(12) United States Patent
Nakao et al.

(10) Patent No.: US 7,238,714 B2
(45) Date of Patent: Jul. 3, 2007

(54) ARYL OR HETEROARYL AMIDE COMPOUNDS

(75) Inventors: Kazunari Nakao, Aichi-ken (JP); Seiji Nukui, San Diego, CA (US); Yoshiyuki Okumura, Aichi-ken (JP); Tatsuya Yamagishi, Aichi-ken (JP)

(73) Assignee: Pfizer Japan, Inc., Shibuya-Ku (JP)

( * ) Notice: Subject to any disclaimer, the term of this patent is extended or adjusted under 35 U.S.C. 154(b) by 359 days.

(21) Appl. No.: 10/932,463

(22) Filed: Sep. 2, 2004

(65) Prior Publication Data

US 2005/0065188 A1   Mar. 24, 2005

Related U.S. Application Data

(60) Provisional application No. 60/500,131, filed on Sep. 3, 2003.

(51) Int. Cl.
*C07D 401/02* (2006.01)
*A61K 31/44* (2006.01)

(52) U.S. Cl. ............... 514/332; 514/340; 514/354; 514/616; 546/255; 546/268.4; 546/315; 564/155

(58) Field of Classification Search ........... 514/332, 514/340, 354, 616; 546/255, 315, 268.4; 564/155

See application file for complete search history.

(56) References Cited

U.S. PATENT DOCUMENTS

| 4,181,658 A | 1/1980 | Hitzel et al. |
| 4,221,815 A | 9/1980 | Weyer et al. |

FOREIGN PATENT DOCUMENTS

| DE | 25 00 157 A1 | 7/1976 |
| DE | 27 06 977 A1 | 8/1978 |
| EP | 1 229 034 A1 | 1/2002 |
| WO | WO 98/45268 A1 | 10/1998 |
| WO | WO 00/64876 A1 | 11/2000 |
| WO | WO 03/016254 A1 | 2/2003 |

*Primary Examiner*—Zinna N. Davis
(74) *Attorney, Agent, or Firm*—Philip B. Polster, II; David Kurlandsky

(57) ABSTRACT

This invention provides a compound of the formula (I):

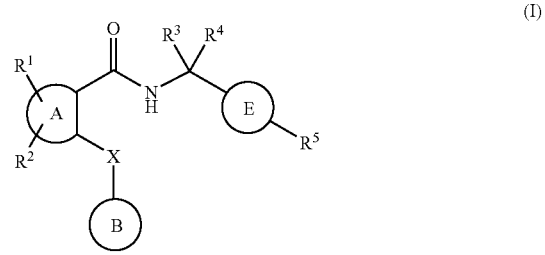

wherein A represents a phenyl group or the like: B represents an aryl or the like: E represents a 1,4-phenylene group; $R^1$ and $R^2$ independently represent a hydrogen atom or the like: $R^3$ and $R^4$ independently represent a hydrogen atom or the like: $R^5$ represents —$CO_2H$ or the like: $R^6$ represents an alkyl group having from 1 to 6 carbon atoms or the like: X represents a methylene group or the like. These compounds are useful for the treatment of disease conditions mediated by prostaglandin such as pain, or the like in mammalian. This invention also provides a pharmaceutical composition comprising the above compound.

27 Claims, No Drawings

ARYL OR HETEROARYL AMIDE COMPOUNDS

This application is a United States utility application, which claims the benefit of priority to U.S. Provisional Application No. 60/500,131, filed Sep. 3, 2003.

TECHNICAL FIELD

This invention relates to novel aryl or heteroaryl amide compounds and to their use in therapy. These compounds are useful as antagonists of the prostaglandin $E_2$ receptor, and are thus useful for the treatment of pain and inflammation and other inflammation-associated disorders, such as arthritis, and in treating disorders or medical conditions selected from pain, inflammatory diseases and the like in mammals, especially humans. The present invention also relates to a pharmaceutical composition comprising the above compounds.

BACKGROUND ART

Prostaglandins are mediators of pain, fever and other symptoms associated with inflammation. Prostaglandin $E_2$ ($PGE_2$) is the predominant eicosanoid detected in inflammation conditions. In addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis or the like.

Four $PGE_2$ receptor subtypes ($EP_1$, $EP_2$, $EP_3$ and $EP_4$) displaying different pharmacological properties have been cloned. The $EP_4$ subtype, a Gs-coupled receptor, stimulates cAMP production, and is distributed in a wide variety of tissue suggesting a major role in $PGE_2$-mediated biological events.

Certain compounds of the present invention are generally disclosed in WO98/45268 and EP-A-1229034 as PDE4 inhibitors, in WO03/16254 as EP4 receptor antagonists, in WO00/64876 as PPAR ligand receptor binders, and in DE2500157 (U.S. Pat. No. 4,221,815) and DE2706977 (U.S. Pat. No. 4,181,658) as antidiabetic agents. WO00/20371 describes a family of PGE receptor antagonists differing from the present compounds by having an ortho-substitution pattern in the phenyl ring. WO01/57036 describes a series of nicotinamide PDE4 inhibitors.

The invention addresses the problem of providing $EP_4$ receptor modulators (e.g., agonists and antagonists) which have improved $EP_4$ receptor modulating activities (e.g., agonist or antagonist activities). In particular, it relates to the provision of EP4 receptor antagonists useful in therapy, particularly for the treatment of pain and inflammation conditions.

BRIEF DISCLOSURE OF THE INVENTION

It has now been found that aryl or heteroaryl amide compounds are $EP_4$ receptor selective antagonists with analgesic activity by systemic administration.

The compounds of the present invention may show less toxicity, good absorption, good distribution, good solubility, low protein binding affinity, less drug-drug interaction, and good metabolic stability.

The present invention provides a compound of the following formula (I):

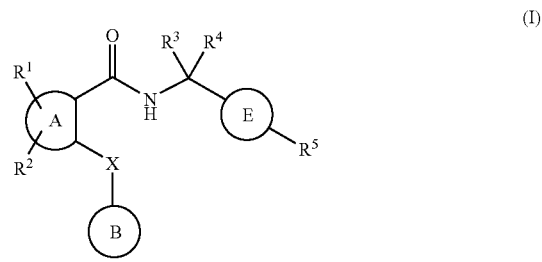

wherein A represents a phenyl group or a pyridyl group;
B represents an aryl group or a heteroaryl group;
E represents a 1,4-phenylene group;
$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;
$R^3$ and $R^4$ independently represent a hydrogen atom or an alkyl group having from 1 to 4 carbon atoms; or $R^3$ and $R^4$ groups may be joined together to form an alkylene chain having 2 to 6 carbon atoms;
$R^5$ represents
—$CO_2H$, $CO_2W$,

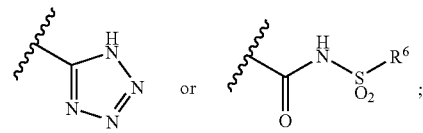

$R^6$ represents an alkyl group having from 1 to 6 carbon atoms, a cycloalkyl group having from 3 to 7 ring atoms, an aryl group or a heteroaryl group;
X represents a methylene group, an oxygen atom or a sulfur atom;
said aryl groups have from 6 to 10 carbon atoms;
said heteroaryl groups are 5- to 10-membered aromatic heterocyclic groups containing from 1 to 3 heteroatoms selected from the group consisting of sulfur atoms, oxygen atoms and nitrogen atoms;
said aryl groups and said heteroaryl groups referred to in the definitions of B are unsubstituted or are substituted by at least one substituent selected from the group consisting of substituents α;
said 1,4-phenylene group referred to in the definition of E is unsubstituted or is substituted by at least one substituent selected from the group consisting of substituents β;
said aryl groups and said heteroaryl groups referred to in the definitions of $R^6$ and α are unsubstituted or are substituted by at least one substituent selected from the group consisting of substituents β;
said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent a groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

W is a pharmaceutically acceptable ester pro-drug group; with the proviso $R^1$ and $R^2$ do not represent a hydrogen atom simultaneously;

or a pharmaceutically acceptable salt thereof.

The aryl or heteroaryl amide compounds of this invention have an antagonistic action towards prostaglandin and are thus useful in therapeutics, particularly for the treatment of a disorder or condition selected from the group consisting of pain, neuropathic pain, visceral pain, inflammatory pain, nociceptive pain, chronic pain, acute pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia, other bleeding problems; kidney disease; thrombosis; occlusive vascular disease; presurgery; and anti-coagulation; sympathetically maintained pain; pain resulting from amputation, skin conditions (e.g. eczema, psoriasis); ophthalmic diseases such as glaucoma, retinitis, retinopathies, uveitis and of acute injury to the eye tissue (e.g. conjunctivitis); lung disorders (e.g. bronchitis, emphysema, allergic rhinitis, respiratory distress syndrome pigeon fancier's disease, farmer's lung, COPD); gastrointestinal tract disorders (e.g. aphthous ulcer, Crohn's disease atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendonitis, bursitis, and Sjogren's; abnormal platelet function (e.g. occlusive vascular diseases); diuretic action; impotence or erectile dysfunction; bone disease characterised by abnormal bone metabolism or resorption such as osteoporosis; hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis; bone resorption, the hemodynamic side effects of NSAIDs and COX-2 inhibitors, cardiovascular diseases, hypertention or myocardial ischemia; functional or organic venous insufficiency; varicose therapy; haemorrhoids; and shock states associated with a marked drop in arterial pressure (e.g. septic shock); neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mile cognitive impairment associated with ageing, particularly Age Associated Memory Impairment; neuroprotection, neurodegeneration following stroke, cardiac arrest, pulmonary bypass, traumatic brain injury, spinal cord injury; tinnitus, complications of Type 1 diabetes (e.g. diabetic microangiopathy, diabetic nephropathy, macular degeneration, glaucoma), nephrotic syndrome, aplastic anaemia, uveitis, Kawasaki disease and sarcoidosi; kidney dysfuncion (e.g. nephritis particularly mesangial proliferative glomerulonephritis, nephritic syndrome), liver dysfunction (hepatitis, cirrhosis), gastrointestinal dysfunction (diarrhea), alcoholic cirrhosis, amyloidosis, atherosclerosis, cardiac disease, sclerosis, organ transplantation reactions, glucocorticoid induced osteoporosis, tooth loss, bone fractures, multiple myeloma, various edema, hypertension, premenstrual tension, urinary calculus, oliguria, hyperphosphaturia, prutitus urticaria, contact-type dermatitis, rhus dermatitis, pollakiuria, learning disability, gingiritis, predontitis, lung injury, liver injury, and constipation, or the like in mammalian subjects, especially humans.

The compound of formula (I) are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compound of formula (I) have also diuretic activity with a various characteristic such as a lower kaluretic activity relative to natriuretic effect, a larger phosphorus excretion.

The compounds of the present invention are useful for the general treatment of pain, particularly inflammatory or neuropathic pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1–164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765–1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13–44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain have both nociceptive and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13–44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumber facet joints, sacroiliac joints, paraspinal muscles or the posterior longitudinal ligament.

Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959–1964). The symptoms of neuropathic pain are difficult to treat, as they are often heterogeneous even between patients with the same disease (Woolf & Decosterd 1999 Pain Supp. 6: S141–S147; Woolf and Mannion 1999 Lancet 353: 1959–1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45–56). Arthritic pain makes up the majority of the inflammatory pain population. Rheumatoid disease is one of the commonest chronic inflammatory conditions in developed countries and rheumatoid arthritis is a common cause of disability. The exact aetiology of RA is unknown, but current hypotheses suggest that both genetic and microbiological factors may be important (Grennan & Jayson 1994 Textbook of Pain 397–407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679–686; McCarthy et al., 1994 Textbook of Pain 387–395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD).

Other types of pain include but are not limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardical infarction, mitral stenosis, pericarditis, Raynaud's phenomenon, scleredoma, scleredoma, skeletal muscle ischemia.

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Head pain including but not limited to migraine, migraine with aura, migraine without aura cluster headache, tension-type headache.

Orofacial pain including but not limited to dental pain, temporomandibular myofascial pain.

The present invention provides a method for the treatment of a disease condition mediated by prostaglandin, in a mammalian subject, which comprises administering to said subject a therapeutically effective amount of a compound of formula (I) or salt thereof.

Further, the present invention also provides a composition which comprises a therapeutically effective amount of the aryl or heteroaryl amide compound of formula (I) or its pharmaceutically acceptable salt together with a pharmaceutically acceptable carrier. The composition is preferably for the treatment of disease defined above, particularly pain, inflammation, osteoarthritis or rheumatoid arthritis.

Also, the present invention provides a compound of formula (I), or a pharmaceutically acceptable salt thereof, as a medicament.

Also, the present invention provides a method for the treatment of disease conditions defined above, particularly pain, inflammation, osteoarthritis or rheumatoid arthritis, which comprises administering to said subject a therapeutically effective amount of a compound of formula (I) or salt thereof.

Further, the present invention provides a method for the treatment of disease conditions defined above, particularly pain, inflammation, osteoarthritis or rheumatoid arthritis, in a mammal, preferably human, which comprises administering to said subject a therapeutically effective amount of a compound of formula (I) or salt thereof.

Yet further, the present invention provides the use of a therapeutically effective amount of a compound of formula (I) or salt thereof in the manufacture of a medicament for the treatment of the disease conditions defined above, particularly pain, inflammation, osteoarthritis or rheumatoid arthritis.

Yet further, the present invention provides a combination, comprising a compound of formula (I), or salt thereof and, one or more other pharmacologically active ingredient(s) for examplea COX-2 selective, COX-1 selective or non-selective NSAID(nonsteroidal anti-inflammatory drug), opioid, anticonvulsant, antidepressant, local anesthetic, disease-modifying anti-rheumatoid drug, or steroid.

Also, the present invention provides a compound of the following formula (II) as a prodrug or a reaction intermediate:

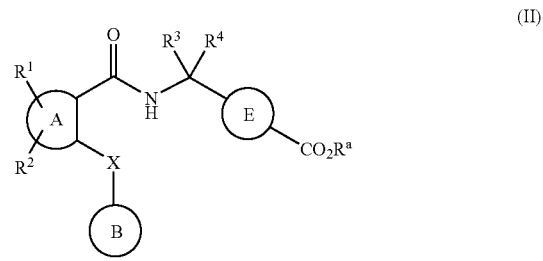

(II)

wherein A represents a phenyl group or a pyridyl group;

B represents an aryl group or a heteroaryl group;

E represents a 1,4-phenylene group;

$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

$R^3$ and $R^4$ independently represent a hydrogen atom or an alkyl group having from 1 to 4 carbon atoms; or $R^3$ and $R^4$ groups may be joined together to form an alkylene chain having 2 to 6 carbon atoms;

$R^a$ represents an alkyl group having from 1 to 6 carbon atoms or an aralkyl group having from 7 to 12 carbon atoms, X represents a methylene group, an oxygen atom or a sulfur atom;

said aryl groups have from 6 to 10 carbon atoms;

said heteroaryl groups are 5- to 10-membered aromatic heterocyclic groups containing from 1 to 3 heteroatoms selected from the group consisting of sulfur atoms, oxygen atoms and nitrogen atoms;

said aryl groups and said heteroaryl groups referred to in the definitions of B are unsubstituted or are substituted by at least one substituent selected from the group consisting of substituents α;

said 1,4-phenylene group referred to in the definition of E is unsubstituted or is substituted by at least one substituent selected from the group consisting of substituents β;

said aryl groups and said heteroaryl groups referred to in the definitions of $R^6$ and α are unsubstituted or are substituted by at least one substituent selected from the group consisting of substituents β;

said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent α groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

with the proviso $R^1$ and $R^2$ do not represent a hydrogen atom simultaneously;

or a pharmaceutically acceptable salt thereof.

Also, the present invention provides an intermediate compound of the following formula (III):

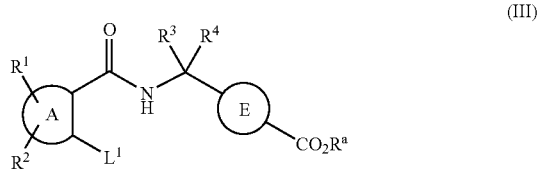

wherein A represents a phenyl group or a pyridyl group;
E represents a 1,4-phenylene group;
$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;
$R^3$ and $R^4$ independently represent a hydrogen atom or an alkyl group having from 1 to 4 carbon atoms; or $R^3$ and $R^4$ groups may be joined together to form an alkylene chain having 2 to 6 carbon atoms;
$R^a$ represents an alkyl groups having from 1 to 6 carbon atoms or an aralkyl group having from 7 to 12 carbon atoms,
$L^1$ represents a halogen atom, an alkanesulfonyloxy group having from 1 to 4 carbon atoms, an arylsulfonyloxy group optionally substituted by an alkyl group having from 1 to 4 carbon atoms, a haloalkanesulfonyloxy group having from 1 to 4 carbon atoms or a boronic acid $(B(OH)_2)$ group;
said 1,4-phenylene group referred to in the definition of E is unsubstituted or is substituted by at least one substituent selected from the group consisting of substituents β;
said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;
with the proviso $R^1$ and $R^2$ do not represent a hydrogen atom simultaneously;
or a pharmaceutically acceptable salt thereof.

DETAILED DESCRIPTION OF THE INVENTION

As used herein, the term "halogen" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "alkylene", as used herein, means a saturated hydrocarbon (straight chain or branched) wherein a hydrogen atom is removed from each of the terminal carbons such as methylene, ethylene, methylethylene, propylene, butylene, pentylene, hexylene and the like.

As used herein, the term "alkenylene", as used herein, means a hydrocarbon radical having at least one double bond (straight chain or branched) wherein a hydrogen atom is removed from each of the terminal carbons such as ethenylene, propenylene, and the like.

As used herein, the term "alkenyl" means a hydrocarbon radical having at least one double bond including, but not limited to, ethenyl, propenyl, 1-butenyl, 2-butenyl and the like.

As used herein, the term "alkynyl", as used herein, means a hydrocarbon radical having at least one triple bond including, but not limited to, ethynyl, propynyl, 1-butynyl, 2-butynyl and the like.

As used herein, the term "alkoxy" means alkyl-O—, including, but not limited to methoxy, ethoxy, n-propoxy, isopropoxy, n-butoxy, iso-butoxy, secondary-butoxy, tertiary-butoxy.

As used herein, the term "cycloalkyl", as used herein, means a saturated carbocyclic radical ring of 3 to 8 carbon atoms, including, but not limited to, cyclopropyl, cyclobutyl, cyclohexyl, cycloheptyl, cyclooctyl, cyclononyl, cyclodecyl and the like.

As used herein, the term "alkanoyl" means a group having carbonyl such as R'—C(O)— wherein R' is H, $C_{1-6}$ alkyl, phenyl or $C_{3-6}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)—, cyclopentyl-C(O)—, cyclohexyl-C(O)—, and the like.

As used herein, the term "aryl" means a monocyclic or bicyclic aromatic carbocyclic ring of 6 to 10 carbon atoms; or bicyclic partially saturated carbocyclic ring of 6 to 10 carbon atoms including, but not limited to, phenyl, naphthyl, indanyl, indenyl, tetralinyl, preferably phenyl, indanyl and naphthyl.

As used herein, the term "haloalkyl", as used herein, means an alkyl radical which is substituted by halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

As used herein, the term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

The term "heteroaryl" means a 5- to 10-membered aromatic or partially saturated hetero mono- or bi-cyclic ring which consists of from 1 to 3 heteroatoms independently selected from the group consisting of sulfur atoms, oxygen atoms and nitrogen atoms including, but not limited to, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl, indolinyl, benzothienyl, benzofuranyl, benzoimidazolinyl, quinolyl, piperidyl, 4-piperidonyl, pyrrolidinyl, 2-pyrrolidonyl, tetrahydrofuranyl, tetrahydroquinolyl, tetrahydroisoquinolyl, decahydroquinolyl or octahydroisoquinolyl, piperazinyl, and the like.

As used herein, the term "aralkyl" means an alkyl radical which is substituted by an aryl group as defined above, e.g. benzyl.

As used herein, the term "aralkoxy" means aralkyl-O—, in which the term aralkyl is defined above, including, but not limited to benzyloxy.

Where the compounds of formula (1) contain hydroxy groups, they may form esters. Examples of such esters include esters with a hydroxy group and esters with a carboxy group. The ester residue may be an ordinary protecting group or a protecting group which can be cleaved in vivo by a biological method such as hydrolysis.

The term "ordinary protecting group" means a protecting group, which can be cleaved by a chemical method such as hydrogenolysis, hydrolysis, electrolysis or photolysis.

"W" means an ester prodrug group which can be cleaved in vivo by a biological method such as hydrolysis and forms a free acid or salt thereof of a compound of the formula (I). Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of groups for an ester of a carboxyl group or a hydroxy group include: lower aliphatic acyl groups, for example: alkanoyl groups, such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups, such as the chloroacetyl, dichloroacetyl, trichloroacetyl, and trifluoroacetyl groups; alkoxyalkylcarbonyl groups, such as the methoxyacetyl group; and unsaturated alkylcarbonyl groups, such as the acryloyl, propioloyl, methacryloyl, crotonoyl, isocrotonoyl and (E)-2-methyl-2-butenoyl groups; more preferably, the lower aliphatic acyl groups having from 1 to 6 carbon atoms; aromatic acyl groups, for example: arylcarbonyl groups, such as the benzoyl, α-naphthoyl and β-naphthoyl groups; halogenated arylcarbonyl groups, such as the 2-bromobenzoyl and 4-chlorobenzoyol groups; lower alkylated arylcarbonyl groups, such as the 2,4,6-trimethylbenzoyl and 4-toluoyl groups; lower alkoxylated arylcarbonyl groups, such as the 4-anisoyl group; nitrated arylcarbonyl groups, such as the 4-nitrobenzoyl and 2-nitrobenzoyl groups; lower alkoxycarbonylated arylcarbonyl groups, such as the 2-(methoxycarbonyl)benzoyl group; and arylated arylcarbonyl groups, such as the 4-phenylbenzoyl group; alkoxycarbonyl groups, for example: lower alkoxycarbonyl groups, such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(lower alkyl) silyl-substituted lower alkoxycarbonyl groups, such as the 2,2,2-trichloroethoxycarbonyl and 2-trimethylsilylethoxycarbonyl groups;

tetrahydropyranyl or tetrahydrothiopyranyl groups, such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups, such as: tetrahydrofuran-2-yl and tetrahydrothiofuran-2-yl groups; silyl groups, for example: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri (lower alkyl)silyl groups substituted by 1 or 2 aryl groups, such as the diphenylmethylsilyl, diphenylbutylsilyl, diphenylisopropylsilyl and phenyldiisopropylsilyl groups; alkoxymethyl groups, for example: lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups; lower alkoxylated lower alkoxymethyl groups, such as the 2-methoxyethoxymethyl group; and halo(lower alkoxy)methyl groups, such as the 2,2,2-trichloroethoxymethyl and bis(2-chloroethoxy)methyl groups; substituted ethyl groups, for example: lower alkoxylated ethyl groups, such as the 1-ethoxyethyl and 1-(isopropoxy)ethyl groups; and halogenated ethyl groups, such as the 2,2,2-trichloroethyl group; aralkyl groups, for example: lower alkyl groups substituted by from 1 to 3 aryl groups, such as the benzyl, α-naphthylmethyl, β-naphthylmethyl, diphenylmethyl, triphenylmethyl, α-naphthyldiphenylmethyl and 9-anthrylmethyl groups; and lower alkyl groups substituted by from 1 to 3 substituted aryl groups, where one or more of the aryl groups is substituted by one or more lower alkyl, lower alkoxy, nitro, halogen or cyano substituents, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups: such as the vinyloxycarbonyl and aryloxycarbonyl groups; and aralkyloxycarbonyl groups in which the aryl ring may be substituted by 1 or 2 lower alkoxy or nitro groups: such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "treating", as used herein, refers to curative, prophylactic of palliative treatment, i.e. reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred compound of formula (I) of this invention is that wherein E represents an unsubstituted 1,4-phenylene group.

Another preferred compound of formula (I) of this invention is that wherein E represents a 1,4-phenylene group substituted by at least one substituent selected from the group consisting of halogen atoms (e.g. fluoro, chloro) or alkyl groups having from 1 to 4 carbon atoms (e.g. methyl).

A preferred compound of formula (I) of this invention is that wherein B represents an aryl or heteroaryl group such as phenyl, naphthyl, pyridyl, quinolyl or isoquinolyl. B is preferably unsubstituted or is substituted by at least one substituent selected from the group consisting of substituents a; said substituents a are selected from the group consisting halogen atoms (e.g. fluoro, chloro), alkyl groups having from 1 to 4 carbon atoms (e.g. methyl, ethyl), alkoxy groups having from 1 to 4 carbon atoms (e.g. methoxy), haloalkoxy groups having from 1 to 4 carbon atoms (e.g. trifluoromethoxy), cyano groups, alkynyl groups having from 2 to 6 carbon atoms (e.g. ethynyl), alkanoyl groups having from 1 to 5 carbon atoms (e.g. acetyl), cycloalkyl groups having from 3 to 7 ring atoms (e.g. cyclopentyl), heteroaryl groups (e.g. 2-, 3- or 4-pyridyl, 1-methylimidazol-2-yl, thiazol-2-yl, 2-methylthiazol-4-yl), aryl groups (e.g. phenyl), aralkoxy groups having from 7 to 10 carbon atoms (e.g. benzyloxy), arylcarbonyl groups (e.g. benzoyl), two adjacent α groups are optionally joined together to form an alkylene chain having 3 carbon atoms, alkylthio groups having from 1 to 4 carbon atoms (e.g. methylthio) and di-alkylaminoalkyl groups having from 1 to 6 carbon atoms in the alkyl part; said heteroaryl groups referred to in the definitions of α are unsubstituted or are substituted by alkyl groups having from 1 to 4 carbon atoms (e.g. methyl). More preferably B represents a phenyl group optionally substituted by substituent selected from the group consisting of substituents α; said substituents a are selected from the group consisting of halogen atoms (e.g. fluoro, chloro), alkyl groups having from 1 to 4 carbon atoms (e.g. methyl, ethyl), alkoxy groups having from 1 to 4 carbon atoms (e.g. methoxy), haloalkoxy groups having from 1 to 4 carbon atoms (e.g. trifluoromethoxy), cyano groups, alkynyl groups having from 2 to 6 carbon atoms (e.g. ethynyl), alkanoyl groups having from 1 to 4 carbon atoms (e.g. acetyl), cycloalkyl groups having from 3 to 7 ring atoms (e.g. cyclopentyl), alkylthio groups having from 1 to 4 carbon atoms (e.g. methylthio), di-alkylaminoalkyl groups having from 1 to 6 carbon atoms in the alkyl part, thiazolyl groups, isothiazolyl groups, oxazolyl groups, isoxazolyl groups, imidazolyl groups, pyridyl groups, benzyloxy groups, phenyl groups or benzoyl groups; said thiazolyl groups, isothiazolyl groups, oxazolyl groups, isoxazolyl groups, imidazolyl groups and pyridyl groups referred to in the definitions of α are unsubstituted or are substituted by alkyl groups having from 1 to 4 carbon atoms. More preferably B represents a phenyl group optionally substituted by substituent selected from the group consisting of substituents α; said substituents α are selected from the group consisting of fluorine atoms, chlorine atoms, methyl groups, ethyl groups, methoxy groups, trifluoromethoxy groups, cyano groups, ethynyl groups, acetyl groups, cyclopentyl groups, methylthio groups, dimethylaminoethyl groups, phenyl groups, imidazolyl groups optionally substituted by methyl groups, thiazolyl groups optionally substituted by methyl groups, pyridyl groups or benzyloxy groups. More preferably, B represents a phenyl group substituted by 1 or 2 fluoro or chloro substituents. More preferably, B represents a phenyl group substituted by 1 fluoro or chloro substituent. Most preferably, B represents 3-fluorophenyl.

A preferred compound of formula (I) of this invention is that wherein X represents a methylene group or an oxygen atom. Preferably, X represents an oxygen atom.

A preferred compound of formula (I) of this invention is that wherein $R^1$ and $R^2$ independently represent a hydrogen atom, a fluorine atom, a chlorine atom, trifluoromethyl, cyano or aminocarbonyl.

A preferred compound of formula (I) of this invention is that wherein $R^1$ represents a halogen atom (e.g. fluoro, chloro) and $R^2$ represents a hydrogen atom.

A preferred compound of formula (I) of this invention is that wherein $R^3$ and $R^4$ independently represent a hydrogen atom or an alkyl group having from 1 to 4 carbon atoms (e.g. methyl, ethyl). More preferably $R^3$ represents an alkyl group having from 1 to 4 carbon atoms (e.g. methyl, ethyl) and $R^4$ represents a hydrogen atom. Most preferably $R^3$ represents a methyl group and $R^4$ represents a hydrogen atom.

A preferred compound of formula (I) of this invention is that wherein $R^5$ represents
—$CO_2H$,

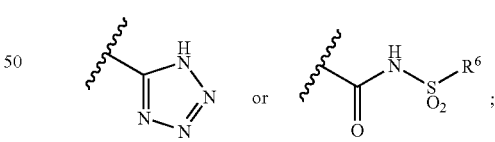

and $R^6$ represents an aryl group optionally substituted by halogen atoms or is a heteroaryl group. More preferably, $R^5$ represents
—$CO_2H$,

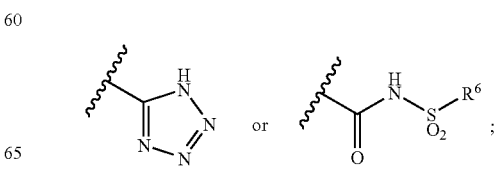

and R⁶ represents an aryl group optionally substituted by halogen atoms. Preferably R⁶ is methyl, cyclohexyl, 2-, 3- or 4-chlorophenyl, 3-fluorophenyl, 3-methylphenyl, 3-methoxyphenyl or 5-methyl-2-pyridyl. Further more preferably R⁵ represents
—CO₂H,

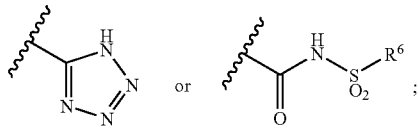

and R⁶ represents a phenyl group optionally substituted by halogen atoms. Most preferably R⁵ represents
—CO₂H or

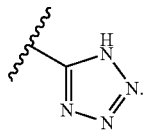

In the definition of B, aryl is preferably phenyl or naphthyl and heteroaryl is a 5- to 10-membered aromatic heterocyclic group containing either from 1 to 3 nitrogen heteroatoms, or 1 or 2 nitrogen heteroatoms and/or 1 oxygen or 1 sulphur heteroatom.

Particularly preferred compounds of the invention include those in which each variable in Formula (I) is selected from the preferred groups for each variable. Even more preferable compounds of the invention include those where each variable in Formula (I) is selected from the more preferred groups for each variable.

A preferred individual compound of this invention is selected from 4-((1S)-1-{[5-chloro-2-(4-fluorophenoxy)benzoyl]amino}ethyl)benzoic acid;
4-[(1S)-1-({[5-chloro-2-(4-fluorophenoxy)pyridin-3-yl]carbonyl}amino)ethyl]benzoic acid;
4-[(1S)-1-({[5-chloro-2-(3-cyanophenoxy)pyridin-3-yl]carbonyl}amino)ethyl]benzoic acid;
4-[(1S)-1-({[5-chloro-2-(3-fluorophenoxy)pyridin-3-yl]carbonyl}amino)ethyl]benzoic acid;
4-[(1S)-1-({[5-chloro-2-(3-chlorophenoxy)pyridin-3-yl]carbonyl}amino)ethyl]benzoic acid;
4-((1S)-1-{[5-chloro-2-(3-fluorophenoxy)benzoyl]amino}ethyl)benzoic acid;
4-((1S)-1-{[5-chloro-2-(3-methoxyphenoxy)benzoyl]amino}ethyl)benzoic acid;
4-((1S)-1-{[5-chloro-2-(3-chlorophenoxy)benzoyl]amino}ethyl)benzoic acid;
4-[(1S)-1-({[5-chloro-2-(2,4-difluorophenoxy)pyridin-3-yl]carbonyl}amino)ethyl]benzoic acid;
4-[(1S)-1-({[5-chloro-2-(4-chloro-3-fluorophenoxy)pyridin-3-yl]carbonyl}amino)ethyl]benzoic acid;
4-[(1S)-1-({[5-chloro-2-(2-chloro-4-fluorophenoxy)pyridin-3-yl]carbonyl}amino)ethyl]benzoic acid;
4-[(1S)-1-({[5-chloro-2-(2,6-difluorophenoxy)pyridin-3-yl]carbonyl}amino)ethyl]benzoic acid;
4-[(1S)-1-({[5-chloro-2-(3,4-difluorophenoxy)pyridin-3-yl]carbonyl}amino)ethyl]benzoic acid;
4-{(1S)-1-[({5-chloro-2-[3-(1,3-thiazol-2-yl)phenoxy]pyridin-3-yl}carbonyl)amino]ethyl}benzoic acid;
4-[(1S)-1-({[5-chloro-2-(2,3-difluorophenoxy)pyridin-3-yl]carbonyl}amino)ethyl]benzoic acid;
4-[(1S)-1-({[5-chloro-2-(2,5-difluorophenoxy)pyridin-3-yl]carbonyl}amino)ethyl]benzoic acid;
4-[(1S)-1-({[5-chloro-2-(4-chlorophenoxy)pyridin-3-yl]carbonyl}amino)ethyl]benzoic acid;
4-[(1S)-1-({[5-chloro-2-(4-chloro-2-fluorophenoxy)pyridin-3-yl]carbonyl}amino)ethyl]benzoic acid;
4-[(1S)-1-({[5-chloro-2-(2-chloro-5-fluorophenoxy)pyridin-3-yl]carbonyl}amino)ethyl]benzoic acid;
4-[(1S)-1-({[5-chloro-2-(3-methylphenoxy)pyridin-3-yl]carbonyl}amino)ethyl]benzoic acid;
4-[(1S)-1-({[5-chloro-2-(4-fluoro-3-methylphenoxy)pyridin-3-yl]carbonyl}amino)ethyl]benzoic acid;
4-[(1S)-1-({[5-chloro-2-(3,5-difluorophenoxy)pyridin-3-yl]carbonyl}amino)ethyl]benzoic acid;
4-((1S)-1-{[5-chloro-2-(2,3-difluorophenoxy)benzoyl]amino}ethyl)benzoic acid;
4-((1S)-1-{[5-chloro-2-(2,4-difluorophenoxy)benzoyl]amino}ethyl)benzoic acid;
4-((1S)-1-{[5-chloro-2-(3,4-difluorophenoxy)benzoyl]amino}ethyl)benzoic acid;
4-[(1S)-1-({[5-chloro-2-(3-chloro-5-fluorophenoxy)pyridin-3-yl]carbonyl}amino)ethyl]benzoic acid;
4-[(1S)-1-({[5-chloro-2-(3-chloro-2-methylphenoxy)pyridin-3-yl]carbonyl}amino)ethyl]benzoic acid;
4-((1S)-1-{[5-chloro-2-(3,5-difluorophenoxy)benzoyl]amino}ethyl)benzoic acid;
4-((1S)-1-{[5-chloro-2-(2,5-difluorophenoxy)benzoyl]amino}ethyl)benzoic acid;
4-[(1S)-1-({[5-chloro-2-(3-chloro-2-fluorophenoxy)pyridin-3-yl]carbonyl}amino)ethyl]benzoic acid;
4-[(1S)-1-({[5-chloro-2-(3-pyridin-2-ylphenoxy)pyridin-3-yl]carbonyl}amino)ethyl]benzoic acid;
4-[(1S)-1-({[5-chloro-2-(4-pyridin-2-ylphenoxy)pyridin-3-yl]carbonyl}amino)ethyl]benzoic acid;
4-[(1S)-1-({[5-chloro-2-(4-pyridin-4-ylphenoxy)pyridin-3-yl]carbonyl}amino)ethyl]benzoic acid;
4-[(1S)-1-({[5-chloro-2-(3-chloro-5-methylphenoxy)pyridin-3-yl]carbonyl}amino)ethyl]benzoic acid;
4-((1S)-1-{[5-chloro-2-(3-methylphenoxy)benzoyl]amino}ethyl)benzoic acid;
4-((1S)-1-{[5-chloro-2-(3-chloro-5-fluorophenoxy)benzoyl]amino}ethyl)benzoic acid;
4-((1S)-1-{[5-chloro-2-(2,6-difluorophenoxy)benzoyl]amino}ethyl)benzoic acid;
4-((1S)-1-{[(5-chloro-2-phenoxypyridin-3-yl)carbonyl]amino}ethyl)benzoic acid;
4-[(1S)-1-({[5-chloro-2-(2,3-dimethylphenoxy)pyridin-3-yl]carbonyl}amino)ethyl]benzoic acid;
4-[(1S)-1-({[5-chloro-2-(2,3-dichlorophenoxy)pyridin-3-yl]carbonyl}amino)ethyl]benzoic acid;
4-[(1S)-1-({[5-chloro-2-(3,4-dichlorophenoxy)pyridin-3-yl]carbonyl}amino)ethyl]benzoic acid;
4-[(1S)-1-({[5-chloro-2-(3,5-dichlorophenoxy)pyridin-3-yl]carbonyl}amino)ethyl]benzoic acid; and 4-[(1S)-1-({[5-chloro-2-(3-fluoro-4-methylphenoxy)pyridin-3-yl]carbonyl}amino)ethyl]benzoic acid;
or a pharmaceutically acceptable salt thereof.

A further preferred individual compound of this invention is selected from
4-((1S)-1-{[5-chloro-2-(4-fluorophenoxy)benzoyl]amino}ethyl)benzoic acid;
4-[(1S)-1-({[5-chloro-2-(4-fluorophenoxy)pyridin-3-yl]carbonyl}amino)ethyl]benzoic acid;
4-[(1S)-1-({[5-chloro-2-(3-cyanophenoxy)pyridin-3-yl]carbonyl}amino)ethyl]benzoic acid;
4-[(1S)-1-({[5-chloro-2-(3-fluorophenoxy)pyridin-3-yl]carbonyl}amino)ethyl]benzoic acid;
4-[(1S)-1-({[5-chloro-2-(3-chlorophenoxy)pyridin-3-yl]carbonyl}amino)ethyl]benzoic acid;
4-((1S)-1-{[5-chloro-2-(3-fluorophenoxy)benzoyl]amino}ethyl)benzoic acid;
4-((1S)-1-{[5-chloro-2-(3-chlorophenoxy)benzoyl]amino}ethyl)benzoic acid;
4-[(1S)-1-({[5-chloro-2-(2-chloro-4-fluorophenoxy)pyridin-3-yl]carbonyl}amino)ethyl]benzoic acid;
4-[(1S)-1-({[5-chloro-2-(2,6-difluorophenoxy)pyridin-3-yl]carbonyl}amino)ethyl]benzoic acid;
4-[(1S)-1-({[5-chloro-2-(3,4-difluorophenoxy)pyridin-3-yl]carbonyl}amino)ethyl]benzoic acid;
4-[(1S)-1-({[5-chloro-2-(2,3-difluorophenoxy)pyridin-3-yl]carbonyl}amino)ethyl]benzoic acid;
4-[(1S)-1-({[5-chloro-2-(2,5-difluorophenoxy)pyridin-3-yl]carbonyl}amino)ethyl]benzoic acid;
4-[(1S)-1-({[5-chloro-2-(2-chloro-5-fluorophenoxy)pyridin-3-yl]carbonyl}amino)ethyl]benzoic acid;
4-[(1S)-1-({[5-chloro-2-(3-methylphenoxy)pyridin-3-yl]carbonyl}amino)ethyl]benzoic acid;
4-[(1S)-1-({[5-chloro-2-(3,5-difluorophenoxy)pyridin-3-yl]carbonyl}amino)ethyl]benzoic acid;
4-((1S)-1-{[5-chloro-2-(2,3-difluorophenoxy)benzoyl]amino}ethyl)benzoic acid;
4-((1S)-1-{[5-chloro-2-(3,4-difluorophenoxy)benzoyl]amino}ethyl)benzoic acid;
4-[(1S)-1-({[5-chloro-2-(3-chloro-5-fluorophenoxy)pyridin-3-yl]carbonyl}amino)ethyl]benzoic acid;
4-((1S)-1-{[5-chloro-2-(3,5-difluorophenoxy)benzoyl]amino}ethyl)benzoic acid;
4-((1S)-1-{[5-chloro-2-(2,5-difluorophenoxy)benzoyl]amino}ethyl)benzoic acid;
4-[(1S)-1-({[5-chloro-2-(3-chloro-5-methylphenoxy)pyridin-3-yl]carbonyl}amino)ethyl]benzoic acid;
4-((1S)-1-{[5-chloro-2-(3-methylphenoxy)benzoyl]amino}ethyl)benzoic acid;
4-((1S)-1-{[5-chloro-2-(3-chloro-5-fluorophenoxy)benzoyl]amino}ethyl)benzoic acid;
4-((1S)-1-{[5-chloro-2-(2,6-difluorophenoxy)benzoyl]amino}ethyl)benzoic acid;
4-((1S)-1-{[(5-chloro-2-phenoxypyridin-3-yl)carbonyl]amino}ethyl)benzoic acid;
4-[(1S)-1-({[5-chloro-2-(2,3-dichlorophenoxy)pyridin-3-yl]carbonyl}amino)ethyl]benzoic acid;
4-[(1S)-1-({[5-chloro-2-(3,4-dichlorophenoxy)pyridin-3-yl]carbonyl}amino)ethyl]benzoic acid;
4-[(1S)-1-({[5-chloro-2-(3,5-dichlorophenoxy)pyridin-3-yl]carbonyl}amino)ethyl]benzoic acid; and
4-[(1S)-1-({[5-chloro-2-(3-fluoro-4-methylphenoxy)pyridin-3-yl]carbonyl}amino)ethyl]benzoic acid;
or a pharmaceutically acceptable salt thereof.

General Synthesis

The compounds of the present invention may be prepared by a variety of processes well known for the preparation of compounds of this type, for example as shown in the following reaction Schemes. Unless otherwise indicated $R^1$ through $R^6$ and A, B, E and X in the reaction Schemes and discussion that follow are defined as above. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1991).

The following reaction Schemes illustrate the preparation of compounds of formula (I).

Scheme 1:
This illustrates the preparation of compounds of formula (Ia) wherein $R^5$ represents —$CO_2H$.

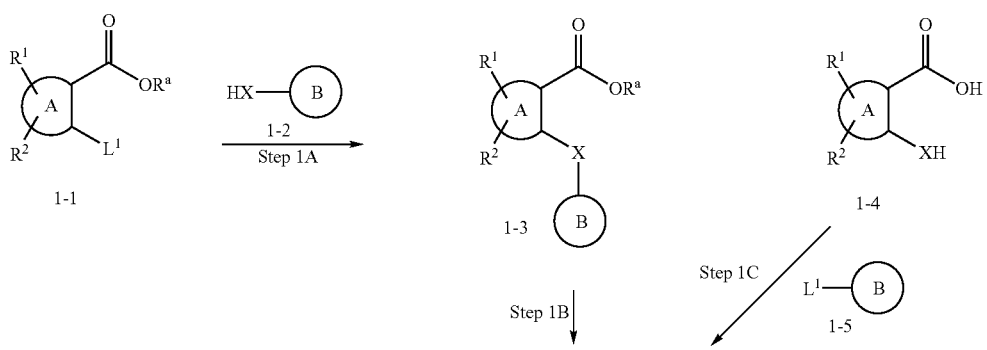

Scheme 1

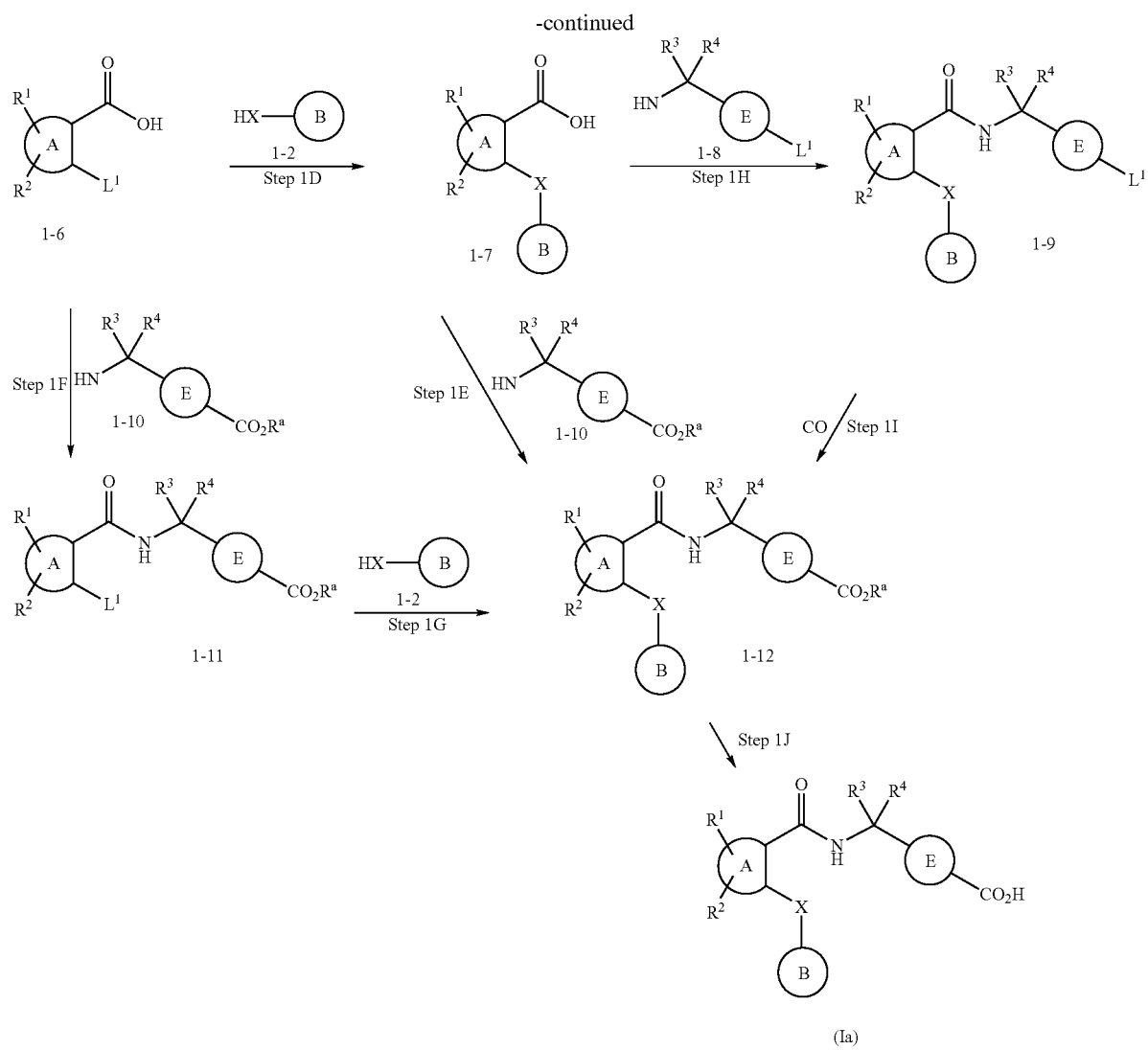

(Ia)

In the above formula, $L^1$ represents a halogen atom such as, chlorine, bromine or iodine; an alkanesulfonyloxy group such as, a methanesulfonyl group; an arylsulfonyloxy group such as, a p-toluenesulfonyloxy group; a haloalkanesulfonyloxy group such as, a trifluoromethanesulfonyloxy group; or a boronic acid group; $R^a$ represents an alkyl groups having from 1 to 6 carbon atoms or an aralkyl group having from 7 to 12 carbon atoms; and all other symbols are as already defined.

Step 1A

In this Step, a compound of formula 1-3 may be prepared by the coupling reaction of an ester compound of formula 1-1 with a cyclic compound of formula 1-2 in an inert solvent.

The coupling reaction may be carried out in the absence or presence of a base in a reaction inert solvent or without solvent. A preferred base is selected from, for example, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, cesium carbonate or potassium carbonate, 2-tert-butylimino-2-diethylamino-1,3-dimethyl-perhydro-1,3,2-diazaphosphorine (BEMP), tert-butylimino-tri (pyrrolidino)phosphorane (BTPP), cesium fluoride (CsF), potassium fluoride, sodium hydride or potassium hydride, or an amine such as triethylamine, tributylamine, diisopropylethylamine, 2,6-lutidine, pyridine or dimethylaminopyridine. Preferred reaction inert solvents include, for example, acetone, benzene, toluene, xylene, o-dichlorobenzene, nitrobenzene, nitromethane, pyridine, dichloromethane, dichloroethane, tetrahydrofuran, dimethylformamide (DMF), dimethylacetamide (DMA), dioxane, dimethylsulfoxide (DMSO), acetonitrile, sulfolane, N-methylpyrrolidinone (NMP), methyl ethyl ketone (2-butanone), tetrahydrofuran (THF), dimethoxyethane (DME) or mixtures thereof. Reaction temperatures are generally in the range of 0 to 200° C., preferably in the range of room temperature to 150° C. Reaction times are, in general, from 1 minute to a day, preferably from 1 hour to 10 hours. If desired, the reaction may be conducted in the presence of metal catalyst such as copper (e.g. copper bronze or cuprous iodide) and nickel.

When $L^1$ represents a boronic acid group, the reaction may be carried out in the presence of a suitable catalyst to form the compound of formula 1-3 by any synthetic procedure applicable to structure-related compounds known to those skilled in the literature (e.g., Lam, P. Y. S.; Clark, C. G.; Saubern, S; Adams, J; Winters, M. P.; Chan, D. M. T.; Combs, A., *Tetrahedron Lett.*, 1998, 39, 2941–2944., Kiyomori, A.; Marcoux, J.; Buchwald, S. L., *Tetrahedron Lett.*, 1999, 40, 2657–2660., Lam, P. Y. S.; Deudon, S.; Averill, K. M.; Li, R.; He, M. Y.; DeShong, P.; Clark, C. G., *J. Am. Chem. Soc.*, 2000, 122, 7600–7601., Collman, J. P.; Zhong, M., *Org. Lett.*, 2000, 2, 1233–1236.). A preferred reaction catalyst is selected from, for example, tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, or copper(II) trifluoromethanesulfonate.

Step 1B

In this Step, an acid compound of formula 1-7 may be prepared by hydrolysis of the ester compound of formula 1-3 in a solvent.

The hydrolysis may be carried out by conventional procedures. In a typical procedure, the hydrolysis carried out under the basic condition, e.g. in the presence of sodium hydroxide, potassium hydroxide or lithium hydroxide. Suitable solvents include, for example, alcohols such as methanol, ethanol, propanol, butanol, 2-methoxyethanol, and ethylene gylcol; ethers such as tetrahydrofuran (THF), 1,2-dimethoxyethane (DME), and 1,4-dioxane; amides such as N,N-dimethylformamide (DMF) and hexamethylphospholictriamide; and sulfoxides such as dimethyl sulfoxide (DMSO). This reaction may be carried out at a temperature in the range from –20 to 100° C., usually from 20° C. to 65° C. for 30 minutes to 24 hours, usually 60 minutes to 10 hour.

The hydrolysis may also be carried out under the acidic condition, e.g. in the presence of e.g. in the presence of hydrogen halides, such as hydrogen chloride and hydrogen bromide; sulfonic acids, such as p-toluenesulfonic acid and benzenesulfonic acid; pyridium p-toluenesulfonate; and carboxylic acid, such as acetic acid and trifluoroacetic acid. Suitable solvents include, for example, alcohols such as methanol, ethanol, propanol, butanol, 2-methoxyethanol, and ethylene gylcol; ethers such as tetrahydrofuran (THF), 1,2-dimethoxyethane (DME), and 1,4-dioxane; amides such as N,N-dimethylformamide (DMF) and hexamethylphospholictriamide; and sulfoxides such as dimethyl sulfoxide (DMSO). This reaction may be carried out at a temperature in the range from –20 to 100° C., usually from 20° C. to 65° C. for 30 minutes to 24 hours, usually 60 minutes to 10 hour.

Step 1C

In this Step, the acid compound of formula 1-7 may also be prepared by coupling reaction of an acid compound of formula 1-4 with a cyclic compound of formula 1-5. This reaction is essentially the same as and may be carried out in the same manner as and using the same reagents and reaction conditions as Step 1A in Scheme 1.

Step 1D

In this Step, the acid compound of formula 1-7 may also be prepared by coupling reaction of an acid compound of formula 1-6 with the cyclic compound of formula 1-2. This reaction is essentially the same as and may be carried out in the same manner as and using the same reagents and reaction conditions as Step 1A in Scheme 1.

Step 1E

In this Step, an amide compound of formula 1-12 may be prepared by the coupling reaction of an amine compound of formula 1-10 with the acid compound of formula 1-7 in the presence or absence of a coupling reagent in an inert solvent. If desired, this reaction may be carried out in the presence or absence of an additive such as 1-hydroxybenzotriazole or 1-hydroxyazabenzotriazole.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone, nitromethane, DMF, sulfolane, DMSO, NMP, 2-butanone, acetonitrile; halogenated hydrocarbons, such as dichloromethane, dichloroethane, chloroform; and ethers, such as tetrahydrofuran and dioxane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –20° C. to 100° C., more preferably from about 0° C. to 60° C. The time required for the reaction may also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice.

Suitable coupling reagents are those typically used in peptide synthesis including, for example, diimides (e.g., dicyclohexylcarbodiimide (DCC), water soluble carbodiimide (WSC)), 2-ethoxy-N-ethoxycarbonyl-1,2-dihydroquinoline, 2-bromo-1-ethylpyridinium tetrafluoroborate (BEP), 2-chloro-1,3-dimethylimidazolinium chloride, benzotriazol-1-yloxy-tris(dimethylamino)phosphonium hexafluorophosphate (BOP), diethyl azodicarboxylate-triphenylphosphine, diethylcyanophosphate, diethylphosphorylazide, 2-chloro-1-methylpyridinium iodide, N,N'-carnbonyldiimidazole, benzotriazole-1-yl diethyl phosphate, ethyl chloroformate or isobutyl chloroformate. If desired, the reaction may be carried out in the presence of a base such as, N,N-diisopropylethylamine, N-methylmorpholine and triethylamine. The amide compound of formula 1-12 may be formed via an acylhalide, which may be obtained by the reaction with halogenating agents such as oxalylchloride, phosphorus oxychloride and thionyl chloride. The resulting acylhalide may be converted to the corresponding amide compound by treating with the amine compound of formula 1-10 under the similar conditions as described in this Step.

Step 1F

In this Step, an amide compound of formula 1-11 may be prepared by coupling reaction of the acid compound of formula 1-6 with the amine compound of formula 1-10. This reaction is essentially the same as and may be carried out in the same manner as and using the same reagents and reaction conditions as Step 1E in Scheme 1.

Step 1G

In this Step, the amide compound of formula 1-12 may also be prepared by coupling reaction of the compound of formula 1-11 with the cyclic compound of formula 1-2. This reaction is essentially the same as and may be carried out in the same manner as and using the same reagents and reaction conditions as Step 1A in Scheme 1.

Step 1H

In this Step, an amide compound of formula 1-9 may be prepared by coupling reaction of the acid compound of formula 1-7 with an amino compound of formula 1-8. This reaction is essentially the same as and may be carried out in the same manner as and using the same reagents and reaction conditions as Step 1E in Scheme 1.

Step 1I

In this Step, the amide compound of formula 1-12 may also be prepared by reacting the amide compound of formula 1-9 with carbon monoxide and alcohol (e.g. methanol or ethanol) in the presence of a catalyst and/or base in an inert solvent.

Example of suitable catalysts include: palladium reagents, such as palladium acetate and palladium dibenzylacetone. Example of suitable bases include: N,N-diisopropylethylamine, N-methylmorpholine and triethylamine. If desired, this reaction may be carried out in the presence or absence of an additive such as 1,1'-bis(diphenylphosphino)ferrocene, triphenylphosphine or 1,3-bis-(diphenylphosphino)propane (DPPP).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone, nitromethane, DMF, sulfolane, DMSO, NMP, 2-butanone, acetonitrile; halogenated hydrocarbons, such as dichloromethane, dichloroethane, chloroform; and ethers, such as tetrahydrofuran and dioxane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from about 50° C. to 80° C. The time required for the reaction may also vary widely, depending on many factors, notably the reaction temperature and the nature of the reagents and solvent employed. However, provided that the reaction is effected under the preferred conditions outlined above, a period of 30 minutes to 24 hours, more preferably 1 hour to 10 hours, will usually suffice.

Step 1J

In this Step, an acid compound of formula Ia may be prepared by hydrolysis of the ester compound of formula 1-12.

This reaction is essentially the same as and may be carried out in the same manner as and using the same reagents and reaction conditions as Step 1B in Scheme 1.

Scheme 2:

This illustrates the preparation of compounds of formula (Ib) wherein $R^5$ represents —$CO_2H$; and X represents a group of formula:

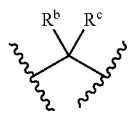

wherein $R^b$ and $R^c$ independently represents a hydrogen atom or an alkyl group having from 1 to 3 carbon atoms.

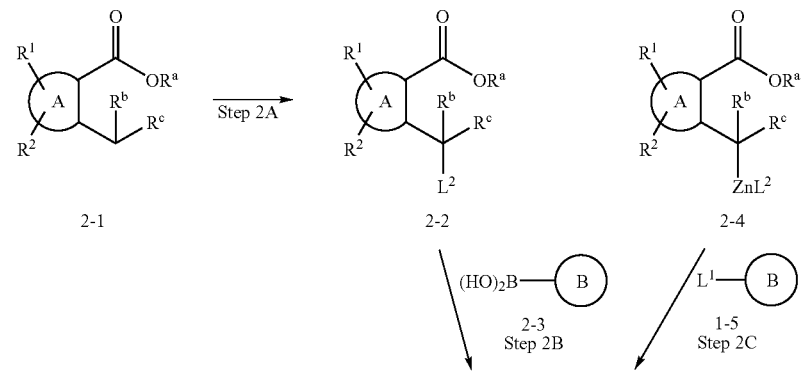

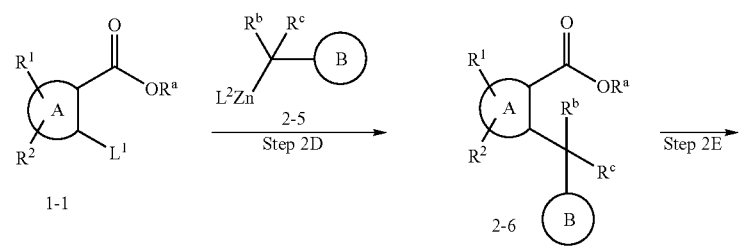

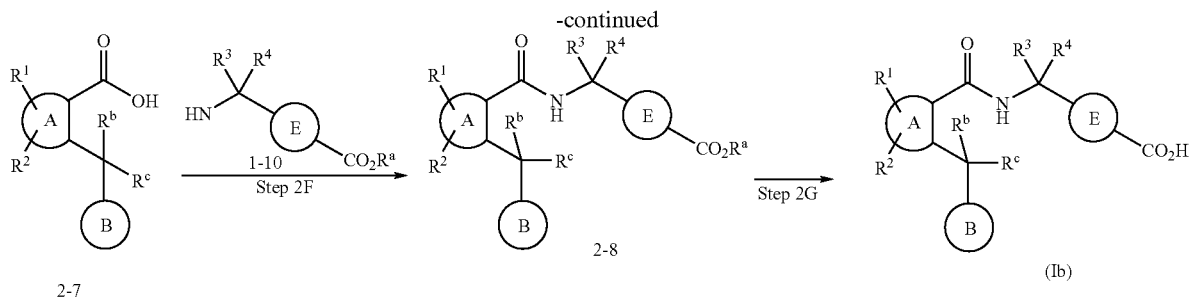

In the above formula, L² represents a halogen atom such as, chlorine, bromine or iodine; and all other symbols are as already defined.

Step 2A

In this Step, a 2-alkyl cyclic ester compound of formula 2-1 may be converted to compound with a leaving group $L^2$ of formula 2-2 under conditions known to those skilled in the art.

The halogenated compound 2-2 may be generally prepared by halogenation with a halogenating reagent in a reaction-inert solvent. Examples of suitable solvents include: such as aqueous or non-aqueous organic solvents such as tetrahydrofuran, dioxane, dimethylformamide, acetonitrile; alcohols, such as methanol or ethanol; halogenated hydrocarbons, such as dichloromethane, dichloroethane or chloroform; and acetic acid. Suitable halogenating reagents include, for example, bromine, chlorine, iodine, N-chlorosuccimide, N-bromosuccimide, 1,3-dibromo-5,5-dimethylhydantoin, bis(dimethylacetamide)hydrogen tribromide, tetrabutylammonium tribromide, bromodimethylsulfonium bromide, hydrogen bromide-hydrogen peroxide, nitrodibromoacetonitrile or copper(II) bromide. The reaction can be carried out at a temperature of from 0° C. to 200° C., more preferably from 20° C. to 120° C. Reaction times are, in general, from 5 minutes to 48 hours, more preferably 30 minutes to 24 hours, will usually suffice.

Step 2B

In this Step, a compound of formula 2-5 may be prepared by the coupling reaction of the halogenated compound of formula 2-2 with a boronic acid compound of formula 2-3 in an inert solvent.

Examples of suitable solvents include: aromatic hydrocarbons, such as benzene, toluene, xylene, nitrobenzene, and pyridine; halogenated hydrocarbons, such as methylene chloride, chloroform, carbon tetrachloride and dichloroethane; ethers, such as diethyl ether, diisopropyl ether, DME, tetrahydrofuran and dioxane; ethyl acetate, acetonitrile, N,N-dimethylformamide, dimethylsulfoxide and water.

The reaction can be carried out at a temperature of from −100° C. to 250° C., more preferably from 0° C. to the reflux temperature. Reaction times are, in general, from 1 minute to 10 day, more preferably from 20 minutes to 5 days, will usually suffice from 1 minute to a day, preferably from 1 hour to 10 hours.

This reaction may be carried out in the presence a suitable catalyst. There is likewise no particular restriction on the nature of the catalysts used, and any catalysts commonly used in reactions of this type may equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper (II) trifluoromethanesulfonate, copper(II) acetate, copper(II) bromide, copper(II) chloride, copper(II) iodide, copper(II) oxide, copper(II) trifluoromethanesulfonate palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride.

This reaction may be carried out in the presence of a suitable additive agent. Examples of such additive agents include: tiphenylphosphine, tri-tert-butylphosphine, 1,1'-bis (diphenylphosphino)ferrocene, tri-2-furylphosphine, tri-o-tolylphosphine, 2-(dichlorohexylphosphino)biphenyl or triphenylarsine.

This reaction may be carried out in the presence or absence of a base. There is likewise no particular restriction on the nature of the bases used, and any base commonly used in reactions of this type may equally be used here. Examples of such bases include: lithium hydroxide, sodium hydroxide, potassium hydroxide, barium hydroxide, sodium carbonate, potassium carbonate, sodium bicarbonate, cesium carbonate, thallium(I) carbonate, sodium ethoxide, potassium tert-butoxide, potassium acetate, cesium fluoride, tetrabutylammonium fluoride, tetrabutylammonium chloride, tetrabutylammonium iodide, pyridine, 1,8-diazabicyclo [5.4.0]undecan, picoline, 4-(N,N-dimethylamino)pyridine, triethylamine, tributylamine, diisopropylethylamine, N-methylmorphorine and N-methylpiperidine. This reaction may be carried out in the presence or absence of a dehydrating reagent. There is likewise no particular restriction on the nature of the dehydrating reagents used, and any dehydrating reagents commonly used in reactions of this type may equally be used here. Examples of such dehydrating reagents include: molecular sieves.

Step 2C

In this Step, the compound of formula 2-7 may be prepared by the coupling reaction of a zinc compound of formula 2-4 with the compound of formula 1-5 in an inert solvent.

Examples of suitable solvents include: aromatic hydrocarbons, such as benzene, toluene, xylene, nitrobenzene, and pyridine; halogenated hydrocarbons, such as methylene chloride, chloroform, carbon tetrachloride and dichloroethane; ethers, such as diethyl ether, diisopropyl ether, tetrahydrofuran and dioxane; ethyl acetate, acetonitrile, N,N-dimethylformamide, dimethylsulfoxide. This reaction may be carried out in the presence a suitable catalyst. Example of suitable catalysts include: dichlorobis[triphenylphosphine]nickel, tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride.

This reaction can be carried out at temperature of −50° C. to 150° C., preferably from about −10° C. to 80° C. for 5 minutes to 48 hours, preferably 30 minutes to 24 hours.

Step 2D

In this Step, the compound of formula 2-7 may be prepared by the coupling reaction of a zinc compound of formula 2-6 with the compound of formula 1-1 in an inert solvent.

This reaction is essentially the same as and may be carried out in the same manner as and using the same reagents and reaction conditions as Step 2C in Scheme 2.

Step 2E

In this Step, an acid compound of formula 2-8 may be prepared by hydrolysis of the ester compound of formula 2-7.

This reaction is essentially the same as and may be carried out in the same manner as and using the same reagents and reaction conditions as Step 1B in Scheme 1.

Step 2F

In this Step, an amide compound of formula 2-9 may be prepared by coupling reaction of the acid compound of formula 2-8 with the amino compound of formula 1-10. This reaction is essentially the same as and may be carried out in the same manner as and using the same reagents and reaction conditions as Step 1E in Scheme 1.

Step 2F

In this Step, an acid compound of formula Ib may be prepared by hydrolysis of the ester compound of formula 2-9.

This reaction is essentially the same as and may be carried out in the same manner as and using the same reagents and reaction conditions as Step 1B in Scheme 1.

Scheme 3:

This illustrates the preparation of compounds of formula (Ic) wherein $R^5$ represents

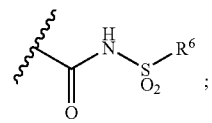

and $R^6$ represents an alkyl group having from 1 to 6 carbon atoms, a cycloalkyl group having from 3 to 7 ring atoms, an aryl group or a heteroaryl group.

Scheme 3

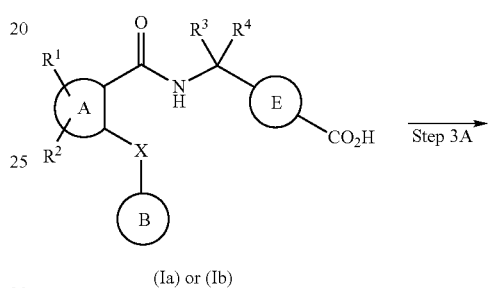

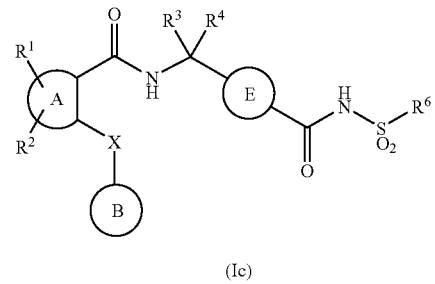

In the above formula all symbols are as already defined.

Step 3A

In this Step, the desired compound of formula Ic may be prepared by the coupling of the compound of formula Ia or Ib, prepared as described in Step 1J in Scheme 1 and Step 2F in Scheme 2 respectively, with a compound of formula $R^6SO_2NH_2$ in an inert solvent.

This reaction is essentially the same as and may be carried out in the same manner as and using the same reagents and reaction conditions as Step 1E in Scheme 1.

Scheme 4:

This illustrates the preparation of compounds of formula (Id) wherein $R^5$ represents

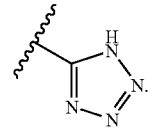

Scheme 4

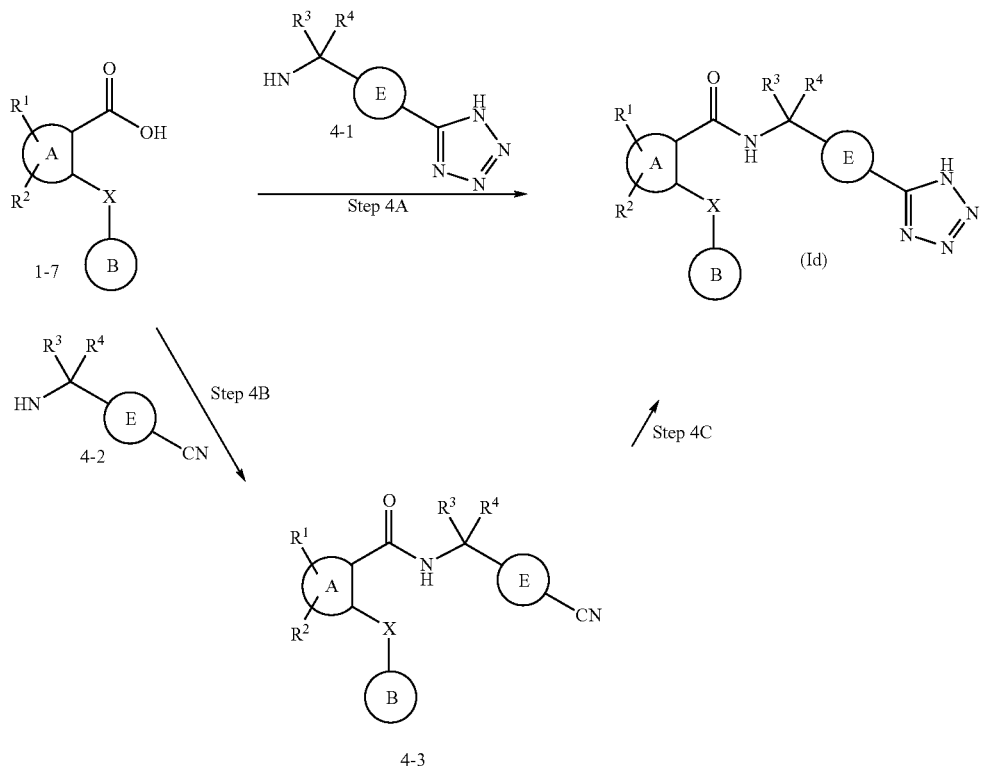

In the above formula all symbols are as already defined.

Step 4A

In this Step, a tetrazole compound of formula Id may be prepared by the coupling of the acid compound of formula 1-7 with an amino compound of formula 4-1. This reaction is essentially the same as and may be carried out in the same manner as and using the same reagents and reaction conditions as Step 1E in Scheme 1.

Step 4B

In this Step, an amide compound of formula 4-3 may be prepared by the coupling of the acid compound of formula 1-7 with an amino compound of formula 4-2. This reaction is essentially the same as and may be carried out in the same manner as and using the same reagents and reaction conditions as Step 1E in Scheme 1.

Step 4C

In this Step, the tetrazole compound of formula Id may also be prepared by converting a nitrile group of the compound of formula 4-3 into the tetrazole group in a inert solvent.

Examples of suitable solvents include: aromatic hydrocarbons such as benzene or toluene; DMF, DMSO, 2-methoxyethanol, water and THF. Examples of suitable tetrazole forming reagents include: sodium azide, lithium azide, trialkyltinazide(alkyl is typically methyl or butyl) and trimethylsilylazide. This reaction may be carried out in the presence or absence of a catalyst. Exmaple of suitable catalysts include dialkyltin oxide(alkyl is typically methyl or butyl), alkylamino hydrochloride, alkylamino hydrobromide or lithium chloride. If desired, this reaction may be carried out in the presence or absence of an acid or a base. Examples of suitable bases include: trimethyl amine, triethyl amine and N,N-diisopropyl ethyl amine. Examples of suitable acids include: ammonium chloride, hydrogen chloride, aluminum chloride or zinc bromide. This reaction may be carried out at temperature of 50° C. to 200° C., preferably from about 80° C. to 150° C. for 5 minutes to 48 hours, preferably 30 minutes to 30 hours. If desired, this reaction may be carried out in a sealable tube.

The starting materials in the aforementioned general syntheses may be commercially available or obtained by conventional methods known to those skilled in the art.

In the above Schemes from 1 to 4, examples of suitable solvents include a mixture of any two or more of those solvents described in each Step.

The compounds of formula (I), and the intermediates above-mentioned preparation methods can be isolated and purified by conventional procedures, such as recrystallization or chromatographic purification.

Also, the compounds of formula (I) may be expected to have more effective therapeutic effects with being co-administered with a COX-2 selective NSAID.

Further, the present invention also encompasses a combination, for the treatment of inflammation, rheumatoid arthritis, pain, common cold, osteoarthritis, neuropathic pain, brain tumor, diuresis, or the like, which comprises a therapeutically effective amount of a compound of formula (I) or salt thereof and a COX-2 selective NSAID.

The compounds of the invention may advantageously be employed in combination with one or more other therapeutic ingredients for example, a COX-2 selective, COX-1 selective or non-selective NSAID, opioid, anticonvulsant, antidepressant, local anesthetic, disease-modifying anti-rheumatoid drug, or a steroid.

The combination with a COX-2 selective NSAID is particularly favored for use in the prophylaxis and treatment of pain and arthritis. Examples of a COX-2 selective NSAID are nimesulide, celecoxib, rofecoxib and valdecoxib.

The compounds of Formula (I) have been found to possess an activity as prostaglandin $E_2$ receptor antagonist, preferably as $EP_4$ receptor antagonist. Preferably, these compounds are useful as an analgesic, anti-inflammatory, diuretic, and the like, in mammalian subjects, especially humans in need of such agents. The affinity, antagonist activities and analgesic activity can be demonstrated by the following tests respectively.

Method for Assessing Biological Activities

In Vitro Assays

Human EP Receptor Cell Membrane Binding Assay:

Stable Expression of Human EP1, 2, 3 and 4 Receptors in the Human Embryonic Kidney (HEK293) Cell Line The cDNA clones of human EP1, 2, 3 and 4 receptors are obtained by polymerase chain reaction (PCR) from rat kidney or heart cDNA libraries (Clontech). Human embryonic kidney cells (HEK 293) are stably transfected with expression vectors for human EP1, 2, 3 and 4 receptors in according to the method described in the article; the journal of biological chemistry vol. 271 No. 39, pp 23642–23645.

Preparation of Membrane Fraction:

The EP1, 2, 3 and 4 transfectant are grown in Dulbecco's modified Eagle's medium containing 10% fetal bovine serum, 50 U/ml penicillin, 50 μg/ml streptomycin and 500 μg/ml G418 (selection medium) at 37° C. in a humidified atmosphere of 5% $CO_2$ in air. For the membrane preparation, cells are harvested with phosphate buffered saline (PBS) and centrifuged at 400×g for 5 min. The pellet is suspended with child (4° C.) PBS containing 1/100 volume of protease inhibitor cocktail (SIGMA) (1 mM (4-(2-aminoethyl)-benzenesulfonyl fluoride (AEBSF)), 0.8 μM Aprotinin, 22 μM Leupeptin, 40 μM Bestatin, 15 μM Pepstatin A and 14 μM E-64). Cells are lysed with ultrasonic cell disrupter for 60-sec sonication. Then cell mixtures are centrifuged at 1,000×g for 10 minutes. The supernatant μs centrifuged at 160,000×g for 30 minutes at 4° C. The pellet is resuspended in assay buffer (10 mM 2-morpholinoeth-anesulfonic acid (MES)-KOH, 1 mM etylenediamine tetra-acetic acid (EDTA), 10 mM $MgCl_2$, pH 6.0), and protein concentration is determined by Bradford method (Bio-Rad assay). This membrane preparation is stored at −80° C. freezer until use for binding assay.

Binding Assay:

Membrane Binding Assay $[^3H]$-$PGE_2$ membrane binding assays are performed in the reaction mixture of 10 mM MES/KOH (pH6.0), 10 mM $MgCl_2$, 1 mM EDTA, 1 nM $[^3H]$-$PGE_2$ (Amersham TRK431, 164 Ci/mmol), 2~10 μg of protein from membrane fraction (human EP1, 2, 3 and 4/HEK293 transfectant) and test compound (total volume is 0.1 ml in 96 well polypropylene plate). Incubation is conducted for 60 min at room temperature prior to separation of the bound and free radioligand by rapid filtration through glass fiber filters (Printed Filtermat B, 1205-404, glass fiber, double thickness, size 102×258 mm, Wallac inc., presoaked in 0.2% polyethylen-imine). Filters are washed with assay buffer and the residual $[^3H]$-$PGE_2$ bound to the filter is determined by liquid scintillation counter (1205 Betaplate™). Specific binding is defined as the difference between total binding and nonspecific binding which is determined in the presence of 10 μM $PGE_2$.

cAMP Assay in Human $EP_4$ Transfectant

HEK293 cells expressing human $EP_4$ receptors (h$EP_4$ cells) are maintained in DMEM containing 10% FBS and 500 μg/ml geneticin. For harvesting h$EP_4$ cells, culture medium is aspirated and cells in 75 $cm^2$ flask are washed with 10 ml of phosphate buffered saline (PBS). Another 10 ml of PBS is added to the cells and incubated for 20 min at room temperature. Human $EP_4$ cells are harvested by pipetting and centrifuged at 300×g for 4 min. Cells are resuspended in DMEM without neutral red at a density of $7\times10^5$ cells/ml containing 0.2 mM IBMX (PDE inhibitor), 1 nM $PGE_2$ and test compounds in PCR-tubes, and incubated at 37° C. for 10 min. The reaction is stopped by heating at 100° C. for 10 min with thermal cycler. Concentration of cAMP in reaction mixtures is determined with SPA cAMP Kit (Amersham) or cAMP Screen™ (Applied Biosystems) according to the manufacture's instruction.

Reference: Eur. J. Pharmacol. 340 (1997) 227–241

TABLE

Result of human EP receptor binding assay (under acidic and hypotonic buffer condition, MME buffer) and functional assay

| Example Number | Binding assay hEP4 Ki (nM) | functional assay human EP4 $IC_{50}$ (nM) vs 1 nM $PGE_2$ |
|---|---|---|
| 45 | 0.3 | 28 |
| 48 | 1.0 | 19 |
| 55 | 0.7 | 20 |
| 56 | 20 | 820 |
| 57 | 92 | 1800 (75% Inh. @ 5000 nM) |
| 68 | 2.4 | 43 |
| 74 | 4.0 | 140 |
| 76 | 1.8 | 100 |
| 79 | 0.7 | 21 |
| 148 | 0.7 | 3.6 |

In Vivo Assays

Carrageenan Induced Mechanical Hyperalgesia in Rats:

Male 4-week-old SD rats were fasted over night. Hyperalgesia was induced by intraplantar injection of λ-carrageenin (0.1 ml of 1% w/v suspension in saline, Zushikagaku). The test compounds (1 ml of 0.1% methylcellulose/100 g body weight) were given per orally at 5.5 hours after the carrageenin injection. The machanical pain threshold was measured by analgesy meter (Ugo Basile) at 4, 5, 6.5 and 7.5 hours after the carrageenin injection and the change of pain threshold was calculated.

Reference: Randall L. O. & Selitto I. J., Arch. Int. Pharmacodyn. 111, 409–419, 1957

Prostaglandin $E_2$($PGE_2$)-Induced Thermal Hyperalgesia in Rats:

Male 4-week-old SD rats were fasted over night. Hyperalgesia was induced by intraplantar injection of 100 ng of PGE2 in 0.05% ethanol/saline (100 ul) into the right hindpaw of the rats. Animals were given orally or intravenously either vehicle (po: 0.1% methyl cellulose, iv: 10% DMSO/saline) or a test compound prior to $PGE_2$ injection, respectively. Rats were placed in plastic cages of plantar test apparatus (Ugo Basile) and the mobile radiant heat source was focused on right hind paw of the rats. The thermal paw-withdrawal latency (sec.) was measured at 15 min after $PGE_2$ injection.

Reference: Hargreaves K. et al., Pain 32, 77–88, 1988.

Drug Substance

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269–1288 by Haleblian (August 1975).

Hereinafter all references to compounds of formula (I) include references to salts, solvates and complexes thereof and to solvates and complexes of salts thereof.

The compounds of the invention include compounds of formula (1) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (D) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of formula (I) contains a carboxylic acid functionality (—COOH), an ester thereof, for example, replacement of the hydrogen with $(C_1-C_8)$alkyl;

(ii) where the compound of formula (I) contains an alcohol functionality (—OH), an ether thereof, for example, replacement of the hydrogen with $(C_1-C_6)$alkanoyloxymethyl; and (iii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety such as tetrazolyl group, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Drug Product

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981–986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1–14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955–958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound (s) of the invention comprising, for example, ethanol, aqueous ethanol, or a suitable alternative agent for dispersing, solubilising, or extending release of the active, a propellant (s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 □g to 10 mg of the compound of formula (I). The overall daily dose will typically be in the range 1 □g to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula I in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range from 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance spectra (NMR), infrared red absorption spectra (IR) or microanalysis. Yields are given for illustrative purposes only. Flash column chromatography was carried out using Merck silica gel 60 (230–400 mesh ASTM). Low-resolution mass spectral data (EI) were obtained on a Integrity (Waters) mass spectrometer. Low-resolution mass spectral data (ESI) were obtained on a ZMD (Micromass) mass spectrometer. NMR data was determined at 270 MHz (JEOL JNM-LA 270 spectrometer) or 300 MHz (JEOL JNM-LA300 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimadzu infrared spectrometer (IR-470). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

Example 1

4-[({[5-FLUORO-2-(4-FLUOROPHENOXY)PYRIDIN-3-YL]CARBONYL}AMINO)METHYL]BENZOIC ACID

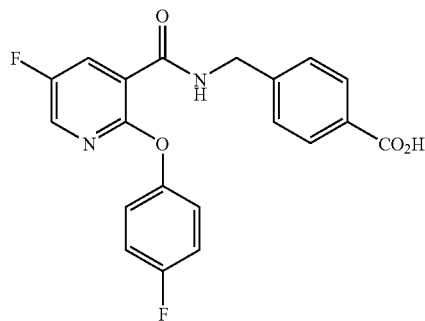

Step 1. Methyl 5-fluoro-2-(4-fluorophenoxy)nicotinate

A mixture of 2-chloro-5-fluoronicotinic acid (2.61 g, 14.9 mmol), 4-fluorophenol (2.02 g, 18 mmol), potassium carbonate (4.56 g, 33 mmol), copper bronze (211 mg, 3.3 mmol), and cuprous iodide (230 mg, 1.2 mmol) in N,N-dimethylforamide (40 mL) was heated under reflux in an oil bath for 6 h. The reaction mixture was filtered through a pad of Celite®. The filtrate was partitioned between ethyl acetate (200 mL) and 2 N hydrochloric acid (200 mL). The organic phase was separated and the aqueous phase was extracted with ethyl acetate (200 mL). The combined organic extracts were washed with brine (50 mL) and dried (sodium sulfate). After removal of solvent, the residual oil was dissolved in methanol (50 mL). To the solution were added conc. hydrochloric acid (1 mL) and the mixture was heated under reflux for 4 h. The volatile components were removed under reduced pressure, and the residue was purified by flash column chromatography on silica gel (150 g) eluting with hexane/ethyl acetate (3/1) to afford 2.63 g (67%) of the title compound: $^1$H-NMR (CDCl$_3$) δ 8.11 (1H, d, J=3.1 Hz), 8.02 (1H, dd, J=7.7, 3.1 Hz), 7.11–7.07 (4H, m), 3.96 (3H, s); MS (ESI) m/z 266 (M+H)$^+$.

Step 2. 5-Fluoro-2-(4-fluorophenoxy)nicotinic acid

To a stirred solution of methyl 5-fluoro-2-(4-fluorophenoxy)nicotinate (step 1, 2.63 g, 9.9 mmol) in methanol (50 mL) was added 2 N sodium hydroxide aqueous solution (10 mL). The reaction mixture was stirred at 40° C. for 3 h. After cooling, the pH value was adjusted to 4.0 by the addition of 2 N hydrochloric acid. The mixture was diluted with water (100 mL), and extracted with dichloromethane (100 mL×3). The combined organic layer was washed with brine (100 mL), dried (sodium sulfate), and concentrated to afford 2.26 g (91%) of the title compound as off white solids: $^1$H-NMR (CDCl$_3$) δ 8.25 (1H, dd, J=7.5, 3.1 Hz), 8.16 (1H, d, J=3.1 Hz), 7.16–7.13 (4H, m); MS (ESI) m/z 252 (M+H)$^+$.

Step 3. Methyl 4-[({[5-fluoro-2-(4-fluorophenoxy)pyridin-3-yl]carbonyl}amino)methyl]benzoate To a stirred solution of 5-fluoro-2-(4-fluorophenoxy)nicotinic acid (step 2, 300 mg, 1.2 mmol) and methyl 4-(aminomethyl)benzoate hydrochloride (284 mg, 1.4 mmol) in dichloromethane (10 mL) were successively added 1-(3-dimethylaminopropyl)-3-ethylcarbodiimide hydrochloride (EDCI) (670 mg, 3.5 mmol), 1-hydroxybenzotriazole hydrate (HOBT) (368 mg, 2.4 mmol), and triethylamine (3 mL). After being stirred overnight, the reaction was quenched by the addition of saturated sodium bicarbonate aqueous solution (50 mL). The aqueous layer was extracted with dichloromethane (50 mL×2) and the combined organic layers were washed with brine (50 mL), dried (sodium sulfate), and evaporated. The remaining residue was purified by flush column chromatography on silica gel (50 g) eluting with hexane/ethyl acetate (3/1) to afford 407 mg (85%) of the title compounds as white solids: $^1$H-NMR (CDCl$_3$) δ 8.39 (1H, dd, J=8.3, 3.1 Hz), 8.28 (1H, br.s), 8.05 (1H, d, J=3.1 Hz), 8.01 (2H, d, J=8.1 Hz), 7.42 (2H, d, J=8.1 Hz), 7.17–7.05 (4H, m), 4.76 (2H, d, J=5.9 Hz), 3.91 (3H, s); MS (ESI) m/z 399 (M+H)$^+$, 397 (M−H)$^-$.

Step 4. 4-[({[5-Fluoro-2-(4-fluorophenoxy)pyridin-3-yl]carbonyl}amino)methyl]benzoic acid To a stirred solution of methyl 4-[({[5-fluoro-2-(4-fluorophenoxy)pyridin-3-yl]carbonyl}amino)methyl]benzoate (step 3, 407 mg, 1.02 mmol) in methanol (10 ml) was added 2 N sodium hydroxide aqueous solution (2 mL). The reaction mixture was stirred at room temperature for 3 h and then evaporated. The residue was partitioned between ethyl acetate (100 mL) and 2 N hydrochloric acid (100 mL). The organic phase was separated and the aqueous phase was extracted with ethyl acetate (100 mL). The combined organic extracts were washed with brine (50 mL), dried (sodium_sulfate), and concentrated. The residual solids were recrystallized from ethyl acetate to afford 248 mg (64%) of the title compound as white solids: $^1$H-NMR (CDCl$_3$) δ 8.40 (1H, dd, J=8.3, 3.1 Hz), 8.30 (1H, br.s), 8.09–8.04 (3H, m), 7.45 (2H, d, J=8.1 Hz), 7.17–7.06 (4H, m), 4.79 (2H, d, J=5.9 Hz); MS (EI) m/z 384 (M$^+$), (ESI) m/z 385 (M+H)$^+$, 383 (M−H)$^-$.

Example 2

4-[1-({[5-FLUORO-2-(4-FLUOROPHENOXY)PYRIDIN-3-YL]CARBONYL}AMINO)ETHYL]BENZOIC ACID

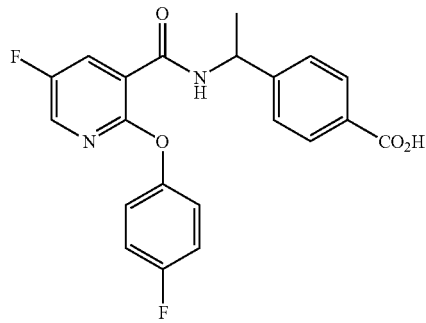

Step 1. N-[1-(4-Bromophenyl)ethyl]-5-fluoro-2-(4-fluorophenoxy)nicotinamide The title compound was prepared according to the procedure described in step 3 of Example 1 from 5-fluoro-2-(4-fluorophenoxy)nicotinic acid (step 2 of Example 1) and [1-(4-bromophenyl)ethyl]amine: $^1$H-NMR (CDCl$_3$) δ 8.31 (1H, ddd, J=8.2, 3.1, 0.9 Hz), 8.14 (1H, d, J=7.2 Hz), 8.03 (1H, dd, J=3.1, 1.1 Hz), 7.45 (2H, dd, J=7.0, 0.9 Hz), 7.25–7.09 (6H, m), 5.28 (1H, dq, J=7.2, 7.0 Hz), 1.57 (3H, d, J=7.0 Hz); MS (ESI) m/z 433 (M+H)$^+$, 431 (M–H)$^-$.

Step 2. Methyl 4-[1-({[5-fluoro-2-(4-fluorophenoxy)pyridin-3-yl]carbonyl}amino)ethyl]benzoate A mixture of N-[1-(4-bromophenyl)ethyl]-5-fluoro-2-(4-fluorophenoxy)nicotinamide (step 1, 398 mg, 0.92 mmol), 1,3-bis(diphenylphosphino)-propane (38 mg, 0.09 mmol), palladium (II) acetate (21 mg, 0.09 mmol), triethylamine (0.38 mL, 2.76 mmol), N,N-dimethylforamide (6 mL) and methanol (4 mL) was stirred at 80° C. for 16 h under carbon monoxide atmosphere. After cooling to room temperature, the mixture was diluted with ether (100 mL) and washed with water (60 mL×3). The organic layer was dried over magnesium sulfate and evaporated. The residue was purified by flush column chromatography on silica gel eluting with hexane/ethyl acetate (2:1) to afford 296 mg (78%) of the title compounds as white solids: $^1$H-NMR (CDCl$_3$) δ 8.32 (1H, dd, J=8.1, 3.1 Hz), 8.21 (1H, d, J=7.3 Hz), 8.04–7.99 (3H, m), 7.43 (2H, d, J=8.2 Hz), 7.27–7.13 (4H, m), 5.38 (1H, dq, J=7.3, 6.9 Hz), 3.90 (3H, s), 1.60 (3H, d, J=6.9 Hz); MS (ESI) m/z 413 (M+H)$^+$, 411 (M–H)$^-$.

Step 3. 4-[1-({[5-Fluoro-2-(4-fluorophenoxy)pyridin-3-yl]carbonyl}amino)ethyl]benzoic acid The title compound was prepared according to the procedure described in step 4 of Example 1 from methyl 4-[1-({[5-fluoro-2-(4-fluorophenoxy)pyridin-3-ylcarbonyl}amino)ethyl]benzoate (step 2): $^1$H-NMR (DMSO-d$_6$) δ 9.01 (1H, d, J=7.9 Hz), 8.23 (1H, dd, J=3.1, 1.3 Hz), 8.02 (1H, ddd, J=7.9, 3.1, 1.3 Hz), 7.86 (2H, d, J=8.3 Hz), 7.52 (2H, d, J=7.5 Hz), 7.30–7.24 (4H, m), 5.18 (1H, dq, J=7.9, 7.0 Hz), 1.46 (3H, d, J=7.0 Hz); MS (ESI) m/z 399 (M+H)$^+$, 397 (M–H)$^-$.

Example 3

4-[1-({[5-FLUORO-2-(4-FLUOROPHENOXY)PYRIDIN-3-YL]CARBONYL}AMINO)PROPYL]BENZOIC ACID

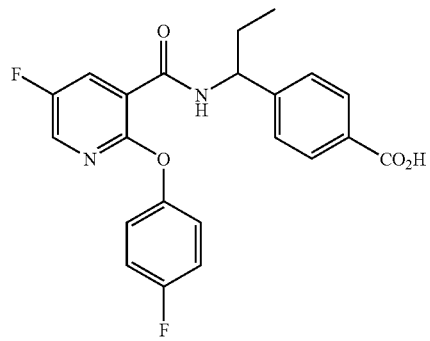

Step 1. Methyl 4-[1-({[5-fluoro-2-(4-fluorophenoxy)pyridin-3-yl]carbonyl}amino)propyl]benzoate The title compound was prepared according to the procedure described in step 3 of Example 1 from 5-fluoro-2-(4-fluorophenoxy)nicotinic acid (step 3 of Example 1) and methyl 4-(1-aminopropyl)benzoate: $^1$H-NMR (CDCl$_3$) δ 8.33–8.26 (2H, m), 8.05–7.99 (3H, m), 7.39 (2H, d, J=8.4 Hz), 7.20–7.15 (4H, m), 5.15 (1H, q, J=7.3 Hz), 3.90 (3H, s), 1.92 (2H, dq, J=7.3, 7.3 Hz), 0.95 (3H, t, J=7.3 Hz); MS (ESI) m/z 427 (M+H)$^+$, 425 (M–H)$^-$.

Step 2. 4-[1-({[5-Fluoro-2-(4-fluorophenoxy)pyridin-3-yl]carbonyl}amino)propyl]benzoic acid The title compound was prepared according to the procedure described in step 4 of Example 1 from methyl 4-[1-({[5-fluoro-2-(4-fluorophenoxy)pyridin-3-yl]carbonyl}amino)propyl]benzoate (step 1): $^1$H-NMR (DMSO-d$_6$) δ 8.97 (1H, d, J=8.0 Hz), 8.23 (1H, d, J=2.9 Hz), 7.99 (1H, dd, J=7.9, 3.1 Hz), 7.86 (2H, d, J=8.3 Hz), 7.50 (2H, d, J=8.3 Hz), 7.30–7.21 (4H, m), 4.96 (1H, q, J=7.7 Hz), 1.77 (2H, dq, J=7.7, 7.2 Hz), 0.92 (3H, t, J=7.2 Hz); MS (ESI) m/z 413 (M+H)$^+$, 411 (M–H)$^-$.

Example 4

4-[1-({[5-FLUORO-2-(4-FLUOROPHENOXY)PYRIDIN-3-YL]CARBONYL}AMINO)-1-METHYLETHYL]BENZOIC ACID

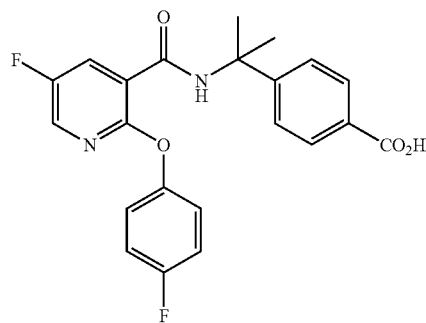

Step 1. Methyl 4-[1-({[5-Fluoro-2-(4-fluorophenoxy)pyridin-3-yl]carbonyl}amino)-1-methylethyl]benzoate The title compound was prepared according to the procedure described in step 3 of Example 1 from 5-fluoro-2-(4-fluorophenoxy)nicotinic acid (step 3 of Example 1) and methyl 4-(1-amino-1-methylethyl)benzoate: $^1$H-NMR (CDCl$_3$) δ 8.33 (1H, br.s), 8.24 (1H, dd, J=8.2, 3.1 Hz), 8.04–7.99 (3H, m), 7.51 (2H, dd, J=6.7, 1.9 Hz), 7.18–7.16 (4H, m), 3.90 (3H, s), 1.80 (6H, s); MS (ESI) m/z 427 (M+H)$^+$, 425 (M−H)$^−$.

Step 2. 4-[1-({[5-Fluoro-2-(4-fluorophenoxy)pyridin-3-yl]carbonyl}amino)-1-methylethyl]benzoic acid The title compound was prepared according to the procedure described in step 4 of Example 1 from methyl 4-[1-({[5-Fluoro-2-(4-fluorophenoxy)pyridin-3-yl]carbonyl}amino)-1-methylethyl]benzoate (step 1): $^1$H-NMR (DMSO-d$_6$) δ 8.82 (1H, s), 8.23 (1H, d, J=3.1 Hz), 8.00 (1H, dd, J=7.9, 3.1 Hz), 7.83 (2H, d, J=8.4 Hz), 7.57 (2H, d, J=8.4 Hz), 7.29–7.27 (4H, m), 1.65 (6H, s); MS (ESI) m/z 413 (M+H)$^+$, 411 (M−H)$^−$.

Example 5

4-[(1S)-1-({[5-FLUORO-2-(4-FLUOROPHENOXY)PYRIDIN-3-YL]CARBONYL}AMINO)ETHYL]BENZOIC ACID

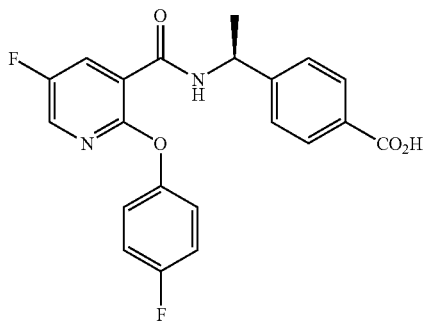

Step 1. tert-Butyl [(1S)-1-(4-bromophenyl)ethyl]carbamate

A mixture of [(1S)-1-(4-bromophenyl)ethyl]amine (10.00 g, 50.0 mmol) and di-tert-butyl dicarbonate (11.45 g, 52.5 mmol), triethylamine (7.66 mL, 55.0 mmol) in dichloromethane (200 mL) was stirred at room temperature for 1 h. The mixture was diluted with dichloromethane (500 mL) and washed with 1N hydrochloric acid (300 mL), saturated sodium hydrogen carbonate aqueous (300 mL), and brine (300 mL). The organic layer was dried over magnesium sulfate, and concentrated under reduced pressure. The residue was washed with cold hexane to afford 14.73 g (98%) of the title compounds as white solids: $^1$H-NMR (CDCl$_3$) δ 7.47–7.42 (2H, m), 7.18 (2H, d, J=8.4 Hz), 5.30 (2H, br.s), 1.41 (12H, br.s).

Step 2. Methyl 4-{(1S)-1-[(tert-butoxycarbonyl)amino]ethyl}benzoate

A mixture of tert-butyl [(1S)-1-(4-bromophenyl)ethyl]carbamate (step 1, 14.73 g, 49.1 mmol), 1,3-bis(diphenylphosphino)-propane (2.03 g, 4.91 mmol), palladium (II) acetate (1.10 g, 4.91 mmol), triethylamine (20.5 mL, 147 mmol), N,N-dimethylforamide (120 mL) and methanol (180 mL) was stirred at 80° C. for 16 h under carbon monoxide atmosphere. After cooling to room temperature, the mixture was diluted with ether (800 mL) and washed with water (500 mL×3). The organic layer was dried over magnesium sulfate and evaporated. The residue was purified by flush column chromatography on silica gel eluting with hexane/ethyl acetate (5:1) to afford 12.83 g (94%) of the title compounds as white solids: $^1$H-NMR (CDCl$_3$) δ 8.02–7.99 (2H, m), 7.37 (2H, d, J=8.4 Hz), 4.83 (2H, br.s), 3.91 (3H, s), 1.46–1.42 (12H, m).

Step 3. Methyl 4-[(1S)-1-aminoethyl]benzoate hydrochloride

Methyl 4-{(1S)-1-[(tert-butoxycarbonyl)amino]ethyl}benzoate (12.83 g, 45.9 mmol) was treated with trifluoroacetic acid (100 mL) and dichloromethane (100 mL) at room temperature for 16 h. After removal of the solvent, the residue was diluted with 10% hydrogen chloride solution in methanol (100 mL). The mixture was concentrated under reduced pressure and the residue was washed with ethyl acetate to give 9.40 g (95%) of the title compounds as white solids: $^1$H-NMR (DMSO-d$_6$) δ 8.67 (2H, br.s), 8.01 (2H, d, J=8.4 Hz), 7.68 (2H, d, J=8.4 Hz), 4.49 (1H, q, J=6.9 Hz), 3.87 (3H, s), 1.53 (3H, d, J=6.9 Hz).

Step 4. Methyl 4-[(1S)-1-({[5-fluoro-2-(4-fluorophenoxy)pyridin-3-yl]carbonyl}amino)ethyl]benzoate The title compound was prepared according to the procedure described in step 3 of Example 1 from 5-fluoro-2-(4-fluorophenoxy)nicotinic acid (step 3 of Example 1) and methyl 4-[(1S)-1-aminoethyl]benzoate hydrochloride (step 3): $^1$H-NMR (CDCl$_3$) the data of the title compound were identical with that of the racemate (step 2 of Example 2); MS (ESI) m/z 413 (M+H)$^+$, 411 (M−H)$^−$.

Step 5. 4-[(1S)-1-({[5-Fluoro-2-(4-fluorophenoxy)pyridin-3-yl]carbonyl}amino)ethyl]benzoic acid The title compound was prepared according to the procedure described in step 4 of Example 1 from methyl 4-[(1S)-1-({[5-fluoro-2-(4-fluorophenoxy)pyridin-3-yl]carbonyl}amino)ethyl]benzoate (step 4): $^1$H-NMR (DMSO-d$_6$) the data of the title compound were identical with that of the racemate (step 3 of Example 2); MS (ESI) m/z 399 (M+H)$^+$, 397 (M−H)$^−$.

Example 6

4-[(1S)-1-({[5-FLUORO-2-(3-FLUOROPHENOXY)PYRIDIN-3-YL]CARBONYL}AMINO)ETHYL]BENZOIC ACID

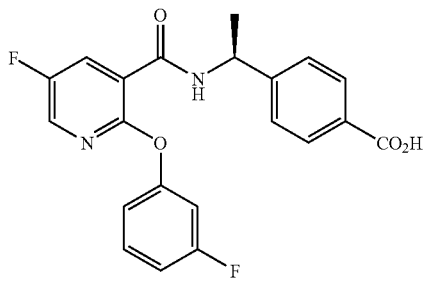

Step 1. 5-Fluoro-2-(3-fluorophenoxy)nicotinic acid

The title compound was prepared according to the procedure described in step 1 & 2 of Example 1 from 2-hydroxy-5-fluoronicotinic acid and 3-fluorophenol; $^1$H-NMR (DMSO-d$_6$) δ 8.37 (1H, m), 8.23–8.15(1H, m), 7.49–7.35 (1H, m), 7.10–6.90 (3H, m).

Step 2. Methyl 4-[(1S)-1-({[5-fluoro-2-(3-fluorophenoxy)pyridin-3-yl]carbonyl}amino)ethyl]benzoate The title compound was prepared according to the procedure described in step 3 of Example 1 from 5-fluoro-2-(3-fluorophenoxy)nicotinic acid (step 1) and methyl 4-[(1S)-1-aminoethyl]benzoate hydrochloride (step 3 of Example 5): $^1$H-NMR (CDCl$_3$) δ 8.33 (1H, dd, J=8.2, 3.1 Hz), 8.12–7.98 (4H, m), 7.47–7.38 (3H, m), 7.05–6.89 (3H, m), 5.36 (1H, m), 3.90 (3H, s), 1.60 (3H, d, J=6.9 Hz).

Step 3. 4-[(1S)-1-({[5-Fluoro-2-(3-fluorophenoxy)pyridin-3-yl]carbonyl}amino)ethyl]benzoic acid The title compound was prepared according to the procedure described in step 4 of Example 1 from methyl 4-[(1S)-1-({[5-fluoro-2-(3-fluorophenoxy)pyridin-3-yl]carbonyl}amino)ethyl]benzoate (step 2): $^1$H-NMR (CDCl$_3$) δ 8.34 (1H, dd, J=8.2, 3.1 Hz), 8.14–8.02 (4H, m), 7.47–7.38 (3H, m), 7.27–6.89 (3H, m), 5.36 (1H, m), 1.59 (3H, d, J=6.9 Hz); MS (ESI) m/z 399 (M+H)$^+$, 397 (M−H)$^−$.

Example 7

4-[({[5-FLUORO-2-(4-FLUOROPHENOXY)PYRIDIN-3-YL]CARBONYL}AMINO)METHYL]-3-METHYLBENZOIC ACID

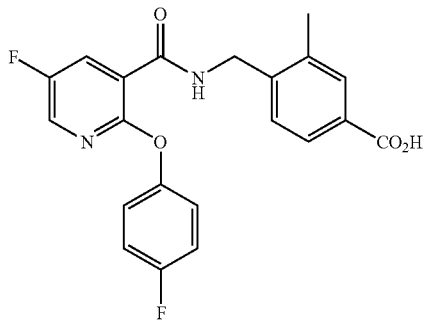

Step 1. Methyl 4-[({[5-fluoro-2-(4-fluorophenoxy)pyridin-3-yl]carbonyl}amino)methyl]-3-methylbenzoate The title compound was prepared according to the procedure described in step 3 of Example 1 from 5-fluoro-2-(4-fluorophenoxy)nicotinic acid (step 3 of Example 1) and methyl 4-(aminomethyl)-3-methylbenzoate: $^1$H-NMR (CDCl$_3$) δ 8.36 (1H, dd, J=8.2, 3.1 Hz), 8.25–8.18 (1H, m), 8.04 (1H, d, J=3.1 Hz), 7.85–7.81 (2H, m), 7.37 (1H, d, J=7.7 Hz), 7.15–7.07 (4H, m), 4.73 (2H, d, J=5.8 Hz), 3.89 (3H, s), 2.40 (3H, s); MS (ESI) m/z 413 (M+H)$^+$, 411 (M−H)$^−$.

Step 2. 4-[({[5-Fluoro-2-(4-fluorophenoxy)pyridin-3-yl]carbonyl]amino)methyl]-3-methylbenzoic acid The title compound was prepared according to the procedure described in step 4 of Example 1 from methyl 4-[({[5-fluoro-2-(4-fluorophenoxy)pyridin-3-yl]carbonyl}amino)methyl]-3-methylbenzoate (step 1): $^1$H-NMR (DMSO-d$_6$) δ 9.05 (1H, t, J=6.1 Hz), 8.25 (1H, d, J=2.9 Hz), 8.09 (1H, dd, J=8.1, 3.1 Hz), 7.74 (1H, s), 7.68 (1H, d, J=7.9 Hz), 7.44 (1H, d, J=8.1 Hz), 7.31–7.25 (4H, m), 4.54 (2H, d, J=5.9 Hz), 2.36 (3H, s); MS (ESI) m/z 399 (M+H)$^+$, 397 (M−H)$^−$.

Example 8

3-FLUORO-4-[({[5-FLUORO-2-(4-FLUOROPHENOXY)PYRIDIN-3-YL]CARBONYL}AMINO)METHYL]BENZOIC ACID

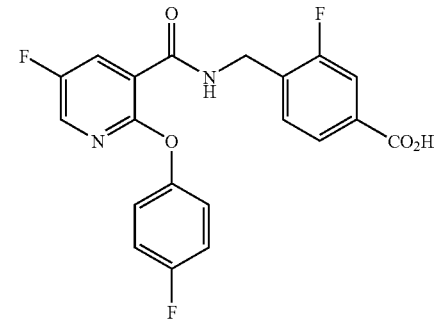

Step 1. Methyl 3-fluoro-4-[({[5-fluoro-2-(4-fluorophenoxy)pyridin-3-yl]carbonyl}amino)methyl]benzoate The title compound was prepared according to the procedure described in step 3 of Example 1 from 5-fluoro-2-(4-fluorophenoxy)nicotinic acid (step 3 of Example 1) and methyl 4-(aminomethyl)-3-fluorobenzoate: $^1$H-NMR (CDCl$_3$) δ 8.45–8.33 (2H, m), 8.04 (1H, d, J=3.1 Hz), 7.80 (1H, dd, J=7.9, 1.5 Hz), 7.71 (1H, dd, J=10.5, 1.5 Hz), 7.49 (1H, t, J=7.6 Hz), 7.17–7.12 (4H, m), 4.78 (2H, d, J=6.1 Hz), 3.91 (3H, s); MS (ESI) m/z 417 (M+H)$^+$, 415 (M−H)$^−$.

Step 2. 3-Fluoro-4-[({[5-fluoro-2-(4-fluorophenoxy)pyridin-3-yl]carbonyl}amino)methyl]benzoic acid The title compound was prepared according to the procedure described in step 4 of Example 1 from methyl 3-fluoro-4-[({[5-fluoro-2-(4-fluorophenoxy)pyridin-3-yl]carbonyl}amino)methyl]benzoate (step 1): $^1$H-NMR (DMSO-d$_6$) δ 9.14 (1H, t, J=5.9 Hz), 8.26 (1H, d, J=3.1 Hz), 8.11 (1H, dd, J=8.3, 3.1 Hz), 7.72–7.53 (3H, m), 7.31–7.25 (4H, m), 4.62 (2H, d, J=5.9 Hz); MS (ESI) m/z 403 (M+H)$^+$, 401 (M−H)$^−$.

Example 9

4-[({[5-FLUORO-2-(4-FLUOROPHENOXY)PYRIDIN-3-YL]CARBONYL}AMINO)METHYL]-2-METHYLBENZOIC ACID

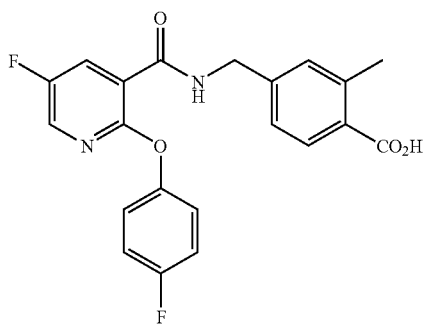

Step 1. Methyl 4-[({[5-fluoro-2-(4-fluorophenoxy)pyridin-3-yl]carbonyl}amino)methyl]-2-methylbenzoate The title compound was prepared according to the procedure described in step 3 of Example 1 from 5-fluoro-2-(4-fluorophenoxy)nicotinic acid (step 3 of Example 1) and methyl 4-(aminomethyl)-2-methylbenzoate: $^1$H-NMR (CDCl$_3$) δ 8.38 (1H, dd, J=8.1, 3.1 Hz), 8.30–8.24 (1H, m), 8.05 (1H, d, J=3.1 Hz), 7.88 (1H, d, J=8.1 Hz), 7.26–7.08 (6H, m), 4.71 (2H, d, J=5.9 Hz), 3.90 (3H, s), 3.87 (3H, s); MS (ESI) m/z 413 (M+H)$^+$, 411 (M−H)$^−$.

Step 2. 4-[({[5-Fluoro-2-(4-fluorophenoxy)pyridin-3-yl]carbonyl}amino)methyl]-2-methylbenzoic acid The title compound was prepared according to the procedure described in step 4 of Example 1 from methyl 4-[({[5-fluoro-2-(4-fluorophenoxy)pyridin-3-yl]carbonyl}amino)methyl]-2-methylbenzoate (step 1): $^1$H-NMR (DMSO-d$_6$) δ 9.10 (1H, t, J=5.9 Hz), 8.24 (1H, d, J=3.1 Hz), 8.09 (1H, dd, J=8.3, 3.1 Hz), 7.76 (1H, d, J=8.3 Hz), 7.27–7.25 (6H, m), 4.54 (2H, d, J=5.9 Hz), 2.42 (3H, s); MS (ESI) m/z 399 (M+H)$^+$, 397 (M−H)$^−$.

The Synthetic Proceduire of Example 10–Example 42

The compounds disclosed hereinafter were prepared according to the following procedure:

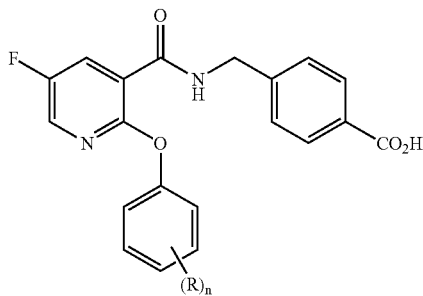

Step 1. tert-Butyl 4-({[(2-chloro-5-fluoropyridin-3-yl)carbonyl]amino}methyl)benzoate To a stirred solution of 2-chloro-5-fluoronicotinic acid (2.0 g, 10 mmol) and tert-butyl 4-(aminomethyl)benzoate (1.65 g, 8 mmol) in dichloromethane (25 mL) were successively added 1-(3-dimethylaminopropyl)-3-ethylcarbodiimide hydrochloride (EDCI) (2.88 g, 15 mmol), 1-hydroxybenzotriazole hydrate (HOBT) (1.53 g, 10 mmol), and triethylamine (5 mL). After being stirred overnight, the reaction mixture was poured into water (100 mL). The organic layer was separated and the aqueous layer was extracted with dichloromethane (50 mL×2). The combined organic layers were washed with brine (100 mL), dried (sodium sulfate), and evaporated. The residue was purified by flush column chromatography on silica gel (200 g) eluting with dichloromethane/ethyl acetate (20/1) to afford 2.39 g (82%) of the title compounds as white solids: $^1$H-NMR (CDCl$_3$) δ 8.33 (1H, d, J=3.1 Hz), 7.97 (2H, d, J=8.4 Hz), 7.91 (1H, dd, J=7.9, 3.1 Hz), 7.40 (2H, d, J=8.4 Hz), 7.04 (1H, br.s), 4.70 (2H, d, J=5.9 Hz), 1.58 (9H, s).

Step 2. 4-[({[5-Fluoro-2-(substituted-phenoxy)pyridin-3-yl]carbonyl}amino)methyl]benzoic acid To a solution of substituted-phenol (0.15 mmol) were added a solution of tert-butyl 4-({[(2-chloro-5-fluoropyridin-3-yl)carbonyl]amino}methyl)benzoate (step 1, 0.05 mmol) in toluene (0.6 mL) and 2-tert-Butylimino-2-diethylamino-1,3-dimethyl-perhydro-1,3,2-diazaphosphorine on polystyrene (PS-BEMP, 0.15 mmol). Then the mixture was agitated at 110° C. overnight. To the resultant mixture were added AcOEt (0.5 mL) and 0.5 N aq.HCl (0.5 mL). The organic layer was extracted and concentrated in vacuo. The crude product was purified by preparative LCMS (XTerra® C18, 20×50 mm) eluting with H$_2$O/MeOH/1% aqueous HCO$_2$H (90/5/5 to 10/85/5). After a TFA-DCE solution (1-1, 0.6 mL) was added to the purified material, the mixture was left at room temperature for 1.5 h. Then the mixture was concentrate in vacuo to afford the desired product.

Example 10

4-[({[5-FLUORO-2-(3-METHOXY-5-METHYLPHENOXY)PYRIDIN-3-YL]CARBONYL}AMINO)METHYL]BENZOIC ACID

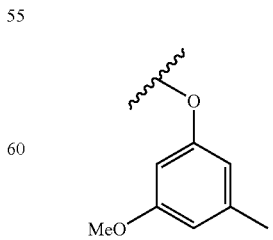

Observed MS (ESI) m/z 411.01 (M+H)$^+$

Exact Mass calcd for C22 H19 F N2 O5: m/z 410.13.

Example 11

4-[({[2-(2-CHLOROPHENOXY)-5-FLUOROPYRIDIN-3-YL]CARBONYL}AMINO)METHYL]BENZOIC ACID

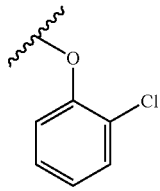

Observed MS (ESI) m/z 400.96 (M+H)$^+$
Exact Mass calcd for C20 H14 Cl F N2 O4: m/z 400.06.

Example 12

4-[({[2-(3-CHLOROPHENOXY)-5-FLUOROPYRIDIN-3-YL]CARBONYL}AMINO)METHYL]BENZOIC ACID

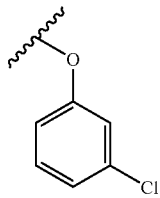

Observed MS (ESI) m/z 400.96 (M+H)$^+$
Exact Mass calcd for C20 H14 Cl F N2 O4: m/z 400.06.

Example 13

4-[({[2-(2,3-DIHYDRO-1H-INDEN-5-YLOXY)-5-FLUOROPYRIDIN-3-YL]CARBONYL}AMINO) METHYL]BENZOIC ACID

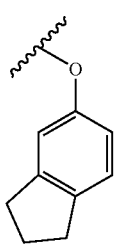

Observed MS (ESI) m/z 407.05 (M+H)$^+$
Exact Mass calcd for C23 H19 F N2 O4: m/z 406.13.

Example 14

4-[({[2-(BIPHENYL-4-YLOXY)-5-FLUOROPYRIDIN-3-YL]CARBONYL}AMINO)METHYL]BENZOIC ACID

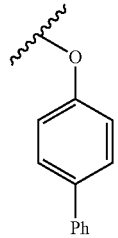

Observed MS (ESI) m/z 443.03 (M+H)$^+$
Exact Mass calcd for C26 H19 F N2 O4: m/z 442.13.

Example 15

4-[({[2-(3-CHLORO-4-METHYLPHENOXY)-5-FLUOROPYRIDIN-3-YL]CARBONYL}AMINO) METHYL]BENZOIC ACID

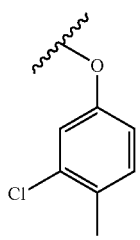

Observed MS (ESI) m/z 414.96 (M+H)$^+$
Exact Mass calcd for C21 H16 Cl F N2 O4: m/z 414.08.

Example 16

4-[({[2-(3,5-DIFLUOROPHENOXY)-5-FLUOROPYRIDIN-3-YL]CARBONYL}AMINO)METHYL] BENZOIC ACID

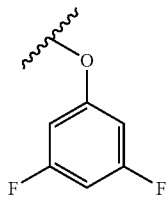

Observed MS (ESI) m/z 402.97 (M+H)$^+$
Exact Mass calcd for C20 H13 F3 N2 O4: m/z 402.08.

Example 17

4-[({[2-(4-CYCLOPENTYLPHENOXY)-5-FLUOROPYRIDIN-3-YL]CARBONYL}AMINO)METHYL]BENZOIC ACID

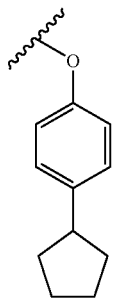

Observed MS (ESI) m/z 435.05 (M+H)+
Exact Mass calcd for C25 H23 F N2 O4: m/z 434.16.

Example 18

4-[({[5-FLUORO-2-(3-METHOXYPHENOXY)PYRIDIN-3-YL]CARBONYL}AMINO)METHYL]BENZOIC ACID

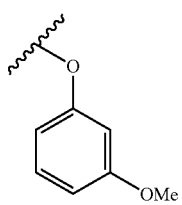

Observed MS (ESI) m/z 397.01 (M+H)+
Exact Mass calcd for C21 H17 F N2 O5: m/z 396.11.

Example 19

4-({[(5-FLUORO-2-PHENOXYPYRIDIN-3-YL)CARBONYL]AMINO}METHYL)BENZOIC ACID

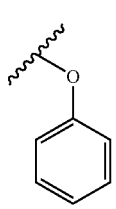

Observed MS (ESI) m/z 367.01 (M+H)+
Exact Mass calcd for C20 H15 F N2 O4: m/z 366.1.

Example 20

4-[({[5-FLUORO-2-(2-FLUOROPHENOXY)PYRIDIN-3-YL]CARBONYL}AMINO)METHYL]BENZOIC ACID

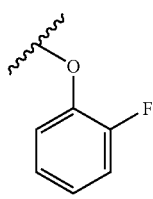

Observed MS (ESI) m/z 385.02 (M+H)+
Exact Mass calcd for C20 H14 F2 N2 O4: m/z 384.09.

Example 21

4-{[({2-[4-(BENZYLOXY)PHENOXY]-5-FLUOROPYRIDIN-3-YL}CARBONYL)AMINO]METHYL}BENZOIC ACID

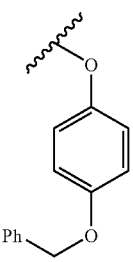

Observed MS (ESI) m/z 473.04 (M+H)+
Exact Mass calcd for C27 H21 F N2 O5: m/z 472.14.

Example 22

4-[({[5-FLUORO-2-(3-FLUOROPHENOXY)PYRIDIN-3-YL]CARBONYL}AMINO)METHYL]BENZOIC ACID

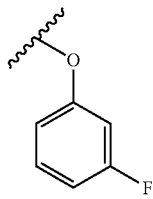

Observed MS (ESI) m/z 385.02 (M+H)+
Exact Mass calcd for C20 H14 F2 N2 O4: m/z 384.09.

Example 23

4-[({[2-(3-ETHYNYLPHENOXY)-5-FLUOROPYRIDIN-3-YL]CARBONYL}AMINO)METHYL]BENZOIC ACID

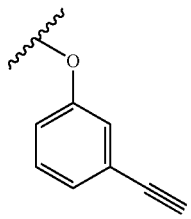

Observed MS (ESI) m/z 390.98 (M+H)$^+$
Exact Mass calcd for C22 H15 F N2 O4: m/z 390.1.

Example 24

4-[({[2-(2-CHLORO-5-METHYLPHENOXY)-5-FLUOROPYRIDIN-3-YL]CARBONYL}AMINO)METHYL]BENZOIC ACID

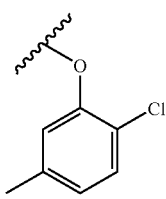

Observed MS (ESI) m/z 414.96 (M+H)$^+$
Exact Mass calcd for C21 H16 Cl F N2 O4: m/z 414.08.

Example 25

4-[({[2-(3-CHLORO-4-FLUOROPHENOXY)-5-FLUOROPYRIDIN-3-YL]CARBONYL}AMINO)METHYL]BENZOIC ACID

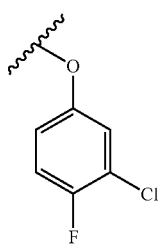

Observed MS (ESI) m/z 418.95 (M+H)$^+$
Exact Mass calcd for C20 H13 Cl F2N2 O4: m/z 418.05.

Example 26

4-[({[2-(2,6-DIFLUOROPHENOXY)-5-FLUOROPYRIDIN-3-YL]CARBONYL}AMINO)METHYL]BENZOIC ACID

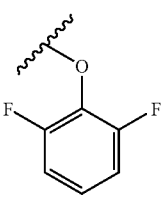

Observed MS (ESI) m/z 402.97 (M+H)$^+$
Exact Mass calcd for C20 H13 F3 N$_2$ O$_4$: m/z 402.08.

Example 27

4-[({[2-(3-ETHYLPHENOXY)-5-FLUOROPYRIDIN-3-YL]CARBONYL}AMINO)METHYL]BENZOIC ACID

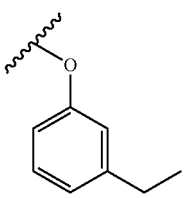

Observed MS (ESI) m/z 395.06 (M+H)$^+$
Exact Mass calcd for C22 H19 F N2 O4: m/z 394.13.

Example 28

4-[({[2-(3,4-DIFLUOROPHENOXY)-5-FLUOROPYRIDIN-3-YL]CARBONYL}AMINO)METHYL]BENZOIC ACID

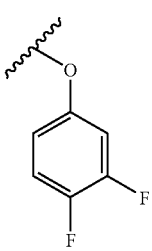

Observed MS (ESI) m/z 402.97 (M+H)$^+$
Exact Mass calcd for C20 H13 F3 N2 O4: m/z 402.08.

Example 29

4-{[({5-FLUORO-2-[3-(TRIFLUOROMETHOXY)PHENOXY]PYRIDIN-3-YL}CARBONYL)AMINO]METHYL}BENZOIC ACID

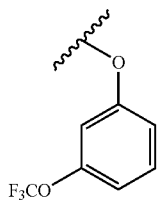

Observed MS (ESI) m/z 451.00 (M+H)+
Exact Mass calcd for C21 H14 F4 N2 O5: m/z 450.08.

Example 30

4-[({[5-FLUORO-2-(4-FLUORO-3-METHYLPHENOXY)PYRIDIN-3-YL]CARBONYL}AMINO)METHYL]BENZOIC ACID

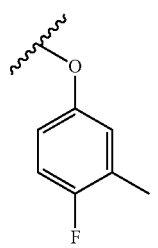

Observed MS (ESI) m/z 399.02 (M+H)+
Exact Mass calcd for C21 H16 F2 N2 O4: m/z 398.11.

Example 31

4-[({[2-(BIPHENYL-3-YLOXY)-5-FLUOROPYRIDIN-3-YL]CARBONYL}AMINO)METHYL]BENZOIC ACID

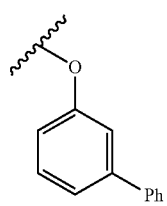

Observed MS (ESI) m/z 443.03 (M+H)+
Exact Mass calcd for C26 H19 F N2 O4: m/z 442.13.

Example 32

4-[({[5-FLUORO-2-(3-METHYLPHENOXY)PYRIDIN-3-YL]CARBONYL}AMINO)METHYL]BENZOIC ACID

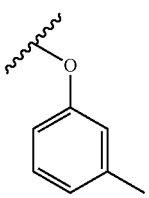

Observed MS (ESI) m/z 381.00 (M+H)+
Exact Mass calcd for C21 H17 F N2 O4: m/z 380.12.

Example 33

4-[({[2-(3-ACETYLPHENOXY)-5-FLUOROPYRIDIN-3-YL]CARBONYL}AMINO)METHYL]BENZOIC ACID

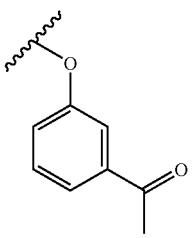

Observed MS (ESI) m/z 409.00 (M+H)+
Exact Mass calcd for C22 H17 F N2 O5: m/z 408.11.

Example 34

4-[({[5-FLUORO-2-(2-NAPHTHYLOXY)PYRIDIN-3-YL]CARBONYL}AMINO)METHYL]BENZOIC ACID

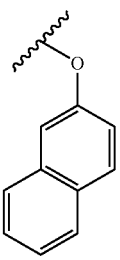

Observed MS (ESI) m/z 417.03 (M+H)+
Exact Mass calcd for C24 H17 F N2 O4: m/z 416.12.

Example 35

4-[({[5-FLUORO-2-(1-NAPHTHYLOXY)PYRIDIN-3-YL]CARBONYL}AMINO)METHYL]BENZOIC ACID

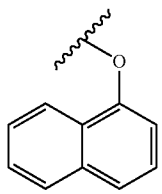

Observed MS (ESI) m/z 417.02 (M+H)+
Exact Mass calcd for C24 H17 F N2 O4: m/z 416.12.

Example 36

4-{[({2-[(4-CHLORO-1-NAPHTHYL)OXY]-5-FLUOROPYRIDIN-3-YL}CARBONYL)AMINO]METHYL}BENZOIC ACID

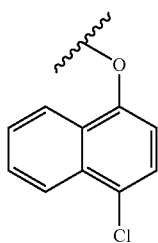

Observed MS (ESI) m/z 450.98 (M+H)+
Exact Mass calcd for C24 H16 Cl F N2 O4: m/z 450.08.

Example 37

4-[({[2-(3-BENZOYLPHENOXY)-5-FLUOROPYRIDIN-3-YL]CARBONYL}AMINO)METHYL]BENZOIC ACID

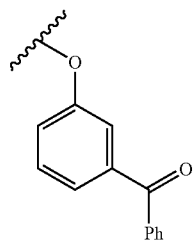

Observed MS (ESI) m/z 471.03 (M+H)+
Exact Mass calcd for C27 H19 F N2 O5: m/z 470.13.

Example 38

4-[{[5-FLUORO-2-(2-METHYLPHENOXY)PYRIDIN-3-YL]CARBONYL}AMINO)METHYL]BENZOIC ACID

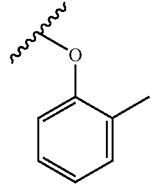

Observed MS (ESI) m/z 381.00 (M+H)+
Exact Mass calcd for C21 H17 F N2 O4: m/z 380.12.

Example 39

4-[({[5-FLUORO-2-(QUINOLIN-8-YLOXY)PYRIDIN-3-YL]CARBONYL}AMINO)METHYL]BENZOIC ACID

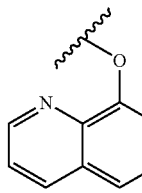

Observed MS (ESI) m/z 418.01 (M+H)+
Exact Mass calcd for C23 H16 F N3 O4: m/z 417.11.

Example 40

4-{[({5-FLUORO-2-[4-(2-METHYL-1,3-THIAZOL-4-YL)PHENOXY]PYRIDIN-3-YL}CARBONYL)AMINO]METHYL}BENZOIC ACID

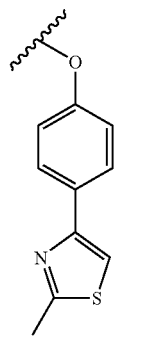

Observed MS (ESI) m/z 463.96 (M+H)+
Exact Mass calcd for C24 H18 F N3 O4 S: m/z 463.10.

Example 41

4-{[({5-FLUORO-2-[(5-FLUOROQUINOLIN-8-YL)OXY]PYRIDIN-3-YL}CARBONYL)AMINO]METHYL}BENZOIC ACID

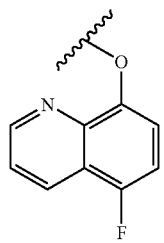

Observed MS (ESI) m/z 435.97 (M+H)$^+$
Exact Mass calcd for C23 H15 F2 N3 O4: m/z 435.1.

Example 42

4-[({[5-FLUORO-2-(4-PYRIDIN-2-YLPHENOXY)PYRIDIN-3-YL]CARBONYL}AMINO)METHYL]BENZOIC ACID

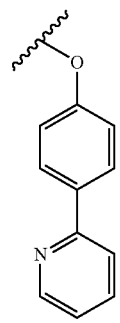

Observed MS (ESI) m/z 444.00 (M+H)$^+$
Exact Mass calcd for C25 H18 F N3 O4: m/z 443.13.

Example 43

4-[({[5-CHLORO-2-(4-FLUOROPHENOXY)PYRIDIN-3-YL]CARBONYL}AMINO)METHYL]BENZOIC ACID

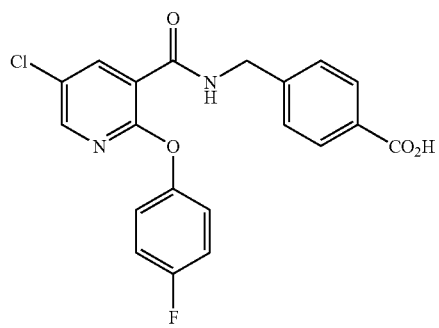

Step 1. Methyl 4-[({[5-chloro-2-(4-fluorophenoxy)pyridin-3-yl]carbonyl}amino)methyl]benzoate To a stirred solution of 5-chloro-2-(4-fluorophenoxy)nicotinic acid (150 mg, 0.56 mmol), methyl 4-(aminomethyl)benzoate hydrochloride (136 mg, 0.67 mmol), and triethylamine (0.31 mL, 2.24 mmol) in dichloromethane (8 mL) was added 2-bromo-1-ethylpyridinium tetrafluoroborate (230 mg, 0.84 mmol) at 0° C. The resulting mixture was warmed to room temperature and stirred for 16 h. The mixture was diluted with dichloromethane (50 mL) and washed with 1N hydrochloric acid (30 mL), saturated aqueous sodium hydrogen carbonate solution (30 mL), and brine (30 mL). The organic layer was dried over magnesium sulfate, and concentrated under reduced pressure. The residue was purified by flush column chromatography on silica gel eluting with hexane/ethyl acetate (2:1) to afford 155 mg (67%) of the title compounds as white solids: $^1$H-NMR (CDCl$_3$) δ 8.59 (1H, dd, J=2.6, 0.9 Hz), 8.26–8.17 (1H, m), 8.13 (1H, dd, J=2.8, 0.9 Hz), 8.00 (2H, d, J=8.1 Hz), 7.41 (2H, d, J=8.1 Hz), 7.15–7.07 (4H, m), 4.76 (2H, d, J=5.9 Hz), 3.90 (3H, s); MS (ESI) m/z 415 (M+H)$^+$, 413 (M–H)$^-$.

Step 2. 4-[({[5-Chloro-2-(4-fluorophenoxy)pyridin-3-yl]carbonyl}amino)methyl]benzoic acid A mixture of methyl 4-[({[5-chloro-2-(4-fluorophenoxy)pyridin-3-yl]carbonyl}amino)methyl]benzoate (step 1, 154 mg, 0.37 mmol), tetrahydrofuran (2 mL), methanol (2 mL), and 2 N sodium hydroxide (2 mL) was stirred at room temperature for 4 h. The mixture was poured into 1N hydrochloric acid (30 mL), and extracted with ethyl acetate (50 mL). The organic layer was dried over magnesium sulfate and evaporated. The residue was purified by TLC [dichloromethane/ethyl acetate (1:2)] to give 98 mg (66%) of the title compound as white solids: $^1$H-NMR (DMSO-d$_6$) δ 9.13 (1H, t, J=6.0 Hz), 8.29 (1H, dd, J=2.6, 1.5 Hz), 8.22 (1H, dd, J=2.6, 1.5 Hz), 7.88 (2H, d, J=8.1 Hz), 7.47 (2H, d, J=8.1 Hz), 7.29–7.26 (4H, m), 4.60 (2H, d, J=6.0 Hz); MS (ESI) m/z 401 (M+H)$^+$, 399 (M–H)$^-$.

Example 44

4-[(1S)-1-({[5-CHLORO-2-(4-FLUOROPHENOXY)PYRIDIN-3-YL]CARBONYL}AMINO)ETHYL]BENZOIC ACID

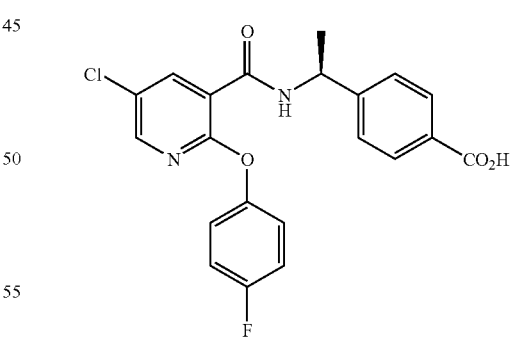

Step 1. 4-((1S)-1-{[(Benzyloxy)carbonyl]amino}ethyl)benzoic acid

To a cooled (0° C.) mixture of 4-[(1S)-1-aminoethyl]benzoic acid (Chem. Eur. J. 1999, 5, 1095, 16.2 g, 98 mmol) and 2 N sodium hydroxide aqueous solution (100 mL) was added benzyl chloroformate (20.5 g, 120 mmol) dropwise over 30 min period followed by the addition of additional 2

N sodium hydroxide aqueous solution (70 mL). The reaction mixture was stirred overnight at room temperature and then acidified to pH 1 with concentrated hydrochloric acid. The resulting precipitate was filtered, washed with water (100 mL), and then vacuum dried to yield 26 g (88%) of the title compounds as white solids: $^1$H-NMR (CDCl$_3$) δ 7.95 (2H, d, J=8.1 Hz), 7.40–7.15 (7H, m), 5.12–4.94 (3H, m), 4.82 (1H, br.s), 1.40 (3H, d, J=7.0 Hz); MS (ESI) m/z 300 (M+H)$^+$, 298 (M−H)$^−$.

Step 2. tert-Butyl 4-((1S)-1-{[(benzyloxy)carbonyl]amino}ethyl)benzoate

To a solution of 4-((1S)-1-{[(benzyloxy)carbonyl]amino}ethyl)benzoic acid (step 1, 3.7 g, 12.4 mmol) and benzyltriethylammonium chloride (3.0 g, 13 mmol) in N,N-dimethylacetamide (100 mL) was added anhydrous potassium carbonate (47 g, 340 mmol) followed by 2-bromo-2-methylpropane (89 g, 650 mmol). The resulting mixture stirred for 24 h at 55° C. After cooling to room temperature, the reaction mixture was poured into cold water (500 mL) under stirring. The resulting solution was extracted with ethyl acetate (500 mL). The organic phase was washed with water (300 mL) and brine (200 mL), dried (sodium sulfate), and evaporated. The residue was purified by flush column chromatography on silica gel (150 g) eluting with hexane/ethyl acetate (3/1) to afford 3.48 g (79%) of the title compounds as white solids: $^1$H-NMR (CDCl$_3$) δ 7.95 (2H, d, J=8.3 Hz), 7.44–7.24 (7H, m), 5.15–4.99 (3H, m), 4.88 (1H, br.s), 1.58 (9H, s), 1.47 (3H, d, J=7.0 Hz).

Step 3. tert-Butyl 4-[(1S)-1-aminoethyl]benzoate

To a stirred solution of tert-butyl 4-((1S)-1-{[(benzyloxy)carbonyl]amino}ethyl)benzoate (step 2, 3.48 g, 9.8 mmol) in a mixture of ethanol (25 mL) and acetic acid (25 mL) was added 10% palladium-carbon (400 mg). The mixture was stirred at room temperature for 2 h under hydrogen atmosphere. The palladium catalyst was removed by filtration and washed with ethanol (100 mL). The filtrate was concentrated under reduced pressure and the residue was partitioned between ethyl acetate (200 mL) and saturated sodium bicarbonate aqueous solution (200 mL). The organic phase was separated and the aqueous phase was extracted with ethyl acetate (200 mL). The combined organic extracts were washed with brine (200 mL) and dried (sodium sulfate), and concentrated to give 2.02 g (93%) of the title compounds as white solids: $^1$H-NMR (CDCl$_3$) δ 7.95 (2H, d, J=8.3 Hz), 7.39 (2H, d, J=8.3 Hz), 4.22–4.12 (1H, dq, J=7.3, 6.6 Hz), 1.80 (2H, br.s), 1.58 (9H, s), 1.38 (3H, d, J=6.6 Hz).

Step 4. tert-Butyl 4-[(1S)-1-({[5-Chloro-2-(4-fluorophenoxy)pyridin-3-yl]carbonyl}amino)ethyl]benzoate The title compound was prepared according to the procedure described in step 3 of Example 1 from 5-chloro-2-(4-fluorophenoxy)nicotinic acid and tert-butyl 4-[(1S)-1-aminoethyl]benzoate (step 3): $^1$H-NMR (CDCl$_3$) δ 8.54 (1H, d, J=2.7 Hz), 8.14 (1H, br.s), 8.13 (1H, d, J=2.7 Hz), 7.95 (2H, d, J=8.3 Hz), 7.39 (2H, d, J=8.3 Hz), 7.17–7.11 (4H, m), 5.36 (1H, dq, J=7.2, 7.0 Hz), 1.59 (3H, d, J=7.0 Hz), 1.58 (9H, s); MS (ESI) m/z 415 (M+H)$^+$.

Step 5. 4-[(1S)-1-({[5-Chloro-2-(4-fluorophenoxy)pyridin-3-yl]carbonyl}amino)ethyl]benzoic acid Trifluoroacetic acid (10 mL) was added to a solution of tert-butyl 4-[(1S)-1-({[5-Chloro-2-(4-fluorophenoxy)pyridin-3-yl]carbonyl}amino)ethyl]benzoate (step 4, 2.1 g; 4.3 mmol) in dichloromethane (30 mL). The reaction mixture was stirred at room temperature until the starting material was fully consumed (4 h). The solvent and most of the trifluoroacetic acid were removed under reduced pressure. The residue was purified by flush silica gel column chromatography on silica gel (50 g) eluting with dichloromethane/methanol (20/1) and recrystallization (ethyl acetate-diisopropyl ether) to give 1.24 g, (86%) of the title compounds as white crystals: mp 198.2° C.;
$^1$H-NMR (CDCl$_3$) δ 8.56 (1H, d, J=2.6 Hz), 8.16 (1H, br.s), 8.14 (1H, d, J=2.6 Hz), 8.07 (2H, d, J=8.3 Hz), 7.46 (2H, d, J=8.3 Hz), 7.19–7.12 (4H, m), 5.46–5.30 (1H, m), 1.61 (3H, d, J=7.1 Hz); MS (ESI) m/z 415 (M+H)$^+$, 413 (M−H)$^−$.

Example 45

4-{(1S)-[({5-CHLORO-2-[3-(1,3-THIAZOL-2-YL)PHENOXY]PYRIDIN-3-YL}CARBONYL)AMINO]ETHYL}BENZOIC ACID

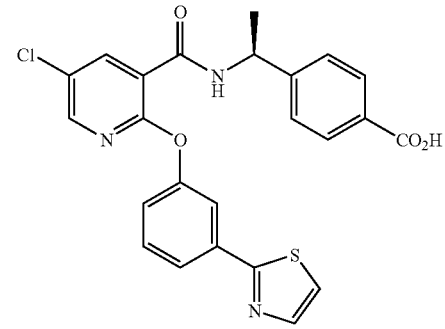

Step 1. tert-Butyl 4-((1S)-1-{[(2,5-dichloropyridin-3-yl)carbonyl]amino}ethyl)benzoate To a stirred solution of 2,5-dichloronicotinic acid (Syn. Commun. 1989, 19, 553–9, 1.92 g, 10 mmol) and tert-butyl 4-[(1S)-1-aminoethyl]benzoate (example 44 step 3, 2.02 g, 9.1 mmol) in dichloromethane (20 mL) were successively added 1-(3-dimethylaminopropyl)-3-ethylcarbodiimide hydrochloride (EDCI) (2.59 g, 13.5 mmol), 1-hydroxybenzotriazole hydrate (HOBT) (2.07 g, 13.5 mmol), and triethylamine (4 mL). After being stirred overnight, the reaction was quenched by the addition of saturated sodium bicarbonate aqueous solution (100 mL). The aqueous layer was extracted with dichloromethane (50 mL×3) and the combined organic layers were washed with brine (100 mL), dried (sodium sulfate), and evaporated. The remaining residue was purified by flush column chromatography on silica gel (100 g) eluting with dichloromethane/ethyl acetate (20/1) to afford 2.51 g (70%) of the title compounds as white solids: $^1$H-NMR (CDCl$_3$) δ 8.41 (1H, d, J=2.6 Hz), 8.09 (1H, d, J=2.6 Hz), 7.99 (2H, d, J=8.3 Hz), 7.43 (2H, d, J=8.3 Hz), 6.81 (1H, d, J=7.2 Hz), 5.33 (1H, dq, J=7.2, 7.0 Hz), 1.62 (3H, d, J=7.0 Hz), 1.58 (9H, s).

Step 2. tert-Butyl 4-{(1S)-1-[({5-chloro-2-[3-(1,3-thiazol-2-yl)phenoxy]pyridin-3-yl}carbonyl)amino]ethyl}benzoate A mixture of tert-butyl 4-((1S)-1-{[(2,5-dichloropyridin-3-yl)carbonyl]amino}ethyl)benzoate (step 1, 178 mg, 0.45 mmol), 3-(1,3-thiazol-2-yl)phenol (162 mg, 0.91 mmol) and 2-tert-butylimino-2-diethylamino-1,3-dimethylperhydro-1,3,2-diazaphosphorine (BEMP, 217 μL, 0.75 mmol) in toluene (2 mL) was stirred at 110° C. for 5 h. After removal of solvent, the residue was eluted on silica gel short column (hexane/ethyl acetate (4/1)) to afford 259 mg (quant.) of the title compound as a white amorphous: $^1$H-NMR (CDCl$_3$) δ 8.57 (1H, d, J=2.7 Hz), 8.15–8.11 (2H, m), 7.97–7.94 (2H, m), 7.90–7.83 (3H, m), 7.58–7.38 (3H, m), 7.34–7.20 (2H, m), 5.42–5.32 (1H, m), 1.61–1.57 (12H, m); MS (ESI) m/z 536 (M+H)$^+$, 534 (M–H)$^-$.

Step 3. 4-{(1S)-1-[({5-Chloro-2-[3-(1,3-thiazol-2-yl)phenoxy]pyridin-3-yl}carbonyl)amino]ethyl}benzoic acid The title compound was prepared according to the procedure described in step 5 of Example 44 from tert-butyl 4-{(1S)-1-[({5-chloro-2-[3-(1,3-thiazol-2-yl)phenoxy]pyridin-3-yl}carbonyl)amino]ethyl}benzoate (step 2): $^1$H-NMR (CDCl$_3$) δ 8.56 (1H, d, J=2.7 Hz), 8.16–8.14 (2H, m), 8.07–8.04 (2H, m), 7.90–7.85 (3H, m), 7.58–7.52 (1H, m), 7.48–7.45 (2H, m), 7.39 (1H, d, J=3.2 Hz), 7.29–7.21 (1H, m), 5.44–5.34 (1H, m), 1.61 (3H, d, J=6.8 Hz); MS (ESI) m/z 480 (M+H)$^+$, 478 (M–H)$^-$.

Example 46

4-{(1S)-1-[({5-CHLORO-2-[(5-CHLOROPYRIDIN-3-YL)OXY]PYRIDIN-3YL}CARBONYL)AMINO]ETHYL}BENZOIC ACID

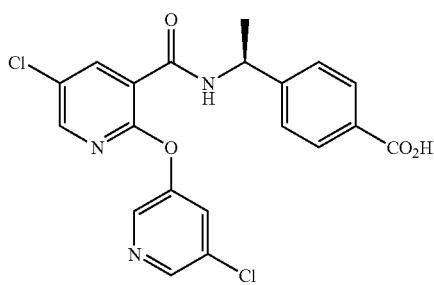

Step 1. 5-Chloro-2-[(5-chloropyridin-3-yl)oxy]nicotinic acid

A mixture of 2,5-dichloronicotinic acid (*Syn. Commun.* 1989, 19, 553–9, 500 mg, 2.6 mmol), 3-chloro-5-hydroxypyridine (404 mg, 3.1 mmol), copper bronze (36 mg, 0.57 mmol), cuprous iodide (40 mg, 0.21 mmol) and potassium carbonate (792 mg, 5.7 mmol) in N,N-dimethylformamide (7 mL) was heated under reflux for 3 h. The reaction mixture was filtered through a pad of Celite® and the filtrate was concentrated. The residue was diluted with water (10 mL) and the mixture was acidified with 2 N hydrochloric acid (2 mL). Precipitateed solids were collected by filtration and dried under reduced presssure at 40° C. to afford 349 mg of the title compound: $^1$H-NMR (CDCl$_3$) δ 8.37 (3H, br.s), 7.96 (2H, br.s), a peak of COOH was not observed; MS (ESI) m/z 285 (M+H)$^+$.

Step 2. tert-Butyl 4-{(1S)-1-[({5-chloro-2-[(5-chloropyridin-3-yl)oxy]pyridin-3-yl}carbonyl)amino]ethyl}benzoate The title compound was prepared according to the procedure described in step 3 of Example 1 from 5-chloro-2-[(5-chloropyridin-3-yl)oxy]nicotinic acid (step 1) and tert-butyl 4-[(1S)-1-aminoethyl]benzoate (step 3 of Example 44): $^1$H-NMR (CDCl$_3$) δ 8.56 (1H, d, J=2.7 Hz), 8.55–8.54 (1H, m), 8.42–8.41 (1H, m), 8.13 (1H, d, J=2.7 Hz), 7.99–7.96 (2H, m), 7.80–7.82 (1H, m), 7.58 (1H, t, J=2.3 Hz), 7.42–7.39 (2H, m), 5.42–5.31 (1H, m), 1.62–1.58 (12H, m); MS (ESI) m/z 488 (M+H)$^+$, 486 (M–H)$^-$.

Step 3. 4-[(1S)-1-[({5-Chloro-2-[(5-chloropyridin-3-yl)oxy]pyridin-3-yl}carbonyl)amino]ethyl]benzoic acid The title compound was prepared according to the procedure described in step 5 of Example 44 from tert-butyl 4-{(1S)-1-[({5-chloro-2-[(5-chloropyridin-3-yl)oxy]pyridin-3-yl}carbonyl)amino]ethyl}benzoate (step 2): $^1$H-NMR (DMSO-d$_6$) δ 9.04 (1H, d, J=7.8 Hz), 8.55 (1H, J=2.3 Hz), 8.52 (1H, d, J=2.3 Hz), 8.34 (1H, d, J=2.6 Hz), 8.19 (1H, d, J=2.6 Hz), 7.98 (1H, t, J=2.3 Hz), 7.89–7.86 (2H, m), 7.53–7.50 (2H, m), 5.21–5.16 (1H, m), 1.46 (3H, d, J=6.8 Hz), a peak of COOH was not observed; MS (ESI) m/z 432 (M+H)$^+$, 430 (M–H)$^-$.

Example 47

4-[(1S)-1-({[5-CHLORO-2-(3-CYANOPHENOXY)PYRIDIN-3-YL]CARBONYL}AMINO)ETHYL]BENZOIC ACID

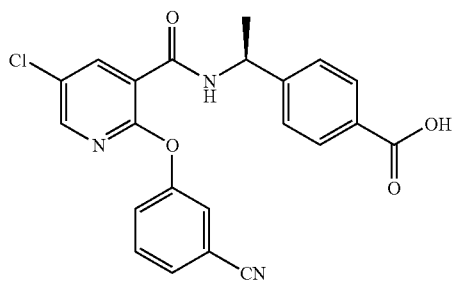

Step 1. 5-Chloro-2-(3-cyanophenoxy)nicotinic acid

The title compound was prepared according to the procedure described in step 1 of Example 46 from 2,5-dichloronicotinic acid (*Syn. Commun.* 1989, 19, 553–9) and 3-hydroxybenzonitrile: $^1$H-NMR (CDCl$_3$) δ 8.40–8.33 (2H, m), 7.74–7.52 (4H, m), a peak of COOH was not observed; MS (ESI) m/z 229 (M–COOH)$^-$.

Step 2. tert-Butyl 4-[(1S)-1-({[5-chloro-2-(3-cyanophenoxy)pyridin-3-yl]carbonyl}amino)ethyl]benzoate The title compound was prepared according to the procedure described in step 3 of Example 1 from 5-chloro-2-(3-cyanophenoxy)nicotinic acid (step 1) and tert-butyl 4-[(1S)-1-aminoethyl]benzoate (step 3 of Example 44): $^1$H-NMR (CDCl$_3$) δ 8.56 (1H, d, J=2.7 Hz), 8.13 (1H, d, J=2.7 Hz), 7.98–7.95 (2H, m), 7.89–7.86 (1H, m), 7.64–7.38 (6H, m), 5.42–5.31 (1H, m), 1.61–1.58 (12H, m); MS (ESI) m/z 476 (M−H)$^-$.

Step 3. 4-[(1S)-1-({[5-Chloro-2-(3-cyanophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(3-cyanophenoxy)pyridin-3-yl]carbonyl}amino)ethyl]benzoate (step 2): $^1$H-NMR (CDCl$_3$) δ 8.56 (1H, d, J=2.7 Hz), 8.15 (1H, d, J=2.7 Hz), 8.09–8.06 (2H, m), 7.91 (1H, d, J=7.0 Hz), 7.64–7.39 (6H, m), 5.39 (1H, quint, J=7.0 Hz), 1.62 (3H, d, J=7.0 Hz), a peak of COOH was not observed; MS (ESI) m/z 422 (M+H)$^+$, 420 (M−H)$^-$.

Example 48

4-[(1S)-1-({[5-CHLORO-2-(3-FLUOROPHENOXY)PYRIDIN-3-YL]CARBONYL}AMINO)ETHYL]BENZOIC ACID

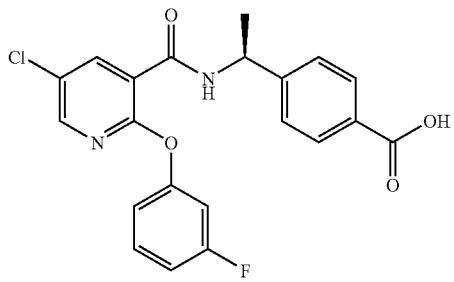

Step 1. Methyl 4-((1S)-1-{[(2,5-dichloropyridin-3-yl)carbonyl]amino}ethyl)benzoate The title compound was prepared according to the procedure described in step 1 of Example 45 from 2,5-dichloronicotinic acid and methyl 4-[(1S)-1-aminoethyl]benzoate hydrochloride (step 3 of Example 5): $^1$H-NMR (CDCl$_3$) δ 8.42 (1H, d, J=2.6 Hz), 8.10 (1H, d, J=2.6 Hz), 8.04 (2H, d, J=8.6 Hz), 7.46 (2H, d, J=8.6 Hz), 6.82 (1H, d, J=7.3 Hz), 5.40–5.30 (1H, m), 3.92 (3H, s), 1.64 (3H, d, J=7.0 Hz); MS (ESI) m/z 353 (M+H)$^+$, 351 (M−H)$^-$.

Step 2. Methyl 4-[(1S)-1-({[5-chloro-2-(3-fluorophenoxy)pyridin-3-yl]carbonyl}amino)ethyl]benzoate A mixture of methyl 4-((1S)-1-{[(2,5-dichloropyridin-3-yl)carbonyl]amino}ethyl)benzoate (step 1, 177 mg, 0.50 mmol), 3-fluorophenol (224 mg, 2.0 mmol) and sodium bicarbonate (105 mg, 1.25 mmol) in 1-methylpyrrolidin-2-one (2 mL) was stirred at 100° C. for 24 h. After cooling, the reaction mixture was partitioned between water (50 mL) and dichloromethane (50 mL) and the organic phase was separated. The aqueous phase was extracted with dichloromethane (50 mL). The combined organic layer was washed with brine (100 mL), dried (sodium sulfate), and concentrated. The residue was purified by flash column chromatography on silica gel (10 g) eluting with hexane/ethyl acetate (4/1) to afford 180 mg (84%) of the title compound as white solids: $^1$H-NMR (CDCl$_3$) δ 8.55 (1H, d, J=2.7 Hz), 8.15 (1H, d, J=2.7 Hz), 8.07–7.98 (3H, m), 7.47–7.37 (3H, m), 7.07–6.99 (1H, m), 6.98–6.88 (2H, m), 5.42–5.31 (1H, m), 3.90 (3H, s), 1.60 (3H, d, J=7.0 Hz); MS (ESI) m/z 429 (M+H)$^+$, 427 (M−H)$^-$.

Step 3. 4-[(1S)-1-({[5-chloro-2-(3-fluorophenoxy)pyridin-3-yl]carbonyl}amino)ethyl]benzoic acid To a stirred solution of methyl 4-[(1S)-1-({[5-chloro-2-(3-fluorophenoxy)pyridin-3-yl]carbonyl}amino)ethyl]benzoate (step 2, 180 mg, 0.42 mmol) in tetrahydrofuran (3 mL) was added 2 N sodium hydroxide aqueous The reaction mixture was stirred at 65° C. for 5 h. After cooling, the reaction mixture was acidified by the addition of 2 N hydrochloric acid (2 mL). The aqueous mixture was partitioned between water (50 mL) and dichloromethane (50 mL) and the organic phase was separated. The aqueous phase was extracted with dichloromethane (50 mL). The combined organic layer was washed with brine (100 mL), dried (sodium sulfate), and concentrated. The residual solids were recrystallized from ethyl acetate to afford 103 mg (60%) of the title compound as white solids: $^1$H-NMR (CDCl$_3$) δ 8.56 (1H, d, J=3.0 Hz), 8.16 (1H, d, J=3.0 Hz), 8.08–8.05 (3H, m), 7.47–7.40 (3H, m), 7.07–6.91 (3H, m), 5.43–5.33 (1H, m), 1.60 (3H, d, J=7.1 Hz), a peak of COOH was not observed; MS (ESI) m/z 415 (M+H)$^+$, 413 (M−H)$^-$.

Example 49

4-[(1S)-1-({[5-CHLORO-2-(3-CHLOROPHENOXY)PYRIDIN-3-YL]CARBONYL}AMINO)ETHYL]BENZOIC ACID

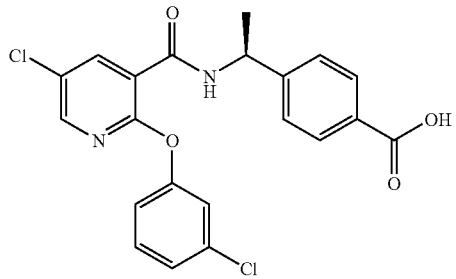

Step 1. Methyl 4-[(1S)-1-({[5-chloro-2-(3-chlorophenoxy)pyridin-3-yl]carbonyl}amino)ethyl]benzoate The title compound was prepared according to the procedure described in step 2 of Example 48 from methyl 4-((1S)-1-{[(2,5-dichloropyridin-3-yl)carbonyl]amino}ethyl)benzoate (step 1 of Example 48) and 3-chlorophenol: $^1$H-NMR (CDCl$_3$) δ 8.55 (1H, d, J=2.7 Hz), 8.15

(1H, d, J=2.7 Hz), 8.05–7.97 (3H, m), 7.45–7.37 (3H, m), 7.33–7.28 (1H, m), 7.21–7.18 (1H, m), 7.09–7.03 (1H, m), 5.42–5.31 (1H, m), 3.90 (3H, s), 1.60 (3H, d, J=7.0 Hz); MS (ESI) m/z 445 (M+H)+, 443 (M−H)−.

Step 2. 4-[(1S)-1-({[5-chloro-2-(3-chlorophenoxy)pyridin-3-yl]carbonyl}amino)ethyl]benzoic acid The title compound was prepared according to the procedure described in step 3 of Example 48 from methyl 4-[(1S)-1-({[5-chloro-2-(3-chlorophenoxy)pyridin-3-yl]carbonyl}amino)ethyl]benzoate (step 1): $^1$H-NMR (CDCl$_3$) δ 8.56 (1H, d, J=2.7 Hz), 8.16 (1H, d, J=2.7 Hz), 8.08–8.03 (3H, m), 7.47–7.38 (3H, m), 7.33–7.30 (1H, m), 7.21–7.20 (1H, m), 7.08–7.05 (1H, m), 5.38 (1H, quint, J=7.0 Hz), 1.60 (3H, d, J=7.0 Hz), a peak of COOH was not observed; MS (ESI) m/z 431 (M+H)+, 429 (M−H)−.

Example 50

4-[(1S)-1-({[5-CHLORO-2-(3-METHOXYPHENOXY)PYRIDIN-3-YL]CARBONYL}AMINO)ETHYL]BENZOIC ACID

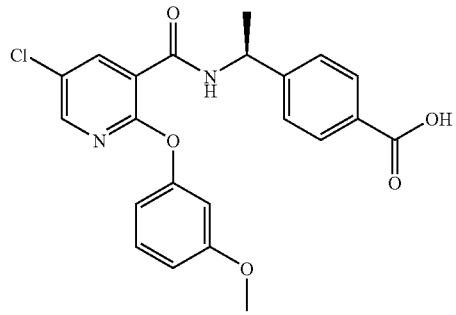

Step 1. tert-Butyl 4-[(1S)-1-({[5-chloro-2-(3-methoxyphenoxy)pyridin-3-yl]carbonyl}amino)ethyl]benzoate The title compound was prepared according to the procedure described in step 2 of Example 45 substituting 3-methoxyphenol for 3-fluorophenol: $^1$H-NMR (CDCl$_3$) δ 8.55 (1H, d, J=2.7 Hz), 8.18–8.15 (2H, m), 7.96–7.94 (2H, m), 7.41–7.34 (3H, m), 6.88–6.84 (1H, m), 6.76–6.70 (2H, m), 5.40–5.31 (1H, m), 3.83 (3H, s), 1.69–1.57 (12H, m); MS (ESI) m/z 483 (M+H)+, 481 (M−H)−.

Step 2. 4-[(1S)-1-({[5-chloro-2-(3-methoxyphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(3-methoxyphenoxy)pyridin-3-yl]carbonyl}amino)ethyl]benzoate (step 1): $^1$H-NMR (CDCl$_3$) δ 8.55 (1H, d, J=2.7 Hz), 8.20–8.16 (2H, m), 8.07–8.05 (2H, m), 7.47–7.44 (2H, m), 7.37 (1H, t, J=8.1 Hz), 6.88–6.85 (1H, m), 6.76–6.70 (2H, m), 5.43–5.33 (1H, m), 3.83 (3H, s), 1.59 (3H, d, J=7.0 Hz), a peak of COOH was not observed; MS (ESI) m/z 427 (M+H)+, 425 (M−H)−.

Example 51

4-[(1S)-1-({[5-CHLORO-2-(2,4-DIFLUOROPHENOXY)PYRIDIN-3-YL]CARBONYL}AMINO)ETHYL]BENZOIC ACID)

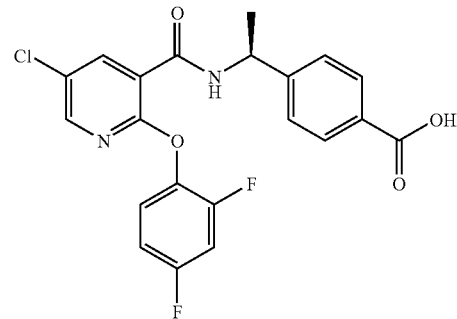

Step 1. Methyl 4-[(1S)-1-({[5-chloro-2-(2,4-difluorophenoxy)pyridin-3-yl]carbonyl}amino)ethyl]benzoate The title compound was prepared according to the procedure described in step 2 of Example 48 from methyl 4-((1S)-1-{[(2,5-dichloropyridin-3-yl)carbonyl]amino}ethyl)benzoate (step 1 of Example 48) and 2,4-difluorophenol: $^1$H-NMR (CDCl$_3$) δ 8.54 (1H, d, J=2.7 Hz), 8.11 (1H, d, J=2.7 Hz), 8.05–7.98 (3H, m), 7.44 (2H, d, J=8.6 Hz), 7.35–7.27 (1H, m), 7.06–6.93 (2H, m), 5.442–5.32 (1H, m), 3.90 (3H, s), 1.61 (3H, d, J=7.0 Hz); MS (ESI) m/z 447 (M+H)+, 445 (M−H)−.

Step 2. 4-[(1S)-1-({[5-chloro-2-(2,4-difluorophenoxy)pyridin-3-yl]carbonyl}amino)ethyl]benzoic acid The title compound was prepared according to the procedure described in step 3 of Example 48 from methyl 4-[(1S)-1-({[5-chloro-2-(2,4-difluorophenoxy)pyridin-3-yl]carbonyl}amino)ethyl]benzoate (step 1): $^1$H-NMR (CDCl$_3$) δ 8.54 (1H, d, J=2.6 Hz), 8.11 (1H, d, J=2.6 Hz), 8.09–8.02 (3H, m), 7.49–7.46 (2H, m), 7.36–7.28 (1H, m), 7.06–6.94 (2H, m), 5.45–5.34 (1H, m), 1.62 (3H, d, J=7.0 Hz), a peak of COOH was not observed; MS (ESI) m/z 433 (M+H)+, 431 (M−H)−.

Example 52

4-[(1S)-1-({[5-CHLORO-2-(4-CHLORO-3-FLUOROPHENOXY)PYRIDIN-3-YL]CARBONYL}AMINO)ETHYL]BENZOIC ACID

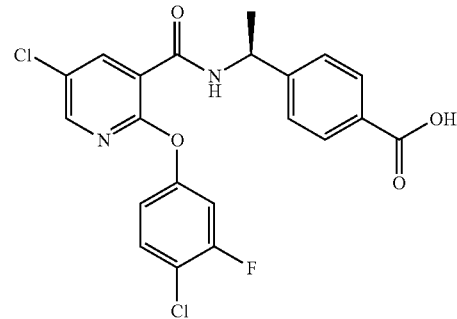

Step 1. tert-Butyl 4-[(1S)-1-({[5-chloro-2-(4-chloro-3-fluorophenoxy)pyridin-3-yl]carbonyl}amino)ethyl]benzoate The title compound was prepared according to the procedure described in step 2 of Example 45 substituting 4-chloro-3-fluorophenol for 3-fluorophenol: $^1$H-NMR (CDCl$_3$) δ 8.55 (1H, d, J=3.0 Hz), 8.14 (1H, d, J=3.0 Hz), 7.98–7.94 (2H, m), 7.91–7.89 (1H, m), 7.51–7.45 (1H, m), 7.41–7.38 (2H, m), 7.04–7.00 (1H, m), 6.94–6.89 (1H, m), 5.41–5.30 (1H, m), 1.60–1.58 (12H, m); MS (ESI) m/z 505 (M+H)$^+$, 503 (M–H)$^−$.

Step 2. 4-[(1S)-1-({[5-chloro-2-(4-chloro-3-fluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-chloro-3-fluorophenoxy)pyridin-3-yl]carbonyl}amino)ethyl]benzoate (step 1): $^1$H-NMR (CDCl$_3$) δ 8.56 (1H, d, J=2.7 Hz), 8.15 (1H, d, J=2.7 Hz), 8.09–8.06 (2H, m), 7.94–7.92 (1H, m), 7.52–7.44 (3H, m), 7.04 (1H, dd, J=9.2, 2.7 Hz), 6.93 (1H, ddd, J=8.6, 2.7, 1.4 Hz), 5.43–5.35 (1H, m), 1.61 (3H, d, J=7.0 Hz), a peak of COOH was not observed; MS (ESI) m/z 449 (M+H)$^+$, 447 (M–H)$^−$.

Example 53

4-[(1S)-1-({[5-CHLORO-2-(2-CHLORO-4-FLUOROPHENOXY)PYRIDIN-3-YL]CARBONYL}AMINO)ETHYL]BENZOIC ACID

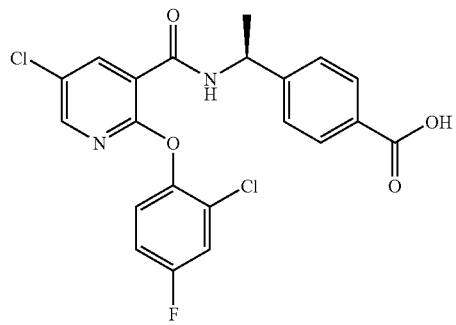

Step 1. Methyl 4-[(1S)-1-({[5-chloro-2-(2-chloro-4-fluorophenoxy)pyridin-3-yl]carbonyl}amino)ethyl]benzoate The title compound was prepared according to the procedure described in step 2 of Example 48 from methyl 4-((1S)-1-{[(2,5-dichloropyridin-3-yl)carbonyl]amino}ethyl)benzoate (step 1 of Example 48) and 2-chloro-4-fluorophenol: $^1$H-NMR (CDCl$_3$) δ 8.54 (1H, d, J=2.6 Hz), 8,12 (1H, br.s), 8.09 (1H, d, J=2.6 Hz), 8.04–7.98 (2H, m), 7.48–7.41 (2H, m), 7.32–7.25 (2H, m), 7.15–7.07 (1H, m), 5.45–5.33 (1H, m), 3.90 (3H, s), 1.61 (3H, d, J=7.0 Hz); MS (ESI) m/z 463 (M+H)$^+$, 461 (M–H)$^−$.

Step 2. 4-[(1S)-1-({[5-chloro-2-(2-chloro-4-fluorophenoxy)pyridin-3-yl]carbonyl}amino)ethyl]benzoic acid The title compound was prepared according to the procedure described in step 3 of Example 48 from methyl 4-[(1S)-1-({[5-chloro-2-(2-chloro-4-fluorophenoxy)pyridin-3-yl]carbonyl}amino)ethyl]benzoate (step 1): $^1$H-NMR (CDCl$_3$) δ 8.55 (1H, d, J=2.6 Hz), 8.13–8.05 (4H, m), 7.49–7.46 (2H, m), 7.34–7.26 (2H, m), 7.15–7.08 (1H, m), 5.45–5.35 (1H, m), 1.62 (3H, d, J=7.0 Hz), a peak of COOH was not observed; MS (ESI) m/z 449 (M+H)$^+$, 447 (M–H)$^−$.

Example 54

4-[(1S)-1-({[5-CHLORO-2-(2,6-DIFLUOROPHENOXY)PYRIDIN-3-YL]CARBONYL}AMINO)ETHYL]BENZOIC ACID

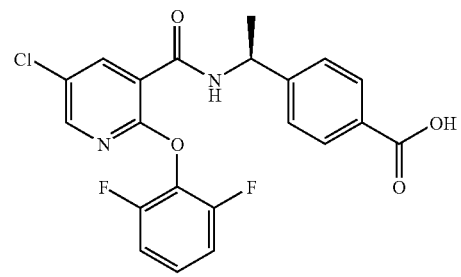

Step 1. Methyl 4-[(1S)-1-({[5-chloro-2-(2,6-difluorophenoxy)pyridin-3-yl]carbonyl}amino)ethyl]benzoate The title compound was prepared according to the procedure described in step 2 of Example 48 from methyl 4-((1S)-1-{[(2,5-dichloropyridin-3-yl)carbonyl]amino}ethyl)benzoate (step 1 of Example 48) and 2,6-difluorophenol: $^1$H-NMR (CDCl$_3$) δ 8.54 (1H, d, J=2.7 Hz), 8.11 (1H, d, J=2.7 Hz), 8.05–7.94 (3H, m), 7.48–7.42 (2H, m), 7.33–7.23 (1H, m), 7.12–7.02 (2H, m), 5.45–5.33 (1H, m), 3.90 (3H, s), 1.61 (3H, d, J=7.0 Hz); MS (ESI) m/z 447 (M+H)$^+$, 445 (M–H)$^−$.

Step 2. 4-[(1S)-1-({[5-chloro-2-(2,6-difluorophenoxy)pyridin-3-yl]carbonyl}amino)ethyl]benzoic acid The title compound was prepared according to the procedure described in step 3 of Example 48 from methyl 4-[(1S)-1-({[5-chloro-2-(2,6-difluorophenoxy)pyridin-3-yl]carbonyl}amino)ethyl]benzoate (step 1): $^1$H-NMR (CDCl$_3$) δ 8.54 (1H, d, J=2.6 Hz), 8.13–8.06 (3H, m), 8.00–7.91 (1H, m), 7.50–7.47 (2H, m), 7.34–7.23 (1H, m), 7.12–7.05 (2H, m), 5.45–5.35 (1H, m), 1.62 (3H, d, J=7.0 Hz), a peak of COOH was not observed; MS (ESI) m/z 433 (M+H)$^+$, 431 (M–H)$^−$.

Example 55

4-[(1S)-1-({[5-CHLORO-2-(3,4-DIFLUOROPHENOXY)PYRIDIN-3-YL]CARBONYL}AMINO)ETHYL]BENZOIC ACID

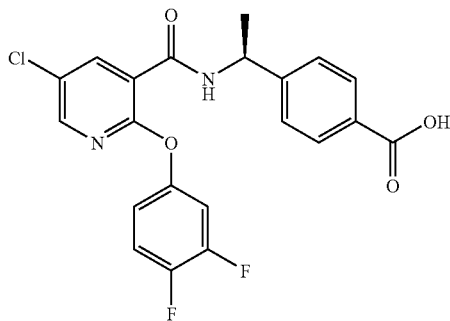

Step 1. tert-Butyl 4-[(1S)-1-({[5-chloro-2-(3,4-difluorophenoxy)pyridin-3-yl]carbonyl}amino)ethyl]benzoate The title compound was prepared according to the procedure described in step 2 of Example 45 substituting 3,4-difluorophenol for 3-fluorophenol: $^1$H-NMR (CDCl$_3$) δ 8.54 (1H, d, J=2.6 Hz), 8.13 (1H, d, J=2.6 Hz), 8.00–7.91 (3H, m), 7.41–7.38 (2H, m), 7.30–7.20 (1H, m), 7.08–7.00 (1H, m), 6.93–6.86 (1H, m), 5.36 (1H, quint, J=7.0 Hz), 1.61–1.58 (12H, m); MS (ESI) m/z 489 (M+H)$^+$, 487 (M–H)$^-$.

Step 2. 4-[(1S)-1-({[5-Chloro-2-(3,4-difluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(3,4-difluorophenoxy)pyridin-3-yl]carbonyl}amino)ethyl]benzoate (step 1): $^1$H-NMR (CDCl$_3$) δ 8.55 (1H, d, J=2.7 Hz), 8.14 (1H, d, J=2.7 Hz), 8.09–8.06 (2H, m), 7.99–7.96 (1H, m), 7.47–7.44 (2H, m), 7.31–7.21 (1H, m), 7.09–7.02 (1H, m), 6.94–6.88 (1H, m), 5.44–5.34 (1H, m), 1.61 (3H, d, J=7.0 Hz), a peak of COOH was not observed; MS (ESI) m/z 433 (M+H)$^+$, 431 (M–H)$^-$.

Example 56

4-[({[2-(4-FLUOROPHENOXY)-5-(TRIFLUOROMETHYL)PYRIDIN-3-YL]CARBONYL}AMINO)METHYL]BENZOIC ACID

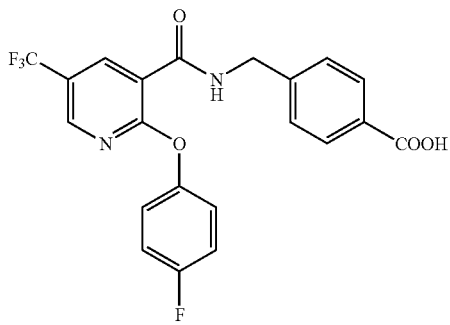

Step 1. Methyl 2-(4-fluorophenoxy)-5-iodonicotinate

To a solution of 4-fluorophenol (224 mg, 2.0 mmol) in DMF (5.0 mL) was added sodium hydride (48 mg, 2.0 mmol) at room temperature. After stirring for 10 min, methyl 2-chloro-5-iodonicotinate (J. Org. Chem. 1989, 54, 3618, 594 mg, 2.0 mmol) was added to the reaction mixture. The reaction mixture was stirred under reflux for 16 h. Then the reaction mixture was poured into water (50 mL) and extracted with ether (50 mL×3). The combined organic extracts were washed with brine (50 mL) and dried (sodium sulfate). After removal of the solvent, the residue was purified by flash column chromatography on silica gel (50 g) eluting with hexane/ethyl acetate (2/1) to afford 644 mg (86%) of the title compound: $^1$H-NMR (CDCl$_3$) δ 8.51 (1H, d, J=2.3 Hz), 8.41 (1H, s), 7.09 (4H, d, J=6.2 Hz), 3.95 (3H, s); MS (ESI) m/z 374 (M+H)$^+$.

Step 2. Methyl 2-(4-fluorophenoxy)-5-(trifluoromethyl)nicotinate

A mixture of methyl 2-(4-fluorophenoxy)-5-iodonicotinate (step 1, 373 mg, 1.0 mmol), sodium trifluoroacetate (1.36 g, 10 mmol), and copper(I) iodide (960 mg, 5.0 mmol) in 1-methyl-pyrolidine (8.0 mL) was stirred at 160° C. for 16 h under nitrogen atmosphere. The reaction mixture was poured into water (20 mL) and extacted with dichloromethane (50 mL×3). The combined organic extracts were washed with brine (50 mL) and dried (sodium sulfate). After removal of the solvent, the residue was purified by TLC plate developing with hexane/ethyl acetate (1/1) to afford 32 mg (10%) of the title compound: $^1$H-NMR (CDCl$_3$) δ 8.5 (2H, s), 7.13 (1H, d, J=6.3 Hz), 3.99 (3H, s); MS (ESI) m/z 316 (M+H)$^+$.

Step 3. 2-(4-Fluorophenoxy)-5-(trifluoromethyl)nicotinic acid

A mixture of methyl 2-(4-fluorophenoxy)-5-(trifluoromethyl)nicotinate (step 2, 32 mg, 0.10 mmol) and 4.0 M lithium hydroxide aqueous solution (1.0 mL, 4.0 mmol) in a mixture of tetrahydrofuran (2 mL) and dioxane (10 mL) was stirred for 3 h at room temperature. The pH value was adjusted to 4.0 by the addition of 2 N hydrochloric acid. The mixture was diluted with water (100 mL) and extracted with dichloromethane (20 mL×3). The combined organic extracts were washed with brine (50 mL), dried (sodium sulfate), and concentrated to afford 29 mg (99%) of the title compound: MS (ESI) m/z 256 (M–45)$^-$.

Step 4. Methyl 4-[({[2-(4-fluorophenoxy)-5-(trifluoromethyl)pyridin-3-yl]carbonyl}amino)methyl]benzoate The title compound was prepared according to the procedure described in step 3 of Example 1 from 2-(4-fluorophenoxy)-5-(trifluoromethyl)nicotinic acid (step 3) and methyl 4-(aminomethyl)benzoate hydrochloride: $^1$H-NMR (CDCl$_3$) δ 8.90 (1H, d, J=2.7 Hz), 8.45 (1H, s), 8.01 (2H, d, J=8.2 Hz), 7.43 (2H, d, J=8.2 Hz), 4.78 (2H, d, J=5.9 Hz), 3.90 (3H, s); MS (ESI) m/z 449 (M+H)$^+$.

Step 5. 4-[({[2-(4-Fluorophenoxy)-5-(trifluoromethyl)pyridin-3-yl]carbonyl}amino)methyl]benzoic acid The title compound was prepared according to the procedure described in step 2 of Example 56 from methyl 4-[({[2-(4-fluorophenoxy)-5-(trifluoromethyl)pyridin-3-yl]carbonyl}amino)methyl]benzoate: $^1$H-NMR (CDCl$_3$) δ 8.90 (1H, d, J=2.1 Hz), 8.46 (1H, s), 8.22 (2H, br.s), 7.45 (2H, br.s), 7.23–7.10 (4H, m), 4.80 (2H, d, J=6.8 Hz); MS (ESI) m/z 435 (M+H)$^+$, 433 (M–H)$^+$.

Example 57

4-[({[5-CYANO-2-(4-FLUOROPHENOXY)PYRIDIN-3-YL]CARBONYL}AMINO)METHYL]BENZOIC ACID

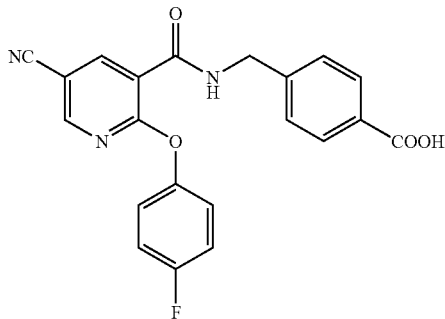

Step 1. Methyl 5-bromo-2-(4-fluorophenoxy)nicotinate

The title compound was prepared according to the procedure described in step 1 of Example 56 from methyl 5-bromo-2-chloronicotinate (*J. Org. Chem.* 1989, 54, 3618–3624) and 4-fluorophenol: $^1$H-NMR (CDCl$_3$) δ 8.37 (1H, d, J=2.5 Hz), 8.27 (1H, d, J=2.5 Hz), 7.10 (2H, d, J=6.2 Hz), 3.95 (3H, s); MS (ESI) m/z 326 (M+H)$^+$.

Step 2. Methyl 5-cyano-2-(4-fluorophenoxy)nicotinate

A mixture of methyl 5-bromo-2-(4-fluorophenoxy)nicotinate (step 1, 163 mg, 0.50 mmol), sodium cyanide (49 mg, 1.0 mmol), tetrakis(triphenylphohphine) palladium(0) (29 mg, 0.025 mmol), and copper iodide (9.5 mg, 0.05 mmol) in propionitrile (4.0 mL) was heated under reflux for 4.5 h with stirring. The reaction mixture was filtered through a pad of Celite®. The filtrate was partitioned between water (10 mL) and dichloromethane (30 mL). The organic phase was separated, dried (sodium sulfate), and concentrated. The residue was purified by TLC plate developing with hexane/ethyl acetate (3/1) to afford 97 mg (71%) of the title compound: $^1$H-NMR (CDCl$_3$) δ 8.5 (2H, m), 7.14 (2H, d, J=1.2 Hz), 7.12 (2H, s), 3.99 (3H, s); MS (ESI) m/z 272 (M+).

Step 3. 5-Cyano-2-(4-fluorophenoxy)nicotinic acid

The title compound was prepared according to the procedure described in step 2 of Example 56 from methyl 5-cyano-2-(4-fluorophenoxy)nicotinate (step 2): $^1$H-NMR (CDCl$_3$) δ 8.66 (1H, d, J=1.8 Hz), 8.54 (1H, d, J=2.3 Hz), 7.15 (4H, d, J=6.3 Hz); MS (ESI) m/z 259 (M+H)$^+$, 257 (M–H)$^+$.

Step 4. Methyl 4-[({[5-cyano-2-(4-fluorophenoxy)pyridin-3-yl]carbonyl}amino)methyl]benzoate The title compound was prepared according to the procedure described in step 3 of Example 1 from 5-cyano-2-(4-fluorophenoxy)nicotinic acid (step 3) and methyl 4-(aminomethyl)benzoate hydrochloride: $^1$H-NMR (CDCl$_3$) δ 8.91 (1H, d, J=1.8 Hz), 8.48 (1H, d, J=1.8 Hz), 8.03 (2H, d, J=8.1 Hz), 7.43 (2H, d, J=8.1 Hz), 7.17–7.12 (4H, m), 4.78 (2H, d, J=5.4 Hz), 3.91 (3H, s); MS (ESI) m/z 406 (M+H)$^+$, 404 (M+H)$^+$.

Step 5. 4-[({[5-Cyano-2-(4-fluorophenoxy)pyridin-3-yl]carbonyl}amino)methyl]benzoic acid The title compound was prepared according to the procedure described in step 2 of Example 56 from methyl 4-[({[5-cyano-2-(4-fluorophenoxy)pyridin-3-yl]carbonyl}amino)methyl]benzoate: $^1$H-NMR (DMSO-d$_6$) δ 8.87 (1H, d, J=2.3 Hz), 8.46 (1H, d, J=2.3 Hz), 8.02 (2H, d, J=8.2 Hz), 7.41 (2H, d, J=8.2 Hz), 7.15–7.10 (4H, m), 4.76 (2H, d, J=5.7 Hz); MS (ESI) m/z 392 (M+H)$^+$, 390 (M–H)$^+$.

Example 58

4-[({[5-FLUORO-2-(4-FLUOROBENZYL)PYRIDIN-3-YL]CARBONYL}AMINO)METHYL]BENZOIC ACID

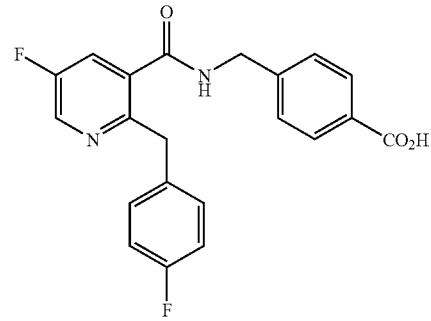

Step 1. Methyl 5-fluoro-2-(4-fluorobenzyl)nicotinate

2-Chloro-5-fluoronicotinic acid (1.00 g, 5.70 mmol) was treated with 2 M solution of (Trimethylsilyl)diazomethane in hexane (5.70 m]L, 11.4 mmol), methanol (4 mL), and dichloromethane (14 mL) at 0° C. for 1 h. The mixture was quenched with acetic acid and concentrated under reduced pressure. The residue was purified by flush column chromatography on silica gel eluting with hexane/ethyl acetate (10/1) to afford 0.78 g (72%) of the title compounds as colorless oil: $^1$H-NMR (CDCl$_3$) δ 8.41 (1H, d, J=3.1 Hz), 7.93 (1H, dd, J=7.6, 3.1 Hz), 3.98 (3H, s).

Step 2. Methyl 5-fluoro-2-(4-fluorobenzyl)nicotinate

To a stirred solution of methyl 2-chloro-5-fluoronicotinate (step 1, 350 mg, 1.85 mmol) and dichlorobis[triphenylphosphine]nickel (II) (362 mg, 0.55 mmol) in tetrahydrofuran (15 mL) was added a 0.5 M solution of 4-fluorobenzylzinc chloride in tetrahydrofuran (5.54 mL, 2.77 mmol) at 0° C. under nitrogen. The resulting mixture was warmed to room temperature and stirred for 16 h. The mixture was poured into saturated aqueous ammonium chloride solution (50 mL) and extracted with ethyl acetate (100 mL). The organic layer was dried over magnesium sulfate and concentrated under reduced pressure. The residue was purified by flush column chromatography on silica gel eluting with hexane/ethyl acetate (10/1) to afford 439 mg (90%) of the title compounds as colorless oil: $^1$H-NMR (CDCl$_3$) δ 8.56 (1H, d, J=2.8 Hz), 7.91 (1H, dd, J=8.6, 2.9 Hz), 7.26–7.19 (2H, m), 6.98–6.92 (2H, m), 4.52 (2H, s), 3.89 (3H, s); MS (ESI) m/z 264 (M+H)$^+$e.

Step 3. 5-Fluoro-2-(4-fluorobenzyl)nicotinic acid

The title compound was prepared according to the procedure described in step 2 of Example 1 from methyl 5-fluoro-2-(4-fluorobenzyl)nicotinate (step 2): MS (ESI) m/z 250 (M+H)$^+$.

Step 4. Methyl 4-[({[5-fluoro-2-(4-fluorobenzyl) pyridin-3-yl]carbonyl}amino)methyl]benzoate The title compound was prepared according to the procedure described in step 3 of Example 1 from 5-fluoro-2-(4-fluorobenzyl)nicotinic acid (step 3) and methyl 4-(aminomethyl)benzoate hydrochloride: $^1$H-NMR (CDCl$_3$) δ 8.49 (1H, d, J=2.8 Hz), 8.01–7.97 (2H, m), 7.44 (1H, dd, J=7.9, 2.8 Hz), 7.27 (2H, dd, J=4.6, 4.0 Hz), 7.14–7.09 (2H, m), 6.93–6.86 (2H, m), 6.08 (1H, br.s), 4.56 (2H, d, J=5.9 Hz), 4.29 (2H, s), 3.92 (3H, s); MS (ESI) m/z 397 (M+H)$^+$, 395 (M−H)$^-$.

Step 5. 4-[({[5-Fluoro-2-(4-fluorobenzyl)pyridin-3-yl]carbonyl}amino)methyl]benzoic acid The title compound was prepared according to the procedure described in step 4 of Example 1 from methyl 4-[({[5-fluoro-2-(4-fluorobenzyl)pyridin-3-yl]carbonyl}amino)methyl]benzoate (step 4): $^1$H-NMR (DMSO-d$_6$) δ 9.20 (1H, t, J=5.7 Hz), 8.60 (1H, d, J=2.8 Hz), 7.90 (2H, d, J=2.8 Hz), 7.82 (1H, dd, J=8.9, 2.8 Hz), 7.38 (2H, d, J=8.1 Hz), 7.18–7.14 (2H, m), 7.02 (2H, dd, J=8.8, 8.6 Hz), 4.50 (2H, d, J=5.7 Hz), 4.20 (2H, s); MS (ESI) m/z 383 (M+H)$^+$, 381 (M−H)$^-$.

Example 59

4-[(1S)-1-({[5-FLUORO-2-(4-FLUOROBENZYL) PYRIDIN-3-YL]CARBONYL}AMINO)ETHYL] BENZOIC ACID

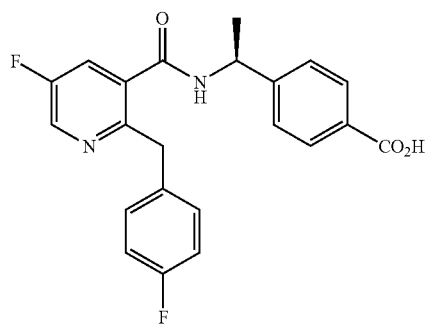

Step 1. Methyl 4-[(1S)-1-({[5-fluoro-2-(4-fluorobenzyl)pyridin-3-yl]carbonyl}amino)ethyl]benzoate The title compound was prepared according to the procedure described in step 3 of Example 1 from 5-fluoro-2-(4-fluorobenzyl)nicotinic acid (step 3 of Example 58) and methyl 4-[(1S)-1-aminoethyl]benzoate hydrochloride (step 3 of Example 5): $^1$H-NMR (CDCl$_3$) δ 9.13 (1H, d, J=7.7 Hz), 8.59 (1H, d, J=3.0 Hz), 7.93 (2H, d, J=8.4 Hz), 7.79 (1H, dd, J=8.7, 2.8 Hz), 7.51 (2H, d, J=8.2 Hz), 7.15–7.09 (2H, m), 7.03–6.96 (2H, m), 5.19–5.09 (1H, m), 4.17 (1H, d, J=13.7 Hz), 4.08 (1H, d, J=13.7 Hz), 3.85 (3H, s), 1.42 (3H, d, J=7.1 Hz); MS (ESI) m/z 411 (M+H)$^+$, 409 (M−H)$^-$.

Step 2. 4-[(1S)-1-({[5-Fluoro-2-(4-fluorobenzyl) pyridin-3-yl]carbonyl}amino)ethyl]benzoic acid The title compound was prepared according to the procedure described in step 4 of Example 1 from methyl 4-[(1S)-1-({[5-fluoro-2-(4-fluorobenzyl)pyridin-3-yl] carbonyl}amino)ethyl]benzoate (step 1): $^1$H-NMR (DMSO-d$_6$) δ 9.11 (1H, d, J=7.9 Hz), 8.59 (1H, d, J=3.0 Hz), 7.91 (2H, d, J=8.2 Hz), 7.79 (1H, dd, J=8.8, 2.9 Hz), 7.48 (2H, d, J=8.4 Hz), 7.15–6.96 (4H, m), 5.20–5.10 (1H, m), 4.18 (1H, d, J=13.9 Hz), 4.09 (1H, d, J=13.9 Hz), 1.42 (3H, d, J=7.1 Hz); MS (ESI) m/z 397 (M+H)$^+$, 395 (M−H)$^-$.

Example 60

4-[(1S)-1-({[5-CHLORO-2-(4-FLUOROBENZYL) PYRIDIN-3-YL]CARBONYL}AMINO)ETHYL] BENZOIC ACID

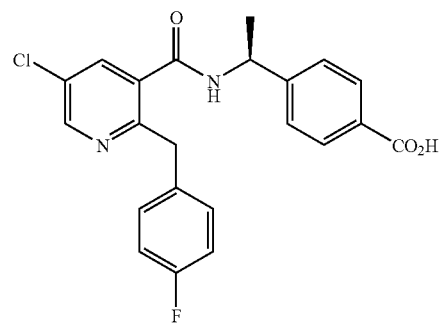

Step 1. Methyl 5-chloro-2-(4-fluorobenzyl)nicotinate

To a stirred solution of methyl 2,5-dichloronicotinate (*Journal of Chemical and Engineering Data* 1981, 26, 332, 350 mg, 1.70 mmol) and tetrakis(triphenylphosphine)palladium(0) (196 mg, 0.17 mmol) in tetrahydrofuran (6 mL) was added a 0.5 M solution of 4-fluorobenzylzinc chloride in tetrahydrofuran (4.08 mL, 2.04 mmol) at 0° C. under nitrogen. The resulting mixture was heated at 60° C. for 16 h. The mixture was poured into water (50 mL) and the aqueous mixture was extracted with ethyl acetate (100 mL). The organic layer was dried over magnesium sulfate and concentrated under reduced pressure. The residue was purified by flush column chromatography on silica gel eluting with hexane/ethyl acetate (6/1) to afford 416 mg (88%) of the title compounds as colorless oil: $^1$H-NMR (CDCl$_3$) δ 8.64 (1H, d, J=2.6 Hz), 8.17 (1H, d, J=2.6 Hz), 7.24–7.20 (2H, m), 6.96–6.90 (2H, m), 4.50 (2H, s), 3.89 (3H, s).

Step 2. 5-Chloro-2-(4-fluorobenzyl)nicotinic acid

The title compound was prepared according to the procedure described in step 2 of Example 1 from methyl 5-chloro-2-(4-fluorobenzyl)nicotinate (step 1): $^1$H-NMR (DMSO-$d_6$) δ 8.73 (1H, d, J=2.5 Hz), 8.22 (1H, d, J=2.5 Hz), 7.24–7.04 (4H, m), 3.35 (2H, s).

Step 3. Methyl 4-[(1S)-1-({[5-chloro-2-(4-fluorobenzyl)pyridin-3-yl]carbonyl}amino)ethyl]benzoate The title compound was prepared according to the procedure described in step 3 of Example 1 from 5-chloro-2-(4-fluorobenzyl)nicotinic acid (step 2) and methyl 4-[(1S)-1-aminoethyl]benzoate hydrochloride (step 3 of Example 5): $^1$H-NMR (CDCl$_3$) δ 9.15 (1H, d, J=7.7 Hz), 8.63 (1H, d, J=2.4 Hz), 7.96–7.92 (3H, m), 7.50 (2H, d, J=8.4 Hz), 7.15–6.96 (4H, m), 5.19–5.09 (1H, m), 4.17 (1H, d, J=14.0 Hz), 4.08 (1H, d, J=14.0 Hz), 3.85 (3H, s), 1.42 (2H, d, J=7.0 Hz); MS (ESI) m/z 427 (M+H)$^+$, 425 (M−H)$^−$.

Step 4. 4-[(1S)-1-({[5-Chloro-2-(4-fluorobenzyl)pyridin-3-yl]carbonyl}amino)ethyl]benzoic acid The title compound was prepared according to the procedure described in step 4 of Example 1 from methyl 4-[(1S)-1-({[5-chloro-2-(4-fluorobenzyl)pyridin-3-yl]carbonyl}amino)ethyl]benzoate (step 3): $^1$H-NMR (DMSO-$d_6$) δ 9.13 (1H, d, J=7.6 Hz), 8.63 (1H, d, J=2.5 Hz), 7.95–7.90 (3H, m), 7.47 (2H, d, J=8.2 Hz), 7.15–6.96 (4H, m), 5.19–5.09 (1H, m), 4.18 (1H, d, J=14.0 Hz), 4.09 (1H, d, J=14.0 Hz), 1.42 (3H, d, J=6.9 Hz); MS (ESI) m/z 413 (M+H)$^+$, 411 (M−H)$^−$.

Example 61

4-[(1S)-1-({[5-CHLORO-2-(3-FLUOROBENZYL)PYRIDIN-3-YL]CARBONYL}AMINO)ETHYL]BENZOIC ACID

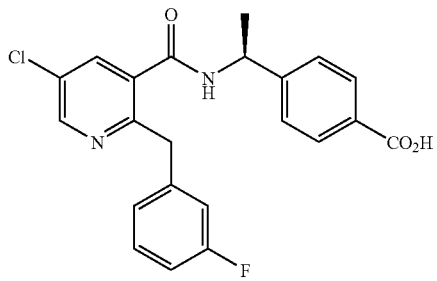

Step 1. Methyl 5-chloro-2-(3-fluorobenzyl)nicotinate

The title compound was prepared according to the procedure described in step 2 of Example 58 from methyl 2,5-dichloronicotinate and 3-fluorobenzylzinc chloride: $^1$H-NMR (CDCl$_3$) δ 8.65 (1H, d, J=2.4 Hz), 8.19 (1H, d, J=2.6 Hz), 7.26–6.84 (4H, m), 4.54 (2H, s), 3.89 (3H, s).

Step 2. 5-Chloro-2-(3-fluorobenzyl)nicotinic acid

The title compound was prepared according to the procedure described in step 2 of Example 1 from methyl 5-chloro-2-(3-fluorobenzyl)nicotinate (step 1): $^1$H-NMR (DMSO-$d_6$) δ 8.74 (1H, d, J=2.6 Hz), 8.24 (1H, d, J=2.6 Hz), 7.34–7.26 (1H, m), 7.03–6.98 (3H, m), 4.48 (2H, s).

Step 3. Methyl 4-[(1S)-1-({[5-chloro-2-(3-fluorobenzyl)pyridin-3-yl]carbonyl}amino)ethyl]benzoate The title compound was prepared according to the procedure described in step 3 of Example 1 from 5-chloro-2-(3-fluorobenzyl)nicotinic acid (step 2) and methyl 4-[(1S)-1-aminoethyl]benzoate hydrochloride (step 3 of Example 5): $^1$H-NMR (CDCl$_3$) δ 9.18 (1H, d, J=7.7 Hz), 8.65 (1H, d, J=2.6 Hz), 7.96 (1H, d, J=2.6 Hz), 7.93 (2H, d, J=8.3 Hz), 7.50 (2H, d, J=8.4 Hz), 7.27–7.20 (1H, m), 7.02–6.89 (3H, m), 5.20–5.10 (1H, m), 4.20 (1H, d, J=14.1 Hz), 4.13 (1H, d, J=14.1 Hz), 3.85 (3H, s), 1.42 (3H, d, J=7.2 Hz); MS (ESI) m/z 427 (M+H)$^+$, 425 (M−H)$^−$.

Step 4. 4-[(1S)-1-({[5-Chloro-2-(3-fluorobenzyl)pyridin-3-yl]carbonyl}amino)ethyl]benzoic acid The title compound was prepared according to the procedure described in step 4 of Example 1 from methyl 4-[(1S)-1-({[5-chloro-2-(3-fluorobenzyl)pyridin-3-yl]carbonyl}amino)ethyl]benzoate (step 3): $^1$H-NMR (DMSO-$d_6$) δ 9.16 (1H, d, J=7.7 Hz), 8.65 (1H, d, J=2.5 Hz), 7.97 (1H, d, J=2.3 Hz), 7.90 (2H, d, J=8.2 Hz), 7.47 (2H, d, J=8.4 Hz), 7.28–7.20 (1H, m), 7.01–6.91 (3H, m), 5.18–8.08 (1H, m), 4.21 (1H, d, J=14.2 Hz), 4.13 (1H, d, J=14.2 Hz), 1.42 (3H, d, J=7.1 Hz); MS (ESI) m/z 413 (M+H)$^+$, 411 (M−H)$^−$.

Example 62

4-[(1S)-1-({[5-CHLORO-2-(3-CHLOROBENZYL)PYRIDIN-3-YL]CARBONYL}AMINO)ETHYL]BENZOIC ACID

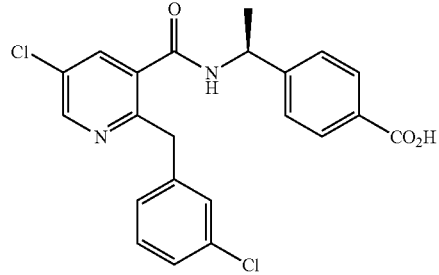

Step 1. Methyl 5-chloro-2-(3-chlorobenzyl)nicotinate

The title compound was prepared according to the procedure described in step 2 of Example 58 from methyl 2,5-dichloronicotinate and 3-chlorobenzylzinc chloride: $^1$H-NMR (CDCl$_3$) δ 8.65 (1H, d, J=2.6 Hz), 8.17 (1H, d, J=2.6 Hz), 7.26–7.12 (4H, m), 4.52 (2H, s), 3.89 (3H, s).

Step 2. 5-Chloro-2-(3-chlorobenzyl)nicotinic acid

The title compound was prepared according to the procedure described in step 2 of Example 1 from methyl 5-chloro-2-(3-chlorobenzyl)nicotinate (step 1): $^1$H-NMR (DMSO-$d_6$) δ 8.74 (1H, d, J=2.6 Hz), 8.24 (1H, d, J=2.6 Hz), 7.32–7.13 (4H, m), 4.47 (2H, s).

Step 3. Methyl 4-[(1S)-1-({[5-chloro-2-(3-chlorobenzyl)pyridin-3-yl]carbonyl}amino)ethyl]benzoate The title compound was prepared according to the procedure described in step 3 of Example 1 from 5-chloro-2-(3-chlorobenzyl)nicotinic acid (step 2) and methyl 4-[(1S)-1-aminoethyl]benzoate hydrochloride (step 3 of Example 5): $^1$H-NMR (CDCl$_3$) δ 9.19 (1H, d, J=7.7 Hz), 8.65 (1H, d, J=2.4 Hz), 7.98–7.92 (3H, m), 7.51 (2H, d, J=8.4 Hz), 7.23–7.18 (3H, m), 7.09–7.06 (1H, m), 5.20–5.10 (1H, m), 4.18 (1H, d, J=14.2 Hz), 4.12 (1H, d, J=14.2 Hz), 3.85 (3H, s), 1.42 (3H, d, J=7.0 Hz); MS (ESI) m/z 443 (M+H)$^+$, 441 (M−H)$^−$.

Step 4. 4-[(1S)-1-({[5-Chloro-2-(3-chlorobenzyl)pyridin-3-yl]carbonyl}amino)ethyl]benzoic acid The title compound was prepared according to the procedure described in step 4 of Example 1 from methyl 4-[(1S)-1-({[5-chloro-2-(3-chlorobenzyl)pyridin-3-yl]carbonyl}amino)ethyl]benzoate (step 3): $^1$H-NMR (DMSO-$d_6$) δ 9.17 (1H, d, J=7.7 Hz), 8.65 (1H, d, J=2.3 Hz), 7.98–7.90 (3H, m), 7.48 (2H, d, J=8.2 Hz), 7.24–7.19 (3H, m), 7.10–7.06 (1H, m), 5.20–5.10 (1H, m), 4.19 (1H, d, J=13.9 Hz), 4.12 (1H, d, J=13.9 Hz), 1.43 (3H, d, J=7.1 Hz); MS (ESI) m/z 429 (M+H)$^+$, 427 (M−H)$^−$.

Example 63

4-[(1S)-1-({[5-CHLORO-2-(3-METHOXYBENZYL)PYRIDIN-3-YL]CARBONYL}AMINO)ETHYL]BENZOIC ACID

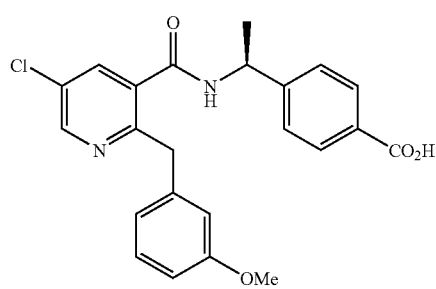

Step 1. Methyl 5-chloro-2-(3-methoxybenzyl)nicotinate

The title compound was prepared according to the procedure described in step 2 of Example 58 from methyl 2,5-dichloronicotinate and 3-methoxybenzylzinc chloride: $^1$H-NMR (CDCl$_3$) δ 8.64 (1H, d, J=2.5 Hz), 8.16 (1H, d, J=2.5 Hz), 7.17 (1H, t, J=7.9 Hz), 6.83–6.70 (3H, m), 4.53 (2H, s), 3.88 (3H, s), 3.75 (3H, s).

Step 2. 5-Chloro-2-(3-methoxybenzyl)nicotinic acid

The title compound was prepared according to the procedure described in step 2 of Example 1 from methyl 5-chloro-2-(3-methoxybenzyl)nicotinate (step 1): $^1$H-NMR (DMSO-$d_6$) δ 8.73 (1H, d, J=2.6 Hz), 8.21 (1H, d, J=2.6 Hz), 7.18–7.13 (1H, m), 6.75–6.71 (3H, m), 4.34 (2H, s), 3.69 (3H, s).

Step 3. Methyl 4-[(1S)-1-({[5-chloro-2-(3-methoxybenzyl)pyridin-3-yl]carbonyl}amino)ethyl]benzoate The title compound was prepared according to the procedure described in step 3 of Example 1 from 5-chloro-2-(3-methoxybenzyl)nicotinic acid (step 2) and methyl 4-[(1S)-1-aminoethyl]benzoate hydrochloride (step 3 of Example 5): $^1$H-NMR (CDCl$_3$) δ 9.15 (1H, d, J=7.5 Hz), 8.63 (1H, d, J=2.4 Hz), 7.94–7.90 (3H, m), 7.49 (2H, d, J=8.4 Hz), 7.09 (1H, t, J=7.8 Hz), 6.74–6.63 (3H, m), 5.18–5.08 (1H, m), 4.17 (1H, d, J=13.8 Hz), 4.09 (1H, d, J=13.8 Hz), 3.85 (3H, s), 3.66 (3H, s), 1.41 (3H, d, J=7.0 Hz); MS (ESI) m/z 439 (M+H)$^+$, 437 (M−H)$^−$.

Step 4. 4-[(1S)-1-({[5-Chloro-2-(3-methoxybenzyl)pyridin-3-yl]carbonyl}amino)ethyl]benzoic acid The title compound was prepared according to the procedure described in step 4 of Example 1 from methyl 4-[(1S)-1-({[5-chloro-2-(3-methoxybenzyl)pyridin-3-yl]carbonyl}amino)ethyl]benzoate (step 3): $^1$H-NMR (DMSO-$d_6$) δ 9.13 (1H, d, J=7.7 Hz), 8.63 (1H, d, J=2.5 Hz), 7.94–7.88 (3H, m), 7.46 (2H, d, J=8.2 Hz), 7.10 (1H, t, J=7.7 Hz), 6.74–6.64 (3H, m), 5.19–5.09 (1H, m), 4.17 (1H, d, J=13.9 Hz), 4.10 (1H, d, J=13.9 Hz), 3.66 (3H, s), 1.41 (3H, d, J=7.1 Hz); MS (ESI) m/z 425 (M+H)$^+$, 423 (M−H)$^−$.

Example 64

4-[(1S)-1-({[5-CHLORO-2-(3-CYANOBENZYL)PYRIDIN-3-YL]CARBONYL}AMINO)ETHYL]BENZOIC ACID

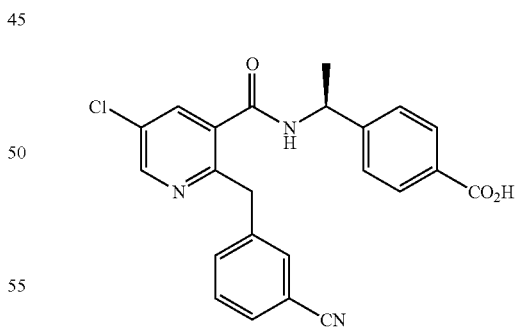

Step 1. Methyl 5-chloro-2-(3-cyanobenzyl)nicotinate

The title compound was prepared according to the procedure described in step 2 of Example 58 from methyl 2,5-dichloronicotinate and 3-cyanobenzylzinc bromide: $^1$H-NMR (CDCl$_3$) δ 8.66 (1H, d, J=2.5 Hz), 8.23 (1H, d, J=2.5 Hz), 7.58–7.34 (4H, m), 4.57 (2H, s), 3.91 (3H, s).

Step 2. 5-Chloro-2-(3-cyanobenzyl)nicotinic acid

The title compound was prepared according to the procedure described in step 2 of Example 1 from methyl 5-chloro-2-(3-cyanobenzyl)nicotinate (step 1): $^1$H-NMR (DMSO-d$_6$) δ 8.74 (1H, d, J=2.6 Hz), 8.26 (1H, d, J=2.6 Hz), 7.68–7.65 (2H, m), 7.55–7.46 (2H, m), 4.52 (2H, s).

Step 3. Methyl 4-[(1S)-1-({[5-chloro-2-(3-cyanobenzyl)pyridin-3-yl]carbonyl}amino)ethyl]benzoate The title compound was prepared according to the procedure described in step 3 of Example 1 from 5-chloro-2-(3-cyanobenzyl)nicotinic acid (step 2) and methyl 4-[(1S)-1-aminoethyl]benzoate hydrochloride (step 3 of Example 5): $^1$H-NMR (CDCl$_3$) δ 8.58 (1H, d, J=2.4 Hz), 8.05–8.02 (2H, m), 7.66 (1H, d, J=2.4 Hz), 7.50–7.27 (6H, m), 6.01 (1H, d, J=8.1 Hz), 5.32–5.23 (1H, m), 4.30 (2H, s), 3.93 (3H, s), 1.54 (3H, d, J=7.0 Hz); MS (ESI) m/z 432 (M–H)$^-$.

Step 4. 4-[(1S)-1-({[5-Chloro-2-(3-cyanobenzyl)pyridin-3-yl]carbonyl}amino)ethyl]benzoic acid The title compound was prepared according to the procedure described in step 4 of Example 1 from methyl 4-[(1S)-1-({[5-chloro-2-(3-cyanobenzyl)pyridin-3-yl]carbonyl}amino)ethyl]benzoate (step 3): $^1$H-NMR (DMSO-d$_6$) δ 9.20 (1H, d, J=7.7 Hz), 8.65 (1H, d, J=2.4 Hz), 8.01 (1H, d, J=2.6 Hz), 7.91 (2H, d, J=8.3 Hz), 7.66–7.40 (6H, m), 5.18–5.08 (1H, m), 4.23 (1H, d, J=14.4 Hz), 4.17 (1H, d, J=14.4 Hz), 1.42 (3H, d, J=7.2 Hz); MS (ESI) m/z 420 (M+H)$^+$, 418 (M–H)$^-$.

Example 65

4-({[5-FLUORO-2-(4-FLUOROPHENOXY)BENZOYL]AMINO}METHYL)BENZOIC ACID

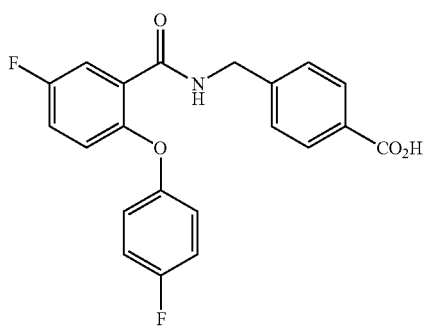

Step 1. Methyl 4-({[5-fluoro-2-(4-fluorophenoxy)benzoyl]amino}methyl)benzoate The title compound was prepared according to the procedure described in step 3 of Example 1 from 5-fluoro-2-(4-fluorophenoxy)benzoic acid (*Anales de la Asociacion Quimica Argentina* 1985, 73, 509) and methyl 4-(aminomethyl)benzoate hydrochloride: $^1$H-NMR (CDCl$_3$) δ 7.99 (4H, m), 7.30 (2H, d, J=7.6 Hz), 7.14–7.03 (3H, m), 6.96–6.92 (2H, m), 6.80 (1H, dd, J=9.2, 4.4 Hz), 4.70 (2H, d, J=5.9 Hz), 3.91 (3H, s); MS (ESI) m/z 398 (M+H)$^+$, 396 (M–H)$^-$.

Step 2. 4-({[5-Fluoro-2-(4-fluorophenoxy)benzoyl]amino}methyl)benzoic acid

The title compound was prepared according to the procedure described in step 4 of Example 1 from methyl 4-({[5-fluoro-2-(4-fluorophenoxy)benzoyl]amino}methyl)benzoate (step 1): $^1$H-NMR (DMSO-d$_6$) δ 8.94 (1H, t, J=5.9 Hz), 7.81 (2H, d, J=8.1 Hz), 7.48 (1H, dd, J=8.8, 3.1 Hz), 7.37–7.19 (5H, m), 7.08–6.99 (3H, m), 4.47 (2H, d, J=5.9 Hz); MS (ESI) m/z 384 (M+H)$^+$, 382 (M–H)$^-$.

Example 66

4-({[4-FLUORO-2-(4-FLUOROPHENOXY)BENZOYL]AMINO}METHYL)BENZOIC ACID

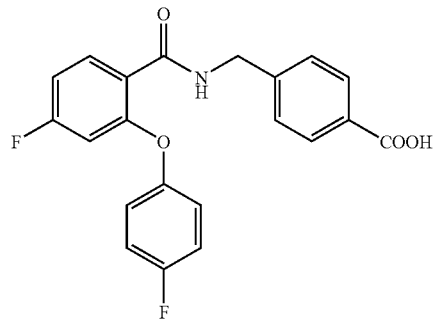

Step 1. 4-Fluoro-2-(4-fluorophenoxy)benzoic acid

A mixture of 2-chloro-4-fluorobenzoic acid (1.74 g, 10 mmol), 4-fluorophenol (2.24 g, 20 mmol), copper (50 mg, 0.78 mmol), copper(I) iodide (50 mg, 0.28 mmol), potassium carbonate (2.76 g, 20 mmol), and pyridine (0.40 mL, 5.0 mmol) in water (6.0 mL) was heated under reflux for 2 h with stirring. The reaction mixture was diluted with water and filtered through a pad of Celite®. The pH value of the filtrate was adjusted to 9.0 by the addition of 2 M aqueous solution of sodium carbonate. The aqueous mixture was extracted with dichloromethane (50 mL×3). The combined organic extracts were washed with brine (50 mL), dried (sodium sulfate), and concentrated to afford 29 mg (99%) of the title compound: MS (ESI) m/z 250 (M$^+$).

Step 2. Methyl 4-({[4-fluoro-2-(4-fluorophenoxy)benzoyl]amino}methyl)benzoate The title compound was prepared according to the procedure described in step 3 of Example 1 from 4-fluoro-2-(4-fluorophenoxy)benzoic acid (step 1) and methyl 4-(aminomethyl)benzoate hydrochloride: $^1$H-NMR (CDCl$_3$) δ 7.99–7.89 (2H, m), 7.38–7.28 (4H, m), 7.12–7.00 (4H, m), 6.41 (1H, dd, J=2.7, 8.1 Hz), 4.63 (2H, br.s), 3.86 (3H, s); MS (ESI) m/z 398 (M+H)$^+$, 396 (M+H)$^+$.

Step 3. 4-({[4-Fluoro-2-(4-fluorophenoxy)benzoyl]amino}methyl)benzoic acid

The title compound was prepared according to the procedure described in step 4 of Example 1 from methyl 4-({[4-fluoro-2-(4-fluorophenoxy)benzoyl]amino}methyl)benzoate (step 2): $^1$H-NMR (CDCl$_3$) δ 8.32 (1H, t, J=8.7

Hz), 8.04 (2H, d, J=7.9 Hz), 7.40 (1H, d, J=7.9 Hz), 7.17–7.03 (4H, m), 6.92 (1H, dt, J=2.5, 8.9 Hz), 6.45 (1H, d, J=8.9 Hz), 4.75 (2H, d, J=5.7 Hz); MS (ESI) m/z 384 (M+H)$^+$, 382 (M–H)$^-$.

Example 67

4-({[5-CHLORO-2-(4-FLUOROPHENOXY)BENZOYL]AMINO}METHYL)BENZOIC ACID

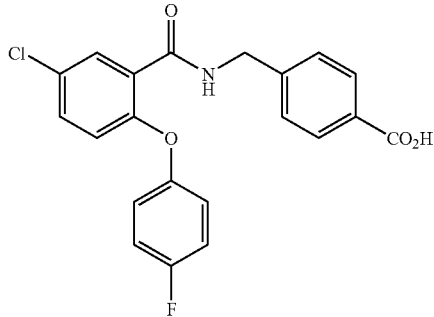

Step 1. Methyl 5-chloro-2-(4-fluorophenoxy)benzoate

To a stirred solution of 4-fluorophenol (1.60 g, 14.3 mmol) and sodium hydride (0.34 g, 14.3 mmol) in N,N-dimethylforamide (30 mL) was added a solution of methyl 5-chloro-2-fluorobenzoate (2.70 g, 14.3 mmol) in N,N-dimethylforamide (30 mL) at 0° C. The resulting mixture was heated at 120° C. for 16 h. After cooling to room temperature, the mixture was diluted with ether (300 mL) and washed with water (150 mL×3). The organic layer was dried over magnesium sulfate and concentrated under reduced pressure. The residue was purified by flush column chromatography on silica gel eluting with hexane/ethyl acetate (20:1) to afford 2.60 g (65%) of the title compounds as slight yellow oil: $^1$H-NMR (CDCl$_3$) δ 7.88 (1H, d, J=2.8 Hz), 7.40 (1H, dd, J=8.8, 2.8 Hz), 7.06–6.85 (5H, m), 3.84 (3H, s).

Step 2. 5-Chloro-2-(4-fluorophenoxy)benzoic acid

A mixture of methyl 5-chloro-2-(4-fluorophenoxy)benzoate (step 1, 2.60 g, 9.26 mmol), tetrahydrofuran (20 mL), methanol (20 mL), and 2 N sodium hydroxide (20 mL) was stirred at room temperature for 3 h. The mixture was poured into 2 N hydrochloric acid (50 mL) and the aqueous mixture was extracted with ethyl acetate (200 mL). The organic layer was dried over magnesium sulfate and evaporated to give 2.41 g (98%) of the title compound as white solids: $^1$H-NMR (CDCl$_3$) δ 8.11 (1H, d, J=2.8 Hz), 7.43 (1H, dd, J=9.0, 2.8 Hz), 7.14–7.02 (4H, m), 6.80 (1H, d, J=8.8 Hz); MS (ESI) m/z 265 (M–H)$^-$.

Step 3. Methyl 4-({[5-chloro-2-(4-fluorophenoxy)benzoyl]amino}methyl)benzoate

The title compound was prepared according to the procedure described in step 3 of Example 1 from 5-chloro-2-(4-fluorophenoxy)benzoic acid (step 2) and methyl 4-(aminomethyl)benzoate hydrochloride: $^1$H-NMR (CDCl$_3$) δ 8.24 (1H, d, J=2.8 Hz), 7.97–7.94 (3H, m), 7.36–7.32 (3H, m), 7.11–6.96 (4H, m), 6.74 (1H, d, J=8.8 Hz), 4.71 (2H, d, J=5.9 Hz), 3.90 (3H, s); MS (ESI) m/z 414 (M+H)$^+$, 412 (M–H)$^-$.

Step 4. 4-({[5-Chloro-2-(4-fluorophenoxy)benzoyl]amino}methyl)benzoic acid

The title compound was prepared according to the procedure described in step 4 of Example 1 from methyl 4-({[5-chloro-2-(4-fluorophenoxy)benzoyl]amino}methyl)benzoate (step 3): $^1$H-NMR (DMSO-d$_6$) δ 8.98 (1H, t, J=5.9 Hz), 7.82 (2H, d, J=8.2 Hz), 7.68 (1H, d, J=2.6 Hz), 7.51 (1H, dd, J=8.7, 2.6 Hz), 7.36–7.08 (6H, m), 6.94 (1H, d, J=8.7 Hz), 4.50 (2H, d, J=5.9 Hz); MS (ESI) m/z 400 (M+H)$^+$, 398 (M–H)$^-$.

Example 68

4-((1S)-1-{[5-CHLORO-2-(4-FLUOROPHENOXY)BENZOYL]AMINO}ETHYL)BENZOIC ACID

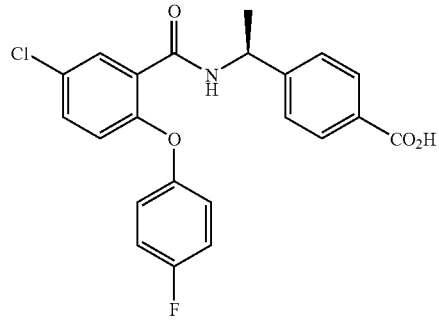

Step 1. Methyl 4-((1S)-1-{[5-chloro-2-(4-fluorophenoxy)benzoyl]amino}ethyl)benzoate The title compound was prepared according to the procedure described in step 3 of Example 1 from 5-chloro-2-(4-fluorophenoxy)benzoic acid (step 2 of Example 67) and methyl 4-[(1S)-1-aminoethyl]benzoate hydrochloride (step 3 of Example 5): $^1$H-NMR (CDCl$_3$) δ 8.16 (1H, d, J=2.6 Hz), 7.95 (2H, dd, J=6.6, 1.8 Hz), 7.88 (1H, d, J=7.4 Hz), 7.36–7.29 (3H, m), 7.23–6.96 (4H, m), 6.78 (1H, d, J=8.7 Hz), 5.32 (1H, dq, J=7.4, 6.9 Hz), 3.90 (3H, s), 1.51 (3H, d, J=6.9 Hz); MS (ESI) m/z 428 (M+H)$^+$, 426 (M–H)$^-$.

Step 2. 4-((1S)-1-{[5-Chloro-2-(4-fluorophenoxy)benzoyl]amino}ethyl)benzoic acid The title compound was prepared according to the procedure described in step 4 of Example 1 from methyl 4-((1S)-1-{[5-chloro-2-(4-fluorophenoxy)benzoyl]amino}ethyl)benzoate (step 1): $^1$H-NMR (DMSO-d$_6$) δ 8.17 (1H, d, J=2.8 Hz), 8.01 (2H, d, J=8.4 Hz), 7.94 (1H, d, J=7.3 Hz), 7.38–7.32 (3H, m), 7.14–6.98 (4H, m), 6.78 (1H, d, J=8.8 Hz), 5.34 (1H, dq, J=7.3, 7.0 Hz), 1.53 (3H, d, J=7.0 Hz); MS (ESI) m/z 414 (M+H)$^+$, 412 (M–H)$^-$.

Example 69

4-({[5-CHLORO-2-(4-FLUOROPHENOXY)BENZOYL]AMINO}METHYL)-2-FLUOROBENZOIC ACID

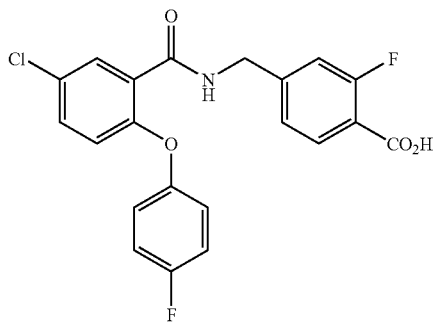

Step 1. Methyl 4-({[5-chloro-2-(4-fluorophenoxy)benzoyl]amino}methyl)-2-fluorobenzoate The title compound was prepared according to the procedure described in step 3 of Example 1 from 5-chloro-2-(4-fluorophenoxy)benzoic acid (step 2 of Example 67) and methyl 4-(aminomethyl)-2-fluorobenzoate: $^1$H-NMR (CDCl$_3$) δ 8.22 (1H, d, J=2.6 Hz), 8.06–7.98 (1H, m), 7.86 (1H, t, J=7.7 Hz), 7.35 (1H, dd, J=8.9, 2.6 Hz), 7.13–6.98 (6H, m), 6.75 (1H, d, J=8.9 Hz), 4.69 (2H, d, J=5.9 Hz), 3.91 (3H, s); MS (ESI) m/z 432 (M+H)$^+$, 430 (M−H)$^−$.

Step 2. 4-({[5-Chloro-2-(4-fluorophenoxy)benzoyl]amino}methyl)-2-fluorobenzoic acid The title compound was prepared according to the procedure described in step 4 of Example 1 from methyl 4-({[5-chloro-2-(4-fluorophenoxy)benzoyl]amino}methyl)-2-fluorobenzoate (step 1): $^1$H-NMR (DMSO-d$_6$) δ 8.19 (1H, d, J=2.8 Hz), 8.09 (1H, t, J=6.0 Hz), 7.86 (1H, t, J=7.8 Hz), 7.35–6.97 (8H, m), 6.73 (1H, d, J=8.8 Hz), 4.66 (2H, d, J=6.1 Hz); MS (ESI) m/z 418 (M+H)$^+$, 416 (M−H)$^−$.

Example 70

4-((1S)-1-{[5-CHLORO-2-(3-CHLOROPHENOXY)BENZOYL]AMINO}ETHYL)BENZOIC ACID

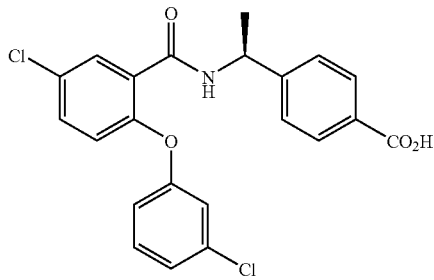

Step 1. Methyl 5-chloro-2-(3-chlorophenoxy)benzoate

The title compound was prepared according to the procedure described in step 1 of Example 67 from methyl 5-chloro-2-fluorobenzoate and 3-chlorophenol: $^1$H-NMR (CDCl$_3$) δ 7.92 (1H, d, J=2.8 Hz), 7.46 (1H, dd, J=8.8, 2.8 Hz), 7.25–6.80 (5H, m), 3.81 (3H, s).

Step 2. 5-Chloro-2-(3-chlorophenoxy)benzoic acid

The title compound was prepared according to the procedure described in step 2 of Example 67 from methyl 5-chloro-2-(3-chlorophenoxy)benzoate (step 1): $^1$H-NMR (CDCl$_3$) δ 8.13 (1H, d, J=2.8 Hz), 7.45 (1H, dd, J=9.0, 2.8 Hz), 7.14–6.80 (5H, m).

Step 3. Methyl 4-((1S)-1-{[5-chloro-2-(3-chlorophenoxy)benzoyl]amino}ethyl)benzoate The title compound was prepared according to the procedure described in step 3 of Example 1 from 5-chloro-2-(3-chlorophenoxy)benzoic acid (step 2) and methyl 4-[(1S)-1-aminoethyl]benzoate hydrochloride (step 3 of Example 5): $^1$H-NMR (CDCl$_3$) δ 8.17 (1H, d, J=2.8 Hz), 7.93 (2H, m), 7.65 (1H, d, J=7.4 Hz), 7.42–7.19 (5H, m), 6.97–6.81 (3H, m), 5.32 (1H, dq, J=7.4, 6.9 Hz), 3.90 (3H, s), 1.49 (3H, d, J=6.9 Hz).

Step 4. 4-((1S)-1-{[5-Chloro-2-(3-chlorophenoxy)benzoyl]amino}ethyl)benzoic acid The title compound was prepared according to the procedure described in step 4 of Example 1 from methyl 4-((1S)-1-{[5-chloro-2-(3-chlorophenoxy)benzoyl]amino}ethyl)benzoate (step 3): $^1$H-NMR (DMSO-d$_6$) δ 8.91 (1H, d, J=7.9 Hz), 7.81 (2H, d, J=8.2 Hz), 7.61–7.54 (2H, m), 7.40–7.34 (3H, m), 7.19–6.91 (4H, m), 5.03 (1H, dq, J=7.9, 7.0 Hz), 1.35 (3H, d, J=7.0 Hz); MS (ESI) m/z 430 (M+H)$^+$, 428 (M−H)$^−$.

Example 71

4-((1S)-1-{[5-CHLORO-2-(3-FLUOROPHENOXY)BENZOYL]AMINO}ETHYL)BENZOIC ACID

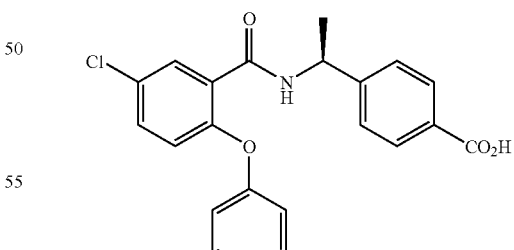

Step 1. Methyl 5-chloro-2-(3-fluorophenoxy)benzoate

The title compound was prepared according to the procedure described in step 1 of Example 67 from methyl 5-chloro-2-fluorobenzoate and 3-fluorophenol: $^1$H-NMR (CDCl$_3$) δ 7.91 (1H, d, J=2.8 Hz), 7.46 (1H, dd, J=8.7, 2.8 Hz), 7.31–7.06 (1H, m), 6.99 (1H, d, J=8.7 Hz), 6.83–6.61 (3H, m), 3.81 (3H, s).

Step 2. 5-Chloro-2-(3-fluorophenoxy)benzoic acid

The title compound was prepared according to the procedure described in step 2 of Example 67 from methyl 5-chloro-2-(3-fluorophenoxy)benzoate (step 1): $^1$H-NMR (DMSO-d$_6$) δ 7.85 (1H, d, J=2.8 Hz), 7.66 (1H, dd, J=8.9, 2.8 Hz), 7.42–7.33 (1H, m), 7.15 (1H, d, J=8.9 Hz); 6.98–6.90 (1H, m), 6.84–6.71 (2H, m).

Step 3. Methyl 4-((1S)-1-{[5-chloro-2-(3-fluorophenoxy)benzoyl]amino}ethyl)benzoate The title compound was prepared according to the procedure described in step 3 of Example 1 from 5-chloro-2-(3-fluorophenoxy)benzoic acid (step 2) and methyl 4-[(1S)-1-aminoethyl]benzoate hydrochloride (step 3 of Example 5): $^1$H-NMR (CDCl$_3$) δ 8.17 (1H, d, J=2.8 Hz), 7.93 (2H, d, J=8.4 Hz), 7.65 (1H, d, J=7.4 Hz), 7.42–7.26 (4H, m), 6.94–6.88 (2H, m), 6.74–6.65 (2H, m), 5.28 (1H, dq, J=7.4, 7.3 Hz), 3.90 (3H, s), 1.48 (3H, d, J=7.3 Hz).

Step 4. 4-((1S)-1-{[5-Chloro-2-(3-fluorophenoxy)benzoyl]amino}ethyl)benzoic acid The title compound was prepared according to the procedure described in step 4 of Example 1 from methyl 4-((1S)-1-{[5-chloro-2-(3-fluorophenoxy)benzoyl]amino}ethyl)benzoate (step 3): $^1$H-NMR (CDCl3) δ 8.17 (1H, d, J=2.6 Hz), 7.98 (2H, d, J=8.4 Hz), 7.68 (1H, d, J=7.0 Hz), 7.43–7.29 (4H, m), 6.95–6.89 (2H, m), 6.75–6.67 (2H, m), 5.29 (1H, dq, J=8.4, 7.0 Hz), 1.50 (3H, d, J=7.0 Hz); MS (ESI) m/z 414 (M+H)$^+$, 412 (M–H)$^-$.

Example 72

4-((1S)-1-{[5-CHLORO-2-(3-METHOXYPHENOXY)BENZOYL]AMINO}ETHYL)BENZOIC ACID

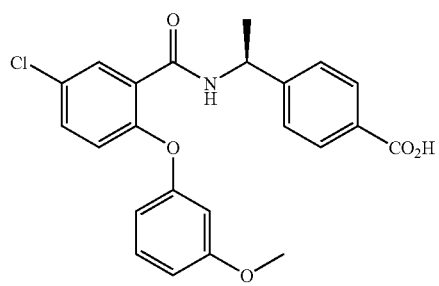

Step 1. Methyl 5-chloro-2-(3-methoxyphenoxy)benzoate

The title compound was prepared according to the procedure described in step 1 of Example 67 from methyl 5-chloro-2-fluorobenzoate and 3-methoxyphenol: $^1$H-NMR (CDCl$_3$) δ 7.89 (1H, d, J=2.8 Hz), 7.41 (1H, dd, J=8.4, 2.8 Hz), 7.24–7.19 (1H, m), 6.95 (1H, d, J=8.4 Hz), 6.67–6.64 (1H, m), 6.53–6.49 (2H, m), 3.83 (3H, s), 3.78 (3H, s).

Step 2. Methyl 4-((1S)-1-{[5-chloro-2-(3-methoxyphenoxy)benzoyl]amino}ethyl)benzoate A mixture of methyl 5-chloro-2-(3-methoxyphenoxy)benzoate (step 1, 220 mg, 0.75 mmol) and 2 N sodium hydroxide (2 mL) in methanol (10 mL) was stirred for 7 h at room temperature. The reaction mixture was poured into 2 N hydrochloric acid (50 mL) and the aqueous mixture was extracted with ethyl acetate (200 mL). The organic layer was dried (sodium sulfate) and evaporated to give 168 mg (80%) of the corresponding carboxylic acid. This acid was used for next reaction without further purification. To a stirred solution of this acid (168 mg, 0.60 mmol) and methyl 4-[(1S)-1-aminoethyl]benzoate hydrochloride (step 3 of Example 5, 143 mg, 0.66 mmol) in dichloromethane (20 mL) were successively added 1-(3-dimethylaminopropyl)-3-ethylcarbodiimide hydrochloride (EDCI) (172 mg, 0.90 mmol), 1-hydroxybenzotriazole hydrate (HOBT) (137 mg, 0.90 mmol), and triethylamine (91 uL). After being stirred overnight, the reaction was quenched by the addition of water (50 mL). The organic layer was separated and the aqueous layer was extracted with dichloromethane (50 mL×2). The combined organic layers were washed with brine (50 mL), dried (sodium sulfate), and evaporated. The residue was purified by flush column chromatography on silica gel (50 g) eluting with hexane/ethyl acetate (4/1) to afford 245 mg (93%) of the title compounds as a colorless oil: $^1$H-NMR (CDCl$_3$) δ 8.17 (1H, d, J=2.8 Hz), 7.94–7.86 (3H, m), 7.38–7.25 (4H, m), 6.87 (1H, d, J=8.7 Hz), 6.77–6.73 (1H, m), 6.57–6.52 (2H, m), 5.29 (1H, m), 3.90 (3H, s), 3.78 (3H, s), 1.49 (3H, d, J=6.9 Hz).

Step 3. 4-((1S)-1-{[5-Chloro-2-(3-methoxyphenoxy)benzoyl]amino}ethyl)benzoic acid The title compound was prepared according to the procedure described in step 4 of Example 1 from methyl 4-((1S)-1-{[5-chloro-2-(3-methoxyphenoxy)benzoyl]amino}ethyl)benzoate (step 3): $^1$H-NMR (DMSO-d$_6$) δ 8.84 (1H, d, J=7.9 Hz), 7.80 (2H, d, J=8.3 Hz), 7.58 (1H, d, J=2.8 Hz), 7.51 (1H, dd, J=7.9, 7.1 Hz), 7.39 (2H, d, J=8.3 Hz), 7.27 (1H, m), 7.03 (1H, d, J=8.8 Hz), 6.74–6.71 (1H, m), 6.58–6.52 (2H, m), 5.06 (1H, dq, J=7.0 Hz), 3.72 (3H, s), 1.37 (3H, d, J=7.1 Hz); MS (ESI) m/z 426 (M+H)$^+$, 424 (M–H)$^-$.

Example 73

5-FLUORO-2-(4-FLUOROPHENOXY)-N-[4-(2H-TETRAZOL-5-YL)BENZYL]NICOTINAMIDE

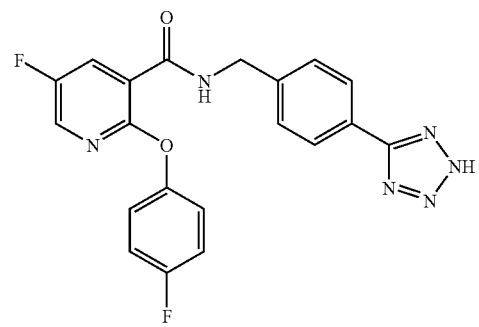

Step 1. N-(4-Cyanobenzyl)-5-fluoro-2-(4-fluorophenoxy)nicotinamide

The title compound was prepared according to the procedure described in step 3 of Example 1 from 5-fluoro-2-(4-fluorophenoxy)nicotinic acid (step 2 of Example 1) and 4-cyanobenzylhexamine hydrobromide (*Synthesis* 1979, 161): $^1$H-NMR (CDCl$_3$) δ 8.38 (1H, dd, J=8.3, 3.1 Hz), 8.33 (1H, br.s), 8.06 (1H, d, J=3.1 Hz), 7.64 (2H, d, J=8.1 Hz), 7.46 (2H, d, J=8.1 Hz), 7.20–7.06 (4H, m), 4.76 (2H, d, J=6.1 Hz); MS (ESI) m/z 366 (M+H)$^+$, 364 (M−H)$^−$.

Step 2. 5-Fluoro-2-(4-fluorophenoxy)-N-[4-(2H-tetrazol-5-yl)benzyl]nicotinamide To a solution of N-(4-cyanobenzyl)-5-fluoro-2-(4-fluorophenoxy)nicotinamide (step 1, 220 mg, 0.60 mmol) in 1-methyl-pyrrolidin-2-one (5 mL) were added sodium azide (117 mg, 1.8 mmol) and triethylamine hydrochloride (248 mg, 1.8 mmol) at room temperature. This mixture was heated at 150° C. for 18 h. The reaction mixture was diluted with dichloromethane (100 mL), and the solution was washed with saturated sodium dihydrogenphosphate solution (50 mL). The organic phase was dried (sodium sulfate) and concentrated. The residue was purified by flash column chromatography on silica gel (50 g) eluting with dichloromethane/methanol/acetic acid (100/5/0.5) to give off white solids. The solids were triturated with ethyl acetate to afford 125 mg (50%) of the title compound as white solids: $^1$H-NMR (DMSO-d$_6$) δ 9.18 (1H, t, J=5.8 Hz), 8.14 (1H, d, J=2.8 Hz), 7.99 (1H, dd, J=8.2, 2.8 Hz), 7.90 (2H, d, J=8.2 Hz), 7.51 (2H, d, J=8.2 Hz), 7.22–7.15 (4H, m), 4.56 (2H, d, J=5.8 Hz); MS (ESI) m/z 409 (M+H)$^+$, 407 (M−H)$^−$.

Example 74

5-CHLORO-2-(4-FLUOROPHENOXY)-N-[4-(2H-TETRAZOL-5-YL)BENZYL]NICOTINAMIDE

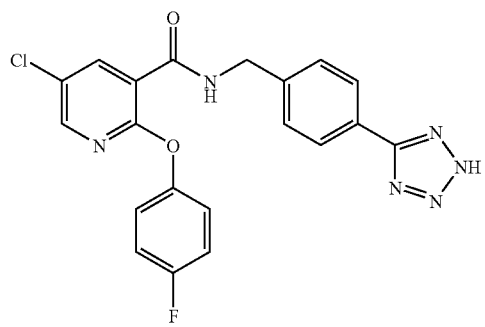

Step 1. 5-Chloro-N-(4-cyanobenzyl)-2-(4-fluorophenoxy)nicotinamide

The title compound was prepared according to the procedure described in step 3 of Example 1 from 5-chloro-2-(4-fluorophenoxy)nicotinic acid and 4-cyanobenzylhexamine hydrobromide (*Synthesis* 1979, 161): MS (ESI) m/z 382 (M+H)$^+$, 380 (M−H)$^−$.

Step 2. 5-Chloro-2-(4-fluorophenoxy)-N-[4-(2H-tetrazol-5-yl)benzyl]nicotinamide The title compound was prepared according to the procedure described in step 2 of Example 73 from 5-chloro-N-(4-cyanobenzyl)-2-(4-fluorophenoxy)nicotinamide (step 1): MS (ESI) m/z 425 (M+H)$^+$, 423 (M−H)$^−$.

Example 75

5-FLUORO-2-(4-FLUOROPHENOXY)-N-[4-(2H-TETRAZOL-5-YL)BENZYL]BENZAMIDE

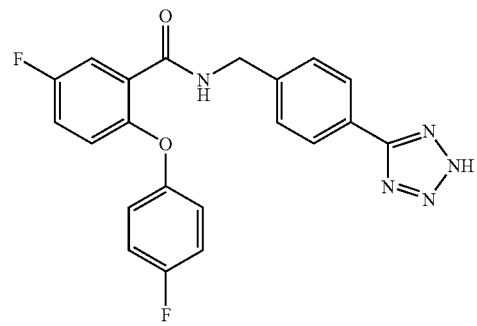

A mixture of 5-fluoro-2-(4-fluorophenoxy)benzoic acid (120 mg, 0.48 mmol), 1-[4-(2H-tetrazol-5-yl)phenyl]methanamine hydrochloride (122 mg, 0.58 mmol), 1-hydroxy-1H-benztriazole monohydrate (110 mg, 0.72 mmol), 1-ethyl-3-(3-dimethylaminopropyl)carbodiimide hydrochloride (138 mg, 0.72 mmol), and triethylamine (0.27 mL, 1.92 mmol) in dichloromethane (8 mL) and N,N-dimethylforamide (2 mL) was stirred at room temperature for 16 h. The mixture was diluted with dichloromethane (50 mL) and washed with 5% aqueous sodium dihydrogenphosphate solution (30 mL). The organic fraction was dried over magnesium sulfate, and concentrated under reduced pressure. The residue was purified by flush column chromatography on silica gel eluting with hexane/ethyl acetate/acetic acid (30:60:1) to afford 143 mg (73%) of the title compounds as white solids: $^1$H-NMR (DMSO-d$_6$) δ 8.99 (1H, t, J=5.9 Hz), 7.91 (2H, d, J=8.2 Hz), 7.53–6.99 (8H, m), 4.50 (2H, d, J=5.9 Hz); MS (ESI) m/z 408 (M+H)$^+$, 406 (M−H)$^−$.

Example 76

5-CHLORO-2-(4-FLUOROPHENOXY)-N-[4-(2H-TETRAZOL-5-YL)BENZYL]BENZAMIDE

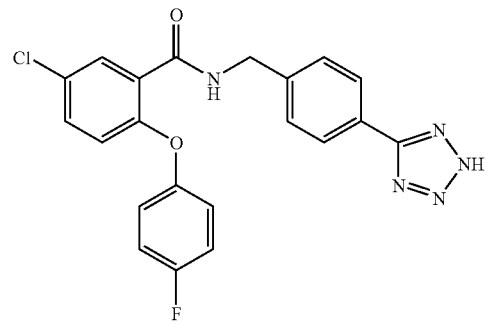

The title compound was prepared according to the procedure described in Example 75 from 5-chloro-2-(4-fluorophenoxy)benzoic acid (step 2 of Example 67) and 1-[4-(2H-tetrazol-5-yl)phenyl]methanamine hydrochloride: $^1$H-NMR (DMSO-d$_6$) δ 9.01 (1H, t, J=6.0 Hz), 7.93 (2H, d, J=8.2 Hz), 7.70 (1H, d, J=2.6 Hz), 7.53–7.46 (3H, m), 7.29–7.10 (4H, m), 6.93 (1H, d, J=8.9 Hz), 4.52 (2H, d, J=6.1 Hz); MS (ESI) m/z 424 (M+H)$^+$, 422 (M–H)$^-$.

Example 77

5-CHLORO-2-(4-FLUOROPHENOXY)-N-{(1S)-1-[4-(2H-TETRAZOL-5-YL)PHENYL]ETHYL}BENZAMIDE

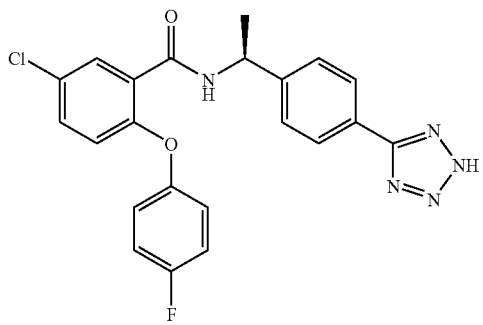

Step 1 tert-Butyl [(1S)-1-(4-cyanophenyl)ethyl]carbamate

A mixture of tert-butyl [(1S)-1-(4-bromophenyl)ethyl]carbamate (step 1 of Example 5, 1.50 g, 5.00 mmol), tetrakis(triphenylphosphine)palladium (0) (0.58 g, 0.50 mmol), zinc cyanide (0.59 g, 5.00 mmol) and N,N-dimethylforamide (30 mL) was stirred at 80° C. for 16 h under nitrogen atmosphere. After cooling to room temperature, the mixture was diluted with ether (200 mL) and washed with water (100 mL×3). The organic layer was dried over magnesium sulfate and evaporated. The residue was purified by flush column chromatography on silica gel eluting with hexane/ethyl acetate (4:1) to afford 1.11 g (90%) of the title compounds as colorless syrup: $^1$H-NMR (CDCl$_3$) δ 7.64–7.61 (2H, m), 7.41 (2H, d, J=8.3 Hz), 4.83 (2H, br.s), 1.44–1.42 (12H, m).

Step 2. tert-Butyl {(1S)-1-[4-(2H-tetrazol-5-yl)phenyl]ethyl}carbamate

A mixture of tert-butyl [(1S)-1-(4-cyanophenyl)ethyl]carbamate (step 1, 1.11 g, 4.51 mmol), sodium azide (1.75 g, 27.1 mmol) and ammonium chloride (1.15 g, 27.1 mmol) in N,N-dimethylforamide (25 mL) was heated at 110° C. for 24 h. After cooling to room temperature, the mixture was diluted with ether (200 mL) and washed with 1 N hydrochloric acid (100 mL). The organic layer was dried over magnesium sulfate and evaporated. The residue was crystallized from dichloromethane and hexane to give 1.19 g (91%) of the title compounds as white solids: $^1$H-NMR (DMSO-d$_6$) δ 7.98 (2H, d, J=8.3 Hz), 7.51 (2H, d, J=8.3 Hz), 4.74–4.63 (1H, m), 1.37–1.32 (12H, m); MS (ESI) m/z 290 (M+H)$^+$, 288 (M–H)$^-$.

Step 3. {(1S)-1-[4-(2H-Tetrazol-5-yl)phenyl]ethyl}amine hydrochloride tert-Butyl {(1S)-1-[4-(2H-tetrazol-5-yl)phenyl]ethyl}carbamate (step 2, 1.19 g, 4.10 mmol) was treated with trifluoroacetic acid (10 mL) and dichloromethane (10 mL) at room temperature for 1 h. After removal of the solvent, the residue was diluted with 4 M solution of hydrogen chloride in ethyl acetate (20 mL). The mixture was concentrated under reduced pressure and the residue was washed with ether to give 0.77 g (83%) of the title compounds as white solids: $^1$H-NMR (DMSO-d$_6$) δ 8.60 (3H, br.s), 8.14 (2H, d, J=8.4 Hz), 7.75 (2H, d, J=8.4 Hz), 4.58–4.45 (1H, m), 1.55 (3H, d, J=6.8 Hz); MS (ESI) m/z 188 (M–H)$^-$.

Step 4. 5-Chloro-2-(4-fluorophenoxy)-n-{(1s)-1-[4-(2h-tetrazol-5-yl)phenyl]ethyl}benzamide The title compound was prepared according to the procedure described in Example 75 from 5-chloro-2-(4-fluorophenoxy)benzoic acid (step 2 of Example 67) and {(1S)-1-[4-(2H-tetrazol-5-yl)phenyl]ethyl}amine hydrochloride (step 3): $^1$H-NMR (DMSO-d$_6$) δ 8.90 (1H, d, J=7.3 Hz), 7.92 (2H, d, J=8.3 Hz), 7.60–7.49 (4H, m), 7.26–7.20 (2H, m), 7.10–7.06 (2H, m), 6.96 (1H, d, J=8.8 Hz), 5.15–5.05 (1H, m), 1.41 (3H, d, J=6.8 Hz); MS (ESI) m/z 438 (M+H)$^+$, 436 (M–H)$^-$.

Example 78

5-FLUORO-2-(4-FLUOROBENZYL)-N-[4-(2H-TETRAZOL-5-YL)BENZYL]NICOTINAMIDE

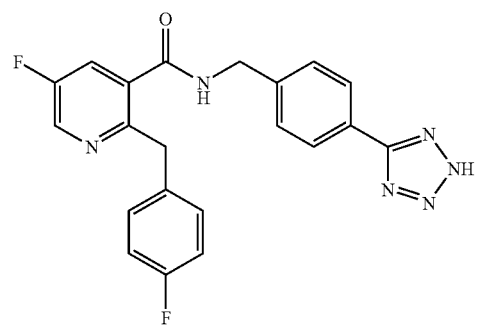

The title compound was prepared according to the procedure described in Example 75 from 5-fluoro-2-(4-fluorobenzyl)nicotinic acid (step 3 of Example 58) and 1-[4-(2H-tetrazol-5-yl)phenyl]methanamine hydrochloride: $^1$H-NMR (DMSO-d$_6$) δ 9.20 (1H, t, J=5.7 Hz), 8.59 (1H, d, J=2.8 Hz), 7.98 (2H, d, J=8.1 Hz), 7.83 (1H, dd, J=8.8, 2.9 Hz), 7.44 (2H, d, J=8.1 Hz), 7.20–7.16 (2H, m), 7.03 (2H, t, J=8.9 Hz), 4.50 (2H, d, J=5.7 Hz), 4.21 (2H, s); MS (ESI) m/z 407 (M+H)$^+$, 405 (M–H)$^-$.

Example 79

5-CHLORO-N-{(1S)-1-[4-({[(3-CHLOROPHE-NYL)SULFONYL]AMINO}CARBONYL)PHE-NYL]ETHYL}-2-(3-FLUOROPHENOXY)NICOTI-NAMIDE

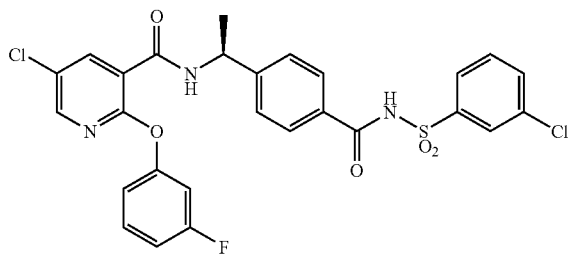

To a stirred solution of 4-[(1S)-1-({[5-Chloro-2-(4-fluorophenoxy)pyridin-3-yl]carbonyl}amino)ethyl]benzoic acid (200 mg, 0.48 mmol) in dry dichloromethane (5 mL) under argon was added 3-chlorobenzenesulfonamide (105 mg, 0.55 mmol), 4-(dimethylamino)pyridine (67 mg, 0.55 mmol), and finally 1-(3-dimethylaminopropyl)-3-ethylcarbodiimide hydrochloride (105 mg, 0.55 mmol). The resulting mixture was stirred at room temperature for 48 h. The reaction mixture was partitioned between dichloromethane (50 mL) and water (50 mL). The organic layer was separated and washed with brine (50 mL), dried (sodium sulfate), and concentrated. The residue was purified by flush column chromatography on silica gel (30 g) eluting with dichloromethane/ethyl acetate (20/1) to give a desired product. Recrystallization of the product from ethyl acetate afforded 68 mg (24%) of the title compounds as a colorless needle: $^1$H-NMR (DMSO-$d_6$) δ 8.99 (1H, d, J=7.6 Hz), 8.26 (1H, d, J=2.5 Hz), 8.09 (1H, d, J=2.5 Hz), 7.97–7.89 (2H, m), 7.80 (4H, d, J=8.3 Hz), 7.67 (1H, dd, J=7.9, 7.9 Hz), 7.51 (2H, d, J=8.3 Hz), 7.29–7.19 (4H, m), 5.15 (1H, dq, J=7.6, 7.0 Hz), 1.42 (3H, d, J=7.0 Hz).

Example 80

4-[(1S)-1-({[5-CHLORO-2-(3,5-DIFLUOROPHE-NOXY)PYRIDIN-3-YL]CARBONYL}AMINO)ETHYL]BENZOIC ACID

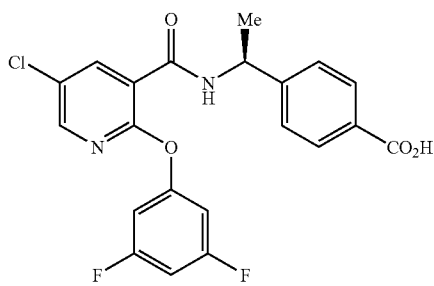

Step 1. tert-Butyl 4-[(1S)-1-({[5-chloro-2-(3,5-difluorophenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 3,5-difluorophenol: $^1$H-NMR (CDCl$_3$) δ 8.53 (1H, d, J=2.6 Hz), 8.18 (1H, d, J=2.6 Hz), 7.95 (1H, dd, J=6.8, 1.8 Hz), 7.38 (2H, d, J=8.1 Hz), 6.83–6.69 (2H, m), 6.40–6.32 (2H, m), 6.25 (1H, br.s), 5.39–5.30 (1H, m), 1.60 (3H, d, J=6.2 Hz), 1.59 (9H, s).

Step 2. 4-[(1S)-1-({[5-Chloro-2-(3,5-difluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(3,5-difluorophenoxy)pyridin-3-yl]carbonyl}amino)ethyl]benzoate (step 1): $^1$H-NMR (DMSO-$d_6$) δ 9.00 (1H, d, J=7.7 Hz), 8.35 (1H, d, J=2.6 Hz), 8.18 (1H, d, J=2.6 Hz), 7.87 (2H, d, J=8.2 Hz), 7.50 (2H, d, J=8.2 Hz), 7.19–7.00 (3H, m), 5.22–5.11 (1H, m), 1.45 (3H, d, J=6.9 Hz); MS (ESI) m/z 433 (M+H)$^+$, 431 (M−H)$^-$.

Example 81

4-[(1S)-1-({[5-CHLORO-2-(3-METHOXY-5-METHYLPHENOXY)PYRIDIN-3-YL]CARBONYL}AMINO)ETHYL]BENZOIC ACID

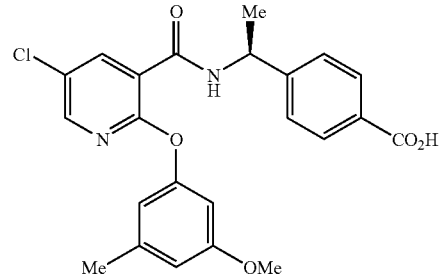

Step 1. tert-Butyl 4-[(1S)-1-({[5-chloro-2-(3-methoxy-5-methylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 3-methoxy-5-methylphenol: $^1$H-NMR (CDCl$_3$) δ 8.54 (1H, d, J=2.6 Hz), 8.17 (2H, d, J=2.8 Hz), 7.95 (2H, dd, J=6.6, 1.8 Hz), 7.39 (2H, d, J=8.1 Hz), 6.67 (1H, br.s), 6.55–6.51 (2H, m), 5.40–5.30 (1H, m), 3.80 (3H, s), 2.37 (3H, s), 1.58 (9H, s), 1.57 (3H, d, J=6.8 Hz).

Step 2. 4-[(1S)-1-({[5-Chloro-2-(3-methoxy-5-methylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(3-methoxy-5-methylphenoxy)pyridin-3-yl]carbonyl}amino)ethyl]benzoate (step 1): $^1$H-NMR (DMSO-$d_6$) δ 8.97 (1H, d, J=7.9 Hz), 8.29 (1H, d, J=2.6 Hz), 8.11 (1H, d, J=2.6 Hz), 7.86 (2H, d, J=8.4 Hz), 7.52 (2H, d, J=8.2 Hz), 6.64–6.57 (3H, m), 5.22–5.11 (1H, m), 3.73 (3H, s), 2.28 (3H, s), 1.45 (3H, d, J=6.9 Hz); MS (ESI) m/z 441 (M+H)⁺, 439 (M−H)⁻.

Example 82

4-((1S)-1-{[5-(AMINOCARBONYL)-2-(3-FLUOROPHENOXY)BENZOYL]AMINO}ETHYL)BENZOIC ACID

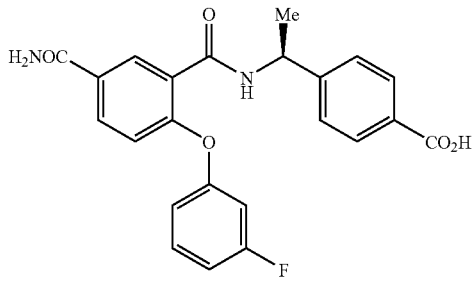

Step 1. Methyl 3-bromo-4-(3-fluorophenoxy)benzoate

The title compound was prepared according to the procedure described in step 1 of Example 67 from methyl 3-bromo-4-fluorobenzoate and 3-fluorophenol: $^1$H-NMR (CDCl$_3$) δ 8.33 (1H, d, J=2.0 Hz), 7.94 (1H, dd, J=8.6, 2.0 Hz), 7.38–7.29 (1H, m), 6.96–6.72 (4H, m), 3.92 (3H, s).

Step 2. 3-Bromo-4-(3-fluorophenoxy)benzoic acid

The title compound was prepared according to the procedure described in step 2 of Example 1 from methyl 3-bromo-4-(3-fluorophenoxy)benzoate (step 1): $^1$H-NMR (CDCl$_3$) δ 8.41 (1H, d, J=2.0 Hz), 8.00 (1H, dd, J=8.6, 2.0 Hz), 7.40–7.32 (1H, m), 6.97–6.76 (4H, m).

Step 3. 3-Bromo-4-(3-fluorophenoxy)benzamide

A mixture of 3-bromo-4-(3-fluorophenoxy)benzoic acid (step 2, 550 mg, 1.77 mmol) and 1,1'-carbonyldiimidazole (430 mg, 2.65 mmol) in N,N-dimethylformamide (10 mL) was stirred at 60° C. for 1 h. After cooling to 0° C., 25% ammonia solution was added slowly to the mixture. The resulting mixture was stirred at room temperature for 16 h. The mixture was pored into 2 M hydrochloric acid (100 mL) and the whole was extracted with ethyl acetate (200 mL). The organic layer was dried over magnesium sulfate and evaporated in vacuo. The residue was purified by flush column chromatography on silica gel eluting with hexane/ethyl acetate (1/1) to give 441 mg (80%) of the title compound as white solids: $^1$H-NMR (CDCl$_3$) δ 8.14 (1H, d, J=2.2 Hz), 7.74 (1H, dd, J=8.6, 2.2 Hz), 7.36–7.27 (1H, m), 6.97–6.59 (6H, m).

Step 4. Methyl 5-(aminocarbonyl)-2-(3-fluorophenoxy)benzoate

The title compound was prepared according to the procedure described in step 2 of Example 2 from 3-bromo-4-(3-fluorophenoxy)benzamide (step 3): $^1$H-NMR (CDCl$_3$) δ 8.39 (1H, d, J=2.1 Hz), 8.00 (1H, dd, J=8.6, 2.1 Hz), 7.36–7.27 (1H, m), 7.03 (1H, d, J=8.7 Hz), 6.90–6.70 (3H, m), 6.31 (2H, br.s), 3.85 (3H, s); MS (ESI) m/z 290 (M+H)⁺.

Step 5. 5-Aminocarbonyl-2-(3-fluorophenoxy)benzoic acid

The title compound was prepared according to the procedure described in step 2 of Example 1 from methyl 5-aminocarbonyl-2-(3-fluorophenoxy)benzoate (step 4): $^1$H-NMR (DMSO-d$_6$) δ 8.38 (1H, d, J=2.2 Hz), 8.12–8.05 (2H, m), 7.47–7.37 (2H, m), 7.13 (1H, d, J=8.4 Hz), 7.01–6.76 (3H, m); MS (ESI) m/z 276 (M+H)⁺, 274 (M−H)⁻.

Step 6. Methyl 4-((1S)-1-{[5-(aminocarbonyl)-2-(3-fluorophenoxy)benzoyl]amino}ethyl)benzoate The title compound was prepared according to the procedure described in step 3 of Example 1 from 5-(Aminocarbonyl)-2-(3-fluorophenoxy)benzoic acid (step 5) and methyl 4-[(1S)-1-aminoethyl]benzoate hydrochloride (step 3 of Example 5): $^1$H-NMR (CDCl$_3$) δ 8.60 (1H, d, J=2.4 Hz), 8.05 (1H, dd, J=8.6, 2.4 Hz), 7.91 (2H, d, J=8.4 Hz), 7.83 (1H, d, J=7.2 Hz), 7.42–7.27 (3H, m), 7.00–6.77 (5H, m), 6.12 (1H, br.s), 5.32–5.22 (1H, m), 3.89 (3H, s), 1.51 (2H, d, J=7.0 Hz); MS (ESI) m/z 437 (M+H)⁺, 435 (M−H)⁻.

Step 7. 4-((1S)-1-{[5-(Aminocarbonyl)-2-(3-fluorophenoxy)benzoyl]amino}ethyl)benzoic acid The title compound was prepared according to the procedure described in step 4 of Example 1 from methyl 4-((1S)-1-{[5-(aminocarbonyl)-2-(3-fluorophenoxy)benzoyl]amino}ethyl)benzoate (step 6): $^1$H-NMR (DMSO-d$_6$) δ 8.87 (1H, d, J=7.9 Hz), 8.08 (2H, d, J=2.0 Hz), 7.98 (1H, dd, J=8.5, 2.3 Hz), 7.82 (2H, d, J=8.3 Hz), 7.46–7.38 (4H, m), 7.10–6.84 (4H, m), 5.13–5.04 (1H, m), 1.38 (2H, d, J=7.0 Hz); MS (ESI) m/z 423 (M+H)⁺, 421 (M−H)⁻.

Example 83

4-[(1S)-1-({[5-CHLORO-2-(3-CHLORO-2-METHYLPHENOXY)PYRIDIN-3-YL]CARBONYL}AMINO)ETHYL]BENZOIC ACID

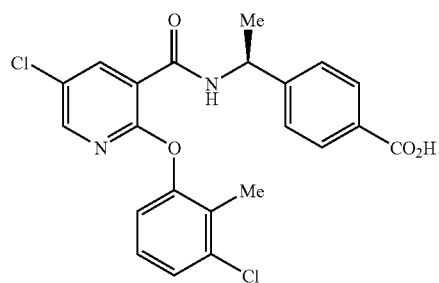

Step 1. Methyl 4-[(1S)-1-({[5-chloro-2-(3-chloro-2-methylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-chloro-2-methylphenol: $^1$H-NMR (CDCl$_3$) δ 8.57 (1H, dd, J=2.6, 0.7 Hz), 8.18–7.99 (4H, m), 7.44–7.34 (3H, m), 7.23 (1H, d, J=8.1 Hz), 7.02 (1H, d, J=8.1 Hz), 5.45–5.35 (1H, m), 3.90 (3H, s), 2.19 (3H, s), 1.60 (3H, d, J=6.9 Hz); MS (ESI) m/z 459 (M+H)$^+$, 457 (M−H)$^−$.

Step 2. 4-[(1S)-1-({[5-Chloro-2-(3-chloro-2-methylphenoxy)pyridin-3-yl]carbonyl}amino)ethyl]benzoic acid A mixture of methyl 4-[(1S)-1-({[5-chloro-2-(3-chloro-2-methylphenoxy)pyridin-3-yl]carbonyl}amino)ethyl]benzoate (step 2, 230 mg, 0.56 mmol), N,N-dimethylformamide (5 mL), and 2 M sodium hydroxide aqueous solution (2.5 mL) was stirred at room temperature for 16 h. The mixture was poured into 2 M hydrochloric acid (30 mL), and extracted with ethyl acetate (100 mL×2). The organic layer was dried over magnesium sulfate and evaporated in vacuo. The residue was purified by flush column chromatography on silica gel eluting with dichloromethane/methanol (20/1) to give 191 mg (86%) of the title compound as white solids: $^1$H-NMR (DMSO-d$_6$) δ 9.06 (1H, d, J=7.9 Hz), 8.25 (1H, d, J=2.6 Hz), 8.15 (1H, d, J=2.6 Hz), 7.88 (2H, d, J=8.1 Hz), 7.53 (2H, d, J=8.2 Hz), 7.46–7.15 (1H, m), 5.24–5.14 (1H, m), 2.10 (3H, s), 1.47 (3H, d, J=6.9 Hz); MS (ESI) m/z 445 (M+H)$^+$, 443 (M−H)$^−$.

Example 84

4-[(1S)-1-({[5-CHLORO-2-(3-PYRIDIN-2-YLPHENOXY)PYRIDIN-3-YL]CARBONYL}AMINO)ETHYL]BENZOIC ACID

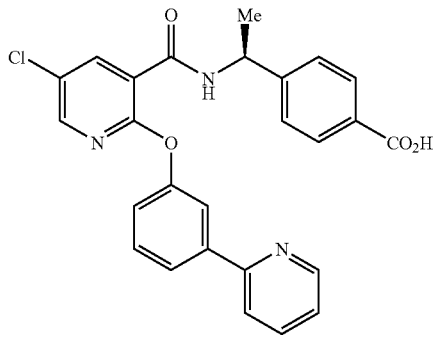

Step 1. Methyl 4-[(1S)-1-({[5-chloro-2-(3-pyridin-2-ylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-pyridin-2-ylphenol (Chem. Pharm. Bull. 1985, 33, 1009): $^1$H-NMR (CDCl$_3$) δ 8.71–8.68 (1H, m), 8.56 (1H, d, J=2.8 Hz), 8.22 (1H, d, J=7.4 Hz), 8.13 (1H, d, J=2.8 Hz), 8.02–7.99 (2H, m), 7.92–7.81 (2H, m), 7.79–7.76 (2H, m), 7.57 (1H, t, J=7.9 Hz), 7.44 (2H, d, J=8.2 Hz), 7.30–7.20 (2H, m), 5.43–5.33 (1H, m), 3.89 (3H, s), 1.60 (3H, d, J=6.9 Hz); MS (ESI) m/z 488 (M+H)$^+$, 486 (M−H)$^−$.

Step 2. 4-[(1S)-1-({[5-Chloro-2-(3-pyridin-2-ylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3-pyridin-2-ylphenoxy)pyridin-3-yl]carbonyl}amino)ethyl]benzoate (step 1): $^1$H-NMR (DMSO-d$_6$) δ 9.08 (1H, d, J=7.7 Hz), 8.67 (1H, d, J=4.9 Hz), 8.29 (1H, d, J=2.6 Hz), 8.15 (1H, d, J=2.6 Hz), 8.00–7.85 (6H, m), 7.60–7.50 (3H, m), 7.40–7.27 (2H, m), 5.25–5.15 (1H, m), 1.47 (3H, d, J=6.9 Hz); MS (ESI) m/z 474 (M+H)$^+$, 472 (M−H)$^−$.

Example 85

4-[(1S)-1-({[5-CHLORO-2-(3-PYRIDIN-3-YLPHENOXY)PYRIDIN-3-YL]CARBONYL}AMINO)ETHYL]BENZOIC ACID

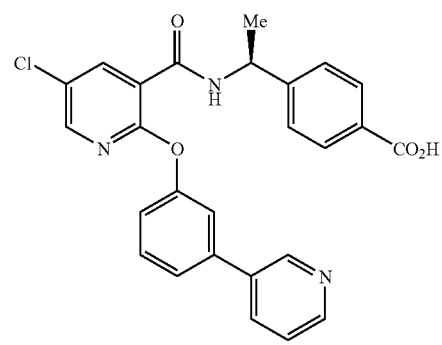

Step 1. Methyl 4-[(1S)-1-({[5-chloro-2-(3-pyridin-3-ylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-pyridin-3-ylphenol (J. Med. Chem. 1981, 24, 1475): $^1$H-NMR (CDCl$_3$) δ 8.86 (1H, d, J=1.8 Hz), 8.63 (1H, dd, J=4.8, 1.5 Hz), 8.57 (1H, d, J=2.6 Hz), 8.17–8.15 (2H, m), 8.02–7.99 (2H, m), 7.90–7.86 (1H, m), 7.62–7.36 (6H, m), 7.22–7.18 (1H, m), 5.45–5.34 (1H, m), 3.89 (3H, s), 1.61 (3H, d, J=6.9 Hz); MS (ESI) m/z 488 (M+H)$^+$, 486 (M−H)$^−$.

Step 2. 4-[(1S)-1-({[5-Chloro-2-(3-pyridin-3-ylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3-pyridin-3-ylphenoxy)pyridin-3-yl]carbonyl}amino)ethyl]benzoate (step 1): $^1$H-NMR (DMSO-d$_6$) δ 9.02 (1H, d, J=7.6 Hz), 8.90 (1H, s), 8.59 (1H, d, J=4.4 Hz), 8.30–8.06 (3H, m), 7.89–7.81 (2H, m), 7.63–7.47 (6H, m), 7.27 (1H, d, J=7.1 Hz), 5.25–5.15 (1H, m), 1.67 (3H, d, J=7.1 Hz); MS (ESI) m/z 474 (M+H)⁺, 472 (M–H)⁻.

Example 86

4-[(1S)-1-({[5-CHLORO-2-(3-PYRIDIN-4-YLPHENOXY)PYRIDIN-3-YL]CARBONYL}AMINO)ETHYL]BENZOIC ACID

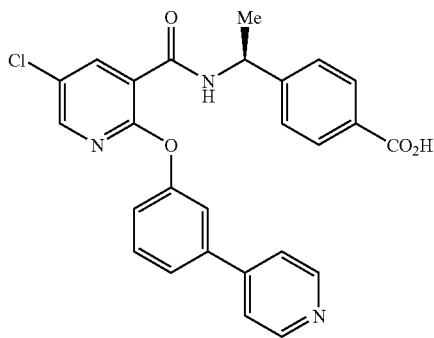

Step 1. Methyl 4-[(1S)-1-({[5-chloro-2-(3-pyridin-4-ylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-pyridin-4-ylphenol (*J. Heterocycl. Chem.* 1991, 28, 933): ¹H-NMR (CDCl₃) δ 8.69 (2H, dd, J=4.4, 1.6 Hz), 8.57 (1H, d, J=2.8 Hz), 8.15 (1H, d, J=2.6 Hz), 8.12 (1H, br.s), 8.00 (2H, dd, J=6.8, 1.9 Hz), 7.61–7.42 (7H, m), 7.27–7.22 (1H, m), 5.45–5.34 (1H, m), 3.89 (3H, s), 1.61 (3H, d, J=6.9 Hz); MS (ESI) m/z 488 (M+H)⁺, 486 (M–H)⁻.

Step 2. 4-[(1S)-1-({[5-Chloro-2-(3-pyridin-4-ylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3-pyridin-4-ylphenoxy)pyridin-3-yl]carbonyl}amino)ethyl]benzoate (step 1): ¹H-NMR (DMSO-d₆) δ 9.03 (1H, d, J=7.7 Hz), 8.65 (2H, d, J=5.8 Hz), 8.30 (1H, d, J=2.6 Hz), 8.16 (1H, d, J=2.8 Hz), 7.84 (2H, d, J=8.4 Hz), 7.74–7.53 (7H, m), 7.34–7.31 (1H, m), 5.25–5.14 (1H, m), 1.47 (3H, d, J=6.9 Hz); MS (ESI) m/z 474 (M+H)⁺, 472 (M–H)⁻.

Example 87

4-((1S)-1-{[(5-CHLORO-2-PHENOXYPYRIDIN-3-YL)CARBONYL]AMINO}ETHYL)BENZOIC ACID

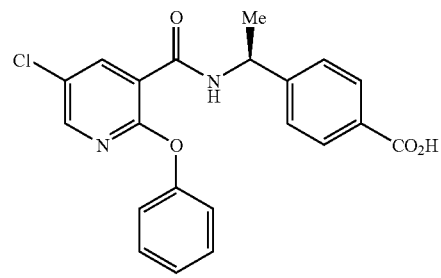

Step 1. Methyl 4-((1S)-1-{[(5-chloro-2-phenoxypyridin-3-yl)carbonyl]amino}ethyl)benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and phenol: ¹H-NMR (CDCl₃) δ 8.54 (1H, d, J=2.8 Hz), 8.21 (1H, d, J=7.3 Hz), 8.13 (1H, d, J=2.6 Hz), 8.00 (2H, dd, J=6.6, 1.8 Hz), 7.50–7.41 (4H, m), 7.34–7.29 (1H, m), 7.20–7.15 (2H, m), 5.42–5.33 (1H, m), 3.89 (3H, s), 1.61 (3H, d, J=7.0 Hz); MS (ESI) m/z 411 (M+H)⁺, 409 (M–H)⁻.

Step 2. 4-((1S)-1-{[(5-Chloro-2-phenoxypyridin-3-yl)carbonyl]amino}ethyl)benzoic acid The title compound was prepared according to the procedure described in step 2 of Example 83 from methyl 4-((1S)-1-{[(5-chloro-2-phenoxypyridin-3-yl)carbonyl]amino}ethyl)benzoate (step 1): ¹H-NMR (DMSO-d₆) δ 9.03 (1H, d, J=7.7 Hz), 8.27 (1H, d, J=2.8 Hz), 8.12 (1H, d, J=2.6 Hz), 7.86 (2H, d, J=8.3 Hz), 7.53 (2H, d, J=8.1 Hz), 7.47–7.41 (2H, m), 7.27–7.18 (3H, m), 5.22–5.13 (1H, m), 1.46 (3H, d, J=7.0 Hz); MS (EST) m/z 397 (M+H)⁺, 395 (M–H)⁻.

Example 88

4-[(1S)-1-({[5-CHLORO-2-(2,4-DIMETHYLPHENOXY)PYRIDIN-3-YL]CARBONYL}AMINO)ETHYL]BENZOIC ACID

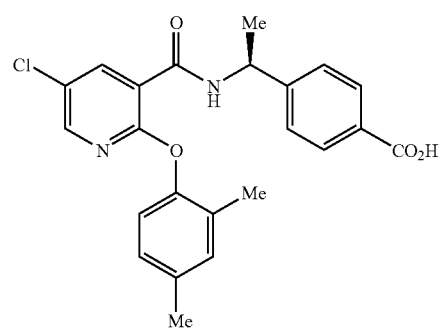

Step 1. Methyl 4-[(1S)-1-({[5-chloro-2-(2,4-dimethylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 2,4-dimethylphenol: $^1$H-NMR (CDCl$_3$) δ 8.56 (1H, d, J=2.8 Hz), 8.32 (1H, d, J=7.5 Hz), 8.11 (1H, d, J=2.6 Hz), 8.02–7.98 (2H, m), 7.43 (2H, d, J=8.3 Hz), 7.26–7.09 (2H, m), 6.99 (1H, d, J=8.1 Hz), 5.45–5.36 (1H, m), 3.90 (3H, s), 2.36 (3H, s), 2.10 (3H, s), 1.59 (3H, d, J=7.0 Hz); MS (ESI) m/z 439 (M+H)$^+$, 437 (M−H)$^−$.

Step 2. 4-[(1S)-1-({[5-Chloro-2-(2,4-dimethylphenoxy)pyridin-3-yl]carbonyl}amino)ethyl]benzoic acid The title compound was prepared according to the procedure described in step 2 of Example 83 from methyl 4-[(1S)-1-({[5-chloro-2-(2,4-dimethylphenoxy)pyridin-3-yl]carbonyl}amino)ethyl]benzoate (step 1): $^1$H-NMR (DMSO-d$_6$) δ 8.99 (1H, d, J=7.5 Hz), 8.21 (1H, d, J=2.6 Hz), 8.11 (1H, d, J=2.6 Hz), 7.87 (2H, d, J=8.4 Hz), 7.53 (2H, d, J=8.3 Hz), 7.09–6.95 (3H, m), 5.24–5.14 (1H, m), 2.29 (3H, s), 2.01 (3H, s), 1.47 (3H, d, J=7.0 Hz); MS (ESI) m/z 425 (M+H)$^+$, 423 (M−H)$^−$.

Example 89

4-[(1S)-1-({[5-CHLORO-2-(2,3-DIMETHYLPHENOXY)PYRIDIN-3-YL]CARBONYL}AMINO)ETHYL]BENZOIC ACID

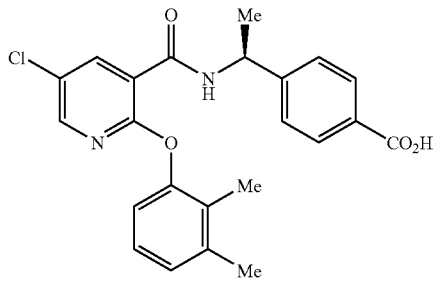

Step 1. Methyl 4-[(1S)-1-({[5-chloro-2-(2,3-dimethylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 2,3-dimethylphenol: $^1$H-NMR (CDCl$_3$) δ 8.56 (1H, d, J=3.0 Hz), 8.32 (1H, d, J=7.4 Hz), 8.11 (1H, d, J=2.8 Hz), 8.02–7.99 (2H, m), 7.43 (2H, d, J=8.4 Hz), 7.23–7.13 (2H, m), 6.95 (1H, d, J=7.7 Hz), 5.46–5.36 (1H, m), 3.90 (3H, s), 2.35 (3H, s), 2.05 (3H, s), 1.59 (3H, d, J=6.9 Hz).

Step 2. 4-[(1S)-1-({[5-Chloro-2-(2,3-dimethylphenoxy)pyridin-3-yl]carbonyl}amino)ethyl]benzoic acid The title compound was prepared according to the procedure described in step 2 of Example 83 from methyl 4-[(1S)-1-({[5-chloro-2-(2,3-dimethylphenoxy)pyridin-3-yl]carbonyl}amino)ethyl]benzoate (step 1): $^1$H-NMR (DMSO-d$_6$) δ 9.02 (1H, d, J=7.9 Hz), 8.21 (1H, d, J=2.6 Hz), 8.12 (1H, d, J=2.6 Hz), 7.87 (2H, d, J=8.4 Hz), 7.53 (2H, d, J=8.3 Hz), 7.16–7.05 (2H, m), 6.97 (1H, d, J=7.2 Hz), 5.24–5.15 (1H, m), 2.27 (3H, s), 1.97 (3H, s), 1.47 (3H, d, J=7.0 Hz); MS (ESI) m/z 425 (M+H)$^+$, 423 (M−H)$^−$.

Example 90

4-[(1S)-1-({[5-CHLORO-2-(3,5-DIMETHYLPHENOXY)PYRIDIN-3-YL]CARBONYL}AMINO)ETHYL]BENZOIC ACID

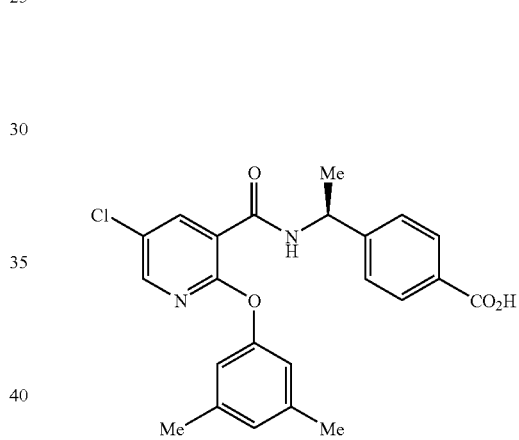

Step 1. Methyl 4-[(1S)-1-({[5-chloro-2-(3,5-dimethylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3,5-dimethylphenol: $^1$H-NMR (CDCl$_3$) δ 8.54 (1H, dd, J=2.6, 0.3 Hz), 8.24 (1H, d, J=7.3 Hz), 8.16 (1H, d, J=3.0 Hz), 8.00 (2H, dd, J=6.6, 1.8 Hz), 7.42 (2H, d, J=8.4 Hz), 6.94 (1H, s), 6.77 (2H, s), 5.42–5.32 (1H, m), 3.90 (3H, s), 2.36 (6H, s), 1.58 (3H, d, J=7.1 Hz).

Step 2. 4-[(1S)-1-({[5-Chloro-2-(3,5-dimethylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3,5-dimethylphenoxy)pyridin-3- yl]carbonyl}amino)ethyl]benzoate (step 1): ¹H-NMR (DMSO-d₆) δ 8.98 (1H, d, J=7.7 Hz), 8.28 (1H, d, J=2.8 Hz), 8.10 (1H, d, J=2.6 Hz), 7.86 (2H, d, J=8.3 Hz), 7.52 (2H, d, J=8.3 Hz), 6.86 (1H, s), 6.78 (2H, s), 5.21–5.12 (1H, m), 2.27 (6H, s), 1.45 (3H, d, J=7.2 Hz); MS (ESI) m/z 425 (M+H)⁺, 423 (M–H)⁻.

Example 91

4-[(1S)-1-({[5-CHLORO-2-(3,4-DIMETHYLPHE-NOXY)PYRIDIN-3-YL]CARBONYL}AMINO)ETHYL]BENZOIC ACID

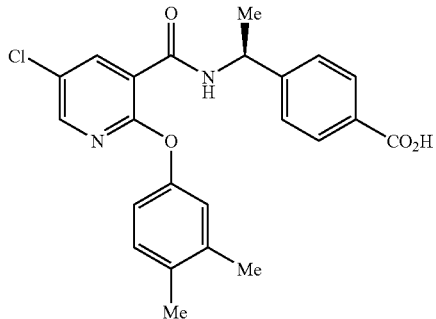

Step 1. Methyl 4-[(1S)-1-({[5-chloro-2-(3,4-dimethylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3,4-dimethylphenol: ¹H-NMR (CDCl₃) δ 8.54 (1H, d, J=2.6 Hz), 8.26 (1H, d, J=7.4 Hz), 8.14 (1H, d, J=2.6 Hz), 8.00 (2H, dd, J=6.6, 1.8 Hz), 7.42 (2H, d, J=8.4 Hz), 7.22 (1H, d, J=8.1 Hz), 6.97–6.87 (2H, m), 5.42–5.32 (1H, m), 3.90 (3H, s), 2.29 (6H, s), 1.58 (3H, d, J=7.1 Hz).

Step 2. 4-[(1S)-1-({[5-Chloro-2-(3,4-dimethylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3,4-dimethylphenoxy)pyridin-3-yl]carbonyl}amino)ethyl]benzoate (step 1): ¹H-NMR (DMSO-d₆) δ 8.98 (1H, d, J=7.7 Hz), 8.25 (1H, d, J=2.6 Hz), 8.09 (1H, d, J=2.6 Hz), 7.86 (2H, d, J=8.3 Hz), 7.52 (2H, d, J=8.3 Hz), 7.17 (1H, d, J=8.1 Hz), 6.97–6.89 (2H, m), 5.22–5.12 (1H, m), 2.22 (6H, s), 1.45 (3H, d, J=7.0 Hz); MS (ESI) m/z 425 (M+H)⁺, 423 (M–H)⁻.

Example 92

4-((1S)-1-{[(5-CHLORO-2-{4-[2-(DIMETHYLAMINO)ETHYL]PHENOXY}PYRIDIN-3-YL)CARBONYL]AMINO}ETHYL)BENZOIC ACID HYDROCHLORIDE

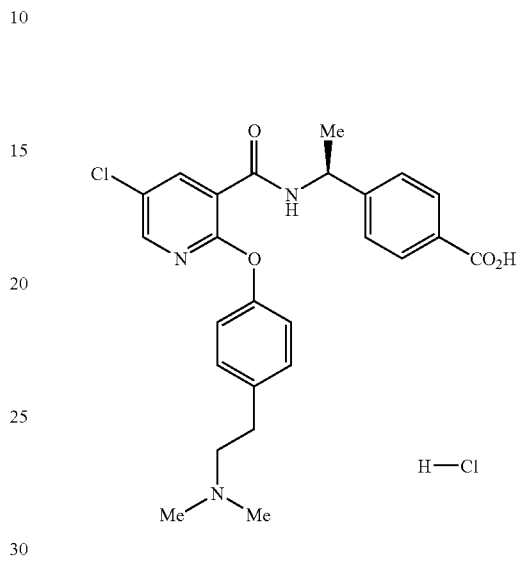

Step 1. Methyl 4-((1S)-1-{[(5-chloro-2-{4-[2-(dimethylamino)ethyl]phenoxy}pyridin-3-yl)carbonyl]amino}ethyl)benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 4-[2-(dimethylamino)ethyl]phenol: ¹H-NMR (CDCl₃) δ 8.53 (1H, d, J=2.6 Hz), 8.23 (1H, d, J=7.5 Hz), 8.13 (1H, d, J=2.8 Hz), 8.02–7.98 (2H, m), 7.43 (2H, d, J=8.3 Hz), 7.33–7.30 (2H, m), 7.11–7.06 (2H, m), 5.39–5.30 (1H, m), 3.90 (3H, s), 2.87–2.82 (2H, m), 2.63–2.58 (2H, m), 2.33 (6H, s), 1.59 (3H, d, J=7.0 Hz).

Step 2. 4-((1S)-1-{[(5-Chloro-2-{4-[2-(dimethylamino)ethyl]phenoxy}pyridin-3-yl)carbonyl]amino}ethyl)benzoic acid hydrochloride The title compound was prepared according to the procedure described in step 2 of Example 83 from methyl 4-((1S)-1-{[(5-chloro-2-{4-[2-(dimethylamino)ethyl]phenoxy}pyridin-3-yl)carbonyl]amino}ethyl)benzoate (step 1) and then converted into the hydrochloride salt with 4 M solution of hydrogen chloride in ethyl acetate: ¹H-NMR (DMSO-d₆) δ 9.04 (1H, d, J=7.9 Hz), 8.26 (1H, d, J=2.8 Hz), 8.12 (1H, d, J=2.6 Hz), 7.85 (2H, d, J=8.4 Hz), 7.53 (2H, d, J=8.3 Hz), 7.34 (2H, d, J=8.6 Hz), 7.17 (2H, d, J=8.6 Hz), 5.22–5.12 (1H, m), 3.29–3.25 (2H, m), 3.04–2.99 (2H, m), 2.80 (6H, s), 1.45 (3H, d, J=7.0 Hz); MS (ESI) m/z 468 (M+H)⁺, 466 (M–H)⁻.

Example 93

4-[(1S)-1-({[5-CHLORO-2-(2,3-DICHLOROPHE-NOXY)PYRIDIN-3-YL]CARBONYL}AMINO)ETHYL]BENZOIC ACID

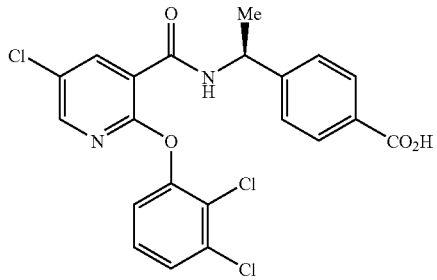

Step 1. Methyl 4-[(1S)-1-({[5-chloro-2-(2,3-dichlorophenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 2,3-dichlorophenol: $^1$H-NMR (CDCl$_3$) δ 8.55 (1H, d, J=2.6 Hz), 8.10–7.99 (4H, m), 7.48–7.21 (5H, m), 5.45–5.34 (1H, m), 3.90 (3H, s), 1.61 (3H, d, J=7.1 Hz).

Step 2. 4-[(1S)-1-({[5-Chloro-2-(2,3-dichlorophenoxy)pyridin-3-yl]carbonyl}amino)ethyl]benzoic acid The title compound was prepared according to the procedure described in step 2 of Example 83 from methyl 4-[(1S)-1-({[5-chloro-2-(2,3-dichlorophenoxy)pyridin-3-yl]carbonyl}amino)ethyl]benzoate (step 1): $^1$H-NMR (DMSO-d$_6$) δ 9.04 (1H, d, J=7.79 Hz), 8.29 (1H, d, J=2.6 Hz), 8.20 (1H, d, J=2.6 Hz), 7.88 (2H, d, J=8.3 Hz), 7.60–7.41 (5H, m), 5.24–5.15 (1H, m), 1.47 (3H, d, J=7.0 Hz); MS (ESI) m/z 465 (M+H)$^+$, 463 (M–H)$^-$.

Example 94

4-[(1S)-1-({[5-CHLORO-2-(2,4-DICHLOROPHE-NOXY)PYRIDIN-3-YL]CARBONYL}AMINO)ETHYL]BENZOIC ACID

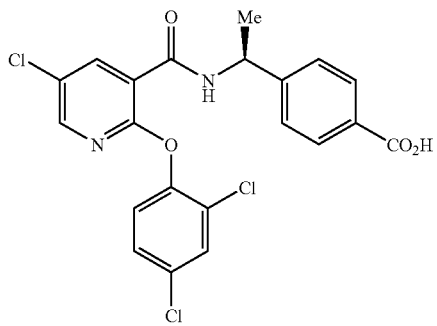

Step 1. Methyl 4-[(1S)-1-({[5-chloro-2-(2,4-dichlorophenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 2,4-dichlorophenol: $^1$H-NMR (CDCl$_3$) δ 8.54 (1H, d, J=2.6 Hz), 8.09–7.99 (4H, m), 7.52 (1H, d, J=2.3 Hz), 7.44 (2H, d, J=8.2 Hz), 7.36 (1H, dd, J=8.7, 2.4 Hz), 7.26 (1H, d, J=8.7 Hz), 5.44–5.34 (1H, m), 3.89 (3H, s), 1.61 (3H, d, J=6.9 Hz).

Step 2. 4-[(1S)-1-({[5-Chloro-2-(2,4-dichlorophenoxy)pyridin-3-yl]carbonyl}amino)ethyl]benzoic acid The title compound was prepared according to the procedure described in step 2 of Example 83 from methyl 4-[(1S)-1-({[5-chloro-2-(2,4-dichlorophenoxy)pyridin-3-yl]carbonyl}amino)ethyl]benzoate (step 1): $^1$H-NMR (DMSO-d$_6$) δ 9.03 (1H, d, J=7.7 Hz), 8.28 (1H, d, J=2.6 Hz), 8.19 (1H, d, J=2.8 Hz), 7.88 (2H, d, J=8.3 Hz), 7.78 (1H, d, J=2.4 Hz), 7.55–7.44 (4H, m), 5.24–5.14 (1H, m), 1.47 (3H, d, J=7.0 Hz); MS (ESI) m/z 465 (M+H)$^+$, 463 (M–H)$^-$.

Example 95

4-[(1S)-1-({[5-CHLORO-2-(2,5-DICHLOROPHE-NOXY)PYRIDIN-3-YL]CARBONYL}AMINO)ETHYL]BENZOIC ACID

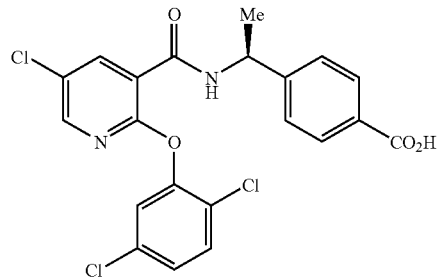

Step 1. Methyl 4-[(1S)-1-({[5-chloro-2-(2,5-dichlorophenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 2,5-dichlorophenol: $^1$H-NMR (CDCl$_3$) δ 8.55 (1H, d, J=2.8 Hz), 8.34 (1H, d, J=2.6 Hz), 8.27–7.99 (3H, m), 7.46–7.43 (3H, m), 7.35 (1H, d, J=2.3 Hz), 7.29–7.25 (1H, m), 5.44–5.34 (1H, m), 3.90 (3H, s), 1.61 (3H, d, J=6.9 Hz).

Step 2. 4-[(1S)-1-({[5-Chloro-2-(2,5-dichlorophenoxy)pyridin-3-yl]carbonyl}amino)ethyl]benzoic acid The title compound was prepared according to the procedure described in step 2 of Example 83 from methyl 4-[(1S)-1-({[5-chloro-2-(2,5-dichlorophenoxy)pyridin-3-yl]

carbonyl}amino)ethyl]benzoate (step 1): $^1$H-NMR (DMSO-$d_6$) δ 8.99 (1H, d, J=7.9 Hz), 8.31 (1H, d, J=2.6 Hz), 8.20 (1H, d, J=2.6 Hz), 7.87 (2H, d, J=8.3 Hz), 7.66–7.61 (2H, m), 7.53 (2H, d, J=8.3 Hz), 7.41 (1H, dd, J=8.6, 2.4 Hz), 5.25–5.15 (1H, m), 1.48 (3H, d, J=7.2 Hz); MS (ESI) m/z 465 (M+H)$^+$, 463 (M−H)$^-$.

Example 96

4-[(1S)-1-({[5-CHLORO-2-(3,4-DICHLOROPHE-NOXY)PYRIDIN-3-YL]CARBONYL}AMINO) ETHYL]BENZOIC ACID

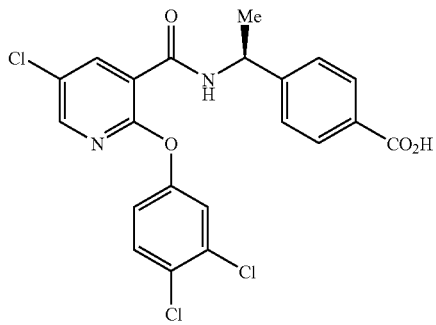

Step 1. Methyl 4-[(1S)-1-({[5-chloro-2-(3,4-dichlorophenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3,4-dichlorophenol: $^1$H-NMR (CDCl$_3$) δ 8.52 (1H, d, J=2.6 Hz), 8.13 (1H, d, J=2.8 Hz), 8.00 (2H, dd, J=6.7, 1.9 Hz), 7.93 (1H, d, J=7.4 Hz), 7.51 (1H, d, J=8.7 Hz), 7.42 (2H, d, J=8.1 Hz), 7.30 (1H, d, J=2.6 Hz), 7.03 (1H, dd, J=8.7, 2.6 Hz), 5.42–5.31 (1H, m), 3.90 (3H, s), 1.60 (3H, d, J=6.9 Hz).

Step 2. 4-[(1S)-1-({[5-Chloro-2-(3,4-dichlorophenoxy)pyridin-3-yl]carbonyl}amino)ethyl]benzoic acid The title compound was prepared according to the procedure described in step 2 of Example 83 from methyl 4-[(1S)-1-({[5-chloro-2-(3,4-dichlorophenoxy)pyridin-3-yl]carbonyl}amino)ethyl]benzoate (step 1): $^1$H-NMR (DMSO-$d_6$) δ 9.01 (1H, d, J=7.9 Hz), 8.32 (1H, d, J=2.6 Hz), 8.16 (1H, d, J=2.8 Hz), 7.87 (2H, d, J=8.4 Hz), 7.71 (1H, d, J=8.8 Hz), 7.59 (1H, d, J=2.8 Hz), 7.51 (2H, d, J=8.4 Hz), 7.27 (1H, dd, J=8.8, 2.8 Hz), 5.22–5.13 (1H, m), 1.46 (3H, d, J=7.2 Hz); MS (ESI) m/z 465 (M+H)$^+$, 463 (M−H)$^-$.

Example 97

4-[(1S)-1-({[5-CHLORO-2-(3,5-DICHLOROPHE-NOXY)PYRIDIN-3-YL]CARBONYL}AMINO) ETHYL]BENZOIC ACID

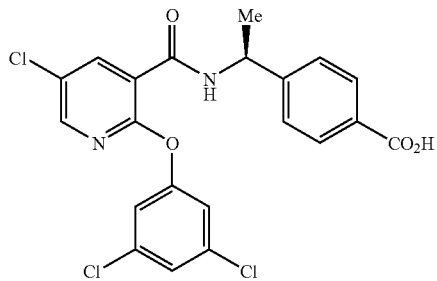

Step 1. Methyl 4-[(1S)-1-({[5-chloro-2-(3,5-dichlorophenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3,5-dichlorophenol: $^1$H-NMR (CDCl$_3$) δ 8.54 (1H, d, J=2.6 Hz), 8.16 (1H, d, J=2.8 Hz), 8.02 (2H, dd, J=6.6, 1.8 Hz), 7.84 (1H, d, J=7.3 Hz), 7.42 (2H, d, J=8.6 Hz), 7.31 (1H, t, J=1.8 Hz), 7.08 (2H, d, J=1.8 Hz), 5.41–5.31 (1H, m), 3.91 (3H, s), 1.60 (3H, d, J=6.9 Hz).

Step 2. 4-[(1S)-1-({[5-Chloro-2-(3,5-dichlorophenoxy)pyridin-3-yl]carbonyl}amino)ethyl]benzoic acid The title compound was prepared according to the procedure described in step 2 of Example 83 from methyl 4-[(1S)-1-({[5-chloro-2-(3,5-dichlorophenoxy)pyridin-3-yl]carbonyl}amino)ethyl]benzoate (step 1): $^1$H-NMR (DMSO-$d_6$) δ 8.99 (1H, d, J=7.9 Hz), 8.35 (1H, d, J=2.8 Hz), 8.17 (1H, d, J=2.6 Hz), 7.87 (2H, d, J=8.3 Hz), 7.52–7.49 (3H, m), 7.39 (2H, d, J=1.8 Hz), 5.22–5.12 (1H, m), 1.46 (3H, d, J=7.0 Hz); MS (ESI) m/z 465 (M+H)$^+$, 463 (M−H)$^-$.

Example 98

4-[(1S)-1-({[5-CHLORO-2-(4-CHLOROPHE-NOXY)PYRIDIN-3-YL]CARBONYL}AMINO) ETHYL]BENZOIC ACID

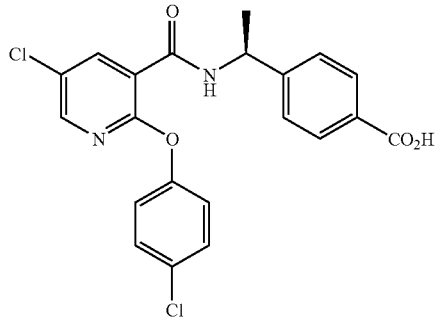

The title compound was prepared according to the two steps procedure described in step 2 and 3 of Example 45. Firstly, tert-butyl 4-((1S)-1-{[(2,5-dichloropyridin-3-yl)carbonyl]amino}ethyl)benzoate (step 1 of Example 45) was reacted with 4-chlorophenol. Next, the crude product was converted to the corresponding carboxylic acid: $^1$H-NMR (CDCl$_3$) δ 8.55 (1H, d, J=2.8 Hz), 8.14 (1H, d, J=2.8 Hz), 8.11–8.02 (3H, m), 7.50–7.39 (4H, m), 7.11 (2H, d, J=9.0 Hz), 5.44–5.31 (1H, m), 1.60 (3H, d, J=7.0 Hz); MS (ESI) m/z 431 (M+H)$^+$, 429 (M−H)$^−$.

Example 99

4-[(1S)-1-({5-CHLORO-2-[(5-FLUOROPYRIDIN-3-YL)OXY]BENZOYL}AMINO)ETHYL]BENZOIC ACID

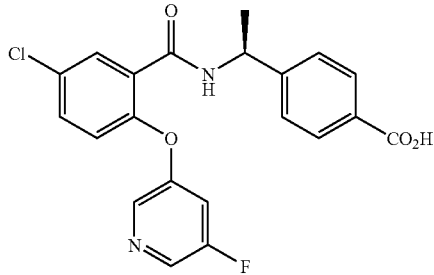

Step 1. Methyl 5-chloro-2-[(5-fluoropyridin-3-yl)oxy]benzoate

The title compound was prepared according to the procedure described in step 1 of Example 67 from methyl 5-chloro-2-fluorobenzoate and 5-fluoropyridin-3-ol: MS (ESI) m/z 282 (M+H)$^+$.

Step 2. 5-Chloro-2-[(5-fluoropyridin-3-yl)oxy]benzoic acid

To a solution of methyl 5-chloro-2-[(5-fluoropyridin-3-yl)oxy]benzoate (80 mg, 0.28 mmol) in methanol (2 mL) was added 2 M sodium hydroxide aqueous solution (2 mL) and the reaction mixture was stirred at room temperature for 12 h. The reaction mixture was acidified with 2 M hydrochloric acid (2.5 mL). The precipitate was collected by filtration to afford 61 mg (80%) of the title compound: $^1$H-NMR (CDCl$_3$) δ 8.24 (1H, br.s), 8.19 (1H, br.s), 8.07 (1H, d, J=2.6 Hz), 7.56 (1H, d, J=8.8, 2.6 Hz), 7.06 (1H, d, J=8.8 Hz), 6.98 (1H, td, J=9.4, 2.2 Hz).

Step 3. Methyl 4-[(1S)-1-({5-chloro-2-[(5-fluoropyridin-3-yl)oxy]benzoyl}amino)ethyl]benzoate The title compound was prepared according to the procedure described in step 3 of Example 1 from 5-chloro-2-[(5-fluoropyridin-3-yl)oxy]benzoic acid (step 2) and methyl 4-[(1S)-1-aminoethyl]benzoate hydrochloride (step 3 of Example 5): $^1$H-NMR (CDCl$_3$) δ 8.33 (1H, d, J=2.3 Hz), 8.23 (1H, d, J=2.3 Hz), 8.11 (1H, d, J=2.7 Hz), 7.95 (2H, d, J=8.2 Hz), 7.45 (1H, dd, J=8.7, 2.8 Hz), 7.38–7.25 (1H, m), 7.30 (2H, d, J=8.2 Hz), 6.95 (1H, td, J=8.9, 2.3 Hz), 6.91 (1H, d, J=8.7 Hz), 5.38–5.25 (1H, m), 3.90 (3H, s), 1.50 (3H, d, J=6.9 Hz).

Step 4. 4-[(1S)-1-({5-Chloro-2-[(5-fluoropyridin-3-yl)oxy]benzoyl}amino)ethyl]benzoic acid The title compound was prepared according to the procedure described in step 2 of Example 99 from methyl 4-[(1S)-1-({5-chloro-2-[(5-fluoropyridin-3-yl)oxy]benzoyl}amino)ethyl]benzoate (step 3): $^1$H-NMR (CDCl$_3$) δ 8.35 (1H, d, J=2.0 Hz), 8.22 (1H, d, J=2.0 Hz), 8.13 (1H, d, J=2.7 Hz), 8.00 (2H, d, J=8.3 Hz), 7.46 (1H, dd, J=8.8, 2.7 Hz), 7.36–7.26 (1H, m), 7.31 (2H, d, J=8.3 Hz), 6.98–6.90 (2H, m), 5.36–5.20 (1H, m), 1.52 (3H, d, J=6.8 Hz); MS (ESI) m/z 415 (M+H)$^+$, 413 (M−H)$^−$.

Example 100

4-[(1S)-1-({5-CHLORO-2-[(5-CHLOROPYRIDIN-3-YL)OXY]BENZOYL}AMINO)ETHYL]BENZOIC ACID

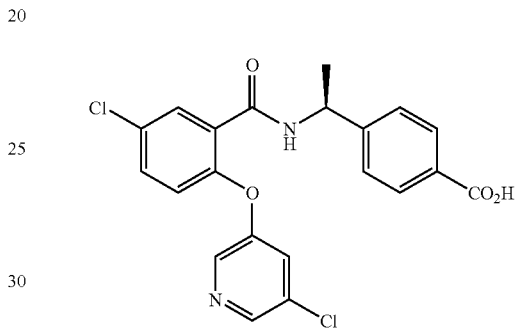

Step 1. 5-Chloro-2-[(5-chloropyridin-3-yl)oxy]benzoic acid

The title compound was prepared according to the two steps procedure described in step 1 of Example 67 and step 2 of Example 99. Firstly, methyl 5-chloro-2-fluorobenzoate was reacted with 5-chloropyridin-3-ol. Next, the crude product was hydrolyzed to the corresponding carboxylic acid: $^1$H-NMR (DMSO-d$_6$) δ 8.36 (1H, d, J=2.0 Hz), 8.25 (1H, d, J=2.4 Hz), 7.87 (1H, d, J=2.6 Hz), 7.70 (1H, dd, J=8.8, 2.6 Hz), 7.50 (1H, dd, J=2.4, 2.0 Hz), 7.29 (1H, d, J=8.8 Hz).

Step 2. Methyl 4-[(1S)-1-({5-chloro-2-[(5-chloropyridin-3-yl)oxy]benzoyl}amino)ethyl]benzoate The title compound was prepared according to the procedure described in step 3 of Example 1 from 5-chloro-2-[(5-chloropyridin-3-yl)oxy]benzoic acid (step 1) and methyl 4-[(1S)-1-aminoethyl]benzoate hydrochloride (step 3 of Example 5): $^1$H-NMR (CDCl$_3$) δ 8.41 (1H, d, J=2.0 Hz), 8.28 (1H, d, J=2.5 Hz), 8.13 (1H, d, J=2.8 Hz), 7.96 (2H, d, J=8.4 Hz), 7.45 (1H, dd, J=8.7, 2.8 Hz), 7.37–7.28 (1H, m), 7.31 (2H, d, J=8.4 Hz), 7.20 (1H, dd, J=2.5, 2.0 Hz), 6.90 (1H, d, J=8.7 Hz), 5.37–5.22 (1H, m), 3.91 (3H, s), 1.51 (3H, d, J=6.9 Hz).

Step 3. 4-[(1S)-1-({5-Chloro-2-[(5-chloropyridin-3-yl)oxy]benzoyl}amino)ethyl]benzoic acid The title compound was prepared according to the procedure described in step 2 of Example 99 from methyl 4-[(1S)-1-({5-chloro-2-[(5-chloropyridin-3-yl)oxy]benzoyl}amino)ethyl]benzoate (step 2): $^1$H-NMR (CDCl$_3$)

δ 8.43 (1H, d, J=2.0 Hz), 8.27 (1H, d, J=2.6 Hz), 8.13 (1H, d, J=2.7 Hz), 8.00 (2H, d, J=8.3 Hz), 7.46 (1H, dd, J=8.6, 2.7 Hz), 7.37–7.29 (1H, m), 7.32 (2H, d, J=8.3 Hz), 7.18 (1H, dd, J=2.6, 2.0 Hz), 6.92 (1H, d, J=8.6 Hz), 5.37–5.23 (1H, m), 1.51 (3H, d, J=7.0 Hz); MS (ESI) m/z 431 (M+H)⁺, 429 (M–H)⁻.

Example 101

4-[(1S)-1-({5-CHLORO-2-[(5-FLUOROPYRIDIN-2-YL)OXY]BENZOYL}AMINO)ETHYL]BENZOIC ACID

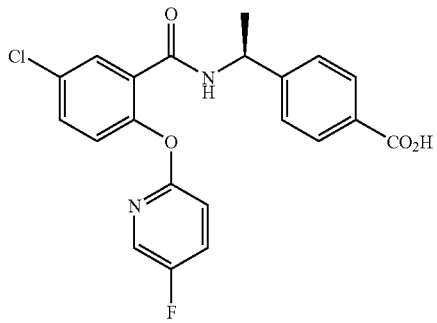

Step 1. Methyl 5-chloro-2-[(5-nitropyridin-2-yl)oxy]benzoate

A mixture of methyl 5-chloro-2-hydroxybenzoate (2.35 g, 12.6 mmol), 2-chloro-5-nitropyridine (2.00 g, 12.6 mmol), and potassium carbonate (5.23 g, 37.8 mmol) in N,N-dimethylformamide (50 mL) was stirred at 120° C. for 1 h. The reaction mixture was poured into water and the aqueous mixture was extracted with a mixture (3/1) of ethyl acetate and toluene. The organic extracts were washed with brine, dried over sodium sulfate, and concentrated. The residue was purified by flush column chromatography on silica gel eluting with hexane/ethyl acetate (4/1) to afford 3.79 g (97%) of the title compound: ¹H-NMR (CDCl₃) δ 8.94 (1H, d, J=2.8 Hz), 8.52 (1H, dd, J=9.0, 2.8 Hz), 8.05 (1H, d, J=2.8 Hz), 7.60 (1H, dd, J=8.6, 2.8 Hz), 7.18 (1H, d, J=8.6 Hz), 7.14 (1H, d, J=9.0 Hz), 3.73 (3H, s).

Step 2. Methyl 2-[(5-aminopyridin-2-yl)oxy]-5-chlorobenzoate

A mixture of methyl 5-chloro-2-[(5-nitropyridin-2-yl)oxy]benzoate (step 1, 1.59 g, 5.2 mmol) and 5% palladium on activated carbon (149 mg) in ethyl acetate (25 mL) was stirred at room temperature for 1 h under hydrogen atmosphere. The reaction mixture was filtered through a pad of Celite® and the filtrate was evaporated. The residue was purified by flush column chromatography on silica gel eluting with dichloromethane/methanol (50/1) to afford 301 mg (21%) of the title compound: ¹H-NMR (CDCl₃) δ 7.92 (1H, d, J=2.8 Hz), 7.56 (1H, d, J=2.6 Hz), 7.47 (1H, dd, J=8.7, 2.6 Hz), 7.11 (1H, dd, J=8.6, 2.8 Hz), 7.08 (1H, d, J=8.7 Hz), 6.82 (1H, d, J=8.6 Hz), 3.74 (3H, s), 3.49 (2H, br.s).

Step 3. Methyl 5-chloro-2-[(5-fluoropyridin-2-yl)oxy]benzoate

To a solution of sodium nitrite (224 mg, 3.25 mmol) in water (5 mL) was added methyl 2-[(5-aminopyridin-2-yl)oxy]-5-chlorobenzoate (907 mg, 3.25 mmol) and 48% tetrafluoroboric acid in water (5 mL) at 0° C. The reaction mixture was stirred for 5 h. The resulting precipitate was collected by filtration and dried under reduced pressure at room temperature. To the solids of tetrafluoroborate were added chlorobenzene (5 mL) and the mixture was heated at 140° C. for 40 min. The reaction mixture was diluted with ethyl acetate. The solution was washed with brine and concentrated. The residue was purified by flush column chromatography on silica gel eluting with hexane/ethyl acetate (8/1) to afford 382 mg (42%) of the title compound: ¹H-NMR (CDCl₃) δ 7.98 (1H, d, J=2.8 Hz), 7.90 (1H, d, J=3.1 Hz), 7.59–7.41 (2H, m), 7.14 (1H, d, J=8.6 Hz), 6.99 (1H, dd, J=8.9, 3.5 Hz), 3.72 (3H, s).

Step 4. 5-Chloro-2-[(5-fluoropyridin-2-yl)oxy]benzoic acid

To a solution of methyl 5-chloro-2-[(5-fluoropyridin-2-yl)oxy]benzoate (204 mg, 0.72 mmol) in tetrahydrofuran (3 mL) was added 2 M sodium hydroxide aqueous solution (1.5 mL) and the reaction mixture was stirred at room temperature for 24 h. Then the reaction mixture was acidified with 2 M hydrochloric acid (2 mL). The precipitates were collected by filtration and dried under reduced pressure to afford 184 mg (95%) of the title compound: ¹H-NMR (DMSO-d₆) δ 8.02 (1H, d, J=3.1 Hz), 7.85–7.66 (2H, m), 7.66 (1H, dd, J=8.8, 2.8 Hz), 7.26 (1H, d, J=8.8 Hz), 7.11 (1H, dd, J=9.0, 3.5 Hz).

Step 5. Methyl 4-[(1S)-1-({5-chloro-2-[(5-fluoropyridin-2-yl)oxy]benzoyl}amino)ethyl]benzoate The title compound was prepared according to the procedure described in step 3 of Example 1 from 5-chloro-2-[(5-fluoropyridin-2-yl)oxy]benzoic acid (step 5) and methyl 4-[(1S)-1-aminoethyl]benzoate hydrochloride (step 3 of Example 5): ¹H-NMR (CDCl₃) δ 7.99 (1H, d, J=2.6 Hz), 7.97 (1H, d, J=3.1 Hz), 7.92 (2H, d, J=8.4 Hz), 7.50–7.39 (2H, m), 7.35–7.21 (3H, m), 6.99 (1H, d, J=8.6 Hz), 6.86 (1H, dd, J=8.9, 3.3 Hz), 5.31–5.17 (1H, m), 3.91 (3H, s), 1.42 (3H, d, J=6.9 Hz); MS (ESI) m/z 429 (M+H)⁺, 427 (M–H)⁻.

Step 6. 4-[(1S)-1-({5-Chloro-2-[(5-fluoropyridin-2-yl)oxy]benzoyl}amino)ethyl]benzoic acid The title compound was prepared according to the procedure described in step 2 of Example 99 from methyl 4-[(1S)-1-({5-chloro-2-[(5-fluoropyridin-2-yl)oxy]benzoyl}amino)ethyl]benzoate (step 5): ¹H-NMR (CDCl₃) δ 8.05–7.93 (4H, m), 7.52–7.40 (2H, m), 7.37 (1H, d, J=7.6 Hz), 7.32–7.25 (2H, m), 6.99 (1H, d, J=8.7 Hz), 6.88 (1H, dd, J=8.9, 3.5 Hz), 5.34–5.19 (1H, m), 1.43 (3H, d, J=6.9 Hz); MS (ESI) m/z 415 (M+H)⁺, 413 (M–H)⁻.

Example 102

4-[(1S)-1-({5-CHLORO-2-[(5-CHLOROPYRIDIN-2-YL)OXY]BENZOYL}AMINO)ETHYL]BENZOIC ACID

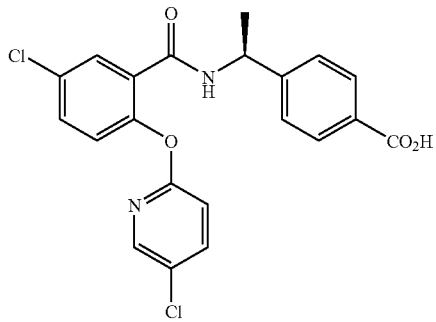

Step 1. Methyl 5-chloro-2-[(5-chloropyridin-2-yl)oxy]benzoate

To a solution of methyl 2-[(5-aminopyridin-2-yl)oxy]-5-chlorobenzoate (step 2 of Example 101, 1.00 g, 3.6 mmol) in 0.66 M hydrochloric acid (11 mL) was added sodium nitrite (252 mg, 3.6 mmol) in water (5 mL) at 0° C. The reaction mixture was stirred for 30 mim at 0° C. The mixture was added dropwise to a stirred suspension of cupper(II) chloride (1.21 g, 9.0 mmol) in acetone (18 mL) and water (5.4 mL). The whole was stirred at 50° C. for 30 min. Then the reaction mixture was poured into water and it was added ammonia solution. The aqueous mixture was extracted with ethyl acetate. The organic phase was washed with brine, dried over sodium sulfate, and concentrated. The residue was purified by flush column chromatography on silica gel eluting with hexane/ethyl acetate (20/1) to afford 347 mg (32%) of the title compound: $^1$H-NMR (CDCl$_3$) δ 8.00 (1H, d, J=2.8 Hz), 7.99 (1H, d, J=2.8 Hz), 7.67 (1H, dd, J=8.7, 2.8 Hz), 7.55 (1H, dd, J=8.6, 2.8 Hz), 7.14 (1H, d, J=8.6 Hz), 6.97 (1H, d, J=8.7 Hz), 3.72 (3H, s).

Step 2. 5-Chloro-2-[(5-chloropyridin-2-yl)oxy]benzoic acid

The title compound was prepared according to the procedure described in step 2 of Example 99 from methyl 5-chloro-2-[(5-chloropyridin-2-yl)oxy]benzoate (step 1): $^1$H-NMR (CDCl$_3$) δ 8.04 (1H, d, J=2.6 Hz), 8.02 (1H, d, J=2.6 Hz), 7.68 (1H, dd, J=8.7, 2.6 Hz), 7.56 (1H, dd, J=8.7, 2.6 Hz), 7.14 (1H, d, J=8.7 Hz), 6.98 (1H, d, J=8.7 Hz).

Step. 3 Methyl 4-[(1S)-1-({5-chloro-2-[(5-chloropyridin-2-yl)oxy]benzoyl}amino)ethyl]benzoate The title compound was prepared according to the procedure described in step 3 of Example 1 from 5-chloro-2-[(5-chloropyridin-2-yl)oxy]benzoic acid (step 2) and methyl 4-[(1S)-1-aminoethyl]benzoate hydrochloride (step 3 of Example 5): $^1$H-NMR (CDCl$_3$) δ 8.04 (1H, d, J=2.6 Hz), 7.94 (1H, d, J=2.6 Hz), 7.91 (2H, d, J=8.3 Hz), 7.63 (1H, dd, J=8.8, 2.6 Hz), 7.43 (1H, dd, J=8.8, 2.6 Hz), 7.22 (2H, d, J=8.3 Hz), 7.18 (1H, d, J=8.0 Hz), 7.00 (1H, d, J=8.8 Hz), 6.80 (1H, d, J=8.8 Hz), 5.28–5.16 (1H, m), 3.91 (3H, s), 1.42 (3H, d, J=7.0 Hz).

Step 4. 4-[(1S)-1-({5-Chloro-2-[(5-chloropyridin-2-yl)oxy]benzoyl}amino)ethyl]benzoic acid The title compound was prepared according to the procedure described in step 2 of Example 99 from methyl 4-[(1S)-1-({5-chloro-2-[(5-chloropyridin-2-yl)oxy]benzoyl}amino)ethyl]benzoate (step 3): $^1$H-NMR (CDCl$_3$) δ 8.07 (1H, d, J=2.6 Hz), 8.04–7.94 (3H, m), 7.66 (1H, dd, J=8.6, 2.6 Hz), 7.44 (1H, dd, J=8.6, 2.6 Hz), 7.33–7.13 (3H, m), 7.01 (1H, d, J=8.6 Hz), 6.83 (1H, d, J=8.6 Hz), 5.30–5.15 (1H, m), 1.43 (3H, d, J=7.0 Hz); MS (ESI) m/z 431 (M+H)$^+$, 429 (M−H)$^−$.

Example 103

5-CHLORO-2-(4-FLUOROPHENOXY)-N-[(1S)-1-(4-{[(METHYLSULFONYL)AMINO]CARBONYL}PHENYL)ETHYL]NICOTINAMIDE

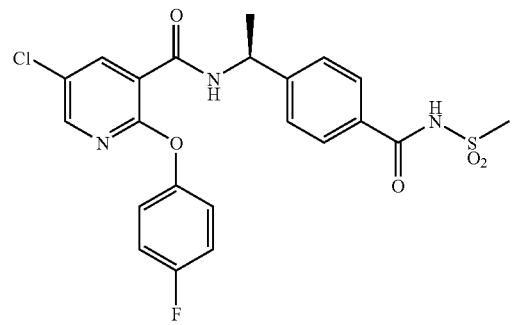

A mixture of 4-[(1S)-1-({[5-chloro-2-(4-fluorophenoxy)pyridin-3-yl]carbonyl}amino)ethyl]benzoic acid (step 5 of Example 44, 250 mg, 0.60 mmol), methanesulfonamide (60 mg, 0.63 mmol), 1-(3-dimethylaminopropyl)-3-ethylcarbodiimide hydrochloride (139 mg, 0.73 mmol) and dimethylaminopyridiene (78 mg, 0.63 mmol) in dichloromethane (5 mL) was stirred at room temperature overnight. The reaction mixture was diluted with ethyl acetate. The solution was washed with 1M hydrochloric acid, water, and brine, dried over sodium sulfate, and evaporated. The residue was purified by flush column chromatography on silica gel eluting with dichloromethane/methanol (40/1) to afford 292 mg (98%) of the title compound: $^1$H-NMR (CDCl$_3$) δ 8.52 (1H, d, J=2.8 Hz), 8.14 (1H, d, J=2.8 Hz), 8.16–8.02 (1H, m), 7.81 (2H, d, J=8.3 Hz), 7.46 (2H, d, J=8.3 Hz), 7.23–7.10 (4H, m), 5.44–5.28 (1H, m), 3.41 (3H, s), 1.59 (3H, d, J=7.0 Hz); MS (ESI) m/z 492 (M+H)$^+$, 490 (M−H)$^−$.

Example 104

5-CHLORO-N-{(1S)-1-[4-({[(2-CHLOROPHE-NYL)SULFONYL]AMINO}CARBONYL)PHE-NYL]ETHYL}-2-(4-FLUOROPHENOXY)NICOTI-NAMIDE

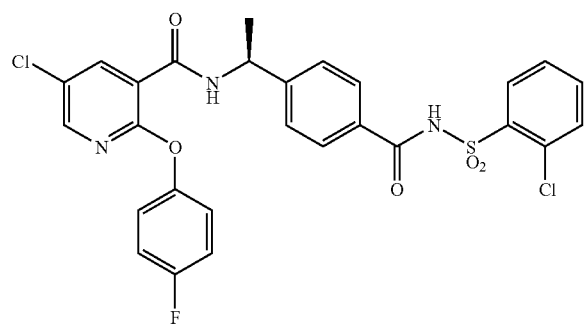

The title compound was prepared according to the procedure described in step 1 of Example 103 from 4-[(1S)-1-({[5-chloro-2-(4-fluorophenoxy)pyridin-3-yl]carbonyl}amino)ethyl]benzoic acid (step 5 of Example 44) and 2-chlorobenzenesulfonamide: $^1$H-NMR (CDCl$_3$) δ 8.54 (1H, d, J=2.6 Hz), 8.23–8.12 (2H, m), 8.04 (1H, d, J=2.6 Hz), 7.87 (1H, d, J=7.3 Hz), 7.47–7.16 (5H, m), 7.15–7.01 (5H, m), 5.45–5.25 (1H, m), 1.48 (3H, d, J=6.4 Hz); MS (ESI) m/z 588 (M+H)$^+$, 586 (M−H)$^−$.

Example 105

4-((1S)-1-{[5-CHLORO-2-(3-CHLORO-5-FLUO-ROPHENOXY)BENZOYL]AMINO}ETHYL)BEN-ZOIC ACID

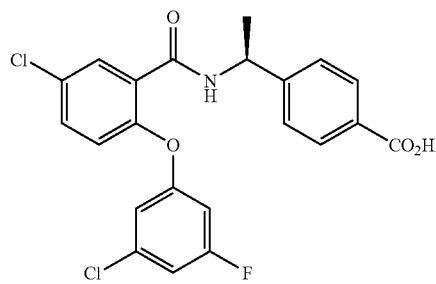

Step 1. Methyl 4-((1S)-1-{[5-chloro-2-(3-chloro-5-fluorophenoxy)benzoyl]amino}ethyl)benzoate The title compound was prepared according to the three steps procedure described in step 1 of Example 67, step 2 of Example 43, and step 3 of Example 1. Firstly, methyl 5-chloro-2-fluorobenzoate was reacted with 3-chloro-5-fluorophenol. Next, the crude product was hydrolyzed to the corresponding carboxylic acid. Finally, the carboxylic acid was condensed with methyl 4-[(1S)-1-aminoethyl]benzoate hydrochloride (step 3 of Example 5): $^1$H-NMR (CDCl$_3$) δ 8.12 (1H, d, J=2.8 Hz), 7.94 (2H, d, J=8.3 Hz), 7.43 (1H, dd, J=8.8, 2.8 Hz), 7.38 (1H, d, J=7.3 Hz), 7.28 (2H, d, J=8.4 Hz), 6.92 (1H, d, J=8.8 Hz), 6.93–6.86 (1H, m), 6.69 (1H, br.s), 6.53 (1H, td, J=9.4, 2.2 Hz), 5.36–5.19 (1H, m), 3.90 (3H, s), 1.49 (3H, d, J=7.0 Hz).

Step 2. 4-((1S)-1-{[5-Chloro-2-(3-chloro-5-fluorophenoxy)benzoyl]amino}ethyl)benzoic acid The title compound was prepared according to the procedure described in step 2 of Example 43 from methyl 4-((1S)-1-{[5-chloro-2-(3-chloro-5-fluorophenoxy)benzoyl]amino}ethyl)benzoate (step 1): $^1$H-NMR (CDCl$_3$) δ 8.14 (1H, d, J=2.8 Hz), 7.99 (2H, d, J=8.4 Hz), 7.44 (1H, dd, J=8.8, 2.8 Hz), 7.39 (1H, d, J=7.7 Hz), 7.31 (2H, d, J=8.4 Hz), 6.94 (1H, d, J=8.8 Hz), 6.94–6.88 (1H, m), 6.72–6.68 (1H, m), 6.53 (1H, td, J=9.4, 2.2 Hz), 5.34–5.23 (1H, m), 1.50 (3H, d, J=7.0 Hz); MS (ESI) m/z 448 (M+H)$^+$, 446 (M−H)$^−$.

Example 106

5-CHLORO-N-{(1S)-1-[4-({[(4-CHLOROPHE-NYL)SULFONYL]AMINO}CARBONYL)PHE-NYL]ETHYL}-2-(4-FLUOROPHENOXY)NICOTI-NAMIDE

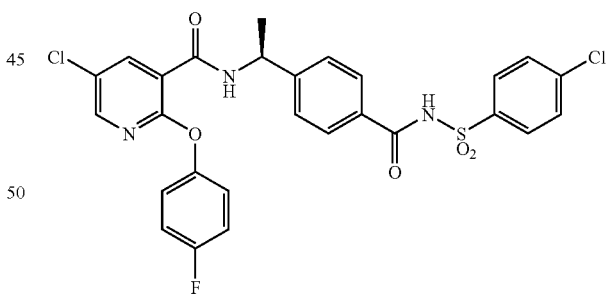

The title compound was prepared according to the procedure described in step 1 of Example 103 from 4-[(1S)-1-({[5-chloro-2-(4-fluorophenoxy)pyridin-3-yl]carbonyl}amino)ethyl]benzoic acid (step 5 of Example 44) and 4-chlorobenzenesulfonamide: $^1$H-NMR (CDCl$_3$) δ 8.51 (1H, d, J=2.6 Hz), 8.13 (1H, d, J=2.6 Hz), 8.16–8.03 (1H, m), 8.08 (2H, d, J=8.7 Hz), 7.75 (2H, d, J=8.2 Hz), 7.52 (2H, d, J=8.7 Hz), 7.43 (2H, d, J=8.2 Hz), 7.21–7.08 (4H, m), 5.39–5.24 (1H, m), 1.57 (3H, d, J=7.4 Hz); MS (ESI) m/z 588 (M+H)$^+$, 586 (M−H)$^−$.

Example 107

5-CHLORO-2-(4-FLUOROPHENOXY)-N-{(1S)-1-[4-({[(5-METHYLPYRIDIN-2-YL)SULFONYL]AMINO}CARBONYL)PHENYL]ETHYL}NICOTINAMIDE

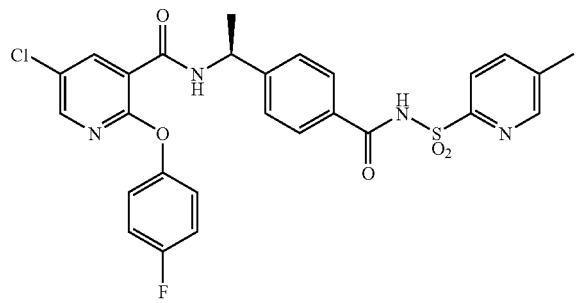

The title compound was prepared according to the procedure described in step 1 of Example 103 from 4-[(1S)-1-({[5-chloro-2-(4-fluorophenoxy)pyridin-3-yl]carbonyl}amino)ethyl]benzoic acid (step 5 of Example 44) and 5-methylpyridine-2-sulfonamide: $^{1}$H-NMR (DMSO-d$_{6}$) δ 8.95 (1H, d, J=8.6 Hz), 8.38 (1H, br.s), 8.26 (1H, d, J=2.6 Hz), 8.10 (1H, d, J=2.6 Hz), 7.92–7.70 (4H, m), 7.40 (2H, d, J=7.9 Hz), 7.30–7.23 (4H, m), 5.22–5.08 (1H, m), 2.34 (3H, s), 1.44 (3H, d, J=6.8 Hz); MS (ESI) m/z 569 (M+H)$^{+}$, 567 (M−H)$^{-}$.

Example 108

5-CHLORO-2-(4-FLUOROPHENOXY)-N-{(1S)-1-[4-({[(3-FLUOROPHENYL)SULFONYL]AMINO}CARBONYL)PHENYL]ETHYL}NICOTINAMIDE

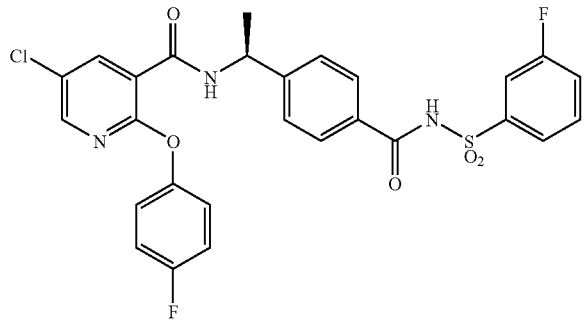

The title compound was prepared according to the procedure described in step 1 of Example 103 from 4-[(1S)-1-({[5-chloro-2-(4-fluorophenoxy)pyridin-3-yl]carbonyl}amino)ethyl]benzoic acid (step 5 of Example 44) and 3-fluorobenzenesulfonamide: $^{1}$H-NMR (CDCl$_{3}$) δ 8.86 (1H, br.s), 8.51 (1H, d, J=2.6 Hz), 8.13 (1H, d, J=2.6 Hz), 8.14–8.08 (1H, m), 7.98–7.91 (1H, m), 7.89–7.81 (1H, m), 7.73 (2H, d, J=8.3 Hz), 7.61–7.50 (1H, m), 7.42 (2H, d, J=8.3 Hz), 7.40–7.30 (1H, m), 7.21–7.08 (4H, m), 5.37–5.24 (1H, m), 1.57 (3H, d, J=6.8 Hz); MS (ESI) m/z 572 (M+H)$^{+}$, 570 (M−H)$^{-}$.

Example 109

5-CHLORO-2-(4-FLUOROPHENOXY)-N-{(1S)-1-[4-({[(3-METHYLPHENYL)SULFONYL]AMINO}CARBONYL)PHENYL]ETHYL}NICOTINAMIDE

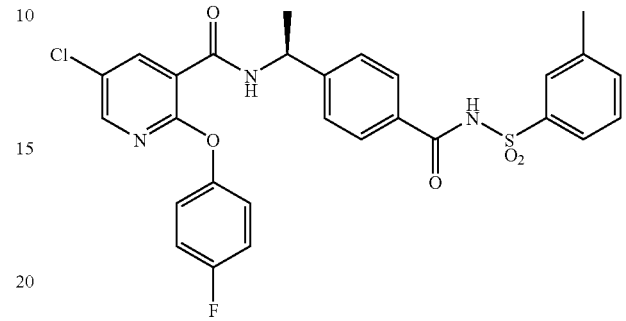

The title compound was prepared according to the procedure described in step 1 of Example 103 from 4-[(1S)-1-({[5-chloro-2-(4-fluorophenoxy)pyridin-3-yl]carbonyl}amino)ethyl]benzoic acid (step 5 of Example 44) and 3-methylbenzenesulfonamide: $^{1}$H-NMR (CDCl$_{3}$) δ 8.90 (1H, br.s), 8.51 (1H, d, J=2.6 Hz), 8.13 (1H, d, J=2.6 Hz), 8.09 (1H, d, J=7.2 Hz), 7.97–7.89 (2H, m), 7.74 (2H, d, J=8.3 Hz), 7.48–7.38 (4H, m), 7.20–7.05 (4H, m), 5.37–5.24 (1H, m), 2.44 (3H, s), 1.56 (3H, d, J=7.0 Hz); MS (ESI) m/z 568 (M+H)$^{+}$, 566 (M−H)$^{-}$.

Example 110

5-CHLORO-2-(4-FLUOROPHENOXY)-N-{(1S)-1-[4-({[(3-METHOXYPHENYL)SULFONYL]AMINO}CARBONYL)PHENYL]ETHYL}NICOTINAMIDE

The title compound was prepared according to the procedure described in step 1 of Example 103 from 4-[(1S)-1-({[5-chloro-2-(4-fluorophenoxy)pyridin-3-yl]carbonyl}amino)ethyl]benzoic acid (step 5 of Example 44) and 3-methoxybenzenesulfonamide: $^{1}$H-NMR (CDCl$_{3}$) δ 8.51 (1H, d, J=2.8 Hz), 8.13 (1H, d, J=2.8 Hz), 8.09 (1H, d, J=7.0 Hz), 7.73 (2H, d, J=8.4 Hz), 7.70–7.64 (2H, m), 7.49–7.39 (3H, m), 7.21–7.08 (5H, m), 5.37–5.25 (1H, m), 3.88 (3H, s), 1.56 (3H, d, J=6.8 Hz); MS (ESI) m/z 584 (M+H)$^{+}$, 582 (M−H)$^{-}$.

Example 111

5-CHLORO-N-[(1S)-1-(4-{[(CYCLOHEXYLSUL-FONYL)AMINO]CARBONYL}PHENYL)ETHYL]-2-(4-FLUOROPHENOXY)NICOTINA-MIDE

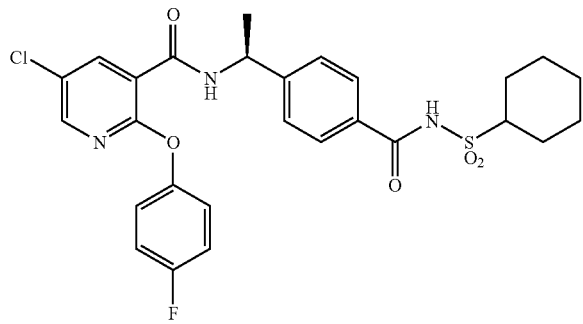

The title compound was prepared according to the procedure described in step 1 of Example 103 from 4-[(1S)-1-({[5-chloro-2-(4-fluorophenoxy)pyridin-3-yl]carbonyl}amino)ethyl]benzoic acid (step 5 of Example 44) and cyclohexanesulfonamide (*Helv. Chim. Acta* 1975, 58, 2321): $^1$H-NMR (CDCl$_3$) δ 8.53 (1H, d, J=2.6 Hz), 8.14 (1H, d, J=2.6 Hz), 8.15–8.08 (1H, m), 7.81 (2H, d, J=8.3 Hz), 7.49 (2H, d, J=8.3 Hz), 7.22–7.10 (4H, m), 5.42–5.30 (1H, m), 3.80–3.65 (1H, m), 2.26–2.16 (2H, m), 1.98–1.85 (2H, m), 1.78–1.50 (4H, m), 1.60 (3H, d, J=7.0 Hz), 1.43–1.15 (2H, m); MS (ESI) m/z 560 (M+H)$^+$, 558 (M−H)$^-$.

Example 112

4-((1S)-1-{[5-CHLORO-2-(3-FLUOROBENZYL)BENZOYL]AMINO}ETHYL)BENZOIC ACID

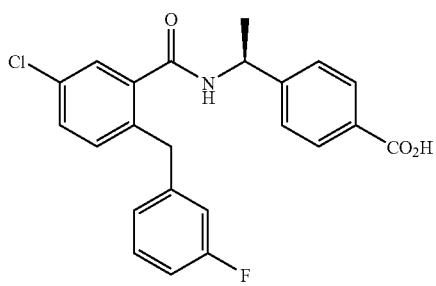

Step 1. Methyl 2-(bromomethyl)-5-chlorobenzoate

A mixture of methyl 5-chloro-2-methylbenzoate (3.13 g, 17.0 mmol), N-bromosuccinimide (3.17 g, 17.8 mmol), benzoyl peroxide (0.41 g, 1.70 mmol), and carbon tetrachloride (80 mL) was stirred at 80° C. for 16 h. After cooling to room temperature, the mixture was diluted with dichloromethane (200 mL) and washed with saturated sodium hydrogen carbonate aqueous (150 mL), and brine (150 mL). The organic layer was dried over magnesium sulfate, and concentrated under reduced pressure. The residue was purified by flush column chromatography on silica gel eluting with hexane/ethyl acetate (60:1) to afford 1.13 g (25%) of the title compounds as colorless oil: $^1$H-NMR (CDCl$_3$) δ 7.96 (1H, d, J=2.2 Hz), 7.46–7.40 (2H, m), 4.92 (2H, s), 3.96 (3H, s).

Step 2. Methyl 5-chloro-2-(3-fluorobenzyl)benzoate

A mixture of methyl 2-(bromomethyl)-5-chlorobenzoate (step 1, 300 mg, 1.14 mmol) and tetrakis(triphenylphosphine)palladium (0) (132 mg, 0.11 mmol) in 1,2-dimethoxyethane (6 mL) was stirred at 50° C. under nitrogen for 30 min. Then 3-fluorophenylboronic acid (191 mg, 1.37 mmol) and 2 M sodium carbonate solution (2.28 mL, 4.55 mmol) was added, and the resulting mixture was heated at 90° C. under nitrogen for 16 h. After cooling to room temperature, the mixture was diluted with ethyl acetate (50 mL) and washed with 1 M hydrochloric acid (30 mL), saturated sodium hydrogen carbonate aqueous (30 mL), and brine (30 mL). The organic layer was dried over magnesium sulfate, and evaporated in vacuo. The residue was purified by TLC [hexane/ethyl acetate (8:1)] to give 107 mg (34%) of the title compound as colorless oil: $^1$H-NMR (CDCl$_3$) δ 7.91 (1H, d, J=2.4 Hz), 7.41 (1H, dd, J=8.4, 2.4 Hz), 7.26–7.14 (2H, m), 6.91–6.79 (3H, m), 4.34 (2H, s), 3.84 (3H, s).

Step 3. 5-Chloro-2-(3-fluorobenzyl)benzoic acid

The title compound was prepared according to the procedure described in step 2 of Example 1 from methyl 5-chloro-2-(3-fluorobenzyl)benzoate (step 2): $^1$H-NMR (CDCl$_3$) δ 8.07 (1H, d, J=2.5 Hz), 7.47 (1H, dd, J=8.4, 2.5 Hz), 7.27–7.15 (2H, m), 6.92–6.80 (3H, m), 4.40 (3H, s).

Step 4. Methyl 4-((1S)-1-{[5-chloro-2-(3-fluorobenzyl)benzoyl]amino}ethyl)benzoate The title compound was prepared according to the procedure described in step 3 of Example 1 from 5-chloro-2-(3-fluorobenzyl)benzoic acid (step 3) and methyl 4-[(1S)-1-aminoethyl]benzoate hydrochloride (step 3 of Example 5): $^1$H-NMR (CDCl$_3$) δ 8.00–7.96 (2H, m), 7.36–7.14 (6H, m), 6.90–6.74 (3H, m), 5.93 (1H, d, J=7.3 Hz), 5.20 (1H, dq, J=7.3, 7.0 Hz), 4.12 (2H, s), 3.92 (3H, s), 1.44 (3H, d, J=7.0 Hz); MS (ESI) m/z 426 (M+H)$^+$, 424 (M−H)$^-$.

Step 5. 4-((1S)-1-{[5-Chloro-2-(3-fluorobenzyl)benzoyl]amino}ethyl)benzoic acid The title compound was prepared according to the procedure described in step 3 of Example 48 from methyl 4-((1S)-1-{[5-chloro-2-(3-fluorobenzyl)benzoyl]amino}ethyl)benzoate (step 4): $^1$H-NMR (DMSO-d$_6$) δ 9.02 (1H, d, J=8.1 Hz), 7.89 (2H, d, J=8.3 Hz), 7.49–7.20 (6H, m), 7.00–6.92 (3H, m), 5.11 (1H, dq, J=7.2, 7.2 Hz), 4.08 (1H, d, J=14.8 Hz), 4.02 (1H, d, J=14.8 Hz), 1.39 (3H, d, J=7.2 Hz); MS (ESI) m/z 412 (M+H)$^+$, 410 (M−H)$^-$.

Example 113

4-[(1S)-1-({[5-CHLORO-2-(3-METHYLPHENOXY)PYRIDIN-3-YL]CARBONYL}AMINO)ETHYL]BENZOIC ACID

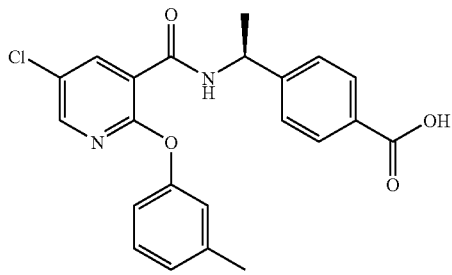

Step 1. tert-Butyl 4-[(1S)-1-({[5-chloro-2-(3-methylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and m-cresol: MS (ESI) m/z 467 (M+H)$^+$, 465 (M−H)$^−$.

Step 2. 4-[(1S)-1-({[5-Chloro-2-(3-methylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(3-methylphenoxy)pyridin-3-yl]carbonyl}amino)ethyl]benzoate (step 1): $^1$H-NMR (DMSO-d$_6$) δ 12.9 (1H, br.s), 9.00 (1H, d, J=7.8 Hz), 8.28 (1H, d, J=2.7 Hz), 8.11 (1H, d, J=2.7 Hz), 7.86 (2H, d, J=8.1 Hz), 7.52 (2H, d, J=8.1 Hz), 7.31 (1H, t, J=7.8 Hz), 7.10–6.90 (3H, m), 5.30–5.05 (1H, m), 2.32 (3H, s), 1.45 (3H, d, J=7.2 Hz); MS (ESI) m/z 411 (M+H)$^+$, 409 (M−H)$^−$.

Example 114

4-((1S)-1-{[5-CHLORO-2-(2,3-DIFLUOROPHENOXY)BENZOYL]AMINO}ETHYL)BENZOIC ACID

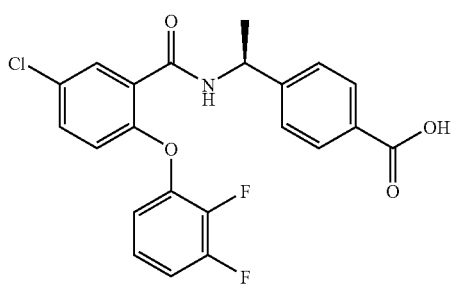

Step 1. Methyl 5-chloro-2-(2,3-difluorophenoxy)benzoate

The title compound was prepared according to the procedure described in step 1 of Example 67 from methyl 5-chloro-2-fluorobenzoate and 2,3-difluorophenol: $^1$H-NMR (CDCl$_3$) δ 7.94 (1H, d, J=2.6 Hz), 7.47 (1H, dd, J=8.7, 2.6 Hz), 7.05–6.86 (3H, m), 6.72–6.60 (1H, m), 3.85 (3H, s).

Step 2. 5-Chloro-2-(2,3-difluorophenoxy)benzoic acid

The title compound was prepared according to the procedure described in step 2 of Example 67 from methyl 5-chloro-2-(2,3-difluorophenoxy)benzoate (step 1): $^1$H-NMR (CDCl$_3$) δ 8.09 (1H, d, J=2.7 Hz), 7.47 (1H, dd, J=8.8, 2.7 Hz), 7.20–7.00 (2H, m), 6.95–6.70 (2H, m).

Step 3. Methyl 4-((1S)-1-{[5-chloro-2-(2,3-difluorophenoxy)benzoyl]amino}ethyl)benzoate The title compound was prepared according to the procedure described in step 3 of Example 1 from methyl 4-[(1S)-1-aminoethyl]benzoate hydrochloride (step 3 of Example 5) and 5-chloro-2-(2,3-difluorophenoxy)benzoic acid (step 2): $^1$H-NMR (CDCl$_3$) δ 8.15 (1H, d, J=2.6 Hz), 7.96 (2H, d, J=8.4 Hz), 7.62 (1H, d, J=7.4 Hz), 7.44–7.31 (3H, m), 7.14–7.00 (2H, m), 6.85 (1H, d, J=8.7 Hz), 6.81–6.68 (1H, m), 5.33 (1H, dq, J=7.4, 7.1 Hz), 3.90 (3H, s), 1.51 (3H, d, J=7.1 Hz); MS (ESI) m/z 446 (M+H)$^+$, 444 (M−H)$^−$.

Step 4. 4-((1S)-1-{[5-Chloro-2-(2,3-difluorophenoxy)benzoyl]amino}ethyl)benzoic acid The title compound was prepared according to the procedure described in step 4 of Example 1 from methyl 4-((1S)-1-{[5-chloro-2-(2,3-difluorophenoxy)benzoyl]amino}ethyl)benzoate (step 3): $^1$H-NMR (DMSO-d$_6$) δ 8.96 (1H, d, J=8.1 Hz), 7.81 (2H, d, J=8.4 Hz), 7.59 (1H, d, J=2.6 Hz), 7.54 (1H, dd, J=8.1, 2.6 Hz), 7.39 (2H, d, J=8.4 Hz), 7.26–7.06 (3H, m), 6.85–6.72 (1H, m), 5.12–4.94 (1H, m), 1.36 (3H, d, J=7.1 Hz); MS (ESI) m/z 432 (M+H)$^+$, 430 (M−H)$^−$.

Example 115

4-((1S)-1-{[5-CHLORO-2-(2,4-DIFLUOROPHENOXY)BENZOYL]AMINO}ETHYL)BENZOIC ACID

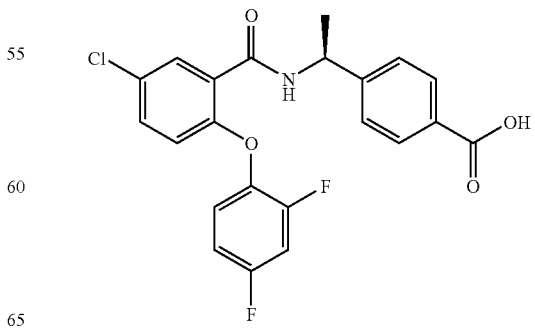

Step 1. Methyl 5-chloro-2-(2,4-difluorophenoxy)benzoate

The title compound was prepared according to the procedure described in step 1 of Example 67 from methyl 5-chloro-2-fluorobenzoate and 2,4-difluorophenol: $^1$H-NMR (CDCl$_3$) δ 7.90 (1H, d, J=2.8 Hz), 7.39 (1H, dd, J=8.8, 2.8 Hz), 7.05–6.91 (2H, m), 6.89–6.80 (1H, m), 6.80 (1H, d, J=8.8 Hz), 3.85 (3H, s).

Step 2. 5-Chloro-2-(2,4-difluorophenoxy)benzoic acid

The title compound was prepared according to the procedure described in step 2 of Example 67 from methyl 5-chloro-2-(2,4-difluorophenoxy)benzoate (step 1): $^1$H-NMR (CDCl$_3$) δ8.11 (1H, d, J=2.8 Hz), 7.43 (1H, dd, J=8.9, 2.8 Hz), 7.18–7.07 (1H, m), 7.06–6.86 (2H, m), 6.75 (1H, d, J=8.9 Hz).

Step 3. Methyl 4-((1S)-1-{[5-chloro-2-(2,4-difluorophenoxy)benzoyl]amino}ethyl)benzoate The title compound was prepared according to the procedure described in step 3 of Example 1 from methyl 4-[(1S)-1-aminoethyl]benzoate hydrochloride (step 3 of Example 5) and 5-chloro-2-(2,4-difluorophenoxy)benzoic acid (step 2): $^1$H-NMR (CDCl$_3$) δ 8.16 (1H, d, J=2.6 Hz), 7.98 (2H, d, J=8.1 Hz), 7.80–7.70 (1H, m), 7.39 (2H, d, J=8.1 Hz), 7.34 (1H, dd, J=8.9, 2.6 Hz), 7.14–6.87 (3H, m), 6.73 (1H, d, J=8.9 Hz), 5.45–5.27 (1H, m), 3.90 (3H, s), 1.55 (3H, d, J=6.9 Hz); MS (ESI) m/z 446 (M+H)$^+$, 444 (M–H)$^-$.

Step 4. 4-((1S)-1-{[5-Chloro-2-(2,4-difluorophenoxy)benzoyl]amino}ethyl)benzoic acid The title compound was prepared according to the procedure described in step 4 of Example 1 from methyl 4-((1S)-1-{[5-chloro-2-(2,4-difluorophenoxy)benzoyl]amino}ethyl)benzoate (step 3): $^1$H-NMR (DMSO-d$_6$) δ 8.93 (1H, d, J=7.9 Hz), 7.83 (2H, d, J=8.2 Hz), 7.53–7.38 (5H, m), 7.26–7.03 (2H, m), 6.92 (1H, d, J=8.6 Hz), 5.17–5.00 (1H, m), 1.39 (3H, d, J=6.9 Hz); MS (ESI) m/z 432 (M+H)$^+$, 430 (M–H)$^-$.

Example 116

4-((1S)-1-{[5-CHLORO-2-(3,4-DIFLUOROPHENOXY)BENZOYL]AMINO}ETHYL)BENZOIC ACID

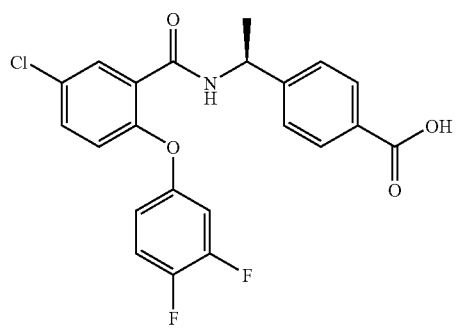

Step 1. Methyl 5-chloro-2-(3,4-difluorophenoxy)benzoate

The title compound was prepared according to the procedure described in step 1 of Example 67 from methyl 5-chloro-2-fluorobenzoate and 3,4-difluorophenol: $^1$H-NMR (CDCl$_3$) δ 7.92 (1H, d, J=2.8 Hz), 7.46 (1H, dd, J=8.7, 2.8 Hz), 7.11 (1H, q, J=9.1 Hz), 6.95 (1H, d, J=8.7 Hz), 6.85–6.72 (1H, m), 6.71–6.59 (1H, m), 3.83 (3H, s).

Step 2. 5-Chloro-2-(3,4-difluorophenoxy)benzoic acid

The title compound was prepared according to the procedure described in step 2 of Example 67 from methyl 5-chloro-2-(3,4-difluorophenoxy)benzoate (step 1): $^1$H-NMR (CDCl$_3$) δ 8.09 (1H, d, J=2.8 Hz), 7.49 (1H, ddt, J=8.7, 2.8, 0.7 Hz), 7.17 (1H, q, J=9.2 Hz), 6.97–6.85 (2H, m), 6.80–6.70 (1H, m).

Step 3. Methyl 4-((1S)-1-{[5-chloro-2-(3.4-difluorophenoxy)benzoyl]amino}ethyl)benzoate The title compound was prepared according to the procedure described in step 3 of Example 1 from methyl 4-[(1S)-1-aminoethyl]benzoate hydrochloride (step 3 of Example 5) and 5-chloro-2-(3,4-difluorophenoxy)benzoic acid (step 2): $^1$H-NMR (CDCl$_3$) δ 8.16 (1H, d, J=2.8 Hz), 7.98–7.93 (2H, m), 7.60 (1H, d, J=7.4 Hz), 7.49 (1H, dd, J=8.7, 2.8 Hz), 7.35–7.29 (2H, m), 7.14 (1H, q, J=8.9 Hz), 6.88–6.78 (2H, m), 6.73–6.66 (1H, m), 5.31 (1H, dq, J=7.4, 6.9 Hz), 3.91 (3H, s), 1.51 (3H, d, J=6.9 Hz); MS (ESI) m/z 446 (M+H)$^+$, 444 (M–H)$^-$.

Step 4. 4-((1S)-1-{[5-Chloro-2-(3,4-difluorophenoxy)benzoyl]amino}ethyl)benzoic acid The title compound was prepared according to the procedure described in step 4 of Example 1 from methyl 4-((1S)-1-{[5-chloro-2-(3,4-difluorophenoxy)benzoyl]amino}ethyl)benzoate (step 3): $^1$H-NMR (DMSO-d$_6$) δ 8.88 (1H, d, J=7.6 Hz), 7.81 (2H, d, J=8.1 Hz), 7.58 (1H, d, J=2.8 Hz), 7.53 (1H, dd, J=8.7, 2.8 Hz), 7.48–7.32 (3H, m), 7.17–7.03 (2H, m), 6.85–6.75 (1H, m), 5.13–4.93 (1H, m), 1.36 (3H, d, J=7.1 Hz); MS (ESI) m/z 432 (M+H)$^+$, 430 (M–H)$^-$.

Example 117

4-[(1S)-1-({[5-CHLORO-2-(3-CHLORO-5-FLUOROPHENOXY)PYRIDIN-3-YL]CARBONYL}AMINO)ETHYL]BENZOIC ACID

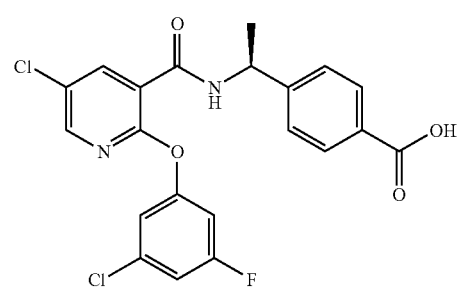

Step 1. tert-Butyl 4-[(1S)-1-({[5-chloro-2-(3-chloro-5-fluorophenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 3-chloro-5-fluorophenol: $^1$H-NMR (CDCl$_3$) δ 8.55 (1H, d, J=2.6 Hz), 8.17 (1H, d, J=2.6 Hz), 7.97 (2H, d, J=8.4 Hz), 7.88–7.80 (1H, m), 7.40 (2H, d, J=8.4 Hz), 7.10–7.02 (1H, m), 7.00–6.94 (1H, m), 6.87–6.80 (1H, m), 5.43–5.27 (1H, m), 1.68–1.55 (12H, m); MS (ESI) m/z 505 (M+H)$^+$, 503 (M–H)$^-$.

Step 2. 4-[(1S)-1-({[5-Chloro-2-(3-chloro-5-fluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(3-chloro-5-fluorophenoxy)pyridin-3-yl]carbonyl}amino)ethyl]benzoate (step 1): $^1$H-NMR (DMSO-d$_6$) δ 9.01 (1H, d, J=7.7 Hz), 8.33 (1H, d, J=2.6 Hz), 8.15 (1H, d, J=2.6 Hz), 7.85 (2H, d, J=8.1 Hz), 7.49 (2H, d, J=8.1 Hz), 7.38–7.26 (1H, m), 7.25–7.11 (2H, m), 5.23–5.06 (1H, m), 1.43 (3H, d, J=7.3 Hz); MS (ESI) m/z 449 (M+H)$^+$, 447 (M–H)$^-$.

Example 118

4-((1S)-1-{[5-CHLORO-2-(3,5-DIFLUOROPHENOXY)BENZOYL]AMINO}ETHYL)BENZOIC ACID

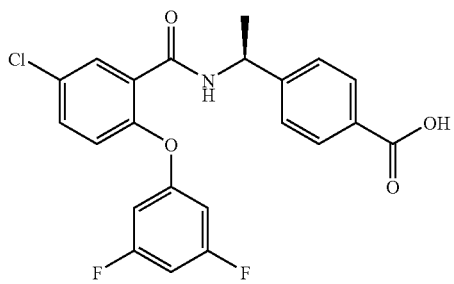

Step 1. Methyl 5-chloro-2-(3,5-difluorophenoxy)benzoate

The title compound was prepared according to the procedure described in step 1 of Example 67 from methyl 5-chloro-2-fluorobenzoate and 3,5-difluorophenol: $^1$H-NMR (CDCl$_3$) δ 8.00–7.90 (1H, m), 7.55–7.47 (1H, m), 7.08–7.00 (1H, m), 6.60–6.35 (3H, m), 3.81 (3H, s).

Step 2. 5-Chloro-2-(3,5-difluorophenoxy)benzoic acid

The title compound was prepared according to the procedure described in step 2 of Example 67 from methyl 5-chloro-2-(3,5-difluorophenoxy)benzoate (step 1): $^1$H-NMR (CDCl$_3$) δ 8.09 (1H, d, J=2.8 Hz), 7.55 (1H, dd, J=8.8, 2.8 Hz), 7.04 (1H, d, J=8.8 Hz), 6.65–6.40 (3H, m).

Step 3. Methyl 4-((1S)-1-{[5-chloro-2-(3,5-difluorophenoxy)benzoyl]amino}ethyl)benzoate The title compound was prepared according to the procedure described in step 3 of Example 1 from methyl 4-[(1S)-1-aminoethyl]benzoate hydrochloride (step 3 of Example 5) and 5-chloro-2-(3,5-difluorophenoxy)benzoic acid (step 2): $^1$H-NMR (CDCl$_3$) δ 8.14 (1H, d, J=2.8 Hz), 7.94 (2H, d, J=8.4 Hz), 7.45 (1H, dd, J=8.8, 2.8 Hz), 7.37 (1H, d, J=7.9 Hz), 7.28 (2H, d, J=8.4 Hz), 6.95 (1H, d, J=8.8 Hz), 6.58–6.68 (1H, m), 6.48–6.38 (2H, m), 5.31 (1H, dq, J=7.9, 7.0 Hz), 3.91 (3H, s), 1.49 (3H, d, J=7.0 Hz); MS (ESI) m/z 446 (M+H)$^+$, 444 (M–H)$^-$.

Step 4. 4-((1S)-1-{[5-Chloro-2-(3,5-difluorophenoxy)benzoyl]amino}ethyl)benzoic acid The title compound was prepared according to the procedure described in step 4 of Example 1 from methyl 4-((1S)-1-{[5-chloro-2-(3,5-difluorophenoxy)benzoyl]amino}ethyl)benzoate (step 3): $^1$H-NMR (DMSO-d$_6$) δ 12.9 (1H, br.s), 8.89 (1H, d, J=7.7 Hz), 7.82 (2H, d, J=8.2 Hz), 7.68–7.55 (2H, m), 7.37 (2H, d, J=8.2 Hz), 7.21 (1H, d, J=8.6 Hz), 7.00–6.90 (1H, m), 6.70–6.58 (2H, m), 5.04 (1H, dq, J=7.7, 6.9 Hz), 1.35 (3H, d, J=6.9 Hz); MS (ESI) m/z 432 (M+H)$^+$, 430 (M–H)$^-$.

Example 119

4-((1S)-1-{[5-CHLORO-2-(3-METHYLPHENOXY)BENZOYL]AMINO}ETHYL)BENZOIC ACID

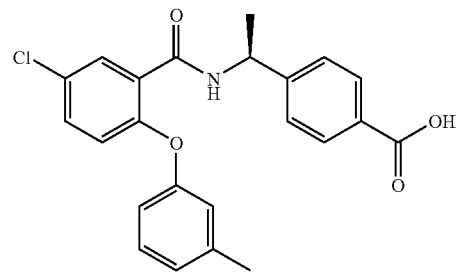

Step 1. Methyl 5-chloro-2-(3-methylphenoxy)benzoate

The title compound was prepared according to the procedure described in step 1 of Example 67 from methyl 5-chloro-2-fluorobenzoate and m-cresol: $^1$H-NMR (CDCl$_3$) δ 7.89 (1H, d, J=2.8 Hz), 7.40 (1H, dd, J=8.8, 2.8 Hz), 7.21 (1H, t, J=7.9 Hz), 6.96–6.87 (2H, m), 6.81–6.72 (2H, m), 3.83 (3H, s), 2.83 (3H, s).

Step 2. 5-Chloro-2-(3-methylphenoxy)benzoic acid

The title compound was prepared according to the procedure described in step 2 of Example 67 from methyl 5-chloro-2-(3-methylphenoxy)benzoate (step 1): $^1$H-NMR (CDCl$_3$) δ 8.15 (1H, d, J=2.8 Hz), 7.42 (1H, dd, J=9.0, 2.8 Hz), 7.31 (1H, t, J=7.9 Hz), 7.10–7.02 (1H, m), 6.93–6.85 (2H, m), 6.83 (1H, d, J=9.0 Hz), 2.37 (3H, s).

Step 3. Methyl 4-((1S)-1-{[5-chloro-2-(3-methylphenoxy)benzoyl]amino}ethyl)benzoate The title compound was prepared according to the procedure described in step 3 of Example 1 from methyl 4-[(1S)-1-aminoethyl]benzoate hydrochloride (step 3 of Example 5) and 5-chloro-2-(3-methylphenoxy)benzoic acid (step 2): $^1$H-NMR (CDCl$_3$) δ 8.18 (1H, d, J=2.6 Hz), 8.00–7.86 (3H, m), 7.40–7.20 (4H, m), 7.07–6.98 (1H, m), 6.98–6.74 (3H, m), 5.38–5.20 (1H, m), 3.88 (3H, s), 2.33 (3H, s), 1.48 (3H, d, J=6.9 Hz); MS (ESI) m/z 424 (M+H)$^+$, 422 (M–H)$^-$.

Step 4. 4-((1S)-1-{[5-Chloro-2-(3-methylphenoxy)benzoyl]amino}ethyl)benzoic acid The title compound was prepared according to the procedure described in step 4 of Example 1 from methyl 4-((1S)-1-{[5-chloro-2-(3-methylphenoxy)benzoyl]amino}ethyl)benzoate (step 3): $^1$H-NMR (DMSO-d$_6$) δ 8.84 (1H, d, J=7.7 Hz), 7.79 (2H, d, J=8.4 Hz), 7.57 (1H, d, J=2.8 Hz), 7.49 (1H, dd, J=8.6, 2.8 Hz), 7.38 (2H, d, J=8.4 Hz), 7.24 (1H, t, J=7.7 Hz), 7.02–6.90 (2H, m), 6.83–6.72 (2H, m), 5.11–4.96 (1H, m), 2.25 (3H, s), 1.35 (3H, d, J=7.0 Hz); MS (ESI) m/z 410 (M+H)$^+$, 408 (M–H)$^-$.

Example 120

4-((1S)-1-{[5-CHLORO-2-(2,6-DIFLUOROPHENOXY)BENZOYL]AMINO}ETHYL)BENZOIC ACID

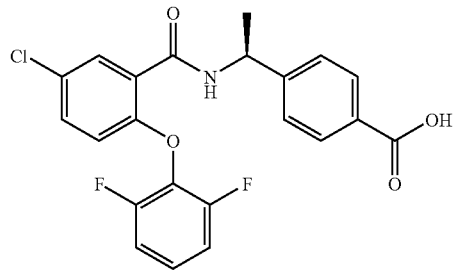

Step 1. Methyl 2-(2,6-difluorophenoxy)-5-nitrobenzoate

The title compound was prepared according to the procedure described in step 1 of Example 67 from methyl 2-fluoro-5-nitrobenzoate (*J. Org. Chem.* 1990, 55, 2034.) and 2,6-difluorophenol: $^1$H-NMR (CDCl$_3$) δ 8.83 (1H, d, J=2.8 Hz), 8.25 (1H, dd, J=9.2, 2.8 Hz), 7.32–7.20 (1H, m), 7.12–7.02 (2H, m), 6.82 (1H, d, J=9.2 Hz), 3.98 (3H, s); MS (ESI) m/z 310 (M+H)$^+$.

Step 2. Methyl 5-amino-2-(2,6-difluorophenoxy)benzoate

A suspension of methyl 2-(2,6-difluorophenoxy)-5-nitrobenzoate (step 1, 365 mg, 1.18 mmol) and 5% Pd/C (37 mg) in methanol (10 mL) was stirred under hydrogen atmosphere for 16 h at room temperature. After filtration through a pad of Celite®, the filtrate was concentrated. The residue was purified by column chromatography on silica gel eluting with hexane/ethyl acetate (5/1 to 1/2) to afford 325 mg of the title compound: $^1$H-NMR (CDCl$_3$) δ 7.21 (1H, d, J=2.9 Hz), 7.12–6.88 (3H, m), 6.77 (1H, dd, J=8.8, 2.9 Hz), 6.64–6.58 (1H, m), 3.87 (3H, s).

Step 3. 5-Amino-2-(2,6-difluorophenoxy)benzoic acid

The title compound was prepared according to the procedure described in step 2 of Example 67 from methyl 5-amino-2-(2,6-difluorophenoxy)benzoate (step 2): $^1$H-NMR (CDCl$_3$) δ 7.25–7.12 (3H, m), 6.99 (1H, d, J=2.8 Hz), 6.63 (1H, dd, J=8.4, 2.8 Hz), 6.50 (1H, d, J=8.4 Hz).

Step 4. 5-Chloro-2-(2,6-difluorophenoxy)benzoic acid

To a solution of methyl 5-amino-2-(2,6-difluorophenoxy)benzoic acid (step 3, 234 mg, 0.88 mmol) in 6 N hydrochloric acid (2.6 mL) was added a solution of sodium nitrite (74 mg, 1.07 mmol) in water (0.5 mL) at 0° C. for 15 min. The mixture was added to a slurry of copper chloride (120 mg) in concentrated hydrochloric acid (1.2 mL). The mixture was stirred for 1 day at room temperature. The mixture was extracted with dichloromethane. The organic layer was purified by column chromatography on silica gel eluting with dichloromethane/methanol (10/1) to afford 210 mg (84%) of the title compound as white solids: $^1$H-NMR (CDCl$_3$) δ 7.77 (1H, d, J=2.7 Hz), 7.51 (1H, dd, J=9.0, 2.7 Hz), 7.40–7.20 (3H, m), 6.80 (1H, d, J=9.0 Hz).

Step 5. Methyl 4-((1S)-1-{[5-chloro-2-(2,6-difluorophenoxy)benzoyl]amino}ethyl)benzoate The title compound was prepared according to the procedure described in step 3 of Example 1 from methyl 4-[(1S)-1-aminoethyl]benzoate hydrochloride (step 3 of Example 5) and 5-chloro-2-(2,6-difluorophenoxy)benzoic acid (step 4): $^1$H-NMR (CDCl$_3$) δ 8.16 (1H, d, J=2.8 Hz), 8.00 (2H, d, J=8.4 Hz), 7.83–7.74 (1H, m), 7.45 (2H, d, J=8.4 Hz), 7.35–7.23 (2H, m), 7.16–7.04 (2H, m), 6.67–6.61 (1H, m), 5.48–5.33 (1H, m), 3.90 (3H, s), 1.59 (3H, d, J=7.0 Hz)); MS (ESI) m/z 446 (M+H)$^+$.

Step 6. 4-((1S)-1-{[5-Chloro-2-(2,6-difluorophenoxy)benzoyl]amino}ethyl)benzoic acid The title compound was prepared according to the procedure described in step 4 of Example 1 from methyl 4-((1S)-1-{[5-chloro-2-(2,6-difluorophenoxy)benzoyl]amino}ethyl)benzoate (step 5): $^1$H-NMR (DMSO-d$_6$) δ 12.8 (1H, br.s), 8.97 (1H, d, J=8.2 Hz), 7.88 (2H, d, J=8.2 Hz), 7.59 (1H, d, J=2.8 Hz), 7.52 (2H, d, J=8.2 Hz), 7.45 (1H, dd, J=8.9, 2.8 Hz), 7.42–7.25 (3H, m), 6.82 (1H, d, J=8.9 Hz), 5.23–5.05 (1H, m), 1.45 (3H, d, J=7.1 Hz); MS (ESI) m/z 432 (M+H)$^+$, 430 (M–H)$^-$.

Example 121

4-[(1S)-1-({[5-CHLORO-2-(2,3-DIFLUOROPHE-NOXY)PYRIDIN-3-YL]CARBONYL}AMINO)ETHYL]BENZOIC ACID

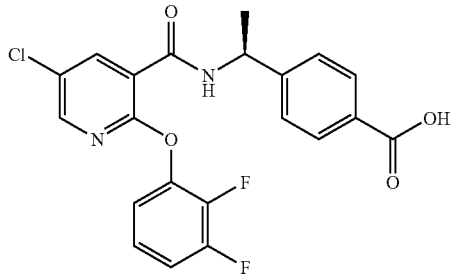

Step 1. tert-Butyl 4-[(1S)-1-({[5-chloro-2-(2,3-difluorophenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 2,3-difluorophenol: $^1$H-NMR (CDCl$_3$) δ 8.54 (1H, d, J=2.7 Hz), 8.11 (1H, d, J=2.7 Hz), 7.98–7.92 (3H, m), 7.43–7.40 (2H, m), 7.23–7.07 (3H, m), 5.43–5.32 (1H, m), 1.61–1.56 (12H, m); MS (ESI) m/z 489 (M+H)$^+$, 487 (M−H)$^−$.

Step 2. 4-[(1S)-1-({[5-Chloro-2-(2,3-difluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(2,3-difluorophenoxy)pyridin-3-yl]carbonyl}amino)ethyl]benzoate (step 1): $^1$H-NMR (CDCl$_3$) δ 8.55 (1H, d, J=2.4 Hz), 8.12 (1H, d, J=2.4 Hz), 8.09–8.06 (2H, m), 7.99–7.97 (1H, m), 7.49–7.46 (2H, m), 7.21–7.09 (3H, m), 5.44–5.34 (1H, m), 1.62 (3H, d, J=7.0 Hz), a peak of COOH was not observed; MS (ESI) m/z 433 (M+H)$^+$, 431 (M−H)$^−$.

Example 122

4-[(1S)-1-({[5-CHLORO-2-(2,5-DIFLUOROPHE-NOXY)PYRIDIN-3-YL]CARBONYL}AMINO)ETHYL]BENZOIC ACID

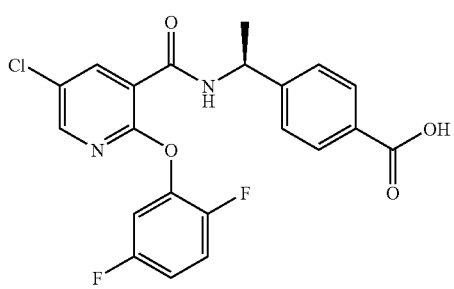

Step 1. tert-Butyl 4-[(1S)-1-({[5-chloro-2-(2,5-difluorophenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 2,5-difluorophenol: $^1$H-NMR (CDCl$_3$) δ 8.54 (1H, d, J=2.6 Hz), 8.12 (1H, d, J=2.6 Hz), 8.00–7.87 (3H, m), 7.43–7.37 (2H, m), 7.25–7.11 (2H, m), 7.05–6.96 (1H, m), 5.42–5.32 (1H, m), 1.61–1.58 (12H, m); MS (ESI) m/z 489 (M+H)$^+$, 487 (M−H)$^−$.

Step 2. 4-[(1S)-1-({[5-Chloro-2-(2,5-difluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(2,5-difluorophenoxy)pyridin-3-yl]carbonyl}amino)ethyl]benzoate (step 1): $^1$H-NMR (CDCl$_3$) δ 8.55 (1H, d, J=2.6 Hz), 8.14 (1H, d, J=2.6 Hz), 8.09–8.06 (2H, m), 8.00–7.98 (1H, m), 7.49–7.46 (2H, m), 7.29–6.97 (3H, m), 5.43–5.34 (1H, m), 1.62 (3H, d, J=6.9 Hz), a peak of COOH was not observed; MS (ESI) m/z 433 (M+H)$^+$, 431 (M−H)$^−$.

Example 123

4-[(1S)-1-({[5-CHLORO-2-(4-CHLORO-2-FLUOROPHENOXY)PYRIDIN-3-YL]CARBONYL}AMINO)ETHYL]BENZOIC ACID

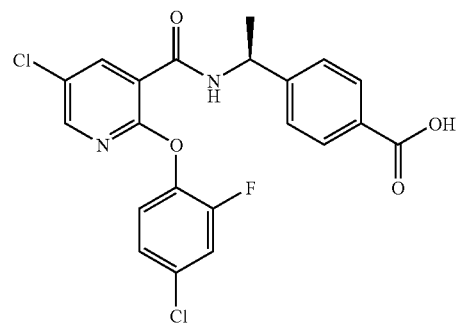

Step 1. tert-Butyl 4-[(1S)-1-({[5-chloro-2-(4-chloro-2-fluorophenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 4-chloro-2-fluorophenol: $^1$H-NMR (CDCl$_3$) δ 8.53 (1H, d, J=2.7 Hz), 8.10 (1H, d, J=2.7 Hz), 7.97–7.94 (3H, m), 7.42–7.39 (2H, m), 7.31–7.21 (3H, m), 5.37 (1H, quint, J=7.0 Hz), 1.61–1.58 (12H, m); MS (ESI) m/z 505 (M+H)$^+$, 503 (M−H)$^−$.

Step 2. 4-[(1S)-1-({[5-Chloro-2-(4-chloro-2-fluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-chloro-2-fluorophenoxy)pyridin-3-yl]carbonyl}amino)ethyl]benzoate (step 1): $^1$H-NMR (CDCl$_3$) δ 9.08–9.06 (1H, m), 8.27 (1H, d, J=2.6 Hz), 8.15 (1H, d, J=2.6 Hz), 7.88–7.85 (2H, m), 7.63 (1H, dd, J=10.5, 2.4 Hz), 7.53–7.34 (4H, m), 5.21–5.11 (1H, m), 1.45 (3H, d, J=7.0 Hz), a peak of COOH was not observed; MS (ESI) m/z 449 (M+H)$^+$, 447 (M–H)$^-$.

Example 124

4-[(1S)-1-({[5-CHLORO-2-(2-CHLORO-5-FLUOROPHENOXY)PYRIDIN-3-YL]CARBONYL}AMINO)ETHYL]BENZOIC ACID

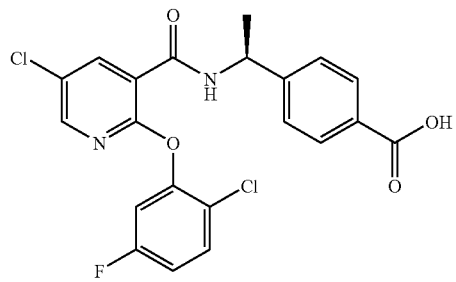

Step 1. tert-Butyl 4-[(1S)-1-({[5-chloro-2-(2-chloro-5-fluorophenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 2-chloro-5-fluorophenol: $^1$H-NMR (CDCl$_3$) δ 8.55 (1H, d, J=2.7 Hz), 8.11 (1H, d, J=2.7 Hz), 8.06–8.04 (1H, m), 7.97–7.94 (2H, m), 7.51–7.45 (1H, m), 7.43–7.40 (2H, m), 7.12–7.00 (2H, m), 5.43–5.32 (1H, m), 1.61–1.58 (12H, m); MS (ESI) m/z 505 (M+H)$^+$, 503 (M–H)$^-$.

Step 2. 4-[(1S)-1-({[5-Chloro-2-(2-chloro-5-fluorophenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(2-chloro-5-fluorophenoxy)pyridin-3-yl]carbonyl}amino)ethyl]benzoate (step 1): $^1$H-NMR (CDCl$_3$) δ 8.98 (1H, d, J=7.8 Hz), 8.29 (1H, d, J=2.7 Hz), 8.18 (1H, d, J=2.7 Hz), 7.87–7.85 (2H, m), 7.64 (1H, dd, J=9.2, 5.9 Hz), 7.53–7.50 (2H, m), 7.40 (1H, dd, J=9.2, 3.0 Hz), 7.24–7.17 (1H, m), 5.22–5.13 (1H, m), 1.45 (3H, d, J=6.9 Hz), a peak of COOH was not observed; MS (ESI) m/z 449 (M+H)$^+$, 447 (M–H)$^-$.

Example 125

4-{(1S)-1-[({5-CHLORO-2-[3-(METHYLTHIO)PHENOXY]PYRIDIN-3-YL}CARBONYL)AMINO]ETHYL}BENZOIC ACID

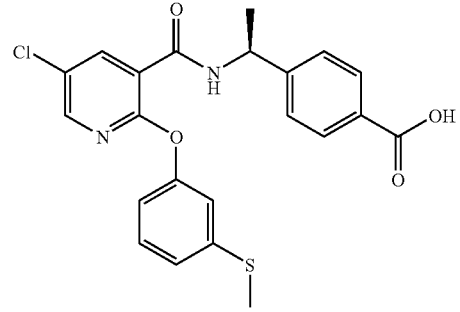

Step 1. tert-Butyl 4-{(1S)-1-[({5-chloro-2-[3-(methylthio)phenoxy]pyridin-3-yl}carbonyl)amino]ethyl}benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 3-(methylthio)phenol (J. Amer. Chem. Soc. 1957, 79, 717): $^1$H-NMR (CDCl$_3$) δ 8.55 (1H, d, J=2.7 Hz), 8.15 (1H, d, J=2.7 Hz), 8.13–8.10 (1H, m), 7.97–7.94 (2H, m), 7.41–7.34 (3H, m), 7.20–7.16 (1H, m), 7.03–7.01 (1H, m), 6.93–6.89 (1H, m), 5.41–5.31 (1H, m), 2.50 (3H, s), 1.60–1.57 (12H, m); MS (ESI) m/z 499 (M+H)$^+$, 497 (M–H)$^-$.

Step 2. 4-[(1S)-1-[({5-Chloro-2-[3-(methylthio)phenoxy]pyridin-3-yl]carbonyl)amino]ethyl}benzoic acid The title compound was prepared according to the procedure described in step 5 of Example 44 from tert-butyl 4-{(1S)-1-[({5-chloro-2-[3-(methylthio)phenoxy]pyridin-3-yl}carbonyl)amino]ethyl}benzoate (step 1): $^1$H-NMR (CDCl$_3$) δ 8.55 (1H, d, J=2.7 Hz), 8.16–8.13 (2H, m), 8.08–8.05 (2H, m), 7.47–7.44 (2H, m), 7.38 (1H, t, J=8.0 Hz), 7.21–7.17 (1H, m), 7.04–7.03 (1H, m), 6.93–6.89 (1H, m), 5.43–5.33 (1H, m), 2.50 (3H, s), 1.60 (3H, d, J=7.0 Hz), a peak of COOH was not observed; MS (ESI) m/z 443 (M+H)$^+$, 441 (M–H)$^-$.

Example 126

4-[(1S)-1-({[5-CHLORO-2-(3-CHLORO-2-FLUOROPHENOXY)PYRIDIN-3-YL]CARBONYL}AMINO)ETHYL]BENZOIC ACID

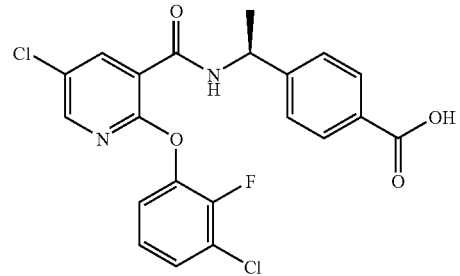

Step 1. Methyl 4-[(1S)-1-({[5-chloro-2-(3-chloro-2-fluorophenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-chloro-2-fluorophenol: $^1$H-NMR (CDCl$_3$) δ 8.55 (1H, d, J=2.7 Hz), 8.11 (1H, d, J=2.7 Hz), 8.03–8.00 (2H, m), 7.96–7.93 (1H, m), 7.45–7.35 (3H, m), 7.27–7.15 (2H, m), 5.43–5.35 (1H, m), 3.90 (3H, s), 1.61 (3H, d, J=7.0 Hz); MS (ESI) m/z 463 (M+H)$^+$, 461 (M–H)$^-$.

Step 2. 4-[(S)-1-({[5-Chloro-2-(3-chloro-2-fluorophenoxy)pyridin-3-yl]carbonyl}amino)ethyl]benzoic acid The title compound was prepared according to the procedure described in step 2 of Example 83 from methyl 4-[(1S)-1-({[5-chloro-2-(3-chloro-2-fluorophenoxy)pyridin-3-yl]carbonyl}amino)ethyl]benzoate: $^1$H-NMR (CDCl$_3$) δ 8.55 (1H, d, J=2.7 Hz), 8.12 (1H, d, J=2.7 Hz), 8.09–8.06 (2H, m), 8.00–7.96 (1H, m), 7.49–7.46 (2H, m), 7.41–7.35 (1H, m), 7.31–7.15 (2H, m), 5.45–5.34 (1H, m), 1.62 (3H, d, J=6.8 Hz), a peak of COOH was not observed; MS (ESI) m/z 449 (M+H)$^+$, 447 (M–H)$^-$.

Example 127

4-{(1S)-1-[({5-CHLORO-2-[3-(1-METHYL-1H-IMIDAZOL-2-YL)PHENOXY]PYRIDIN-3-YL}CARBONYL)AMINO]ETHYL}BENZOIC ACID

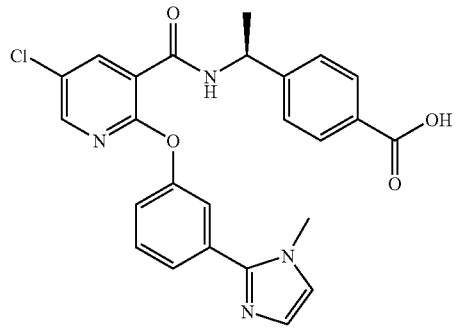

Step 1. 2-(3-Methoxyphenyl)-1-methyl-1H-imidazole

A mixture of 3-iodoanisole (0.6 mL, 5 mmol), 1-methyl-2-(tributylstannyl)-1H-imidazole (*Bull. Chem. Soc. Jpn.* 1986, 59, 677, 2.5 g, 6 mmol), and dichlorobis(triphenylphosphine)palladoim(II) (421 mg, 0.6 mmol) in N,N-dimethylformamide (10 mL) was stirred at 60° C. for 8 h under nitrogen atmosphere. The reaction mixture was poured into 2 N sodium hydroxide aqueous solution (10 mL) and the basic mixture was extracted with ethyl acetate (30 mL×6). The combined organic extracts were washed with brine (10 mL×2) and dried (sodium sulfate). After removal of solvent, the residue was purified by column chromatography on silica gel eluting with dichloromethane/methanol (20/1) to afford 724 mg (77%) of the title compound as pale orange oil: $^1$H-NMR (CDCl$_3$) δ 7.39–7.33 (1H, m), 7.22–7.16 (2H, m), 7.13–7.12 (1H, m), 6.97–6.94 (2H, m), 3.86 (3H, s), 3.76 (3H, s); MS (ESI) m/z 189 (M+H)$^+$.

Step 2. 3-(1-Methyl-1H-imidazol-2-yl)phenol

To a stirred solution of 2-(3-methoxyphenyl)-1-methyl-1H-imidazole (step 1, 724 mg, 3.8 mmol) in dichloromethane (2 mL) was added a solution of boron tribromide (1 M in dichloromethane, 5 mL) at 0° C. The mixture was stirred at 0° C. for 3 h and at room temperature for 40 h. The mixture was poured into aqueous sodium bicarbonate solution (10 mL). The precipitated solids were collected by filtration and dried under reduced pressure to afford 205 mg (31%) of the title compound as a pale brown solid: $^1$H-NMR (CDCl$_3$) δ 7.29–7.22 (2H, m), 7.09–7.07 (2H, m), 6.94 (1H, d, J=1.1 Hz), 6.83–6.78 (1H, m), 3.72 (3H, s); MS (ESI) m/z 175 (M+H)$^+$, 173 (M–H)$^-$.

Step 3. Methyl 4-{(1S)-1-[({5-chloro-2-[3-(1-methyl-1H-imidazol-2-yl)phenoxy]pyridin-3-yl}carbonyl)amino]ethyl}benzoate The title compound was prepared according to the procedure described in step 2 of Example 45 from 3-(1-methyl-1H-imidazol-2-yl)phenol (step 2): $^1$H-NMR (CDCl$_3$) δ 8.53 (1H, d, J=2.7 Hz), 8.14–8.12 (2H, m), 8.01–7.99 (2H, m), 7.58–7.52 (3H, m), 7.44–7.42 (2H, m), 7.23–7.18 (1H, m), 7.13–7.12 (1H, m), 7.00–6.99 (1H, m), 5.42–5.32 (1H, m), 3.90 (3H, s), 3.81 (3H, s), 1.59 (3H, d, J=6.9 Hz); MS (ESI) m/z 491 (M+H)$^+$, 489 (M–H)$^-$.

Step 4. 4-{(1S)-1-[({5-Chloro-2-[3-(1-methyl-1H-imidazol-2-yl)phenoxy]pyridin-3-yl}carbonyl)amino]ethyl}benzoic acid The title compound was prepared according to the procedure described in step 2 of Example 83 from methyl 4-{(1S)-1-[({5-chloro-2-[3-(1-methyl-1H-imidazol-2-yl)phenoxy]pyridin-3-yl}carbonyl)amino]ethyl}benzoate (step 3): $^1$H-NMR (CDCl$_3$) δ □09.04 (1H, d, J=7.0 Hz), 8.30 (1H, d, J=2.7 Hz), 8.14 (1H, d, J=2.7 Hz), 7.87–7.84 (2H, m), 7.56–7.50 (5H, m), 7.28–7.24 (2H, m), 6.98 (1H, d, J=1.1 Hz), 5.24–5.13 (1H, m), 3.76 (3H, s), 1.46 (3H, d, J=7.0 Hz), a peak of COOH was not observed; MS (ESI) m/z 477 (M+H)$^+$, 475 (M–H)$^-$.

Example 128

4-[1-({[5-CHLORO-2-(3-FLUOROPHENOXY)PYRIDIN-3-YL]CARBONYL}AMINO)CYCLOPROPYL]BENZOIC ACID

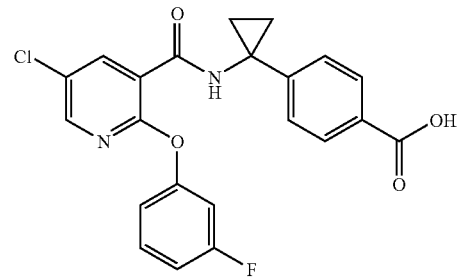

Step 1. 5-Chloro-2-(3-fluorophenoxy)nicotinic acid

To a stirred solution of methyl 2,5-dichloronicotinate (*J. Med. Chem.* 1993, 36, 2676, 353 mg, 1.71 mmol) and 3-fluorophenol (291 mg, 2.6 mmol) in toluene (5 mL) was added potassium carbonate (360 mg, 2.6 mmol) in one portion. The resulting mixture was heated at reflux temperature for 16 h with azeotroping using a Dean Stark apparatus. The mixture was poured into water (50 mL) and the aqueous mixture was extracted with ethyl acetate (100 mL). The organic extracts were washed with water (50 mL) and brine (50 mL), dried (sodium sulfate), and concentrated under reduced pressure to give crude methyl 5-chloro-2-(3-fluorophenoxy)nicotinate. To a stirred solution of the crude ester in methanol (10 mL) was added 2 N sodium hydroxide aqueous solution (2 mL). The reaction mixture was stirred at room temperature for 3 h. The reaction mixture was partitioned between ether (30 mL) and water (30 mL). The organic phase was separated and the aqueous phase was acidified with 2 N hydrochloric acid (10 mL). The acidic mixture was extracted with dichloromethane (50 mL×3). The combined organic layer was washed with brine (100 mL), dried (sodium sulfate), and concentrated to afford 448 mg (93%) of the title compound as off white solids: $^1$H-NMR (CDCl$_3$) δ 8.44 (1H, d, J=2.6 Hz), 8.26 (1H, d, J=2.6 Hz), 7.46–7.36 (1H, m), 7.07–6.89 (3H, m); MS (ESI) m/z 268 (M+H)$^+$.

Step 2. N-[1-(4-Bromophenyl)cyploproryl]-5-chloro-2-(3-fluorophenoxy)nicotinamide The title compound was prepared according to the procedure described in step 3 of Example 1 from 5-chloro-2-(3-fluorophenoxy)nicotinic acid (step 1) and [1-(4-bromophenyl)cyclopropyl]amine (*Org. Lett.* 2003, 5, 753): $^1$H-NMR (CDCl$_3$) δ 8.55 (1H, d, J=2.7 Hz), 8.26 (1H, br.s), 8.15 (1H, d, J=2.7 Hz), 7.48–7.39 (3H, m), 7.23–7.19 (2H, m), 7.08–6.90 (3H, m), 1.36 (4H, s); MS (ESI) m/z 461 (M+H)$^+$, 459 (M–H)$^-$.

Step 3. Methyl 4-[1-({[5-chloro-2-(3-fluorophenoxy)pyridin-3-yl]carbonyl}amino)cyclopropyl]benzoate The title compound was prepared according to the procedure described in step 2 of Example 2 from N-[1-(4-bromophenyl)cycloproryl]-5-chloro-2-(3-fluorophenoxy)nicotinamide (step 2): $^1$H-NMR (CDCl$_3$) δ 8.60 (1H, d, J=2.9 Hz), 8.30 (1H, br.s), 8.17 (1H, d, J=2.9 Hz), 7.98–7.95 (2H, m), 7.48–7.40 (1H, m), 7.32–7.29 (2H, m), 7.07–6.92 (3H, m), 3.90 (3H, s), 1.47–1.45 (4H, m); MS (ESI) m/z 441 (M+H)$^+$, 439 (M–H)$^-$.

Step 4. 4-[1-({[5-Chloro-2-(3-fluorophenoxy)pyridin-3-yl]carbonyl}amino)cyclopropyl]benzoic acid The title compound was prepared according to the procedure described in step 2 of Example 83 from methyl 4-[1-({[5-chloro-2-(3-fluorophenoxy)pyridin-3-yl]carbonyl}amino)cyclopropyl]benzoate (step 3): $^1$H-NMR (CDCl$_3$) δ 9.26 (1H, br.s), 8.33 (1H, d, J=2.6 Hz), 8.20 (1H, d, J=2.6 Hz), 7.84–7.78 (2H, m), 7.54–7.45 (1H, m), 7.34–7.31 (2H, m), 7.19–7.07 (3H, m), 1.36 (4H, s), a peak of COOH was not observed; MS (ESI) m/z 427 (M+H)$^+$, 425 (M–H)$^-$.

Example 129

4-[1-({[5-CHLORO-2-(3-FLUOROPHENOXY)PYRIDIN-3-YL]CARBONYL}AMINO)CYCLOBUTYL]BENZOIC ACID

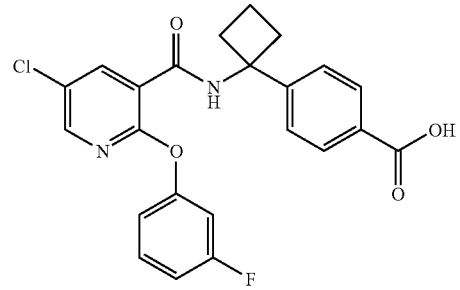

Step 1. N-[1-(4-Bromophenyl)cyclobutyl]-5-chloro-2-(3-fluorophenoxy)nicotinamide A mixture of 1-(4-bromophenyl)cyclobutanecarboxylic acid (200 mg, 0.78 mmol), diphenylphosphoryl azide (202 μL, 0.94 mmol), and triethylamine (131 μL, 0.94 mmol) in toluene (3 mL) was heated under reflux with stirring for 2 h. To the reaction mixture was added concentrated hydrochloric acid (1 mL). The resulting mixture was heated under reflux with stirring for 3 h. Then an ammonium hydroxide solution (5 mL) was added to the reaction mixture and the whole was extracted with ethyl acetate (15 mL×3). The combined organic phase was washed with brine (30 mL) and concentrated to give [1-(4-bromophenyl)cyclopropyl]amine as black oil. The crude amine was reacted with 5-chloro-2-(3-fluorophenoxy)nicotinic acid (step 1 of Example 128) according to the procedure described in step 3 of Example 1 to give the title compound: $^1$H-NMR (CDCl$_3$) δ 8.47 (1H, d, J=2.4 Hz), 8.24 (1H, br.s), 8.14 (1H, d, J=2.4 Hz), 7.51–6.92 (8H, m), 2.74–1.43 (6H, m); MS (ESI) m/z 475 (M+H)$^+$, 473 (M–H)$^-$.

Step 2. Methyl 4-[1-({[5-chloro-2-(3-fluorophenoxy)pyridin-3-yl]carbonyl}amino)cyclobutyl]benzoate The title compound was prepared according to the procedure described in step 2 of Example 2 from N-[1-(4-bromophenyl)cyclobutyl]-5-chloro-2-(3-fluorophenoxy)nicotinamide (step 1): $^1$H-NMR (CDCl$_3$) δ 8.47 (1H, d, J=2.6 Hz), 8.30 (1H, br.s), 8.14 (1H, d, J=2.6 Hz), 8.04–8.01 (2H, m), 7.57–7.55 (2H, m), 7.49–7.41 (1H, m), 7.08–6.95 (3H, m), 3.90 (3H, s), 2.78–2.46 (4H, m), 2.22–2.11 (1H, m), 2.05–1.93 (1H, m); MS (ESI) m/z 455 (M+H)$^+$, 453 (M–H)$^-$.

Step 3. 4-[1-({[5-Chloro-2-(3-fluorophenoxy)pyridin-3-yl]carbonyl}amino)cyclobutyl]benzoic acid The title compound was prepared according to the procedure described in step 2 of Example 83 from methyl 4-[1-({[5-chloro-2-(3-fluorophenoxy)pyridin-3-yl]carbonyl}amino)cyclobutyl]benzoate (step 2): $^1$H-NMR (CDCl$_3$) δ 8.47 (1H, d, J=2.6 Hz), 8.32 (1H, br.s), 8.15 (1H, d, J=2.6 Hz), 8.08–8.05 (2H, m), 7.60–7.54 (2H, m), 7.49–7.41 (1H, m), 7.12–6.87 (3H, m), 2.80–2.56 (4H, m), 2.27–1.94 (2H, m), a peak of COOH was not observed; MS (ESI) m/z 441 (M+H)$^+$, 439 (M–H)$^-$.

Example 130

4-[(1S)-1-({[5-CHLORO-2-(4-FLUORO-3-METHYLPHENOXY)PYRIDIN-3-YL]CARBONYL}AMINO)ETHYL]BENZOIC ACID

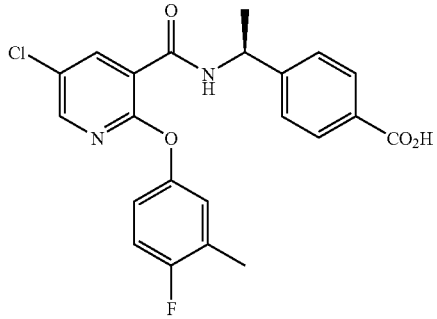

Step 1. tert-Butyl 4-[(1S)-1-({[5-chloro-2-(4-fluoro-3-methylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 4-fluoro-3-methylphenol: $^1$H-NMR (CDCl$_3$) δ 8.55 (1H, d, J=2.6 Hz), 8.23–8.10 (2H, m), 7.96 (2H, d, J=8.4 Hz), 7.41 (2H, d, J=8.4 Hz), 7.15–6.90 (3H, m), 5.50–5.30 (1H, m), 2.32 (3H, s), 1.65–1.55 (3H, m), 1.58 (9H, s); MS (ESI) m/z 485 (M+H)$^+$, 483 (M−H)$^-$.

Step 2.4-[(1S)-1-({[5-Chloro-2-(4-fluoro-3-methylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-fluoro-3-methylphenoxy)pyridin-3-yl]carbonyl}amino)ethyl]benzoate (step 1): $^1$H-NMR (DMSO-d$_6$) δ 8.99 (1H, d, J=7.8 Hz), 8.27 (1H, d, J=2.6 Hz), 8.12 (1H, d, J=2.6 Hz), 7.86 (2H, d, J=8.2 Hz), 7.53 (2H, d, J=8.2 Hz), 7.27–7.02 (3H, m), 5.18 (1H, dq, J=7.8, 6.9 Hz), 2.24 (3H, s), 1.46 (3H, d, J=6.9 Hz); MS (ESI) m/z 429 (M+H)$^+$, 427 (M−H)$^-$.

Example 131

4-[(1S)-1-({[5-CHLORO-2-(4-FLUORO-2-METHYLPHENOXY)PYRIDIN-3-YL]CARBONYL}AMINO)ETHYL]BENZOIC ACID

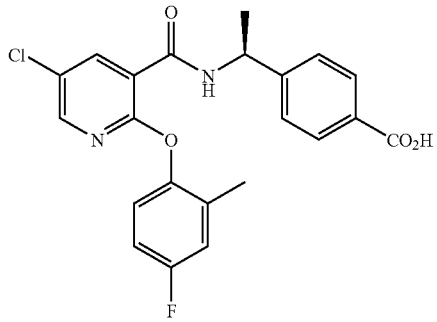

Step 1. tert-Butyl 4-[(1S)-1-({[5-chloro-2-(4-fluoro-2-methylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 4-fluoro-2-methylphenol: $^1$H-NMR (CDCl$_3$) δ 8.57 (1H, d, J=2.6 Hz), 8.22 (1H, d, J=7.6 Hz), 8.11 (1H, d, J=2.6 Hz), 7.96 (2H, d, J=8.4 Hz), 7.41 (2H, d, J=8.4 Hz), 7.13–6.93 (3H, m), 5.39 (1H, dq, J=7.6, 6.9 Hz), 2.12 (3H, s), 1.60 (3H, d, J=6.9 Hz), 1.58 (9H, s); MS (ESI) m/z 485 (M+H)$^+$, 483 (M−H)$^-$.

Step 2. 4-[(1S)-1-({[5-Chloro-2-(4-fluoro-2-methylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-fluoro-2-methylphenoxy)pyridin-3-yl]carbonyl}amino)ethyl]benzoate (step 1): $^1$H-NMR (DMSO-d$_6$) δ 12.87 (1H, br.s), 9.02 (1H, d, J=7.7 Hz), 8.23 (1H, d, J=2.6 Hz), 8.14 (1H, d, J=2.6 Hz), 7.88 (2H, d, J=8.2 Hz), 7.54 (2H, d, J=8.2 Hz), 7.25–7.02 (3H, m), 5.19 (1H, dq, J=7.7, 7.0 Hz), 2.06 (3H, s), 1.47 (3H, d, J=7.0 Hz); MS (ESI) m/z 429 (M+H)$^+$, 427 (M−H)$^-$.

Example 132

4-[(1S)-1-({[5-CHLORO-2-(4-CHLORO-3-METHYLPHENOXY)PYRIDIN-3-YL]CARBONYL}AMINO)ETHYL]BENZOIC ACID

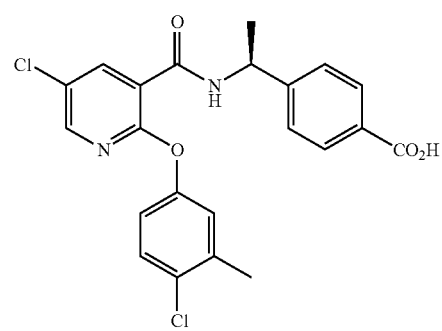

Step 1. tert-Butyl 4-[(1S)-1-({[5-chloro-2-(4-chloro-3-methylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 4-chloro-3-methylphenol: $^1$H-NMR (CDCl$_3$) δ 8.54 (1H, d, J=2.6 Hz), 8.15 (1H, d, J=2.6 Hz), 8.09 (1H, d, J=7.3 Hz), 7.95

(2H, d, J=8.3 Hz), 7.47–7.37 (3H, m), 7.03 (1H, d, J=2.8 Hz), 6.96 (1H, dd, J=8.6, 2.8 Hz), 5.36 (1H, dq, J=7.3, 7.0 Hz), 2.41 (3H, s), 1.60 (3H, d, J=7.0 Hz), 1.58 (9H, s); MS (ESI) m/z 501 (M+H)⁺, 499 (M−H)⁻.

Step 2. 4-[(1S)-1-({[5-Chloro-2-(4-chloro-3-methylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-chloro-3-methylphenoxy)pyridin-3-yl]carbonyl}amino)ethyl]benzoate (step 1): ¹H-NMR (DMSO-d₆) δ 12.88 (1H, br.s), 9.01 (1H, d, J=7.9 Hz), 8.29 (1H, d, J=2.6 Hz), 8.14 (1H, d, J=2.6 Hz), 7.86 (2H, d, J=8.3 Hz), 7.52 (2H, d, J=8.3 Hz), 7.46 (1H, d, J=8.8 Hz), 7.20 (1H, d, J=2.8 Hz), 7.08 (1H, dd, J=8.8, 2.8 Hz), 5.17 (1H, dq, J=7.9, 7.0 Hz), 2.33 (3H, s), 1.45 (3H, d, J=7.0 Hz); MS (ESI) m/z 445 (M+H)⁺, 443 (M−H)⁻.

Example 133

4-[(1S)-1-({[5-CHLORO-2-(4-CHLORO-2-METHYLPHENOXY)PYRIDIN-3-YL]CARBONYL}AMINO)ETHYL]BENZOIC ACID

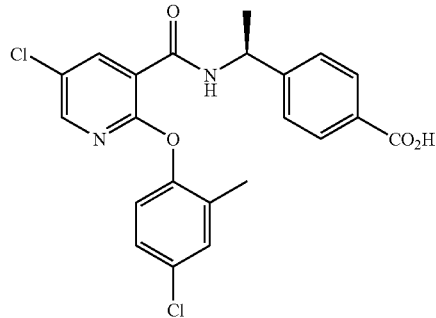

Step 1. Methyl 4-[(1S)-1-({[5-chloro-2-(4-chloro-2-methylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 4-chloro-2-methylphenol: ¹H-NMR (CDCl₃) δ 8.57 (1H, d, J=2.6 Hz), 8.14 (1H, d, J=7.6 Hz), 8.11 (1H, d, J=2.6 Hz), 8.01 (2H, d, J=8.2 Hz), 7.43 (2H, d, J=8.2 Hz), 7.31 (1H, d, J=2.4 Hz), 7.27 (1H, dd, J=8.6, 2.4 Hz), 7.04 (1H, d, J=8.6 Hz), 5.36 (1H, dq, J=7.6, 7.1 Hz), 3.91 (3H, s), 2.11 (3H, s), 1.60 (3H, d, J=7.1 Hz); MS (ESI) m/z 459 (M+H)⁺, 457 (M−H)⁻.

Step 2. 4-[(1S)-1-({[5-Chloro-2-(4-chloro-2-methylphenoxy)pyridin-3-yl]carbonyl}amino)ethyl]benzoic acid The title compound was prepared according to the procedure described in step 2 of Example 83 from methyl 4-[(1S)-1-({[5-chloro-2-(4-chloro-2-methylphenoxy)pyridin-3-yl]carbonyl}amino)ethyl]benzoate (step 1): ¹H-NMR (DMSO-d₆) δ 9.03 (1H, d, J=7.7 Hz), 8.24 (1H, d, J=2.6 Hz), 8.15 (1H, d, J=2.6 Hz), 7.87 (2H, d, J=8.3 Hz), 7.53 (2H, d, J=8.3 Hz), 7.40 (1H, d, J=2.8 Hz), 7.31 (1H, dd, J=8.6, 2.8 Hz), 7.19 (1H, d, J=8.6 Hz), 5.19 (1H, dq, J=7.7, 7.2 Hz), 2.06 (3H, s), 1.47 (3H, d, J=7.2 Hz); MS (ESI) m/z 445 (M+H)⁺, 443 (M−H)⁻.

Example 134

4-[(1S)-1-({[5-CHLORO-2-(2-CHLORO-4-METHYLPHENOXY)PYRIDIN-3-YL]CARBONYL}AMINO)ETHYL]BENZOIC ACID

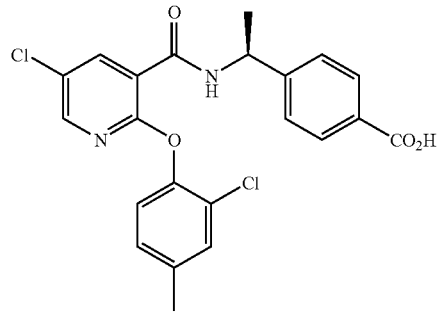

Step 1. Methyl 4-[(1S)-1-({[5-chloro-2-(2-chloro-4-methylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 2-chloro-4-methylphenol: ¹H-NMR (CDCl₃) δ 8.53 (1H, d, J=2.6 Hz), 8.20 (1H, d, J=7.4 Hz), 8.11 (1H, d, J=2.6 Hz), 8.01 (2H, d, J=8.4 Hz), 7.45 (2H, d, J=8.4 Hz), 7.37–7.31 (1H, m), 7.23–7.17 (2H, m), 5.39 (1H, dq, J=7.4, 6.9 Hz), 3.90 (3H, s), 2.40 (3H, s), 1.60 (3H, d, J=6.9 Hz); MS (ESI) m/z 459 (M+H)⁺, 457 (M−H)⁻.

Step 2. 4-[(1S)-1-({[5-Chloro-2-(2-chloro-4-methylphenoxy)pyridin-3-yl]carbonyl}amino)ethyl]benzoic acid The title compound was prepared according to the procedure described in step 2 of Example 83 from methyl 4-[(1S)-1-({[5-chloro-2-(2-chloro-4-methylphenoxy)pyridin-3-yl]carbonyl}amino)ethyl]benzoate (step 1): ¹H-NMR (DMSO-d₆) δ 8.98 (1H, d, J=7.7 Hz), 8.25 (1H, d, J=2.6 Hz), 8.16 (1H, d, J=2.6 Hz), 7.87 (2H, d, J=8.2 Hz), 7.53 (2H, d, J=8.3 Hz), 7.45–7.39 (1H, m), 7.34–7.18 (2H, m), 5.20 (1H, dq, J=7.7, 6.9 Hz), 2.34 (3H, s), 1.47 (3H, d, J=6.9 Hz); MS (ESI) m/z 445 (M+H)⁺, 443 (M−H)⁻.

Example 135

4-[(1S)-1-({[5-CHLORO-2-(3-CHLORO-4-METHYLPHENOXY)PYRIDIN-3-YL]CARBONYL}AMINO)ETHYL]BENZOIC ACID

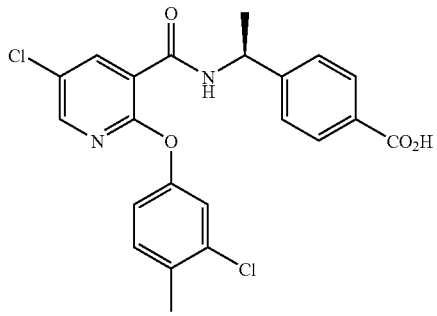

Step 1. Methyl 4-[(1S)-1-({[5-chloro-2-(3-chloro-4-methylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-chloro-4-methylphenol: $^1$H-NMR (CDCl$_3$) δ 8.54 (1H, d, J=2.6 Hz), 8.15 (1H, d, J=2.6 Hz), 8.07 (1H, d, J=7.3 Hz), 8.01 (2H, d, J=8.4 Hz), 7.43 (2H, d, J=8.4 Hz), 7.32 (1H, d, J=8.4 Hz), 7.20 (1H, d, J=2.5 Hz), 6.97 (1H, dd, J=8.4, 2.5 Hz), 5.37 (1H, dq, J=7.3, 7.1 Hz), 3.91 (3H, s), 2.41 (3H, s), 1.59 (3H, d, J=7.1 Hz); MS (ESI) m/z 459 (M+H)$^+$, 457 (M−H)$^-$.

Step 2. 4-[(1S)-1-({[5-Chloro-2-(3-chloro-4-methylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3-chloro-4-methylphenoxy)pyridin-3-yl]carbonyl}amino)ethyl]benzoate (step 1): $^1$H-NMR (DMSO-d$_6$) δ 9.01 (1H, d, J=7.9 Hz), 8.29 (1H, d, J=2.6 Hz), 8.13 (1H, d, J=2.6 Hz), 7.87 (2H, d, J=8.3 Hz), 7.53 (2H, d, J=8.3 Hz), 7.42 (1H, d, J=8.4 Hz), 7.34 (1H, d, J=2.4 Hz), 7.12 (1H, dd, J=8.4, 2.4 Hz), 5.18 (1H, dq, J=7.9, 7.2 Hz), 2.34 (3H, s), 1.46 (3H, d, J=7.2 Hz); MS (ESI) m/z 445 (M+H)$^+$, 443 (M−H)$^-$.

Example 136

4-((1S)-1-{[5-CHLORO-2-(2,5-DIFLUOROPHENOXY)BENZOYL]AMINO}ETHYL)BENZOIC ACID

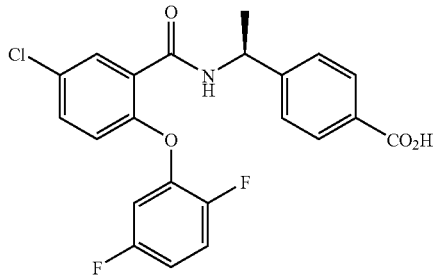

Step 1. Methyl 5-chloro-2-(2,5-difluorophenoxy)benzoate

The title compound was prepared according to the procedure described in step 1 of Example 67 from methyl 5-chloro-2-fluorobenzoate and 2,5-difluorophenol: $^1$H-NMR (CDCl$_3$) δ 7.95 (1H, d, J=2.8 Hz), 7.46 (1H, dd, J=8.8, 2.8 Hz), 7.20–7.10 (1H, m), 6.95 (1H, d, J=8.8 Hz), 6.85–6.73 (1H, m), 6.68–6.56 (1H, m), 3.85 (3H, s).

Step 2. 5-Chloro-2-(2,5-difluorophenoxy)benzoic acid

The title compound was prepared according to the procedure described in step 2 of Example 67 from methyl 5-chloro-2-(2,5-difluorophenoxy)benzoate (step 1): MS (ESI) m/z 283 (M−H)$^-$.

Step 3. Methyl 4-((1S)-1-{[5-chloro-2-(2,5-difluorophenoxy)benzoyl]amino}ethyl)benzoate The title compound was prepared according to the procedure described in step 3 of Example 1 from 5-chloro-2-(2,5-difluorophenoxy)benzoic acid (step 2) and methyl 4-[(1S)-1-aminoethyl]benzoate hydrochloride (step 3 of Example 5): $^1$H-NMR (CDCl$_3$) δ 8.16 (1H, d, J=2.6 Hz), 7.95 (2H, d, J=8.2 Hz), 7.60 (1H, d, J=7.4 Hz), 7.45–7.32 (3H, m), 7.25–7.13 (1H, m), 6.97–6.82 (2H, m), 6.80–6.67 (1H, m), 5.33 (1H, dq, J=7.4, 6.9 Hz), 3.90 (3H, s), 1.53 (3H, d, J=6.9 Hz); MS (ESI) m/z 446 (M+H)$^+$, 444 (M−H)$^-$.

Step 4. 4-((1S)-1-{[5-Chloro-2-(2,5-difluorophenoxy)benzoyl]amino}ethyl)benzoic acid The title compound was prepared according to the procedure described in step 2 of Example 83 from methyl 4-((1S)-1-{[5-chloro-2-(2,5-difluorophenoxy)benzoyl]amino}ethyl)benzoate (step 3): $^1$H-NMR (DMSO-d$_6$) δ 8.94 (1H, d, J=7.8 Hz), 7.83 (2H, d, J=8.2 Hz), 7.61 (1H, d, J=2.6 Hz), 7.56 (1H, dd, J=8.7, 2.6 Hz), 7.52–7.37 (3H, m), 7.12 (1H, d, J=8.7 Hz), 7.08–6.97 (1H, m), 6.96–6.86 (1H, m), 5.06 (1H, dq, J=7.8, 6.9 Hz), 1.46 (3H, d, J=6.9 Hz); MS (ESI) m/z 432 (M+H)$^+$, 430 (M−H)$^-$.

Example 137

4-[(1S)-1-({[2-(2-CHLORO-4-FLUOROPHENOXY)-5-FLUOROPYRIDIN-3-YL]CARBONYL}AMINO)ETHYL]BENZOIC ACID

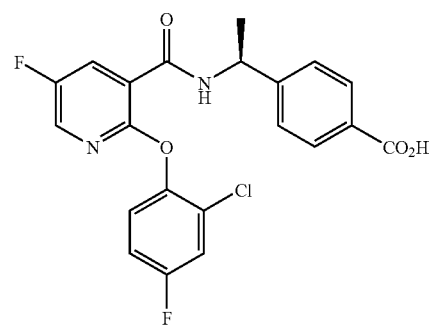

Step 1. Methyl 4-((1S)-1-{[(2-chloro-5-fluoropyridin-3-yl)carbonyl]amino}ethyl)benzoate The title compound was prepared according to the procedure described in step 1 of Example 45 from 2-chloro-5-fluoronicotinic acid and methyl 4-[(1S)-1-aminoethyl]benzoate hydrochloride (step 3 of Example 5): $^1$H-NMR (CDCl$_3$) δ 8.54 (1H, d, J=2.9 Hz), 8.05 (2H, d, J=8.4 Hz), 7.92 (1H, dd, J=7.8, 2.9 Hz), 7.47 (2H, d, J=8.4 Hz), 6.91 (1H, m), 5.36 (1H, m), 3.92 (3H, s), 1.64 (3H, d, J=6.9 Hz).

Step 2. Methyl 4-[(1S)-1-({[2-(2-chloro-4-fluorophenoxy)-5-fluoropyridin-3-yl]carbonyl}amino)ethyl]benzoate The title compound was prepared according to the procedure described in step 2 of Example 45 from methyl 4-((1S)-1-{[(2-chloro-5-fluoropyridin-3-yl)carbonyl]amino}ethyl)benzoate (step 1) and 2-chloro-4-fluorophenol: $^1$H-NMR (CDCl$_3$) δ 8.32 (1H, dd, J=8.1, 2.9 Hz), 8.19 (1H, d, J=7.3 Hz), 8.02–7.99 (3H, m), 7.45 (2H, d, J=8.3 Hz), 7.32–7.25 (2H, m), 7.14–7.08 (1H, m), 5.39 (1H, m), 3.90 (3H, s), 1.61 (3H, d, J=7.0 Hz).

Step 3. 4-[(1S)-1-({[2-(2-Chloro-4-fluorophenoxy)-5-fluoropyridin-3-yl]carbonyl}amino)ethyl]benzoic acid The title compound was prepared according to the procedure described in step 2 of Example 83 from methyl 4-[(1S)-1-({[2-(2-chloro-4-fluorophenoxy)-5-fluoropyridin-3-yl]carbonyl}amino)ethyl]benzoate (step 2): $^1$H-NMR (DMSO-d$_6$) δ 9.00 (1H, d, J=7.7 Hz), 8.22 (1H, d, J=2.9 Hz), 8.07 (1H, dd, J=8.7, 2.9 Hz), 7.86 (2H, d, J=8.2 Hz), 7.61 (1H, dd, J=8.4, 2.9 Hz), 7.53 (2H, d, J=8.2 Hz), 7.55–7.45 (1H, m), 7.31 (1H, m), 5.20 (1H, m), 1.47 (3H, d, J=7.1 Hz); MS (ESI) m/z 433 (M+H)$^+$, 431 (M–H)$^-$.

Example 138

4-((1S)-1-{[5-CYANO-2-(3-FLUOROPHENOXY)BENZOYL]AMINO}ETHYL)BENZOIC ACID

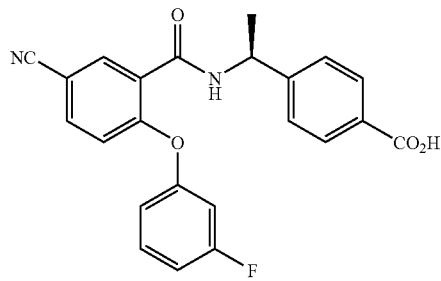

Step 1. 5-Cyano-2-(3-fluorophenoxy)benzoic acid

The title compound was prepared according to the procedure described in step 1 and 2 of Example 67 from methyl 5-cyano-2-fluorobenzoate and 3-fluorophenol: $^1$H-NMR (CDCl$_3$) δ 8.36 (1H, s), 7.73 (1H, m), 7.39 (1H, m), 7.00–6.78 (4H, m).

Step 2. Methyl 4-((1S)-1-{[5-cyano-2-(3-fluorophenoxy)benzoyl]amino}ethyl)benzoate The title compound was prepared according to the procedure described in step 3 of Example 1 from 5-cyano-2-(3-fluorophenoxy)benzoic acid (step 1) and methyl 4-[(1S)-1-aminoethyl]benzoate hydrochloride (step 3 of Example 5): $^1$H-NMR (CDCl$_3$) δ 8.54 (1H, s), 7.97 (2H, d, J=8.4 Hz), 7.77–7.65 (2H, m), 7.47–7.34 (3H, m), 7.04–6.80 (4H, m), 5.35 (1H, m), 3.90 (3H, s), 1.54 (3H, d, J=7.8 Hz).

Step 3. 4-((1S)-1-{[5-Cyano-2-(3-fluorophenoxy)benzoyl]amino}ethyl)benzoic acid To a stirred solution of methyl 4-((1S)-1-{[5-cyano-2-(3-fluorophenoxy)benzoyl]amino}ethyl)benzoate (step 2, 200 mg, 0.47 mmol) in dichloromethane (10 mL) was added a solution of boron tribromide (1 M in dichloromethane, 0.95 mL, 0.95 mmol) dropwise at 0° C. The resulting mixture was stirred at room temperature for 6 h. The reaction mixture was poured into water (10 mL) and the whole was extracted with ethyl acetate (50 mL). The organic layer was dried over magnesium sulfate and concentrated under reduced pressure. The residue was purified by flush column chromatography on silica gel eluting with hexane/ethyl acetate (1/1) to afford 62 mg (33%) of the title compound as white solids: $^1$H-NMR (DMSO-d$_6$) δ 12.86 (1H, br.s), 8.95 (1H, d, J=7.9 Hz), 8.04 (1H, d, J=2.2 Hz), 7.90 (1H, dd, J=8.6, 2.2 Hz), 7.81 (2H, d, J=8.3 Hz), 7.51–7.40 (3H, m), 7.12–6.90 (4H, m), 5.07 (1H, m), 1.37 (3H, d, J=6.9 Hz); MS (ESI) m/z 405 (M+H)$^+$, 403 (M–H)$^-$.

Example 139

4-[(1S)-1-({[5-CHLORO-2-(4-PYRIDIN-2-YLPHENOXY)PYRIDIN-3-YL]CARBONYL}AMINO)ETHYL]BENZOIC ACID

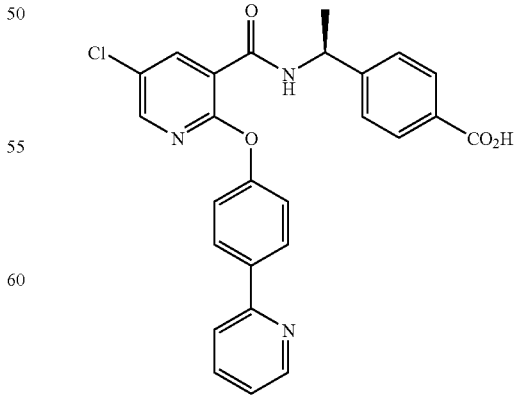

Step 1. tert-Butyl 4-[(1S)-1-({[5-chloro-2-(4-pyridin-2-ylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 4-pyridin-2-ylphenol (*Tetrahedron*, 1998, 54, 1289): ¹H-NMR (CDCl₃) δ 8.71 (1H, m), 8.56 (1H, d, J=2.8 Hz), 8.19–7.71 (8H, m), 7.41 (2H, d, J=1.8 Hz), 7.29–7.25 (3H, m), 5.36 (1H, m), 1.58 (3H, d, J=7.0 Hz), 1.57 (9H, s).

Step 2. 4-[(1S)-1-({[5-Chloro-2-(4-pyridin-2-ylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-pyridin-2-ylphenoxy)pyridin-3-yl]carbonyl}amino)ethyl]benzoate (step 1): ¹H-NMR (DMSO-d₆) δ 9.07 (1H, d, J=7.7 Hz), 8.67 (1H, m), 8.30 (1H, d, J=2.6 Hz), 8.15 (3H, m), 8.14–7.85 (4H, m), 7.54 (2H, d, J=8.1 Hz), 7.38–7.30 (3H, m), 5.18 (1H, m), 1.46 (3H, d, J=7.0 Hz); MS (ESI) m/z 474 (M+H)⁺, 472 (M–H)⁻.

Example 140

4-[(1S)-1-({[5-CHLORO-2-(4-PYRIDIN-3-YLPHENOXY)PYRIDIN-3-YL]CARBONYL}AMINO)ETHYL]BENZOIC ACID

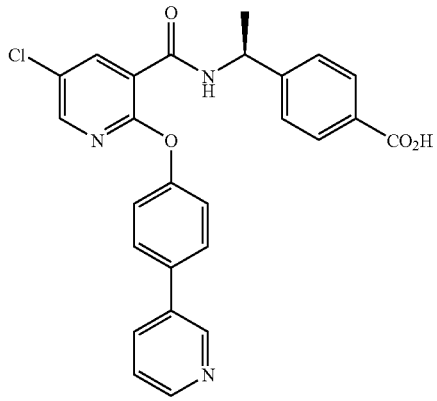

Step 1. tert-Butyl 4-[(1S)-1-({[5-chloro-2-(4-pyridin-3-ylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 4-pyridin-3-ylphenol (*J. Med. Chem.* 1986, 29, 1461): ¹H-NMR (CDCl₃) δ 8.88 (1H, m), 8.64–8.53 (2H, m), 8.17 (1H, d, J=2.6 Hz), 8.13 (1H, d, J=7.5 Hz), 7.96 (2H, d, J=8.4 Hz), 7.69 (2H, d, J=8.6 Hz), 7.47 (1H, d, J=8.6 Hz), 7.42 (2H, d, J=8.4 Hz), 7.29 (2H, d, J=8.6 Hz), 6.97 (1H, d, J=8.6 Hz), 5.38 (1H, m), 1.60 (3H, d, J=7.5 Hz), 1.57 (9H, s).

Step 2. 4-[(1S)-1-({[5-Chloro-2-(4-pyridin-3-ylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-pyridin-3-ylphenoxy)pyridin-3-yl]carbonyl}amino)ethyl]benzoate (step 1): ¹H-NMR (DMSO-d₆) δ 9.03 (1H, d, J=7.7 Hz), 8.90 (1H, m), 8.56 (1H, m), 8.29 (1H, d, J=2.6 Hz), 8.13 (1H, d, J=2.6 Hz), 8.09 (1H, m), 7.85 (2H, d, J=8.2 Hz), 7.77 (2H, d, J=8.7 Hz), 7.52 (2H, d, J=8.2 Hz), 7.47 (1H, m), 7.31 (2H, d, J=8.7 Hz), 5.17 (1H, m), 1.44 (3H, d, J=7.1 Hz); MS (ESI) m/z 474 (M+H)⁺, 472 (M–H)⁻.

Example 141

4-[(1S)-1-({[5-CHLORO-2-(4-PYRIDIN-4-YLPHENOXY)PYRIDIN-3-YL]CARBONYL}AMINO)ETHYL]BENZOIC ACID

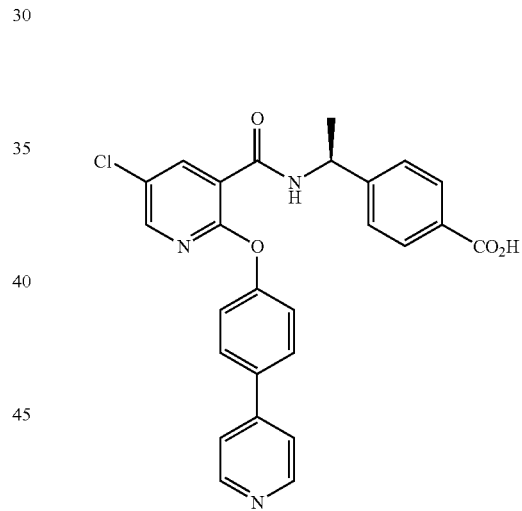

Step 1. tert-Butyl 4-[(1S)-1-({5-chloro-2-(4-pyridin-4-ylphenoxy)pyridin-3-yl]carbonyl}amino)ethyl]benzoate The title compound was prepared according to the procedure described in step 2 of Example 45 from tert-butyl 4-((1S)-1-{[(2,5-dichloropyridin-3-yl)carbonyl]amino}ethyl)benzoate (step 1 of Example 45) and 4-pyridin-4-ylphenol (*J. Med. Chem.* 2003, 46, 3709): ¹H-NMR (CDCl₃) δ 8.68 (2H, d, J=6.0 Hz), 8.57 (1H, d, J=2.6 Hz), 8.16 (1H, d, J=2.6 Hz), 8.10 (1H, d, J=7.9 Hz), 7.96 (2H, d, J=8.2 Hz), 7.73 (2H, d, J=8.7 Hz), 7.52 (2H, d, J=6.0 Hz), 7.41 (2H, d, J=8.2 Hz), 7.29 (2H, d, J=8.7 Hz), 5.38 (1H, m), 1.60 (3H, d, J=7.5 Hz), 1.57 (9H, s).

Step 2. 4-[(1S)-1-({[5-Chloro-2-(4-pyridin-4-ylphenoxy)pyridin-3-yl]carbonyl}amino)ethyl]benzoic acid The title compound was prepared according to the procedure described in step 5 of Example 44 from tert-butyl 4-[(1S)-1-({[5-chloro-2-(4-pyridin-4-ylphenoxy)pyridin-3-yl]carbonyl}amino)ethyl]benzoate (step 1): $^1$H-NMR (DMSO-d$_6$) δ 9.04 (1H, d, J=7.9 Hz), 8.63 (2H, d, J=6.1 Hz), 8.30 (1H, d, J=2.6 Hz), 8.14 (1H, d, J=2.6 Hz), 7.86 (4H, m), 7.72 (2H, d, J=6.1 Hz), 7.52 (2H, d, J=8.3 Hz), 7.34 (2H, d, J=8.6 Hz), 5.19 (1H, m), 1.46 (3H, d, J=7.0 Hz); MS (ESI) m/z 474 (M+H)$^+$, 472 (M−H)$^−$.

Example 142

4-[(1S)-1-({[5-CHLORO-2-(3-CHLORO-5-METHYLPHENOXY)PYRIDIN-3-YL]CARBONYL}AMINO)ETHYL]BENZOIC ACID

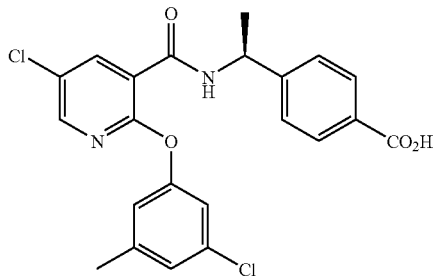

Step 1. Methyl 4-[(1S)-1-({[5-chloro-2-(3-chloro-5-methylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-chloro-5-methylphenol (*J. Org. Chem.* 1996, 61, 6814): $^1$H-NMR (CDCl$_3$) δ 8.54 (1H, d, J=2.8 Hz), 8.15 (1H, d, J=2.6 Hz), 8.01 (3H, m), 7.42 (2H, d, J=8.1 Hz), 7.12 (1H, m), 6.97 (1H, m), 6.85 (1H, m), 5.36 (1H, m), 3.91 (3H, s), 2.38 (3H, s), 1.59 (3H, d, J=7.5 Hz).

Step 2. 4-[(1S)-1-({[5-Chloro-2-(3-chloro-5-methylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3-chloro-5-methylphenoxy)pyridin-3-yl]carbonyl}amino)ethyl]benzoate (step 1): $^1$H-NMR (DMSO-d$_6$) δ 8.99 (1H, d, J=7.7 Hz), 8.31 (1H, d, J=2.6 Hz), 8.13 (1H, d, J=2.6 Hz), 7.86 (2H, d, J=8.1 Hz), 7.51 (2H, d, J=8.1 Hz), 7.14 (2H, m), 6.99 (1H, s), 5.16 (1H, m), 2.32 (3H, s), 1.45 (3H, d, J=7.0 Hz); MS (ESI) m/z 444 (M+H)$^+$, 442 (M−H)$^−$.

Example 143

4-[(1S)-1-({[5-CHLORO-2-(3-FLUORO-2-METHYLPHENOXY)PYRIDIN-3-YL]CARBONYL}AMINO)ETHYL]BENZOIC ACID

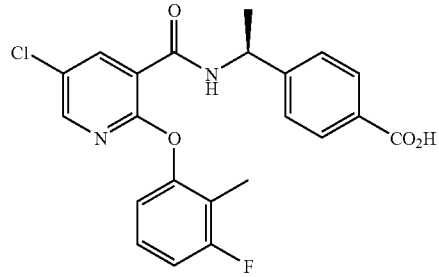

Step 1. Methyl 4-[(1S)-1-({[5-chloro-2-(3-fluoro-2-methylphenoxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and 3-fluoro-2-methylphenol: $^1$H-NMR (CDCl$_3$) δ 8.57 (1H, d, J=2.3 Hz), 8.14 (1H, d, J=7.5 Hz), 8.10 (1H, d, J=2.3 Hz), 8.00 (2H, d, J=8.3 Hz), 7.43 (2H, d, J=8.3 Hz), 7.25 (1H, m), 7.03 (1H, t, J=8.3 Hz), 6.91 (1H, d, J=8.1 Hz), 5.40 (1H, m), 3.90 (3H, s), 2.06 (3H, s), 1.60 (3H, d, J=7.5 Hz).

Step 2. 4-[(1S)-1-({[5-Chloro-2-(3-fluoro-2-methylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3-fluoro-2-methylphenoxy)pyridin-3-yl]carbonyl}amino)ethyl]benzoate (step 1): $^1$H-NMR (DMSO-d$_6$) δ 9.04 (1H, d, J=7.5 Hz), 8.23 (1H, d, J=2.7 Hz), 8.14 (1H, d, J=2.7 Hz), 7.86 (2H, d, J=8.3 Hz), 7.51 (2H, d, J=8.3 Hz), 7.31–7.24 (1H, m), 7.10–6.99 (2H, m), 5.18 (1H, m), 1.97 (3H, s), 1.46 (3H, d, J=7.0 Hz); MS (ESI) m/z 427 (M−H)$^−$.

Example 144

4-[(1S)-1-({[5-CHLORO-2-(ISOQUINOLIN-7-YLOXY)PYRIDIN-3-YL]CARBONYL}AMINO)ETHYL]BENZOIC ACID

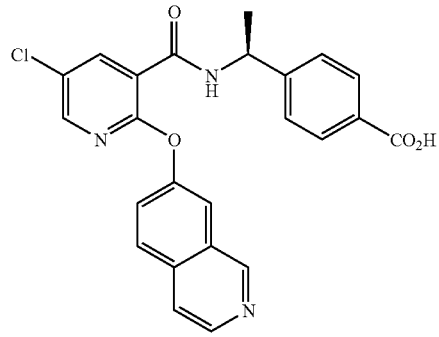

Step 1. Methyl 4-[(1S)-1-({[5-chloro-2-(isoquinolin-7-yloxy)pyridin-3-yl]carbonyl}amino)ethyl]benzoate The title compound was prepared according to the procedure described in step 2 of Example 45 methyl 4-((1S)-1-{[(2,5-dichloropyridin-3-yl)carbonyl]amino}ethyl)benzoate (step 1 of Example 48) and isoquinolin-7-ol: ¹H-NMR (CDCl₃) δ 9.27 (1H, s), 8.59 (2H, m), 8.13–8.10 (2H, m), 8.00 (2H, d, J=8.4 Hz), 7.94 (1H, d, J=8.9 Hz), 7.74 (2H, m), 7.50 (1H, dd, J=8.9, 2.3 Hz), 7.45 (2H, d, J=8.4 Hz), 5.40 (1H, m), 3.89 (3H, s), 1.61 (3H, d, J=7.0 Hz).

Step 2. 4-[(1S)-1-({[5-Chloro-2-(isoquinolin-7-yloxy)pyridin-3-yl]carbonyl}amino)ethyl]benzoic acid The title compound was prepared according to the procedure described in step 2 of Example 83 from methyl 4-[(1S)-1-({[5-chloro-2-(isoquinolin-7-yloxy)pyridin-3-yl]carbonyl}amino)ethyl]benzoate (step 1): ¹H-NMR (DMSO-d₆) δ 9.30 (1H, s), 9.10 (1H, d, J=7.7 Hz), 8.51 (1H, d, J=5.6 Hz), 8.31 (1H, d, J=2.6 Hz), 8.18 (1H, d, J=2.6 Hz), 8.05 (1H, d, J=8.9 Hz), 7.91–7.81 (4H, m), 7.65 (1H, dd, J=8.9, 2.3 Hz), 7.52 (2H, d, J=8.2 Hz), 5.18 (1H, m), 1.46 (3H, d, J=7.1 Hz); MS (ESI) m/z 448 (M+H)⁺, 426 (M–H)⁻.

Example 145

4-[(1S)-1-({[5-CHLORO-2-(QUINOLIN-7-YLOXY)PYRIDIN-3-YL]CARBONYL}AMINO)ETHYL]BENZOIC ACID

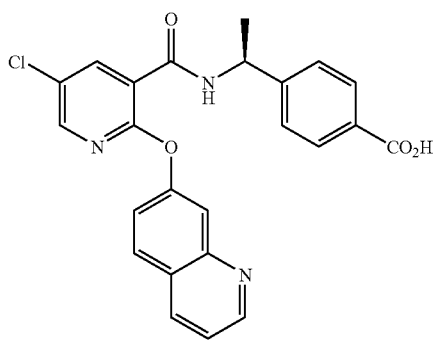

Step 1. Methyl 4-[(1S)-1-({[5-chloro-2-(quinolin-7-yloxy)pyridin-3-yl]carbonyl}amino)ethyl]benzoate The title compound was prepared according to the procedure described in step 2 of Example 45 from methyl 4-((1S)-1-{[(2,5-dichloropyridin-3-yl)carbonyl]amino}ethyl)benzoate (step 1 of Example 48) and quinolin-7-ol: ¹H-NMR (CDCl₃) δ 8.96 (1H, m), 8.60 (1H, d, J=2.8 Hz), 8.24–8.14 (3H, m), 8.00–7.88 (4H, m), 7.47–7.26 (4H, m), 5.39 (1H, m), 3.89 (3H, s), 1.60 (3H, d, J=7.0 Hz).

Step 2. 4-[(1S)-1-({[5-Chloro-2-(quinolin-7-yloxy)pyridin-3-yl]carbonyl}amino)ethyl]benzoic acid The title compound was prepared according to the procedure described in step 2 of Example 83 from methyl 4-[(1S)-1-({[5-chloro-2-(quinolin-7-yloxy)pyridin-3-yl]carbonyl}amino)ethyl]benzoate (step 1): ¹H-NMR (DMSO-d₆) δ 9.09 (1H, d, J=7.9 Hz), 8.90 (1H, m), 8.40 (1H, d, J=7.7 Hz), 8.31 (1H, d, J=2.6 Hz), 8.18 (1H, d, J=2.6 Hz), 8.06 (1H, d, J=8.8 Hz), 7.81 (2H, d, J=8.3 Hz), 7.76 (1H, m), 7.55–7.48 (4H, m), 5.18 (1H, m), 1.46 (3H, d, J=7.0 Hz); MS (ESI) m/z 448 (M+H)⁺, 426 (M–H)⁻.

Example 146

4-((1S)-1-{[4,5-DIFLUORO-2-(4-FLUOROPHENOXY)BENZOYL]AMINO}ETHYL)BENZOIC ACID

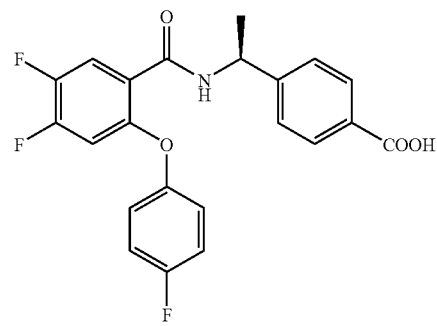

Step 1. 4,5-Difluoro-2-(4-fluorophenoxy)benzoic acid

The title compound was prepared according to the procedure described in step 1 of Example 66 from 2-chloro-4,5-difluorobenzoic acid and 4-fluorophenol: MS (ESI) m/z 222 (M–H)⁻.

Step 2. Methyl 4-((1S)-1-{[4,5-difluoro-2-(4-fluorophenoxy)benzoyl]amino}ethyl)benzoate The title compound was prepared according to the procedure described in step 3 of Example 1 from 4,5-difluoro-2-(4-fluorophenoxy)benzoic acid (step 1) and methyl 4-[(1S)-1-aminoethyl]benzoate (step 3 of Example 5): MS (ESI) m/z 430 (M+H)⁺, 428 (M–H)⁻.

Step 3. 4-((1S)-1-{[4,5-Difluoro-2-(4-fluorophenoxy)benzoyl]amino}ethyl)benzoic acid The title compound was prepared according to the procedure described in step 4 of Example 1 from methyl 4-((1S)-1-{[4,5-difluoro-2-(4-fluorophenoxy)benzoyl]amino}ethyl)benzoate (step 2): ¹H-NMR (CD₃OD) δ 7.86 (2H, d, J=8.3 Hz), 7.65–7.59 (1H, m), 7.40–7.26 (3H, m), 7.08–7.02 (1H, m), 6.91–6.86 (1H, m), 6.78–6.69 (3H, m), 5.10 (1H, m), 1.45 (3H, d, J=7.0 Hz); MS (ESI) m/z 416 (M+H)⁺, 414 (M–H)⁻.

Example 147

4-[(1S)-1-({[5-CHLORO-2-(3-FLUORO-4-METHYLPHENOXY)PYRIDIN-3-YL]CARBONYL}AMINO)ETHYL]BENZOIC ACID

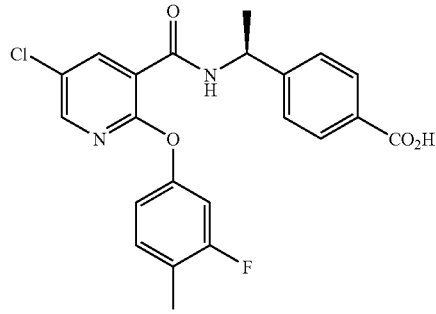

Step 1. Methyl 4-[(1S)-1-({[5-chloro-2-(3-fluoro-4-methylphenoxy)pyridin-3-yl]carbonyl}amino)ethyl]benzoate The title compound was prepared according to the procedure described in step 2 of Example 45 methyl 4-((1S)-1-{[(2,5-dichloropyridin-3-yl)carbonyl]amino}ethyl)benzoate (step 1 of Example 48) and 3-fluoro-4-methylphenol: $^1$H-NMR (CDCl$_3$) δ 8.54 (1H, d, J=2.8 Hz), 8.14 (1H, d, J=2.8 Hz), 8.07 (1H, d, J=7.7 Hz), 8.00 (2H, d, J=8.4 Hz), 7.41 (2H, d, J=8.4 Hz), 7.26 (1H, m), 6.25 (2H, m), 5.36 (1H, m), 3.91 (3H, s), 2.30 (3H, s), 1.59 (3H, d, J=7.0 Hz); MS (ESI) m/z 443 (M+H)$^+$, 441 (M−H)$^−$.

Step 2. 4-[(1S)-1-({[5-Chloro-2-(3-fluoro-4-methylphenoxy)pyridin-3-yl]carbonyl}amino)ethyl]benzoic acid The title compound was prepared according to the procedure described in step 2 of Example 83 from methyl 4-[(1S)-1-({[5-chloro-2-(3-fluoro-4-methylphenoxy)pyridin-3-yl]carbonyl}amino)ethyl]benzoate (step 1): $^1$H-NMR (DMSO-d$_6$) δ 8.99 (1H, d, J=7.7 Hz), 8.28 (1H, d, J=2.6 Hz), 8.11 (1H, d, J=2.6 Hz), 7.84 (2H, d, J=8.4 Hz), 7.50 (2H, d, J=8.4 Hz), 7.33 (1H, m), 7.06 (1H, m), 6.94 (1H, m), 5.16 (1H, m), 2.23 (3H, s), 1.44 (3H, d, J=7.7 Hz); MS (ESI) m/z 429 (M+H)$^+$, 427 (M−H)$^−$.

Example 148

4-((1S)-1-{[5-CHLORO-2-(3-CHLOROBENZYL)BENZOYL]AMINO}ETHYL)BENZOIC ACID

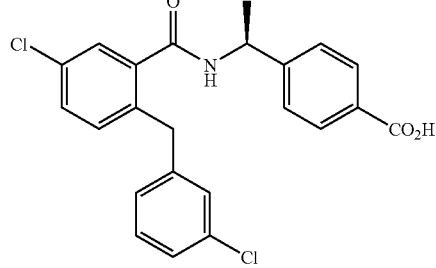

Step 1. Methyl 5-chloro-2-(3-chlorobenzyl)benzoate

The title compound was prepared according to the procedure described in step 2 of Example 112 from methyl 2-(bromomethyl)-5-chlorobenzoate (step 1 of Example 112) and 3-chlorophenylbronic acid: $^1$H-NMR (CDCl$_3$) δ 7.91 (1H, d, J=2.4 Hz), 7.42 (1H, dd, J=8.3 Hz) 7.22–7.10 (4H, m), 7.02–6.99 (1H, m), 4.32 (2H, s), 3.84 (3H, s).

Step 2. 5-Chloro-2-(3-chlorobenzyl)benzoic acid

The title compound was prepared according to the procedure described in step 2 of Example 1 from methyl 5-chloro-2-(3-chlorobenzyl)benzoate (step 1): $^1$H-NMR (CDCl$_3$) δ 8.07 (1H, d, J=2.3 Hz), 7.47 (1H, dd, J=8.2, 2.3 Hz), 7.25–7.00 (5H, m), 4.38 (2H, s).

Step 3. Methyl 4-((1S)-1-{[5-chloro-2-(3-chlorobenzyl)benzoyl]amino}ethyl)benzoate The title compound was prepared according to the procedure described in step 3 of Example 1 from 5-chloro-2-(3-chlorobenzyl)benzoic acid (step 2) and methyl 4-[(1S)-1-aminoethyl]benzoate hydrochloride (step 3 of Example 8): $^1$H-NMR (CDCl$_3$) δ 7.98 (2H, dd, J=6.5, 1.7 Hz), 7.36–7.26 (4H, m), 7.19–7.13 (3H, m), 7.05 (1H, br.s), 6.97–6.94 (1H, m), 5.93 (1H, d, J=7.2 Hz), 5.19 (1H, dq, J=7.2, 7.0 Hz), 4.11 (2H, s), 3.92 (3H, s), 1.44 (3H, d, J=7.0 Hz); MS (ESI) m/z 442 (M+H)$^+$, 440 (M−H)$^−$.

Step 4. 4-((1S)-1-{[5-Chloro-2-(3-chlorobenzyl)benzoyl]amino}ethyl)benzoic acid The title compound was prepared according to the procedure described in step 3 of Example 48 from methyl 4-((1S)-1-{[5-chloro-2-(3-chlorobenzyl)benzoyl]amino}ethyl)benzoate (step 3): $^1$H-NMR (DMSO-d$_6$) δ 9.03 (1H, d, J=7.9 Hz), 7.89 (2H, d, J=8.4 Hz), 7.49–7.33 (5H, m), 7.25–7.17 (3H, m), 7.09–7.05 (1H, m), 5.11 (1H, dq, J=7.2, 7.0 Hz), 4.04 (2H, s), 1.39 (3H, d, J=7.0 Hz); MS (ESI) m/z 428 (M+H)$^+$, 426 (M−H)$^−$.

What is claimed is:
1. A compound of the formula (I):

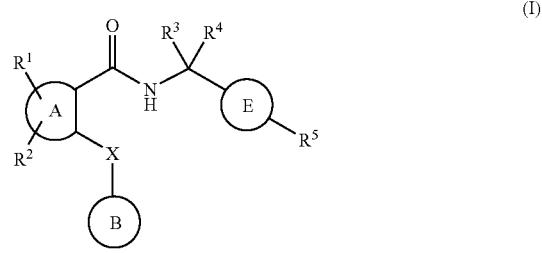

wherein A represents a phenyl group or a pyridyl group;
B represents an aryl group or a heteroaryl group;
E represents a 1,4-phenylene group;
R$^1$ and R$^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;
R$^3$ and R$^4$ independently represent a hydrogen atom or an alkyl group having from 1 to 4 carbon atoms; or R$^3$ and R$^4$ groups may be joined together to form an alkylene chain having 2 to 6 carbon atoms;

R5 represents

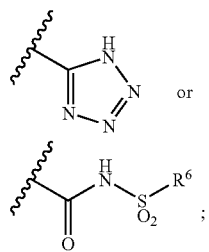

—$CO_2H$, $CO_2W$,
$R^6$ represents an alkyl group having from 1 to 6 carbon atoms, a cycloalkyl group having from 3 to 7 ring atoms, an aryl group or a heteroaryl group;
X represents a methylene group, an oxygen atom or a sulfur atom;
said aryl groups have from 6 to 10 carbon atoms;
said heteroaryl groups are 5- to 10-membered aromatic heterocyclic groups containing from 1 to 3 heteroatoms selected from the group consisting of sulfur atoms, oxygen atoms and nitrogen atoms; said aryl groups and said heteroaryl groups referred to in the definitions of B are unsubstituted or are substituted by at least one substituent selected from the group consisting of substituents α;
said 1,4-phenylene group referred to in the definition of E is unsubstituted or is substituted by at least one substituent selected from the group consisting of substituents β;
said aryl groups and said heteroaryl groups referred to in the definitions of $R^6$ and α are unsubstituted or are substituted by at least one substituent selected from the group consisting of substituents β;
said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms arylcarbonyl groups, two adjacent a groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;
said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;
W is a pharmaceutically acceptable ester pro-drug group;
with the proviso $R^1$ and $R^2$ do not represent a hydrogen atom simultaneously;
or a pharmaceutically acceptable salt thereof.

2. A compound according to claim 1, wherein:
E represents an unsubstituted 1,4-phenylene group.

3. A compound according to claim 1, wherein:
E represents a 1,4-phenylene group substituted by at least one substituent selected from the group consisting of halogen atoms and alkyl groups having from 1 to 4 carbon atoms.

4. A compound according to claim 1, wherein:
B represents a phenyl or pyridyl group;
said group is unsubstituted or is substituted by at least one substituent selected from the group consisting of substituents α;
said substituents a are selected from the group consisting halogen atoms, alkyl groups having from 1 to 4 carbon atoms, alkoxy groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent α groups are optionally joined together to form an alkylene chain having 3 carbon atoms, alkylthio groups having from 1 to 4 carbon atoms, and di-alkylaminoalkyl groups having from 1 to 6 carbon atoms in the alkyl part;
said heteroaryl groups referred to in the definitions of α are unsubstituted or are substituted by alkyl groups having from 1 to 4 carbon atoms.

5. A compound according to claim 1, wherein:
B represents a phenyl group optionally substituted by substituent selected from the group consisting of substituents α;
said substituents α are selected from the group consisting of halogen atoms, alkyl groups having from 1 to 4 carbon atoms, alkoxy groups having from 1 to 4 carbon atoms, haloalkoxy groups having from 1 to 4 carbon atoms, cyano groups, alkynyl groups having from 2 to 6 carbon atoms, alkanoyl groups having from 1 to 4 carbon atoms, cycloalkyl groups having from 3 to 7 ring atoms, alkylthio groups having from 1 to 4 carbon atoms, di-alkylaminoalkyl groups having from 1 to 6 carbon atoms in the alkyl part, thiazolyl groups, isothiazolyl groups, oxazolyl groups, isoxazolyl groups, imidazolyl groups, pyridyl groups, benzyloxy groups, phenyl groups or benzoyl groups;

said thiazolyl groups, isothiazolyl groups, oxazolyl groups, isoxazolyl groups, imidazolyl groups and pyridyl groups referred to in the definitions of α are unsubstituted or are substituted by alkyl groups having from 1 to 4 carbon atoms.

6. A compound according to claim 1, wherein:

B represents a phenyl group optionally substituted by substituent selected from the group consisting of substituents α;

said substituents a are selected from the group consisting of fluorine atoms, chlorine atoms, methyl groups, ethyl groups, methoxy groups, trifluoromethoxy groups, cyano groups, ethynyl groups, acetyl groups, cyclopentyl groups, methylthio groups, dimethylaminoethyl groups, phenyl groups, imidazolyl groups optionally substituted by methyl groups, thiazolyl groups optionally substituted by methyl groups, pyridyl groups or benzyloxy groups.

7. A compound according to claim 1, wherein X represents a methylene group or an oxygen atom.

8. A compound according to claim 1, wherein $R^1$ represents a halogen atom and $R^2$ represents a hydrogen atom.

9. A compound according to claim 1, wherein $R^3$ and $R^4$ independently represent a hydrogen atom or an alkyl group having from 1 to 4 carbon atoms.

10. A compound according to claim 1, wherein $R^3$ represents an alkyl group having from 1 to 4 carbon atoms and $R^4$ represents a hydrogen atom.

11. A compound according to claim 1, wherein $R^3$ represents a methyl group and $R^4$ represents a hydrogen atom.

12. A compound according to claim 1, wherein $R^5$ represents

—CO$_2$H,

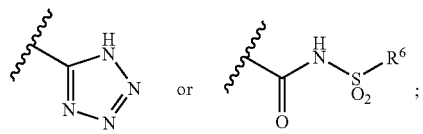

$R^6$ represents an aryl group optionally substituted by halogen atoms or an heteroaryl group.

13. A compound according to claim 1, wherein $R^5$ represents

—CO$_2$H,

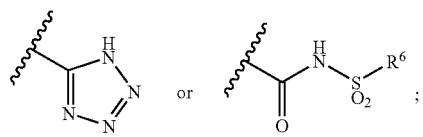

and $R^6$ represents an aryl group optionally substituted by halogen atoms.

14. A compound according to claim 1, wherein $R^5$ represents

—CO$_2$H

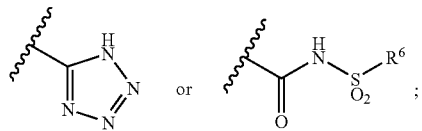

and $R^6$ represents a phenyl group optionally substituted by halogen atoms.

15. A compound according to claim 1, wherein $R^5$ represents

—CO$_2$H or

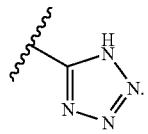

16. A compound according to claim 1 selected from:

4-((1S)-1-{[5-chloro-2-(4-fluorophenoxy)benzoyl]amino}ethyl)benzoic acid;
4-[(1S)-1-({[5-chloro-2-(4-fluorophenoxy)pyridin-3-yl]carbonyl}amino)ethyl]benzoic acid;
4-[(1S)-1-({[5-chloro-2-(3-cyanophenoxy)pyridin-3-yl]carbonyl}amino)ethyl]benzoic acid;
4-[(1S)-1-({[5-chloro-2-(3-fluorophenoxy)pyridin-3-yl]carbonyl}amino)ethyl]benzoic acid;
4-[(1S)-1-({[5-chloro-2-(3-chlorophenoxy)pyridin-3-yl]carbonyl}amino)ethyl]benzoic acid;
4-((1S)-1-{[5-chloro-2-(3-fluorophenoxy)benzoyl]amino}ethyl)benzoic acid;
4-((1S)-1-{[5-chloro-2-(3-methoxyphenoxy)benzoyl]amino}ethyl)benzoic acid;
4-((1S)-1-{[5-chloro-2-(3-chlorophenoxy)benzoyl]amino}ethyl)benzoic acid;
4-[(1S)-1-({[5-chloro-2-(2,4-difluorophenoxy)pyridin-3-yl]carbonyl}amino)ethyl]benzoic acid;
4-[(1S)-1-({[5-chloro-2-(4-chloro-3-fluorophenoxy)pyridin-3-yl]carbonyl}amino)ethyl]benzoic acid;
4-[(1S)-1-({[5-chloro-2-(2-chloro-4-fluorophenoxy)pyridin-3-yl]carbonyl}amino)ethyl]benzoic acid;
4-[(1S)-1-({[5-chloro-2-(2,6-difluorophenoxy)pyridin-3-yl]carbonyl}amino)ethyl]benzoic acid;
4-[(1S)-1-({[5-chloro-2-(3,4-difluorophenoxy)pyridin-3-yl]carbonyl}amino)ethyl]benzoic acid;
4-{(1S)-1-[({5-chloro-2-[3-(1,3-thiazol-2-yl)phenoxy]pyridin-3-yl}carbonyl)amino]ethyl}benzoic acid;
4-[(1S)-1-({[5-chloro-2-(2,3-difluorophenoxy)pyridin-3-yl]carbonyl}amino)ethyl]benzoic acid;
4-[(1S)-1-({[5-chloro-2-(2,5-difluorophenoxy)pyridin-3-yl]carbonyl}amino)ethyl]benzoic acid;
4-[(1S)-1-({[5-chloro-2-(4-chlorophenoxy)pyridin-3-yl]carbonyl}amino)ethyl]benzoic acid;
4-[(1S)-1-({[5-chloro-2-(4-chloro-2-fluorophenoxy)pyridin-3-yl]carbonyl}amino)ethyl]benzoic acid;
4-[(1S)-1-({[5-chloro-2-(2-chloro-5-fluorophenoxy)pyridin-3-yl]carbonyl}amino)ethyl]benzoic acid;
4-[(1S)-1-({[5-chloro-2-(3-methylphenoxy)pyridin-3-yl]carbonyl}amino)ethyl]benzoic acid;
4-[(1S)-1-({[5-chloro-2-(4-fluoro-3-methylphenoxy)pyridin-3-yl]carbonyl}amino)ethyl]benzoic acid;

4-[(1S)-1-({[5-chloro-2-(3,5-difluorophenoxy)pyridin-3-yl]carbonyl}amino)ethyl]benzoic acid;
4-((1S)-1-{[5-chloro-2-(2,3-difluorophenoxy)benzoyl]amino}ethyl)benzoic acid;
4-((1S)-1-{[5-chloro-2-(2,4-difluorophenoxy)benzoyl]amino}ethyl)benzoic acid;
4-((1S)-1-{[5-chloro-2-(3,4-difluorophenoxy)benzoyl]amino}ethyl)benzoic acid;
4-[(1S)-1-({[5-chloro-2-(3-chloro-5-fluorophenoxy)pyridin-3-yl]carbonyl}amino)ethyl]benzoic acid;
4-[(1S)-1-({[5-chloro-2-(3-chloro-2-methylphenoxy)pyridin-3-yl]carbonyl}amino)ethyl]benzoic acid;
4-((1S)-1-{[5-chloro-2-(3,5-difluorophenoxy)benzoyl]amino}ethyl)benzoic acid;
4-((1S)-1-{[5-chloro-2-(2,5-difluorophenoxy)benzoyl]amino}ethyl)benzoic acid;
4-[(1S)-1-({[5-chloro-2-(3-chloro-2-fluorophenoxy)pyridin-3-yl]carbonyl}amino)ethyl]benzoic acid;
4-[(1S)-1-({[5-chloro-2-(3-pyridin-2-ylphenoxy)pyridin-3-yl]carbonyl}amino)ethyl]benzoic acid;
4-[(1S)-1-({[5-chloro-2-(4-pyridin-2-ylphenoxy)pyridin-3-yl]carbonyl}amino)ethyl]benzoic acid;
4-[(1S)-1-({[5-chloro-2-(4-pyridin-4-ylphenoxy)pyridin-3-yl]carbonyl}amino)ethyl]benzoic acid;
4-[(1S)-1-({[5-chloro-2-(3-chloro-5-methylphenoxy)pyridin-3-yl]carbonyl}amino)ethyl]benzoic acid;
4-((1S)-1-{[5-chloro-2-(3-methylphenoxy)benzoyl]amino}ethyl)benzoic acid;
4-((1S)-1-{[5-chloro-2-(3-chloro-5-fluorophenoxy)benzoyl]amino}ethyl)benzoic acid;
4-((1S)-1-{[5-chloro-2-(2,6-difluorophenoxy)benzoyl]amino}ethyl)benzoic acid;
4-((11S)-1-{[(5-chloro-2-phenoxypyridin-3-yl)carbonyl]amino}ethyl)benzoic acid;
4-[(1S)-1-({[5-chloro-2-(2,3-dimethylphenoxy)pyridin-3-yl]carbonyl}amino)ethyl]benzoic acid;
4-[(1S)-1-({[5-chloro-2-(2,3-dichlorophenoxy)pyridin-3-yl]carbonyl}amino)ethyl]benzoic acid;
4-[(1S)-1-({[5-chloro-2-(3,4-dichlorophenoxy)pyridin-3-yl]carbonyl}amino)ethyl]benzoic acid;
4-[(1S)-1-({[5-chloro-2-(3,5-dichlorophenoxy)pyridin-3-yl]carbonyl}amino)ethyl]benzoic acid; and
4-[(1S)-1-({[5-chloro-2-(3-fluoro-4-methylphenoxy)pyridin-3-yl]carbonyl}amino)ethyl]benzoic acid;
or a pharmaceutically acceptable salt thereof.

17. A compound according to claim 1 selected from:
4-((1S)-1-{[5-chloro-2-(4-fluorophenoxy)benzoyl]amino}ethyl)benzoic acid;
4-[(1S)-1-({[5-chloro-2-(4-fluorophenoxy)pyridin-3-yl]carbonyl}amino)ethyl]benzoic acid;
4-[(1S)-1-({[5-chloro-2-(3-cyanophenoxy)pyridin-3-yl]carbonyl}amino)ethyl]benzoic acid;
4-[(1S)-1-({[5-chloro-2-(3-fluorophenoxy)pyridin-3-yl]carbonyl}amino)ethyl]benzoic acid;
4-[(1S)-1-({[5-chloro-2-(3-chlorophenoxy)pyridin-3-yl]carbonyl}amino)ethyl]benzoic acid;
4-((1S)-1-{[5-chloro-2-(3-fluorophenoxy)benzoyl]amino}ethyl)benzoic acid;
4-((1S)-1-{[5-chloro-2-(3-chlorophenoxy)benzoyl]amino}ethyl)benzoic acid;
4-[(1S)-1-({[5-chloro-2-(2-chloro-4-fluorophenoxy)pyridin-3-yl]carbonyl}amino)ethyl]benzoic acid;
4-[(1S)-1-({[5-chloro-2-(2,6-difluorophenoxy)pyridin-3-yl]carbonyl}amino)ethyl]benzoic acid;
4-[(1S)-1-({[5-chloro-2-(3,4-difluorophenoxy)pyridin-3-yl]carbonyl}amino)ethyl]benzoic acid;
4-[(1S)-1-({[5-chloro-2-(2,3-difluorophenoxy)pyridin-3-yl]carbonyl}amino)ethyl]benzoic acid;
4-[(1S)-1-({[5-chloro-2-(2,5-difluorophenoxy)pyridin-3-yl]carbonyl}amino)ethyl]benzoic acid;
4-[(1S)-1-({[5-chloro-2-(2-chloro-5-fluorophenoxy)pyridin-3-l]carbonyl}amino)ethyl]benzoic acid;
4-[(1S)-1-({[5-chloro-2-(3-methylphenoxy)pyridin-3-yl]carbonyl}amino)ethyl]benzoic acid;
4-[(1S)-1-({[5-chloro-2-(3,5-difluorophenoxy)pyridin-3-yl]carbonyl}amino)ethyl]benzoic acid;
4-((1S)-1-{[5-chloro-2-(2,3-difluorophenoxy)benzoyl]amino}ethyl)benzoic acid;
4-((1S)-1-{[5-chloro-2-(3,4-difluorophenoxy)benzoyl]amino}ethyl)benzoic acid;
4-[(1S)-1-({[5-chloro-2-(3-chloro-5-fluorophenoxy)pyridin-3-yl]carbonyl}amino)ethyl]benzoic acid;
4-((1S)-1-{[5-chloro-2-(3,5-difluorophenoxy)benzoyl]amino}ethyl)benzoic acid;
4-((1S)-1-{[5-chloro-2-(2,5-difluorophenoxy)benzoyl]amino}ethyl)benzoic acid;
4-[(1S)-1-({[5-chloro-2-(3-chloro-5-methylphenoxy)pyridin-3-yl]carbonyl}amino)ethyl]benzoic acid;
4-((1S)-1-{[5-chloro-2-(3-methylphenoxy)benzoyl]amino}ethyl)benzoic acid;
4-((1S)-1-{[5-chloro-2-(3-chloro-5-fluorophenoxy)benzoyl]amino}ethyl)benzoic acid;
4-((1S)-1-{[5-chloro-2-(2,6-difluorophenoxy)benzoyl]amino}ethyl)benzoic acid;
4-((1S)-1-{[(5-chloro-2-phenoxypyridin-3-yl)carbonyl]amino}ethyl)benzoic acid;
4-[(1S)-1-({[5-chloro-2-(2,3-dichlorophenoxy)pyridin-3-yl]carbonyl}amino)ethyl]benzoic acid;
4-[(1S)-1-({[5-chloro-2-(3,4-dichlorophenoxy)pyridin-3-yl]carbonyl}amino)ethyl]benzoic acid;
4-[(1S)-1-({[5-chloro-2-(3,5-dichlorophenoxy)pyridin-3-yl]carbonyl}amino)ethyl]benzoic acid; and
4-[(1S)-1-({[5-chloro-2-(3-fluoro-4-methylphenoxy)pyridin-3-yl]carbonyl}amino)ethyl]benzoic acid;
or a pharmaceutically acceptable salt thereof.

18. A pharmaceutical composition, which comprises a compound according to claim 1, or a pharmaceutically acceptable salt thereof, and a suitable pharmaceutically acceptable carrier.

19. A compound of the formula (II):

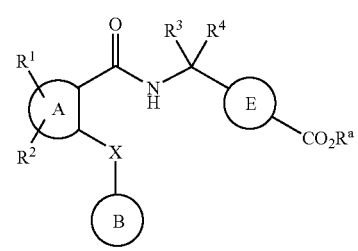

(II)

wherein A represents a phenyl group or a pyridyl group;
B represents an aryl group or a heteroaryl group;
E represents a 1,4-phenylene group;
$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

R³ and R⁴ independently represent a hydrogen atom or an alkyl group having from 1 to 4 carbon atoms; or R³ and R⁴ groups may be joined together to form an alkylene chain having 2 to 6 carbon atoms;

R$^a$ represents an alkyl groups having from 1 to 6 carbon atoms or an aralkyl group having from 7 to 12 carbon atoms, X represents a methylene group, an oxygen atom or a sulfur atom;

said aryl groups have from 6 to 10 carbon atoms;

said heteroaryl groups are 5- to 10-membered aromatic heterocyclic groups containing from 1 to 3 heteroatoms selected from the group consisting of sulfur atoms, oxygen atoms and nitrogen atoms;

said aryl groups and said heteroaryl groups referred to in the definitions of B are unsubstituted or are substituted by at least one substituent selected from the group consisting of substituents α;

said 1,4-phenylene group referred to in the definition of E is unsubstituted or is substituted by at least one substituent selected from the group consisting of substituents β;

said aryl groups and said heteroaryl groups referred to in the definitions of R⁶ and α are unsubstituted or are substituted by at least one substituent selected from the group consisting of substituents β;

said substituents α are selected from the group consisting of halogen atoms, alkyl groups having from 1 to 4 carbon atoms, alkoxy groups having from 1 to 4 carbon atoms haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent α groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

with the proviso R¹ and R² do not represent a hydrogen atom simultaneously;

or a pharmaceutically acceptable salt thereof.

20. A compound of the formula (III):

$$\text{(III)}$$

wherein A represents a phenyl group or a pyridyl group;

E represents a 1,4-phenylene group;

R¹ and R² independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

R³ and R⁴ independently represent a hydrogen atom or an alkyl group having from 1 to 4 carbon atoms; or R³ and R⁴ groups may be joined together to form an alkylene chain having 2 to 6 carbon atoms;

R$^a$ represents an alkyl groups having from 1 to 6 carbon atoms or an aralkyl group having from 7 to 12 carbon atoms, L¹ represents a halogen atom, an alkanesulfonyloxy group having from 1 to 4 carbon atoms, an arylsulfonyloxy group optionally substituted by an alkyl group having from 1 to 4 carbon atoms, a haloalkanesulfonyloxy group having from 1 to 4 carbon atoms or a boronic acid (B(OH)₂) group;

said 1,4-phenylene group referred to in the definition of E is unsubstituted or is substituted by at least one substituent selected from the group consisting of substituents β;

said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

with the proviso R¹ and R² do not represent a hydrogen atom simultaneously.

21. A compound of the formula (I):

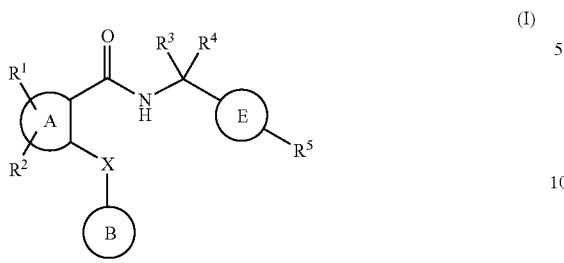

wherein A represents a phenyl group or a pyridyl group;
B represents an aryl group or a heteroaryl group;
E represents a phenylene group;
$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;
$R^3$ and $R^4$ independently represent a hydrogen atom or an alkyl group having from 1 to 4 carbon atoms; or $R^3$ and $R^4$ groups may be joined together to form an alkylene chain having 3 to 6 carbon atoms;
$R^5$ represents
—$CO_2H$,

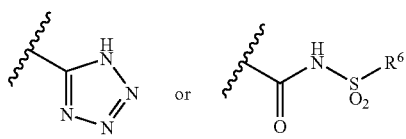

$R^6$ represents an alkyl group having from 1 to 6 carbon atoms, a cycloalkyl group having from 3 to 7 ring atoms, an aryl group or a heteroaryl group;
X represents a methylene group, an oxygen atom or a sulfur atom;
said aryl groups have from 6 to 10 carbon atoms;
said heteroaryl groups are 5- to 10-membered aromatic heterocyclic groups containing from 1 to 3 heteroatoms selected from the group consisting of sulfur atoms, oxygen atoms and nitrogen atoms;
said aryl groups and said heteroaryl groups referred to in the definitions of B are unsubstituted or are substituted by at least one substituent selected from the group consisting of substituents α;
said phenylene groups referred to in the definitions of E are unsubstituted or are substituted by at least one substituent selected from the group consisting of substituents β;
said aryl groups and said heteroaryl groups referred to in the definitions of $R^6$ and α are unsubstituted or are substituted by at least one substituent selected from the group consisting of substituents β;
said substituents α are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent α groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in the alkanoyl and alkyl part, alkanoyl(alkyl)aminoalkyl groups having from 1 to 6 carbon atoms in the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di-alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in the alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part or alkylsulfonylamino groups having from 1 to 4 carbon atoms;
said substituents β are selected from the group consisting of halogen atoms, alkyl groups having from 1 to 4 carbon atoms, alkoxy groups having from 1 to 4 carbon atoms, haloalkyl groups having from 1 to 4 carbon atoms or haloalkoxy groups having from 1 to 4 carbon atoms or cyano groups;
or a pharmaceutically acceptable ester of such compound; or a pharmaceutically acceptable salt thereof.

22. A compound according to claim 21, wherein E represents an unsubstituted 1,4-phenylene group.

23. A compound according to claim 21, wherein E represents a 1,4-phenylene group substituted by at least one substituent selected from the group consisting of halogen atoms and alkyl groups having from 1 to 4 carbon atoms.

24. The compound 4-[(1S)-1-({[5-chloro-2-(3-fluorophenoxy)pyridin-3-yl]carbonyl}amino)ethyl]benzoic acid or a pharmaceutically acceptable salt thereof.

25. A pharmaceutical composition comprising 4-[(1S)-1-({[5-chloro-2-(3-fluorophenoxy)pyridin-3-yl]carbonyl}amino)ethyl]benzoic acid or a pharmaceutically acceptable salt thereof and a pharmaceutically acceptable excipient.

26. A method of treating pain, inflammation, osteoarthritis or rheumatoid arthritis, the method comprising administering to a subject in need thereof a therapeutically effective amount of 4-[(1S)-1-({[5-chloro-2-(3-fluorophenoxy)pyridin-3-yl]carbonyl}amino)ethyl]benzoic acid or a pharmaceutically acceptable salt thereof.

27. A method of treating osteoarthritis, the method comprising administering to a subject in need thereof a therapeutically effective amount of 4-[(1S)-1-({[5-chloro-2-(3-fluorophenoxy)pyridin-3-yl]carbonyl}amino)ethyl]benzoic acid or a pharmaceutically salt thereof.

* * * * *